US012599637B2

(12) United States Patent
Gangaiah et al.

(10) Patent No.: US 12,599,637 B2
(45) Date of Patent: Apr. 14, 2026

(54) **GENETICALLY MODIFIED *LACTOBACILLUS* AND USES THEREOF**

(71) Applicant: ELANCO US INC., Greenfield, IN (US)

(72) Inventors: Dharanesh Mahimapura Gangaiah, Fishers, IN (US); Arvind Kumar, Fishers, IN (US); Lin Liu, Greenfield, IN (US); Shrinivasrao Peerajirao Mane, Zionsville, IN (US); Valerie Elyse Ryan, Greenfield, IN (US)

(73) Assignee: BiomEdit, Inc., Fishers, IN (US)

( * ) Notice: Subject to any disclaimer, the term of this patent is extended or adjusted under 35 U.S.C. 154(b) by 1199 days.

(21) Appl. No.: 17/428,506

(22) PCT Filed: Feb. 4, 2020

(86) PCT No.: PCT/US2020/016522

§ 371 (c)(1),
(2) Date: Aug. 4, 2021

(87) PCT Pub. No.: WO2020/163284

PCT Pub. Date: Aug. 13, 2020

(65) Prior Publication Data

US 2022/0127628 A1     Apr. 28, 2022

Related U.S. Application Data

(60) Provisional application No. 62/801,307, filed on Feb. 5, 2019.

(51) Int. Cl.
| | |
|---|---|
| *A61K 35/747* | (2015.01) |
| *A23K 10/18* | (2016.01) |
| *A23K 20/163* | (2016.01) |
| *A23K 50/75* | (2016.01) |
| *A23L 33/135* | (2016.01) |
| *A61K 35/742* | (2015.01) |
| *A61K 38/00* | (2006.01) |
| *A61P 1/00* | (2006.01) |
| *A61P 31/04* | (2006.01) |
| *C07K 14/32* | (2006.01) |
| *C07K 14/335* | (2006.01) |
| *C07K 16/12* | (2026.01) |
| *C07K 16/1282* | (2026.01) |
| *C12N 1/20* | (2026.01) |
| *C12N 1/205* | (2026.01) |
| *C12N 15/74* | (2006.01) |
| *C12R 1/225* | (2006.01) |

(52) U.S. Cl.
CPC ........... *A61K 35/747* (2013.01); *A23K 10/18* (2016.05); *A23K 20/163* (2016.05); *A23K 50/75* (2016.05); *A23L 33/135* (2016.08); *A61K 35/742* (2013.01); *A61P 1/00* (2018.01); *A61P 31/04* (2018.01); *C07K 16/1282* (2013.01); *C12N 1/205* (2021.05); *C12N*

*15/746* (2013.01); *A23V 2002/00* (2013.01); *A23V 2400/173* (2023.08); *A61K 38/00* (2013.01); *C07K 14/32* (2013.01); *C07K 14/335* (2013.01); *C07K 2317/22* (2013.01); *C07K 2317/76* (2013.01); *C07K 2319/02* (2013.01); *C07K 2319/035* (2013.01); *C12R 2001/225* (2021.05)

(58) Field of Classification Search
CPC ...... A23K 10/18; A61K 38/00; A61K 35/747; A23L 33/135
See application file for complete search history.

(56) References Cited

U.S. PATENT DOCUMENTS

2018/0221456 A1     8/2018   Schuch et al.

FOREIGN PATENT DOCUMENTS

| | | |
|---|---|---|
| DE | 102011015803 A1 | 10/2012 |
| GB | 2482535 A | 2/2012 |
| WO | 2013184064 A1 | 12/2013 |
| WO | 2017123675 A1 | 7/2017 |
| WO | 2018148847 A1 | 8/2018 |

OTHER PUBLICATIONS

Wang et al. "Preparation and Characterization of a Human ScFv against the Clostridium Perfringens Type a Alpha-Toxin." Toxicon: Official Journal of the International Society on Toxinology, vol. 130, May 2017, pp. 79-86, pubmed.ncbi.nlm.nih.gov/28259756/, https://doi.org/10.1016/j.toxicon.2017.02.021 (Year: 2017).*
Rusch, Sharyn L., and Debra A. Kendall. "Interactions That Drive Sec-Dependent Bacterial Protein Transport." Biochemistry, vol. 46, No. 34, Aug. 2007, pp. 9665-9673, https://doi.org/10.1021/bi7010064. Accessed Feb. 7, 2021. (Year: 2007).*

(Continued)

*Primary Examiner* — Jennifer Dunston

*Assistant Examiner* — Alexandra Rose Lippolis

(74) *Attorney, Agent, or Firm* — Hoffmann & Baron LLP

(57) ABSTRACT

The present invention relates to efficient delivery of anti-infective activity, immunomodulatory factors, or growth-promoting biomolecules directly to the digestive tract of an animal via a live delivery platform. The live delivery platform can be a genetically modified microorganism. Delivery can be accomplished with a *Lactobacillus* sp which colonizes the gastrointestinal tract. The anti-infective activity can be a bacteriocidal or bacteriostatic peptide, an antibody or fragment thereof which specifically recognizes a pathogen, or a phage, or a lytic peptide from a phage which specifically targets a certain pathogen.

19 Claims, 4 Drawing Sheets

Specification includes a Sequence Listing.

(56) References Cited

OTHER PUBLICATIONS

Del Carmen S et al. Current Review of Genetically Modified Lactic Acid Bacteria for the Prevention and Treatment of Colitis Using Murine Models. Gastroenterol Res Pract. 2015; 2015:146972. doi: 10.1155/2015/146972. Epub May 4, 2015. PMID: 26064086; PMCID: PMC4434185. (Year: 2015).*

Börner, Rosa A., et al. "Genome Editing of Lactic Acid Bacteria: Opportunities for Food, Feed, Pharma and Biotech," FEMS Microbiology Letters, vol. 366. No. 1, fny291 (2019).

De Moreno De Leblanc, Alejandra, et al. "Current Review of Genetically Modified Lactic Acid Bacteria for the Prevention and Treatment of Colitis Using Murine Models," Gastroenterology Research and Practice, vol. 2015, Article ID 146972 (2015).

Cano-Garrido, Olivia, et al., "Lactic Acid Bacteria: Reviewing the Potential of a Promising Delivery Live Vector for Biomedical Purposes," Microbial Cell Factories, vol. 14, No. 1, pp. 1-12 (2015).

Gaspar, C., et al. "Bacteriocin Production of the Probiotic Lactobacillus Acidophilus KS400," AMB Express, vol. 8, No. 1, pp. 1-8 (2018).

Michon, Christophe, et al. "Display of Recombinant Proteins at the Surface of Lactic Acid Bacteria: Strategies and Applications," Microbial Cell Factories, vol. 15, No. 1, pp. 1-16 (2016).

Duong, Tri, et al. "Construction of Vectors for Inducible and Constitutive Gene Expression in Lactobacillus," Microbial Biotechnology, vol. 4, No. 3, pp. 357-367 (2011).

Tauer, Christopher, et al. "Tuning Constitutive Recombinant Gene Expression in Lactobacillus Plantarum," Microbial Cell Factories, vol. 13, No. 1, pp. 1-11 (2014).

Perez-Lopez, Araceli, et al. "Mucosal Immunity to Pathogenic Intestinal Bacteria," Nature Reviews Immunology vol. 16, No. 3, pp. 135-148 (2016).

Anonymous, "Lactobacillus Reuteri," UniParc04 May 2017 (May 4, 2017), retrieved from Uniparc Accession No. JPI000A1F8C33 Database, Retrieved from the Internet: URL:Uniprot, XP055691980.

Anonymous, "UPI000F4F6921," Nov. 27, 2018 (Nov. 27, 2018), Retrieved from the Internet: URL:https://www.uniprot.org/uniparc/UPI000F4F6921, XP055692691, (retrieved on May 7, 2020).

Anonymous, "UPI000A2D69E0—Gram_Pos_Anchoring Domain-Containing Protein," Aug. 30, 2017 (Aug. 30, 2017), Retrieved from the Internet: URL:https://www.uniprot.org/uniparc/UPI000A2D69E0, XP055692765, (retrieved on May 7, 2020).

Nishiyama, Keita, et al., "Adhesion Properties of Lactic Acid Bacteria on Intestinal Mucin," Microorganisms, vol. 4, No. 3, pp. 34 (2016).

Cho, Seungchan, et al. "Probiotic Lactobacillus Paracasei Expressing a Nucleic Acid-Hydrolyzing Minibody (3D8 ScFv) Enhances Probiotic Activities in Mice Intestine as Revealed by Metagenomic Analyses," Genes, vol. 9, No. 6, p. 276 (2018).

Schmitz, Stephanie, et al. "The Lantibiotic Mersacidin is an Autoinducing Peptide," Applied and Environmental Microbiology, vol. 72, No. 11, pp. 7270-7277 (2006).

"Glycosyl Hydrolase 53 Family Protein [Limosilactobacillus Reuteri]," NCBI Reference Sequence: WP_08560044.1, retrieved from the internet: https://www.ncbi.nlm.nih.gov/protein/WP_985650044 on Oct. 20, 2021. (Corresponds to Non-Patent Literature No. 9 above.).

"SEC10/PgrA Surface Exclusion Domain-Containing Protein [Limosilactobacillus Reuteri]" NCBI Reference Sequence: WP_086118125.1, retrieved from the internet: https://www.ncbi.nlm.nih.gov/protein/WP_086118125 on Oct. 20, 2021. (Corresponds to Non-Patent Literature No. 11 above.).

PCT/International Search Report corresponding to International Application No. PCT/US2020/016522, dated May 13, 2020.

* cited by examiner

Antimicrobial susceptibility testing of *L. reuteri* strains using AVIPRO PLATE.

| Strain | AMX | CET | CST | CPP | CTX | DOX | ENR | ERY | ERYD | LIN | LIS | NEO | OXA | PEN | RAM | STRE | T/S | TET | TIA | TILM | TLS |
|---|---|---|---|---|---|---|---|---|---|---|---|---|---|---|---|---|---|---|---|---|---|
| 2091 | 2 | 2 | 4 | 4 | 1 | 8 | 2 | 4 | 10 | 4 | 8/32 | 16 | 0.25 | 2 | 50 | 200 | 2/38 | 8 | 8 | 16 | 1 |
| 2094 | 2 | 2 | 4 | 4 | 1 | 8 | 2 | 4 | 10 | 4 | 8/32 | 16 | 2 | 0.5 | 50 | 200 | 2/38 | 8 | 16 | 16 | 1 |
| 2095 | 2 | 2 | 4 | 4 | 1 | 8 | 2 | 4 | 10 | 4 | 8/32 | 16 | 2 | 2 | 50 | 200 | 2/38 | 8 | 16 | 16 | 1 |
| 2097 | 2 | 2 | 4 | 4 | 1 | 8 | 2 | 4 | 10 | 4 | 8/32 | 16 | 2 | 0.5 | 50 | 200 | 2/38 | 8 | 16 | 16 | 1 |
| 2098 | 2 | 2 | 4 | 4 | 1 | 8 | 2 | 1 | 10 | 4 | 8/32 | 16 | 2 | 0.5 | 50 | 200 | 2/38 | 8 | 8 | 16 | 1 |
| 3630 | 2 | 2 | 4 | 4 | 1 | 8 | 2 | 4 | 10 | 4 | 8/32 | 16 | 2 | 2 | 50 | 200 | 2/38 | 8 | 16 | 16 | 1 |
| 3632 | 2 | 2 | 4 | 4 | 1 | 8 | 2 | 4 | 10 | 4 | 8/32 | 16 | 2 | 2 | 50 | 200 | 2/38 | 8 | 16 | 16 | 1 |

Numbers represent concentration (μg/mL) at which the bacterial strain showed either resistance or susceptibility to the tested antibiotic. Strains showing resistance at a given antibiotic concentration are indicated by a bold and underlined concentration. Data are shown as means, representing three independent experiments. AMX: amoxicillin (2, 4, 8, 16 μg/mL); CET: ceftiofur (2 μg/mL); CST: colistin (2, 4 μg/mL); CPP: cefpodaxime-proxetil (4 μg/mL); CTX: cefotaxime (1 μg/mL); Dox: doxycycline (2, 4, 8 μg/mL); ENR: enrofloxacin (0.25, 0.5, 1, 2 μg/mL); ERY: erythromycin (0.25, 0.5, 1, 4 μg/mL); ERYD: erythromycinD (10, 20, 30 μg/mL); LIN: lincomycin (4 μg/mL); LIS: lincomycin-spectinomycin (8 μg/mL LI and 32 μg/mL S); NEO: neomycin (8, 16 μg/mL); OXA: oxacillin (0.25, 2 μg/mL); PEN: penicillin G (0.125, 0.25, 0.5, 2 μg/mL); RAM: rifampicin (50 μg/mL); STRE: streptomycin (200 μg/mL); T/S: trimethoprim-sulfamethoxazole (0.5/9.5, 1/19, 2/38 μg/mL T and S respectively); TET: tetracycline (2, 4, 8 μg/mL); TIA: tiamulin (8, 16 μg/mL); TILM: tilmicosin (8, 16 μg/mL); TLS: tylosin (0.5, 1 μg/mL).

FIG. 1

A. Example suicide vector map with representative expression cassette

B. Chromosomal integration sites

Site 1:

Site 2:

Site 3:

GENETICALLY MODIFIED *LACTOBACILLUS* AND USES THEREOF

CROSS-REFERENCE TO RELATED APPLICATIONS

The present application is a National Stage Application claiming priority from co-pending PCT Application No. PCT/US2020/016522 filed Feb. 4, 2020, which in turn claims benefit of priority to U.S. Provisional Application Ser. No. 62/801,307, filed Feb. 5, 2019, all of which are is hereby incorporated by reference in their its entirety.

FIELD OF THE INVENTION

The present invention relates to a live delivery platform, such as a genetically modified bacterium, to deliver preventative or therapeutic anti-infective activity, immunomodulatory factors, or growth-promoting biomolecules directly to the mucosa of an animal in need thereof.

BACKGROUND OF THE INVENTION

Direct fed microbials (DFMs), often also called probiotics, are microorganisms which colonize the gastrointestinal tract of an animal and provide some beneficial effect to that animal. The microorganisms can be bacterial species, for example those from the genera *Bacillus, Lactobacillus, Lactococcus*, and *Enterococcus*. The microorganisms can also be yeast or even molds. The microorganisms can be provided to an animal orally or mucosally or, in the case of birds, provided to a fertilized egg, i.e. in ovo.

The beneficial activity provided by a DFM can be the synthesis of vitamins or other nutritional molecules needed for a healthy metabolism of the host animal. A DFM can also protect the host animal from disease, disorders, or clinical symptoms caused by other, pathogenic microorganisms. For example, the DFM may naturally produce factors having inhibitory or cytotoxic activity against certain species of pathogens, such as deleterious or disease-causing bacteria. However, the DFM may not be able to produce such factors in sufficient quantity to reduce infection of the host with the pathogen, or the factors may affect only a limited set of pathogens, leaving the host vulnerable to other pathogens.

Stronger or more broad-based antibiotics can be administered to the host animal, for example orally or parenterally, but these would have a limited duration in the host, and thus may require repeated administration. Oral delivery may also result in the degradation of the antibiotics or failure to deliver the antibiotic to the particular anatomical site where the therapeutic effect is most needed. Development of antibiotic resistance by pathogens is another important concern.

What is needed is a delivery system which can constantly deliver anti-infective molecules directly to the gastrointestinal or respiratory tract where pathogenic bacteria are replicating in the host. The gastrointestinal and respiratory systems are also often a point of entry of the pathogen into the host. Preferably, the delivery system is a live genetically modified microorganism, such as a bacterium, which can colonize the gastrointestinal or respiratory tract of a host and directly deliver antibiotic factors to reduce the number of, or block the entry of, a pathogen. For example, in ovo delivery of a live delivery platform could prevent early colonization of an embryo by pathogens, possibly through competitive exclusion or direct or indirect anti-infective effects. In ovo delivery has the further advantage of bypassing any limitations of colonization by the genetically-modified microorganism due to maternal antibody interference. Preferably, the live bacterial delivery system synthesizes the anti-infective factor in sufficient quantity to have the desired effect on a pathogen. A targeted pathogen may be, without limitation, a bacterium of the genera *Salmonella, Clostridium, Campylobacter, Fusobacterium, Staphylococcus*, or *Streptococcus*, or an *E. coli* bacterium, or a parasite such as an *Eimeria* species. Preferably, the live bacterial system persists in the host gastrointestinal tract for a period of time. Preferably, the live bacterial delivery system produces a broad-spectrum anti-infective factor or multiple anti-infective factors, such that a variety of pathogens are targeted. Alternatively, a combination of live delivery systems could be administered to a single animal, with genetically modified bacteria producing multiple anti-infective factors, immunomodulatory molecules, or growth-promoting biomolecules, or any combination thereof. Thus, more than one disease state is prevented or reduced, or diseases and syndromes having multiple causes can be effectively treated.

Provided herein is disclosure of anti-infective peptides, including new mersacidin-like peptides, which target multiple bacterial species. Also disclosed are antibodies, including single chain antibodies, which target specific pathogens and pathogenic molecules. Also disclosed are phage or phage lytic peptides which target pathogenic species. Provided also is a *Lactobacillus* expression system which can produce high levels of at least one or a multiplicity of the above molecules, preferably as surface-displayed or secreted molecules.

SUMMARY OF THE INVENTION

The present invention provides a live delivery platform comprising a genetically modified microorganism. The genetically modified microorganism comprises an expression cassette containing one or more of: a promoter for transcriptional expression, a nucleic acid sequence encoding a signal sequence for secretion, a nucleic acid sequence encoding a cell-wall anchor, at least one heterologous coding region encoding a desired biomolecule, a nucleic acid sequence encoding an expressed peptide tag for detection, and terminators for translation and transcription termination. The genetically modified microorganism may be a bacterium, a yeast, or a fungus. A genetically modified bacterium is preferably a *Bacillus, Lactobacillus, Lactococcus*, or an *Enterococcus*. The genetically modified bacterium may also preferably be an *E. coli* bacterium. The genetically modified bacterium may also preferably be a *Lactobacillus reuteri* strain. The present invention provides an expression cassette within a genetically modified microorganism that may include a promoter for transcriptional expression. The promoter for transcriptional expression may comprise a nucleic acid sequence of SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, and SEQ ID NO: 43.

The present invention provides an expression cassette within a genetically modified microorganism that may include a nucleic acid sequence encoding a signal sequence for secretion. The signal sequence for secretion may be at least 20 amino acids, at least 25 amino acids, at least 30 amino acids, at least 35 amino acids, at least 40 amino acids, at least 44 amino acids, at least 50 amino acids, at least 55 amino acids, at least 60 amino acids, or at least 65 amino acids. The signal sequence for secretion may also be 20-65 amino acids, 20-60 amino acids; 20-55 amino acids; 20-50 amino acids, 20-45 amino acids, 20-40 amino acids, 20-35 amino acids, 20-30 amino acids, 25-65 amino acids, 25-60 amino acids; 25-55 amino acids; 25-50 amino acids, 25-45 amino acids, 25-40 amino acids, 25-35 amino acids, 25-30 amino acids, 30-65 amino acids, 30-60 amino acids; 30-55 amino acids; 30-50 amino acids, 30-45 amino acids, 30-40 amino acids, or 30-35 amino acids. The signal sequence for secretion may comprise an amino acid sequence that is a fragment of SEQ ID NO: 20, SEQ ID NO: 21, SEQ ID NO: 22, SEQ ID NO: 23, and SEQ ID NO: 40, where the fragment has a length as given herein. The signal sequence for secretion may comprise an amino acid sequence that is an amino-terminal fragment of SEQ ID NO: 20, SEQ ID NO: 21, SEQ ID NO: 22, SEQ ID NO: 23, and SEQ ID NO: 40, where the fragment has a length as given herein.

The present invention provides an expression cassette within a genetically modified microorganism that may include a nucleic acid sequence encoding a cell wall anchor peptide. The cell wall anchor peptide may have a length of 100-250 amino acids, 100-225 amino acids, 100-200 amino acids, 100-175 amino acids, 100-150 amino acids, 125-250 amino acids, 125-225 amino acids, 125-200 amino acids, 125-175 amino acids, or 125-150 amino acids. The cell wall anchor may comprise an amino acid sequence that is a fragment of SEQ ID NO: 20, SEQ ID NO: 21, SEQ ID NO: 22, SEQ ID NO: 23, and SEQ ID NO: 40, where the fragment has a length as given herein. The cell wall anchor may comprise an amino acid sequence that is a carboxy-terminal fragment of SEQ ID NO: 20, SEQ ID NO: 21, SEQ ID NO: 22, SEQ ID NO: 23, and SEQ ID NO: 40, where the fragment has a length as given herein.

The present invention provides an expression cassette within a genetically modified microorganism that includes a heterologous coding region encoding a desired biomolecule. The desired biomolecule may be a biomolecule having anti-infective activity, a probiotic factor, an immunomodu-latory factor, or a growth-promoting biomolecule. The biomolecule may have anti-infective activity active against a pathogenic bacterium or a parasite. The parasite may preferably be an *Eimeria* species. The pathogenic bacterium may preferably be a *Salmonella, Clostridium, Campylobacter, Staphylococcus, Streptococcus, Fusobacterium*, and an *E. coli* bacterium.

The present invention provides an expression cassette within a genetically modified microorganism that includes a heterologous coding region encoding a desired biomolecule having anti-infective activity. The anti-infective biomol-ecule may be a bactericidal peptide, an enzyme, a lysin, a phage, or an antibody. The bactericidal peptide may be a mersacidin-like molecule. The mersacidin-like molecule may comprise a sequence disclosed herein as SEQ ID NO: 2 or SEQ ID NO: 4. The desired biomolecule may be an enzyme. The enzyme may comprise a sequence disclosed herein as SEQ ID NO: 5 or SEQ ID NO: 6. The desired biomolecule may be a lysin. The lysin may comprise a sequence disclosed herein as SEQ ID NO: 24, SEQ ID NO: 25, SEQ ID NO: 26, SEQ ID NO: 27, or SEQ ID NO: 28. The desired biomolecule may be a phage, or a phage in a pro-phage form. The phage genetic material may comprise a sequence disclosed herein as SEQ ID NO: 11, SEQ ID NO: 12, or SEQ ID NO: 13. The desired biomolecule may be derived from a *Bacillus* species. The desired biomolecule may be a *Bacillus* bacteriocin. A *Bacillus* anti-infective molecule may comprise a sequence disclosed herein as SEQ ID NO: 44, SEQ ID NO: 45, SEQ ID NO: 46, SEQ ID NO: 47, or SEQ ID NO: 48.

The present invention provides an expression cassette within a genetically modified microorganism that includes a heterologous coding region encoding a desired biomolecule that is an antibody. The antibody may be a single chain antibody. The single chain antibody may be from a camelid. The single chain antibody may specifically recognize a pathogenic microorganism or a molecule produced by a pathogen. The single chain antibody may specifically rec-ognize a bacterial protein, such as for example a toxin or an attachment molecule. The single chain antibody may spe-cifically recognize a bacterial protein from *Clostridium perfringens*. The bacterial protein may be a protein produced by *C. perfringens*. The bacterial protein may be *C. perfrin-gens* alpha toxin or *C. perfringens* NetB toxin.

The present invention provides an expression cassette within a genetically modified microorganism that includes a heterologous coding region encoding a desired biomolecule that is an antibody that recognizes *C. perfringens* alpha toxin or *C. perfringens* NetB toxin. The single chain antibody may comprise an amino acid sequence as disclosed herein as SEQ ID NO: 29, SEQ ID NO: 30, SEQ ID NO: 33, or SEQ ID NO: 34.

The present invention provides an expression cassette within a genetically modified microorganism that includes a heterologous coding region encoding a desired biomolecule that is a probiotic factor. The probiotic factor may be an agglutinin receptor. The agglutinin receptor may comprise a sequence disclosed herein as SEQ ID NO: 9 or SEQ ID NO: 10.

The present invention provides a genetically modified microorganism comprising an expression cassette. The expression cassette may comprise a promoter for transcrip-tional expression, and at least one heterologous coding region encoding a desired biomolecule. The expression cassette may also optionally comprise one or more of a nucleic acid sequence encoding a signal sequence for secre-tion, a nucleic acid sequence encoding a cell-wall anchor, a nucleic acid sequence encoding an expressed peptide tag for detection, and terminators for translation and transcription termination. The expression cassette may comprise a pro-moter having a sequence disclosed herein as SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or SEQ ID NO: 43. The at least one heterologous coding region encoding a desired biomolecule may encode a bio-molecule such as a bactericidal peptide, an enzyme, a lysin, a phage, and an antibody. The at least one heterologous coding region encoding a desired biomolecule may encode a biomolecule having anti-infective activity. The at least one heterologous coding region encoding a desired biomolecule may encode a biomolecule having a sequence disclosed herein as SEQ ID NO: 2, SEQ ID NO: 4, SEQ ID NO: 5, SEQ ID NO: 6, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO:34, SEQ ID NO: 44, SEQ ID NO: 45, SEQ ID NO: 46, SEQ ID NO: 47, SEQ ID NO: 48, SEQ ID NO: 49, or SEQ ID NO: 50.

The present invention provides a genetically modified microorganism comprising an expression cassette, where the genetically modified bacterium is a *Bacillus, Lactobacillus, Lactococcus*, or an *Enterococcus*. The genetically modified bacterium may be a *Lactobacillus reuteri* strain.

The present invention provides a genetically modified microorganism comprising an expression cassette, where the expression cassette is located on a plasmid. The plasmid may comprise a sequence disclosed herein as SEQ ID NO: 8. The present invention provides a genetically-modified microorganism comprising an expression cassette, where the expression cassette is located on a bacterial chromosome.

5                                                6

The expression cassette located on a bacterial chromosome may be inserted into a transposase locus. The expression cassette located on a bacterial chromosome may be inserted into an Uracil phosphoribosyl (UPP) transferase locus. The expression cassette located on a bacterial chromosome may be inserted into a pyrE locus.

The present invention provides a method of reducing colonization of an animal by a pathogenic bacterium. The method may comprise treating an animal in need thereof with a live delivery platform. The live delivery platform comprises a genetically modified microorganism. The genetically modified microorganism comprises an expression cassette containing one or more of: a promoter for transcriptional expression, a nucleic acid sequence encoding a signal sequence for secretion, a nucleic acid sequence encoding a cell-wall anchor, at least one heterologous coding region encoding a desired biomolecule, a nucleic acid sequence encoding an expressed peptide tag for detection, and terminators for translation and transcription termination. The genetically modified microorganism may be a bacterium, a yeast, or a fungus. A genetically modified bacterium is preferably a *Bacillus, Lactobacillus, Lactococcus*, or an *Enterococcus*. The genetically modified bacterium may also preferably be an *E. coli* bacterium. The genetically modified bacterium may also preferably be a *Lactobacillus reuteri* strain.

The present invention provides a method of reducing colonization of an animal by a pathogenic bacterium, where the method comprises treating an animal in need thereof with a genetically modified microorganism. The genetically modified microorganism is modified to contain an expression cassette. The expression cassette may comprise a promoter for transcriptional expression having a sequence disclosed herein as SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or SEQ ID NO: 43. The expression cassette may further comprise a signal sequence for secretion having an amino acid sequence that is a fragment of SEQ ID NO: 20, SEQ ID NO: 21, SEQ ID NO: 22, SEQ ID NO: 23, and SEQ ID NO: 40, where the fragment has a length as given herein. A signal sequence for secretion may comprise an amino acid sequence that is an amino-terminal fragment of SEQ ID NO: 20, SEQ ID NO: 21, SEQ ID NO: 22, SEQ ID NO: 23, and SEQ ID NO: 40, where the fragment has a length as given herein. The expression cassette preferably also includes a heterologous coding region encoding a desired biomolecule. The desired biomolecule may be a biomolecule having anti-infective activity, a probiotic factor, an immunomodulatory factor, or a growth-promoting biomolecule. The biomolecule may have anti-infective activity active against a pathogenic bacterium or a parasite. The parasite may preferably be an *Eimeria* species. The pathogenic bacterium may preferably be a *Salmonella, Clostridium, Campylobacter, Staphylococcus, Streptococcus, Fusobacterium*, and an *E. coli* bacterium. The anti-infective biomolecule may be a bactericidal peptide, an enzyme, a lysin, a phage, or an antibody. The expression cassette may optionally contain a nucleic acid sequence encoding a cell-wall anchor, a nucleic acid sequence encoding an expressed peptide tag for detection, and/or terminators for translation and transcription termination.

The present invention provides a method of reducing colonization of an animal by a pathogenic bacterium, where the method comprises treating an animal in need thereof with a genetically modified microorganism. The animal may be a bird, a human, or a non-human mammal. The treatment may be administered orally, parentally, nasally, or mucosally. When the animal is a bird the treatment may be administered in ovo.

The present invention provides a use of any genetically modified microorganism disclosed herein in therapy. The present invention provides a use in therapy of a bacterium genetically modified to contain any expression cassette as disclosed herein. A therapy may be reducing colonization of an animal by a pathogenic bacterium.

The present invention provides a use of any expression cassette disclosed herein in therapy. The present invention provides a use in therapy of any expression cassette as disclosed herein. A therapy may be reducing colonization of an animal by a pathogenic bacterium. The expression cassette should comprise at least one heterologous coding region encoding a desired biomolecule. The at least one heterologous coding region encoding a desired biomolecule may encode a biomolecule such as a bactericidal peptide, an enzyme, a lysin, a phage, and an antibody. The at least one heterologous coding region encoding a desired biomolecule may encode a biomolecule having anti-infective activity. The at least one heterologous coding region encoding a desired biomolecule may encode a biomolecule having a sequence disclosed herein as SEQ ID NO: 2, SEQ ID NO: 4, SEQ ID NO: 5, SEQ ID NO: 6, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO:34, SEQ ID NO: 44, SEQ ID NO: 45, SEQ ID NO: 46, SEQ ID NO: 47, SEQ ID NO: 48, SEQ ID NO: 49, or SEQ ID NO: 50.

The present invention provides a use of any genetically modified microorganism disclosed herein in the manufacture of a medicament for reducing colonization of an animal by a pathogenic bacterium. The present invention provides for use of a bacterium genetically modified to contain any expression cassette as disclosed herein in the manufacture of a medicament for reducing colonization of an animal by a pathogenic bacterium.

The present invention provides a use of any expression cassette disclosed herein in the manufacture of a medicament for reducing colonization of an animal by a pathogenic bacterium. The present invention provides a use in manufacture of a medicament of any expression cassette as disclosed herein. The medicament may be for reducing colonization of an animal by a pathogenic bacterium. The expression cassette should comprise at least one heterologous coding region encoding a desired biomolecule. The at least one heterologous coding region encoding a desired biomolecule may encode a biomolecule such as a bactericidal peptide, an enzyme, a lysin, a phage, and an antibody. The at least one heterologous coding region encoding a desired biomolecule may encode a biomolecule having anti-infective activity. The at least one heterologous coding region encoding a desired biomolecule may encode a biomolecule having a sequence disclosed herein as SEQ ID NO: 2, SEQ ID NO: 4, SEQ ID NO: 5, SEQ ID NO: 6, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO:34, SEQ ID NO: 44, SEQ ID NO: 45, SEQ ID NO: 46, SEQ ID NO: 47, SEQ ID NO: 48, SEQ ID NO: 49, or SEQ ID NO: 50.

The present invention provides an antibody comprising an amino acid sequence of SEQ ID NO: 29, SEQ ID NO: 49, SEQ ID NO: 30, SEQ ID NO: 33, SEQ ID NO: 50 or SEQ ID NO: 34. The antibody preferably binds a toxin produced by *Clostridium perfringens*. The antibody preferably binds *C. perfringens* alpha toxin or a *C. perfringens* NetB toxin.

The present invention provides use of an antibody comprising an amino acid sequence of SEQ ID NO: 29, SEQ ID NO: 49, SEQ ID NO: 30, SEQ ID NO: 33, SEQ ID NO: 50 or SEQ ID NO: 34 in therapy. The present invention provides use of an antibody comprising an amino acid sequence of SEQ ID NO: 29, SEQ ID NO: 49, SEQ ID NO: 30, SEQ ID NO: 33, SEQ ID NO: 50 or SEQ ID NO: 34 in reducing colonization of an animal by a *C. perfringens* bacterium. The present invention provides use of an antibody comprising an amino acid sequence of SEQ ID NO: 29, SEQ ID NO: 49, SEQ ID NO: 30, SEQ ID NO: 33, SEQ ID NO: 50 or SEQ ID NO: 34 in the manufacture of medicament to reduce colonization of an animal by a *C. perfringens* bacterium. The present invention provides a method of treating an animal for *C. perfringens* infection or colonization, where the method comprises administering an antibody comprising an amino acid sequence of SEQ ID NO: 29, SEQ ID NO: 49, SEQ ID NO: 30, SEQ ID NO: 33, SEQ ID NO: 50 or SEQ ID NO: 34 to an animal in need thereof.

BRIEF DESCRIPTION OF THE DRAWINGS

FIG. 1. Antibiotic resistance or sensitivity of *Lactobacillus reuteri* strains, as determined with an AVIPRO® Plate.

DETAILED DESCRIPTION OF THE INVENTION

Figure 2:
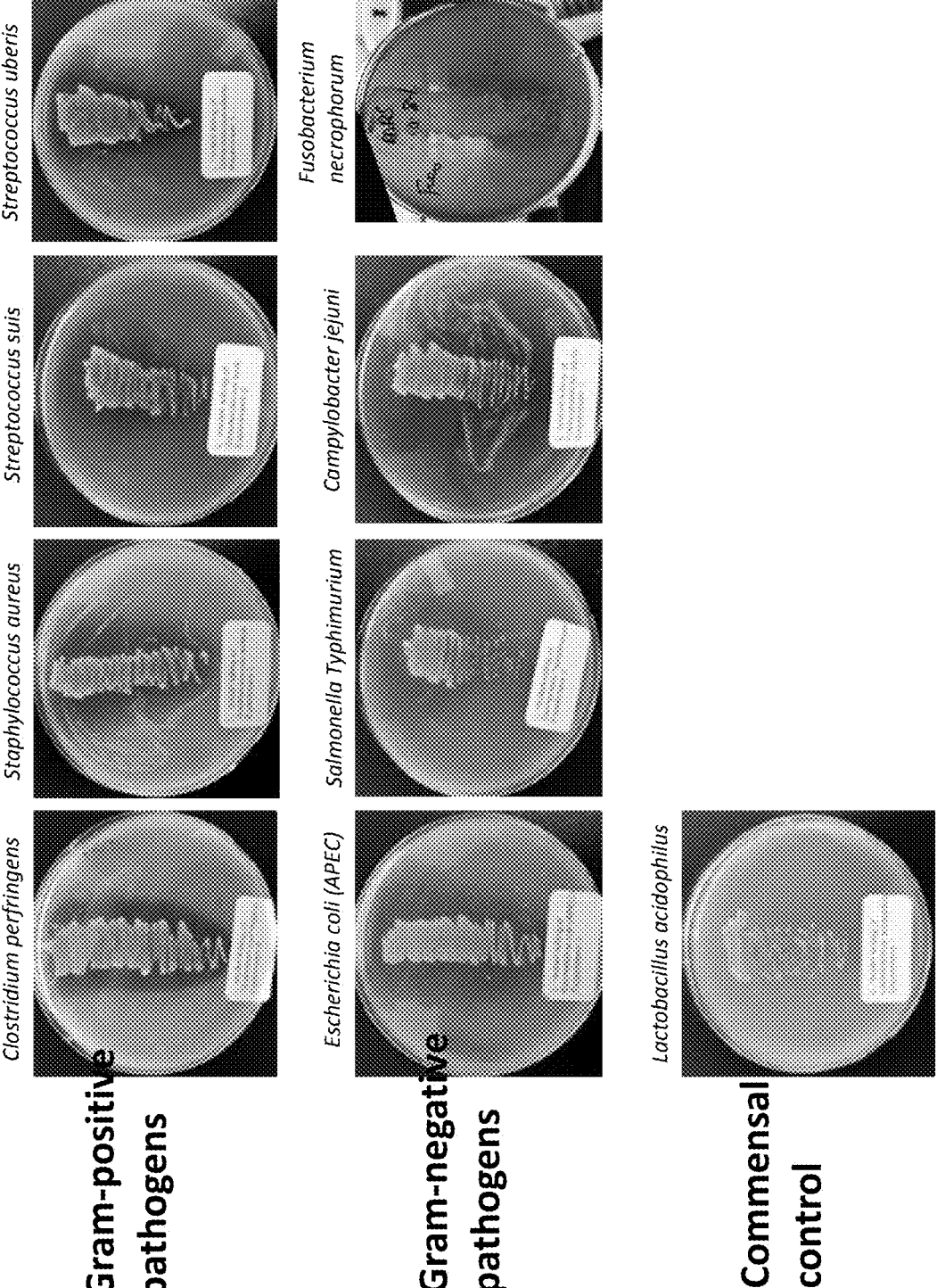
FIG. 2. Pathogenic bacteria, but not nonpathogenic *Lactobacillus acidophilus* are killed by *L. reuteri* strain 3632, as evidenced by a clear "halo" surrounding strain 3632.

As used herein, a "genetically-modified microorganism" means any microorganism which has been altered from the natural state using molecular biological techniques. A genetic modification could be the deletion of a portion of the bacterial chromosome or a naturally-occurring plasmid. The genetic modification could also be the introduction of an artificial or exogenous nucleic acid into a portion of the chromosome. The introduction may or may not disturb or perturb the expression of a bacterial gene. The genetic modification could also be the introduction of an artificial plasmid. The genetically-modified microorganism may be a bacterium, a virus, a yeast, a mold, or a single-celled organism.

An "artificial nucleic acid" or "artificial plasmid" is any nucleic acid or plasmid which does not occur naturally, but rather has been constructed using molecular biological techniques. Portions of the nucleic acid or plasmid may occur naturally, but those portions are in an artificial relationship or organization.

As used herein, an "expression cassette" is an artificial nucleic acid constructed to result in the expression of a desired biomolecule by the genetically-modified microorganism. An expression cassette comprises one or more of a promoter for transcriptional expression, a nucleic acid sequence encoding a signal sequence for secretion, a nucleic acid sequence encoding a cell-wall anchor, at least one heterologous coding region encoding a desired biomolecule, a nucleic acid sequence encoding an expressed peptide tag for detection, and terminators for translation and transcription termination. A promoter directs the initiation of transcription of the coding regions into a messenger RNA and the translation of the mRNA into a peptide. A signal sequence for secretion, or a secretion signal sequence, directs the peptide to be located outside the cell membrane. The extracellular peptide could be a soluble, secreted protein or it may be cell-associated, particularly if the expression cassette contains a cell wall anchor sequence which attaches the extracellular peptide to a bacterial cell wall. An expressed peptide tag is any amino acid sequence which may be recognized by an antibody or other binding protein. The expressed peptide tag may also bind an inorganic substance, such as a six-histidine tag which binds to nickel molecules. Terminators for translation may be a stop codon or a spacer open reading frame containing a stop codon.

As used herein, a "heterologous coding region" is a nucleic acid sequence containing an open reading frame which encodes a peptide. The coding region is heterologous to the associated promoter, meaning the coding region and the promoter are not associated in their natural states.

As used herein, a "protein" is a sequence of amino acids which assumes a three-dimensional structure. A "peptide" can be used interchangeably with protein but may also be a short linear sequence of amino acids without a defined three-dimensional structure.

As used herein, a "desired biomolecule" is any peptide which may be advantageous to a host when administered via a live delivery platform. The desired biomolecule may be a peptide with anti-infective activity, a probiotic factor, an immunomodulatory factor, an anti-antinutritional factor, or a growth-promoting biomolecule. The desired biomolecule may also be an enzyme which produces a substance with anti-infective activity or a probiotic factor such as a vitamin.

As used herein, "anti-infective activity" includes any activity which prevents infection of a host with a pathogenic organism. The following molecules are examples of biomolecules possessing anti-infective activity: an antibacterial peptide; a lysin or lytic enzyme; a prophage, phage or virus; an enzyme, for example one that cleaves or disables a protein made by a pathogen; and an antibody which blocks, inhibits, or clears a pathogenic molecule. An anti-infective may have bacteriostatic activity, which slows, reduces, or prevents the growth of a pathogenic species. A non-limiting example of an antibacterial peptide is a member of the mersacidin family or a mersacidin-like molecule, such as those described in EP0700998. A non-limiting example of lysins are lytic molecules produced by phage. Lysins may have specificity for certain pathogenic species of bacteria and have been suggested for use in substitution for traditional antibiotics. V. A. Fischetti, *Viruses*, vol. 10, no. 310 (2018); and R. Vazquez et al. *Frontiers in Immunology*, vol. 9, article 2252 (2018).

As used herein, a "probiotic factor" is a substance which, when produced by a genetically-modified microorganism, proves beneficial to a host. The probiotic factor may be an attachment molecule or an agglutinizing molecule which promotes colonization of the host with the genetically modified microorganism and/or prolongs the period of time where the genetically modified microorganism colonizes the host. The longer the genetically-modified microorganism persists in the host the longer the beneficial effect is provided.

As used herein, an "immunomodulatory factor" could be a cytokine, lymphokine, chemokine, interleukin, interferon, a colony stimulating factor, or a growth factor. The immunomodulatory factor could provide nonspecific enhancement of an immune response or the immunomodulatory factor could increase the number or tissue distribution of immune cells present in the host. The immunomodulatory factor may also reduce an inappropriate immune response, such as without limitation an autoimmune response.

As used herein, a "growth-promoting biomolecule" could be a growth factor, a transfer factor (such as an iron-chelating molecule), a hormone, or any other factor which promotes healthy metabolic activity.

As used herein, an "anti-nutritional factor" could include protease inhibitors, for example a trypsin inhibitor.

As used herein, "delivery" or "administration" means the act of providing a beneficial activity to a host. The delivery may be direct or indirect. An administration could be by an oral, nasal, or mucosal route. For example without limitation, an oral route may be an administration through drinking water, a nasal route of administration may be through a spray or vapor, and a mucosal route of administration may be through direct contact with mucosal tissue. Mucosal tissue is a membrane rich in mucous glands such as those that line the inside surface of the nose, mouth, esophagus, trachea, lungs, stomach, gut, intestines, and anus. In the case of birds, administration may be in ovo, i.e. administration to a fertilized egg. In ovo administration can be via a liquid which is sprayed onto the egg shell surface, or an injected through the shell.

As used herein, the terms "treating", "to treat", or "treatment", include restraining, slowing, stopping, reducing, ameliorating, or reversing the progression or severity of an existing symptom, disorder, condition, or disease. A treatment may also be applied prophylactically to prevent or reduce the incidence, occurrence, risk, or severity of a clinical symptom, disorder, condition, or disease. As used herein, the term "reducing" may apply to both prophylactic (e.g. preventative) treatments or therapeutic treatments.

The following experimental examples are illustrative of a live delivery system comprising *Lactobacillus* expression cassettes which can be delivered by the disclosed live delivery platform. It will be appreciated that other embodiments and uses will be apparent to those skilled in the art and that the invention is not limited to these specific illustrative examples or preferred embodiments. The descriptive headings of these Examples are for convenience only and should not influence interpretation of any of the results presented therein.

Example 1. *L. reuteri* Strain Identification

Seven *Lactobacillus reuteri* (*L. reuteri*) strains are isolated from older birds at the Research Center, Hannover from the cecal contents received from the Poultry Clinic, University of Hannover. All the seven strains are identified to be *L. reuteri* by 16S rRNA sequencing.

While only limited growth is observed for most strains under aerobic conditions in MRS broth and agar (de Man, J. D.; Rogosa, M.; and Sharpe, M. E. "A Medium for the Cultivation of Lactobacilli". *J. Appl Bact.* 23: 130-135 (1960)), all isolates show very good growth on MRS agar and MRS broth under anaerobic conditions at 39° C. Culturing the bacterial strains on blood agar under anaerobic conditions results mostly in limited growth. None of the strains is able to grow in Mueller Hinton broth under anaerobic conditions. For all further analysis, bacterial strains are grown in MRS medium under anaerobic conditions at 39° C.

Antimicrobial susceptibility of bacterial isolates is tested using the AVIPRO® PLATE (FIG. 1). All strains are resistant against colistin, doxycycline, enrofloxacin, erythromycin, neomycin, oxacillin, penicillin G, trimethroprim-sulfamethoxazole, tetracycline, tilmicosin and tylosin. All strains are resistant to streptomycin except strain 3632, and to tiamulin except strain 2098. In addition, resistance to cefpodaxime-proxetil is observed with strains 2091, 2095, 2097 and 3630; resistance to cefotaxime is observed with strains 2091, 2095 and 2097; and resistance to lincomycin is observed with strains 3630 and 3632. No strain is found to be resistant against amoxicillin, ceftiofur, erythromycin D, lincomycin-spectinomycin and rifampicin under tested concentrations. *Lactobacillus reuteri* strain 3632 was deposited on 19 Jun. 2020 according to the Budapest Treaty in the American Type Culture Collection (ATCC), ATCC Patent Depository, 10801 University Boulevard, Manassas, Va., 20110, USA. The deposit was assigned ATCC Patent Deposit Number PTA-126788. *Lactobacillus reuteri* strain 3630was deposited on 19 Jun. 2020 according to the Budapest Treaty in the American Type Culture Collection (ATCC), ATCC Patent Depository, 10801 University Boulevard, Manassas, Va., 20110, USA. The deposit was assigned ATCC Patent Deposit Number PTA-126787.

Example 2. *L. reuteri* Strain Selection and Anti-Infective Activity

To select the best strain for further engineering, the *L. reuteri* isolates are tested for various desirable probiotic anti-infective properties, such as growth kinetics, ability to produce hydrogen peroxide, auto-aggregation, enzyme profile, survival in the presence of ox bile and pancreatic enzymes, and sensitivity to heat shock and pH changes. The *L. reuteri* strains are also tested for safety using a haemolytic assay.

In general, all strains behave very similar in terms of probiotic properties, including growth kinetics and ability to produce hydrogen peroxide, except for strain 3632, which shows some unique properties, including the ability to auto-aggregate in liquid media (comparable to that of the well-characterized human probiotic strain *L. reuteri* ATCC 23272). None of the strains is found to be hemolytic on blood agar plates, suggesting that these isolates are less likely to be pathogenic to humans.

Whole-genome sequencing is performed for *L. reuteri* strains 2091 and 3632, and an independently isolated *L. reuteri* strain 170331 of European origin, using PACBIO® sequencing (Amplicon Express). Sequencing, assembly and annotation statistics are summarized in TABLE 1. Genomic structures and organization differ among the tested strains.

TABLE 1

| Genome sequencing, assembly and annotation statistics. | | | |
|---|---|---|---|
| Strain | 170331 | 2091 | 3632 |
| Genome size | 2,090,596 bp | 2,231,245 bp | 2,482,713 bp |
| Contigs | 9 | 11 | 7 |
| Coding Sequences (ORFs) | 2,154 | 2,280 | 2,595 |
| Ribosomal Binding Sites | 2,231 | 2.354 | 2,680 |
| Transcription Terminators | 1,123 | 1,123 | 1,375 |
| Operons | 452 | 472 | 541 |
| tRNA | 75 | 61 | 77 |
| rRNA | 18 | 19 | 13 |
| Other RNAs | 39 | 99 | 89 |
| CRISPR | 1 | 0 | 0 |
| Prophages | 7 | 1 | 8 |
| Islands | 30 | 22 | 24 |
| Bacteriocins | 0 | 1 | 4 |

Based on the genome sequencing data, strain 3632 encodes for two bacteriocins belonging to mersacidin family based on homology to the mersacidin conserved domain. These bacteriocins appear to be unique to strain 3632. A cDNA encoding one mersacidin (mersacidin-E1) could be:

```
                                          (SEQ ID NO: 1)
  1  atggacaaag aagaattaga aaaaattgta ggtaataact ttgaggaaat gagtttacaa 61  aaaatgacag aaattcaagg tatgggtgaa taccaagtgg attcaacacc agcagcttct 121  gcgatttcac gggcaacaat tcaagtatca cgtgcatctt ctggaaaatg tctaagttgg 181  ggtagtggtg cagcatttag tgcttatttt actcataaaa gatggtgcta g.
```

(SEQ ID NO: 1). This novel open reading frame would encode a polypeptide of mersacidin-E1:

```
                                          (SEQ ID NO: 2)
MDKEELEKIVGNNFEEMSLQKMTEIQGMGEYQVDSTPAASAISRATIQVS

RASSGKCLSWGSGAAFSAYFTHKRWC.
```

Another cDNA encoding the second form of mersacidin (mersacidin-E2) could be:

```
                                          (SEQ ID NO: 3)
  1  atggaagaaa aagaattaga aggtgtaata gggaattcgt ttgaaagtat gactgtagag 61  gaaatgacaa aaattcaagg tatgggtgaa tatcaagtag attcgacgcc tggatatttt 121  atggaaagtg ctgccttttc agctcttaca gccaatataa caagacatgc tatgcatcat 181  cattaa.
```

This novel open reading frame would encode a polypeptide of mersacidin-E2:

```
                                          (SEQ ID NO: 4)
MEEKELEGVIGNSFESMTVEEMTKIQGMGEYQVDSTPGYFMESAAFSALT

ANITRHAMHHH.
```

*L. reuteri* strain 3632 encodes other polypeptides which contribute anti-infective activity to this strain. Capreomycidine synthase, involved in capreomycin synthesis, is identified to be expressed in both the culture supernatant and pelleted cells.

```
                                          (SEQ ID NO: 5)
MVEIAHFGVEAWLNKWEKSATYDISQSTIASLSMHDLLNLDGNNGEEFYE

MLDKQQMNYGWIEGSPEFKEEVAKLYHHVDPENILQTNGATGANILALYA

LINPGDHVIAEYPSYQQLYDIPKSLGADVDYWHIHEEDNWYPRIDDLKAM

VKPNTKMICLNNANNPTGTVLDKEFLEQVVEIAKSVDAYVLVDEVYLPLD

HPEKFAQIIDLYDKGISTNSLSKTYSVPGVRIGWTATNAEVADIFRKFRD

YTMICGGVFNDQLATYVLRHRDQVLARNRKLVLGNLAIYKDWIDHEDRAS

VIMPQAVSTSFPKLDVPVDIHTFCENLLHDEGVLLVPGDAFDTPGHVRLG

YCAPEATLKEGLKRLSKYMHQYD.
```

Colicin V production protein is also expressed in pelleted cells of strain 3632:

```
                                          (SEQ ID NO: 6)
MILTTFIILILMGCFINGHRRGLLTMTLMLGTYIVAWIVARQGAQLIGG

WLKSLLPSIGTPATFSESLLANVNSNLFFYNGIAFMIIFTIVSILCHWG

IRQLNWIKRIPVVGTVDKIAGGLISFLIGYLITYVVLLIMQLFPAGWWQ

MQIANSELARFMINQTPGIAHLVIDTLVQGG.
```

A person of skill in the art would recognize that, because of the redundancy of the genetic code, multiple nucleic acid sequences could encode the above peptides.

The functionality of these putative bacteriocins is tested by co-plating pathogenic bacteria with strain 3632. As shown in FIG. 2, the pathogenic bacteria *Clostridium perfringens, Staphylococcus aureus, Streptococcus suis, Streptococcus uberis, Escherichia coli* (APEC), *Salmonella typhimurium, Fusobacterium necrophorum*, and *Campylobacter jejuni* are killed by *L. reuteri* 3632. A non-pathogenic control, *Lactobacillus acidophilus*, is not killed. DFM strains such as 3632 may be used to control, limit, prevent, or eliminate infection by pathogenic bacteria in swine (*S. suis*), poultry (*C. perfringens, E. coli, S. typhimurium*, and *C. jejuni*), and cattle (*S. aureus, S. uberis*, and *F. necrophorum*). DFM strains such as 3632 may be used to control, limit, prevent, or eliminate infection by food-borne pathogenic bacteria in humans.

Example 3. Other Genetic Elements of *L. reuteri* Strain 3632

In order to identify any potential plasmids containing antimicrobial resistance genes, native plasmids are isolated and identified by high throughput sequencing (ACGT, Inc). The 3632 strain contains three native plasmids but none with any known antimicrobial resistance genes. However, one of the plasmids is maintained in high copy numbers:

(SEQ ID NO: 7)

```
   1  TTGGCAATCT TTCACCTATC AGCAAAAATC ATTAGTCGAG GAAAAGGGCA ATCAGCAATT

61  GCCTCGGCTG CTTATCGTTC AGGGAACAAA CTTCACGATG AACGATACGA CGAAACACAA

121  GATTACACAA ACAAACGTTT CATCGAACAC TCAGAAATCC AACTTCCAGA GAATGCCCCA

181  GCTAAGTATC AAGATAGGGC AACCCTTTGG AACAGCGTAG AAAAGGCAGA AAAAGCTAAG

241  AATTCGCAGT TAGCTAGAGA AATTGAAATA GCCTTACCAC GAGAGCTAAC ACCAGAACAA

301  CGAGTTAAAT TAGTCCACGA TTACGTTCAG AAAACCTTTG TCGATAAGGG AATGGTAGCC

361  GATTGGTCTA TTCACAACCC ACAACCAGAT AAGGATAATC CAGAAAAGCC AGCAAACCCG

421  CACGCTCATA TCATGCTCAC ACTGCGTAGC TTGCGTTCTA ACGGCTCTTG GGCACCAAAG

481  AAGACAAGTC ACTATGAACT AGACGAAAAC GGCCAGAAGG TGCCTGTAAT CGATCCTGAG

541  ACAGGCAAAC AGAAGTTAGG GGCGAAAAAC CAAAAAATCT GGAAACGAGT AATTACCCCA

601  ACTAATGACT GGAATAACCC CAAAAACGTT GAAAAATGGC GGGCTGAATG GGCGAAGACT

661  TGTAATAAGT ACTTGGCTCC TGACCACCAG ATTGACCACC GCAGTTATAA ACGGCAGGGC

721  AAAAAACAAA TTCCAACAAT CCATGAGGGC TATGTTGCTC GTAAAATGGA ACGAGAAGCC

781  ACAGGAAGCT CAGAGAGGGC TTCTTTTAAC CAAATCGTAA AATATATCAA CAACGAGTTA

841  AAATCGCTTA GAAAGCAAAT TAGGGGCATT ATACGCGAAA TACGGAATCT AGAAAAAGGA

901  CGTGACCAAG ATGAGAAAGT TCGACTTCAG CAAGACACCC GAGCAAATCA AACAAGAACA

961  AGCAGAGATC AAGCGCTGGG AGGAGGAGTT CAACGCACGA TTACAGACAA TCGGGAGCAA

1021  TCCGGAAACG GTAGAGCCAA CGGAACTGCC GAAGAAGCCC AACGAACAGA TCCTAATCAA

1081  CTTCATCAAC AGTCTTTCGG AGAAACAGCA AGAAGAATTT TCCGAGATTT CCGGCTATTT

1141  GCGGAGCGTC AACGAGAAGC TCGACAGCGA CAACGCCGAC TTAGCCAAGG CTTACAACAT

1201  CATCAAGAAA CAGAAAAACG ACTTGAAGCA GGGCAACAAC AACTTACTCG AACAAAACAT

1261  ACAGCTGACG AACGAAAACA ACAGCTTACA GAACGACAAA TTCGAGTTAG AAAAGCTTTT

1321  AGCGACGCTT CTAAGTCCAA AGTCTTGGAA CGATACTACA CTCACTTCCG TCAAACAAAA

1381  ACTCAAGCAA ATCATGCAAA AGGATTAGAC TACCAAGGAC CAATTCTGGG ACATTCCCGA

1441  GGACGCTCAA GGTAGTTATG CTAGAATGAT TAAGCCGTCC GTGGCAACTC CTACGTAAAG

1501  GAGGTGGCAA CATGGCACAT ATACTCCTCT CAGCAGTTTT GAGCCTTCTG GGTTCCTTGA

1561  TAACTGCACT GTTCGCTGAT TGGCTTCGTC GGCGAAAATA GTTTTTGACG GCATGAAGCG

1621  CAAATTAAAA GCCACTCAAC TATTCGCACT AGTTGGGTGG CTTTTTTGCA ACGTGGCAAT

1681  ATACTTCTCT CGGTTAAATT ATAACATGGT TGTTCCAGAA GTGCATTAGG TAGGCGGTTT

1741  GTCCCCCCCC ATGGGTTTTG GCTTCGAAAA TCAATCGTTG AAGTGACCAG CGAAGCTCAG

1801  CTGATGGAGC CCTCATATTC AAGAAGCAGG TCAACGAATG CCAATTCCAA CATGAGGGCC

1861  ATGACTTAGG CCACTGATAC TCGCAAATGA CTGTCACACC AACGGTATTA GCCATTCTGA

1921  TAAGCGAGTC TAACGACTTT TGACGCATAA TCGACCACCT ACCTTATTTT CAAAGCGCCT

1981  CAGAGCTAAT TAGAGTATTC TTCAAGGAGC TTAGCGAGGA TTATAGACGC TTGGCGGACT

2041  TCACTTTCGG CTTGATTGAC CCGTTTAGCG ATCTTGTCAT CATGGCGAGC CACCTTTTCC

2101  AAGTCATGGA GATTATCAGC GATTTGGTCA GTCATGACGG AGTAGTTCTT AATACCCGAC

2161  AGCAGGCTTT CAACGTTAGT ATTCTCAAGG TTTTCGTTGA ATATCATGGT TATTCCTCCT

2221  TATCCTCAAA CTTAGTCATC TTCTGTCTCC TGTTTTAGAG AATTTTCAAT CATGTCTAAT

2281  AATGTTGACA TGTCAATGTT AAATGAATCA AGGCTACCAT ACCGCTTGAT TTGAGTTTTA

2341  ACACTATCCA ATCCATATTC TTCAAGTAAT GCTTTTAATT TACCAGTAAC TTTTTCACCT
```

-continued

```
2401   AAATGCCCAA AATACTGAAG CCAGCTCTTA AGTAATTCTC GGTACTGGTC AAATTTTTCT

2461   TTTTCAGTAA GCTGTTTCTC AACTTCTTCT TGGTCCTCAG AACCGTTAAC TACTTTCCAG

2521   AGGTCAGGGT CAGTAGTACC CAACTTATAA CCAAGTACCC GATCATATGC TCTGGCCTTT

2581   TCCTTTGGAG TCAAATCAGG ATTAAGGTCA ATATTATCTA GCTTCATACG TTGGTCAGCA

2641   TAACGACCTT TTTCAAAGTC ATCGGCATTC TTGGCTTCAG GTTGCCAAGT GAACTCATAG

2701   CCAACAACAG GACGTCCTCT ACCAGCTCCT CGAATAGTTT TTACGGTTAA GCCACGAATA

2761   ACAGGGGTTA GCTCTTCTTT AATTGGACGT AACACTCTTT TTCTTACGTT ACCCTGGTCT

2821   TTCTTGTAGC TCTTGGGTAG ATCTAGTTGC TTAAATAATT CGTCACTGGT TAACTTCAAC

2881   CGCCCTACTG TTCGATATTG TTTAATTAAC ACTCTTTTTC TTACGTTACC CTGGTCTTTC

2941   TTGTAGCTCT TGGGTAGATC TAGTTGCTTA AATAATTCGT CACTGGTTAA CTTCAACCGC

3001   CCTACTGTTC GATATTGTTT AATCAAGCGA AACATGTTCT TAGCATAAGC AGATTGAAGA

3061   CTATTAAACT GAGCTAGTTG AAATCTTGTC CAATGACTTA AATCATTGAA TAGCTTCTGA

3121   AATAGAGGGT TAACTTGAAC AGTCAGAATC TGTTTACTCC TCTGAATCTG AAATACATTC

3181   CAACAAGCAA ATTGAGTAAT GGTGTCTCCA TCATCGGTGT AGGCATTAAT CTCTAATAGC

3241   TTTTTATTAG TTTTCATCAA ATCTTTTACA AAATTAGATG TACTCCGTTC ATACTTACTA

3301   AGACTTTGTA GTTGCGTAAA TGAAACTTT AATTTCTGAG TACCCTTTTG ATACGACTGC

3361   TGAACTAGTG TAATAAATAG ATTTAGCTCA TTAGAGTTCA GTCGGCCAAG TGGAATAGTA

3421   TTAAGCCGAT TACTATACTT CACAATTTCA TTACTCAATT TTCTCACCTC AAATATATTA

3481   TAACATTTTA TCGTACACAA TCAAGAGTAC GTACTTATAG CACACGTACA GTATTAGCGC

3541   GTATATTAAG ACAAAAATTT AGACAAAATG TACCTTATAA CGGACAAAAT GTACCTTATA

3601   AACCGGACAA AATGTACCTT ATAACGGACA AAATGTACCT TATAAAAAAC GAAACTCTTA

3661   CTCTCCCAAG GAGTTTCAAA CCCCTAAAGA GTATTTAAAG AATATATATA AAGATATTTA

3721   AAGAGGCACC ATACGGAAAA TCTCCTTTCT GATTTCAATT TCAGAGAGGA GATTATCACT

3781   AAATTTCAAA ATTCAATTTT TCGCCAAAAA CTTTTTTAGT AGTTTTCGGT AACTAGCAAA

3841   ATCAACTTCG TTGATTATTT TGACTATTTC GAAATTCATC AAAAACTGAA TGCCCGTCTT

3901   TATAGTGAAT TTGTTTAGTG AAGTTCACTA ACTGCTTCAG CATATTCAGT TGACCACGTA

3961   ACCATTGTTC ACTATCAGCA GGACTAATTT GTTCTGATAA TTGCTCTTTT TGGTGGTTAT

4021   AAGCCTTATA AGCCTGATAT TTAGCATAAC CTTGTGGGTC ATCTGATTTA GCCACTCTAG

4081   CCACTTTAGG TACTTTTCTA AGCCCCTTAG CTTGAGCTTG AATATCTTCT AAAACCGCCC

4141   CTTTTTCGAT GAGACGCTTA TTTCGTTGCT TTCTCTTTTC AGTATTGATG CGAGCCATTT

4201   GACGCTCTCG ACGAGCCTTA AACACTGCTT CCTTTTCTTG AAGGCGTTCA AGTTCTGCTT

4261   TCATTTTTTC AATATCAGCC ATAACAAATC CTCCTAATGT GAATAATGTT TTCTGAAATT

4321   CAAATGTTAT CTAGATTATA TGATGTTACA ATTGATTTAA CCACTACGTT TGGTCTCCCT

4381   GTTAAGGGCG CACTTATACA CATTCAAAGA ATGTAATTAC GCCTGACGGC GACGTGCGCT

4441   CTCCGAGGGG ACTTACCCAG TCGGGGCGAC TTCATCGAGA CCATGTCATG GAGATTCAGT

4501   TTCACCGAAA CGGACCACTA ACCCCGTGGA GGGGAGAAGT TTCACTTCTA GGGACCATTC

4561   CATGGAGGGT CGCTTTTTAC AAAAGCAACG CAAAACAAAA GACTAGCTCC CAAGCTTACG

4621   CAAGGTCGTT AGTCCCTAAG GAGGCAGCAC AGA.
```

A putative *L. reuteri* plasmid origin of replication identified based on BLAST analysis could be:

```
                                                      (SEQ ID NO: 8)
   1 TTAGTCATCT TCTGTCTCCT GTTTTAGAGA ATTTTCAATC ATGTCTAATA ATGTTGACAT

61 GTCAATGTTA AATGAATCAA GGCTACCATA CCGCTTGATT TGAGTTTTAA CACTATCCAA

121 TCCATATTCT TCAAGTAATG CTTTTAATTT ACCAGTAACT TTTTCACCTA AATGCCCAAA

181 ATACTGAAGC CAGCTCTTAA GTAATTCTCG GTACTGGTCA AATTTTTCTT TTTCAGTAAG

241 CTGTTTCTCA ACTTCTTCTT GGTCCTCAGA ACCGTTAACT ACTTTCCAGA GGTCAGGGTC

301 AGTAGTACCC AACTTATAAC CAAGTACCCG ATCATATGCT CTGGCCTTTT CCTTTGGAGT

361 CAAATCAGGA TTAAGGTCAA TATTATCTAG CTTCATACGT TGGTCAGCAT AACGACCTTT

421 TTCAAAGTCA TCGGCATTCT TGGCTTCAGG TTGCCAAGTG AACTCATAGC CAACAACAGG

481 ACGTCCTCTA CCAGCTCCTC GAATAGTTTT TACGGTTAAG CCACGAATAA CAGGGGTTAG

541 CTCTTCTTTA ATTGGACGTA ACACTCTTTT TCTTACGTTA CCCTGGTCTT TCTTGTAGCT

601 CTTGGGTAGA TCTAGTTGCT TAAATAATTC GTCACTGGTT AACTTCAACC GCCCTACTGT

661 TCGATATTGT TTAATTAACA CTCTTTTTCT TACGTTACCC TGGTCTTTCT TGTAGCTCTT

721 GGGTAGATCT AGTTGCTTAA ATAATTCGTC ACTGGTTAAC TTCAACCGCC CTACTGTTCG

781 ATATTGTTTA ATCAAGCGAA ACATGTTCTT AGCATAAGCA GATTGAAGAC TATTAAACTG

841 AGCTAGTTGA AATCTTGTCC AATGACTTAA ATCATTGAAT AGCTTCTGAA ATAGAGGGTT

901 AACTTGAACA GTCAGAATCT GTTTACTCCT CTGAATCTGA AATACATTCC AACAAGCAAA

961 TTGAGTAATG GTGTCTCCAT CATCGGTGTA GGCATTAATC TCTAATAGCT TTTTATTAGT

1021 TTTCAT.
```

Analysis of the strain 3632 sequence reveals two agglutinin receptor precursors (ARP) that are uniquely found in *L. reuteri* strain 3632 compared to *L. reuteri* 2091, strain 170331 and *L. reuteri* ATCC 23272 (human). These agglutinin receptor precursors likely result in the increased level of auto-aggregation observed with this strain, and these receptors would contribute to the probiotic potential of a DFM genetically modified to express them. The amino acid sequence of ARP-1 is:

```
                                      (SEQ ID NO: 9)
MNEYNAEMAKLNQGANAPVITTNSVNQALSLKPENNATVDIEALNPRIT

FKRVEEGTKYAGYQIFDKNNAYVNNIDGEFLRVTYTNLKNSTYKGSKIS

KIVVTYSDSTPTGNRITQSGLNAVTEGANDNFLVVFEDPVRGDMHSTTV

TATYQYYDANGNLIDFSGTNNAWLSVGSLNFDQGNDYQGGKNEGNPTSG

ISEGVKLISGAQIKQLAGSSISVHDDGWAYAGFNNYSGTGMNNGINTDN

GGSGWDMDGSPNAYYGAIVFQLTGSSVSLRQGLVSWGGADIASQYNNQF

LNNAWFTAGTTLPETQIKQPIRKTSETHYHYNPSVIRL.
```

The amino acid sequence of ARP-2 is:

```
                                      (SEQ ID NO: 10)
MAQKLMSANSTDKNFKMYKSKKSWVFAYSTTLALAAVAGITLSTTNVHA

DTTNGGDNQVNATAVTQNTTSNTVDQIAANTAQTDNTSTSINIRSLMDD

LASGDDTSSSQNGQEQSQNYASSNQNSQTQQENGTTGQSTASQNGTTSD

QTNSDQSDKNYYVISTRDLDKNGNVNYLTQKNYTSIKGQEVADGTVVTW
```

-continued

```
PLSVSALPANRAQDLKSHVISETLDPHLEYLHYRAYLTNTDGTVTDVTN

HVNLNRSGQTLIFTDDNYLLSIYNNNRYRVQNLPVIKLVTKANGNGYII

PNAFKSSYVFNDGSHDVSFTTTSNNVQIKTFNPGNSKDVEIGGNVQGDP

SGTINGQVVADGSVVTWPMSVGDLPANRAQDVLSHIETDTLYNGLNYEG

YHAYLPQADGSFQDVSSHINVQQNGQDLTFIADDYLIGLYNQDKSTAFK

MPIIDLITSVHGTSIIAPNKFNSQLAFKDGNGQTVINNTSNQVQISTYH

PTNTKDVELGGNVQGDTPNSINDKVVANGAIVTWPMASSELPANRVQDL

QSRVISETLDSHLQYQGYKAWLQNADGKYTDVTSHVKLTQDGQNLTFAD

DEYLLNLYNSNKGTAYKLPIIDLVTKVNGAGITAPNSYTTKYVYSDGDG

NTTINVTSNTVKISTFNPTTNKDVELGDNIHGDTESSIAGKLVSEGTIV

TWPLSTSDLPANRAQDVVSHTAVDALEPTLQYISYTAWLPDSNGQLQDV

TSHVKMTRDGQKLTFTDDDYLIGLYNQNKDIALKMPIIDLVTKATGNTK

LLPNSFDSQFVYNDVDGNTIINVSSNKPTVETFDPTVHKDVELGGNNVQ

GDTPNSIDGKIVAQGTVVTWPMSTSDLPANRTQDVVSHSTSETLNQNLQ

YVGYHAYMPDANGKLQDVTSHVQLQQNGQNLVFTDDSYLINLYNQDKSI

AFKMPIIDLMTKAISDSATIPNTFESQYVFNDGNGNTTFKSTSNTVQII

TYKPKTTKDVELGDNIHGDTNASIAGQMITDGTVVTWPMSTSDLPANRT

QDLQQHVVTDNLNDNLIFQGYTAWLPTANGLVDVTNHIELTRDGQNLTF

TDDAYLLNLYNQNKDTAYKLPIIDLVTKANGNTKLIPNNFDSMFVYNDG
```

-continued

DQQTTVNVTSNTVNISTYDPTATKDVELGDDIEGDTADTINNLMVQIGT

KMTYPLTVSDLPANRADEITAHQSVDTLSDYLEYQGYKAYLPDADGKLQ

DITEHVNLKREGQKLSFNDDDYLINLYNNSKATKQALPVIDLVAKVTGS

NDGKKVHIIPNHFDSTITTKDGKINTTSNTVVINSNDPEAVKDVELGDN

VVGDTPNSVTGTTVADGTIVTWPMSVGSLGANRAQNVIKHTETENLDSG

LTYLSFKAYLPDADGKMQDITEHINIQQDGQKLVFTDDDYLISLYNKDK

SQRFALPVIDLVTRVNGDNKIIPNTFVSQFTFNDGKGNTITSVTSNQVN

VSTFKSNPEKHVTLGTDIEGDDAENADGTVVAQGSEVTWPLSDKSPLPA

NRSQDVKSHTLVDKLDDNLQYNSYKAYLKGTDGKLQDVTDHIKLTRDGQ

NLTFIDDDYLLDLYNKDKSTAFNLPIIDLVTTVVGNDKLIPNKFDSNFV

FSDGNKDTSMKTTSNEVSISTYTPVTNKDAELGDNVVGDTSDSIANETV

PDGTIVTWPLSVSSLPANRSQDVFKHVIEDILDGNLTYNSFKAYLKDAA

-continued

GNLQEVTDHVKLAQEGQHLTFTDDDYLINLYNSSKNKEQSLPIIDLVTT

VHGDSKLIPNEFDNVFVFKDGKGQTTVKTTSNKVTIKTASLPTPTKEET

DDQGNNINGNEVKAGEHVNYTLNWDLSNDKDVKATPEMIKKGFFFIDPI

DSRALSVDDLSKAKVVDQNGNKVDGISFHLYNSLSEVPEFIQEQVKANN

LQDKITGPFVVAQADDLQAFFDKYVKTGAKLKVTIPTIVKSGFTGEFSN

TAYQFGFGKATPTNTVTNYVKPMHKPASPETPAAIAPQVISATAQPMTS

DAPVTPSEKTAKLPQTGNADEGALLGLAAVSLVGSLGLAALGLKQNRND

D.

A person of skill in the art would recognize that, because of the redundancy of the genetic code, multiple nucleic acid sequences could encode the above peptides.

*L. reuteri* strain 3632 contains eight bacteriophage-encoding loci, but only three of these loci appear to encode productive prophages. Bacteriophage loci 1 has a sequence of:

```
                                                        (SEQ ID NO: 11)
   1    CTATTCAAAT TTGAAATTTT GAACAACTTT ATCAAGGTCT TCTTGTTCAA TCCCTAGATA

61    GTGGCGCGTA TTTCGTTCAG AGGAGTGATT AAATAACTGC GAAATGATTT CAACGTTAAC

121    ACCTTTCTTA TAGAGTTGTC GACCAAAAGT TTTTCTAAAA GAGTGTGTTC CAATTTTAGC

181    AACGATTTTA TTATTTTCCG TTTTTCTAGC CATTCGTTGC AACATTTCGT AAAAGCCATG

241    TACTGAAAAA TGACCTTCTT GTTTCCCAGG GAAAAGATAA TCATTCTCGT CTTTATAATT

301    CAAGTCATTA AGATAATCAA TAATTTCGGC AAGACAATTA TTCCAAAAGA GCGTTTTAGC

361    CTTACCTGTT TTTTGCTCAA TAACACGGGT TTTAGTTTTA TTTAGAACAT GACCAACCCT

421    TAACGTTACA ACGTCTGATG CTCGCAATCC GTTATTAAGG GCAATTGCAA TTAGTAATAG

481    GTTTCGGTTA ACCAATTCAG GACGCGAATG CAGCTTAATT GTCTCACGTA ACTGATCATA

541    TTCTTCGAGA GTCAAGAATT AACATTTTC TACCCATATT TTCCGTTTAC CCTTGATTTG

601    ACCATTAGTT TTATTTTTGG GAATATAAAC TCGTTTTTTA GTTGACATAA TATTTCTTCC

661    TTTGTTAATT TGCGAGGTAA TCAACTAAAG CAGGGACGAT TTCCTCTCCT TCTTTCCGCC

721    CAGTTTCATA AAGTGCTCGA ATTTTCTTAA TATTTCCTTC AATCCGCTTA ATTTTAATTG

781    GTTTAGAGGG AGCAATATTA AAGATCTTTC CTTCACAAGA CAAACGATTA ATTTCAGCAG

841    TCTGTTGGTT GTAGAGAAGG GGACGATCAA TCCCCGCTTT AGCAAATTCG GGATAATCTT

901    TATATACCAT GTCGTACAAC TTCTTTACAG CAGAACTAGA TGGCTTCTTT CGGTAGTTAA

961    TATCCCTGGT CCGTACAACA ACAATCTTGT CATAGCCTTG TCGTTGTGCA ATATCAAATG

1021    GAATTGAATC TGTGATCCCA CCATCAAGGC AAGGCCCTTG AGAAGTTTCC TGTGGATCTG

1081    AAAGAAATGG CATTGATGAG GAAGCTTTGA GGGCATTGGT TAGCTCCTCA CCAACAGGAT

1141    CCGTAAATAA AACTGTTTTT CCTGTTTTCA CAGAAGTAGC AACTGCTGTG AAATGAGATG

1201    CTGACCGTCG ATATGCAGCT TCATTAAAAT TCTGCCAAGA ATATCCGTGA TCTTCAAAAA

1261    GATAATCAAG ATTAATTATT TGCTTTTTAA ATACGCGAGC CATCGAGATA TATTGGCGAT

1321    CGTGCCGATG ATCAATATTA ATATTGGCAG CGCGTCCGTA TTGCTTAGAG ACGAAATTAA

1381    CTCCACAAAG TGAACCAGCA GAAACGCCAA TTACACTTCG AAATTCAATA TGGTGAGCGA

1441    GAAATGTATC AACAATTCCG GCAGTATATT GTCCACGGAA TGCGCCACCT TCTAAAACTA

1501    ATGCTGCATT ATATAACATA AAATGAAATA ACTCCTTTTT GTCCGCCAAA AATAGCAAAA
```

-continued

```
1561   ATGACCTAAT TTTTAGTGAG ACACTTTTTC AATAAAATTA TACAACAGTC TCACACGAAA

1621   ATATAGGATT TTAAAAGCTT GTTATATCAA CGTTTATTCT CGGTTACCGT AAGACTCTTT

1681   TATCAAAAGA GTCTTACTGA TTTTGAAATA ACGCAAAAGT AGGGGCAAAA ACGGATTTTG

1741   CCTCTCAGAC GAACTGAAAT TCATTTTGAT GAGTAGTAGG TCGTTACAAT TCGTCTCAGA

1801   AGAAAAACGC ATATTGATAT CAAAAAATGA GTAAATAGAC AGTAAATATT TAAATATGAA

1861   CTTTTTATGA AGAAACTATT GATAATTTAA GATAATCATA ATAAAATAGT GCACAGTTAA

1921   TTGTTAAACG TTTAGCAAAA AAGGTAAAGA AACGGGGTTA TTTCTATGCT AGAACGCAAG

1981   GAACATAAGA AAATGTATAA AAGTGGTAAA AATTGGGCAG TTGTTACACT TTCTACGGCT

2041   GCACTGGTGT TTGGTGTAAC AACTGTAAAC GCATCCGCAG ACACGAATAC TGAAAACAAT

2101   GATTCTTCTA CTGTACAGGT TACAACAGGG GATAATGATA TTGCTGTTAA AAGTGTGACA

2161   CTTGGTAGTG GTCAGGTTAG TGCAGCTAGT GATGCGACTA AAAATTCTGC TAATGCAAAT

2221   AGTGCTTCTT CTGCCGCTAA TACACAAAAT TCTAACAGTC AAGTAGCAAG TTCTGCTGCA

2281   ACAGCTTCAT CTACAAGTTC AGCATCTTCA TCAACTAACA CAGATAGTAA AGCAGCTACA

2341   GAAAATACTA ATGTAGCCAA AGAGGATGAT ACACAAAAAG CTGCACCCGC TAACGAATCC

2401   TCTGAAGCCA AAAAGAACC AGCTGTAAAC ACTAATGATT CTTCAGCTGC CAAAAACGAT

2461   GATCAACAAT CCAGTAAAAA GAATACTGCC GCTAAGTTAA ACAAGGATGC TGAAAACGTT

2521   GTAAAAAAGG CGTGGATTGA TCCTAATAGT TTAACTGATG ACCAGATTAA AGCATTACAT

2581   TAAATAAGAT GAACTTCTCG AAAGCTGCAA AGTCTGGTAC ACAAATGACT TATAATGACC

2641   TTAAAAAGAT TGGTGAGGCT TTAGTTGATC AAGATCCTAA ATACGCTATT CCTTATTTTA

2701   ATGCAAGTCA AATAAAGAAT ATGCCCGCTG CATATACTAG GGATGCTGAA ACAGGTGAAT

2761   ATGCTGATTT AGATATTTGG GATTCATGGC CAGTTCAAGA TCCAGTGACT GGTTATGTTT

2821   CTAATTGGAA TGGCTATCAA CTTGTGATCG CTATGATGGG ACGGCCTCAT CACGAAGATA

2881   ATCATATTTA TTTACTTTAT AATAAGTATG GTGATAATGA TTTTTCACAC TGGCGAAATG

2941   CAGGATCTAT ATTTGGATAT AATGAATCTC CACTAACACA AGAATGGTCC GGGTCTGCTA

3001   TTGTTAATTC TGACAACTCT ATTCAACTCT TTTATACTAT CAATGATACA AATAATGCTA

3061   TTAACCATCA AAAATTAGCA AGTGCTACTA TGTACTTAAC AGCCGACAAT GATGGTGTCC

3121   ATATTAATAA TGTAGAGAAT AATCATGTGG TATTTGCAGG TGATGGTTAT CATTACCAAA

3181   CTTATGATCA ATGGAAAGCT GCAAATAGTT TTGCTGACAA CTACACTTTG CGGGATGGAC

3241   ATGTTGTACA AATGCCAAAT GGTGATCGGT ATTTAGTATT TGAAGGAAAT ACTGGAACTG

3301   AAAATTATCA AGGTGAAGAT CAATTATATA ATTGGTCAAA TTATGGTGGT AACGATCGCT

3361   TTAATATTGA AAGCTTGTTT CATCTTTTAA GTAGTGATGT TGATTATAAA AAAGCTATCT

3421   TTGCTAACGG GGCACTTGGA ATTATTAAAC TAACGAATGA TGAAAAGAAC CCGCAAGTAG

3481   AAGAAGTATA TACTCCATTA GTTACATCAA ATATGGTTAG TGATGAACTT GAACGTCCTA

3541   ATGTTGTTAA ACTTGGAGAT AAGTATTATC TATTCTCGGC TACACGTTTA AGCAGAGGAA

3601   CTAATATCGA TACTCTTAAT AAAGCTAATA AAGTTGTCGG AGATAATGTT GCAATGATTG

3661   GTTACGTAGC CGATAGTCTT ACAGGTCCAT ATAAACCATT AAATGGTTCA GGGGTTGTAG

3721   TGACAGCTTC TGTTCCTGCC AATTGGCGTA CCGCTACTTA TTCTTACTAT GCTGTTCCAG

3781   TAGAAGGAAA AGAAAATCAA TTACTCATTA CTTCGTATAT GACAAATAGA GGCGAAGTTG

3841   CTGGAAAAGG TATGAATTCA ACATGGGCAC CAAGTTTTAT TGTGCAAATT AATCCTGATG

3901   ATACAACTAT GGTATTAGCT AAAGTAACTA ACCAAGGGGA TTGGATTTGG GACGAATCAA

3961   GTAACAATAA TAATATGTTA GGAAACATTC AAACAGCTGC TTTACCTGGG GAATTTGGTA
```

-continued

```
4021   AACCAATTGA TTGGGATTTA ATTGGTGGTT ATGGATTAAA ACCGCATGAT CCTGCTACAC

4081   CAAATGATCC TGAAACGCCA ACTACACCAG AAACCCCTGA GACACCTAAT ACTCCCGAAA

4141   CACCAAAGAC TCCTGAAAAT CCTGGGACAC CTCAAACTCC CGATACACCT AATACTCCGG

4201   AAGTTCCTTT AACTCCAGAA ACGCCTAAGC AACCTGAAAC CCAAACTAAT AATCGTTTAC

4261   CACAAACTGG AAATAACGCC AATAAAGCCA TGATTGGCCT AGGTATGGGA ACATTGCTTA

4321   GTATGTTTGG TCTTGCAGGA ATTAACAAAC GTCGAGTTAA CTAAATACTT TAAAATAAAA

4381   CCGCTAAGCC TTAAATTCAG CTTAACGGTT TTTTATTTTG AAAGTTTTTA TTATCGAAAA

4441   AAACAAATCC TCGTTAATCC TTTAATGCAA TTGTTGTAAA ACCTTGCGAC AGTAATAACA

4501   GTGGATTTGC CCATCTTTGT CAGCTAACTT CCGTGCATGC ATTGCAGAAA AAGTATAGTG

4561   CTCATGACAA AATGGACAAA CATATTGCTT TTTCCCAAAT AGTGAGGTAA TAAAGCCCAA

4621   AATTTTCTCC TCCATAAAAA AATTATACAC CCCTTAACAT TATAGCGAAG ATTATCTTTA

4681   TAGAAAAGGC TTTTATTCAT TTGTTTTTTT ATATGAAGTT TCACTAATTT CTTTAAGAGC

4741   ATCACGCTGC TGTTTCTGGT CAACGTGAGT ATATAAATCG GTAGCAGATG TTCCTTTTTG

4801   TCCCAACTGT TGGGCCACTA ATACTTGATC TTTCGTTACC TCATACATTT CAGAAGCAAG

4861   GGTGTGCCGT AATTTATGGG GAGTAAGAGG ATGGCCAAAT GCGGTTGAAT ACTTTTTGAC

4921   CATTTTTTCA ATTGCATTAG CTGTCATCCG TCGAGTTTGC TTGTGATAAA CGGTTAGGAA

4981   GAAAGCAGTA TCCTTTTTTA AAGCGTGGTA TCGTTGTGCA CGAATCGCTT GGTAAGTTTG

5041   GATATAAGTA ATAGCCCAAG GAGCAATTGG TACCGAATCC CTCTGGCCAC CTTTTCTTGT

5101   TACATCTAGC AGCGATTGTT TTAAGTTTAA ATCACCAAGG TTTACATTTG CCGCCTCGGA

5161   TACCCGGACG CCTGTTCCTA AAATAAGAGC AATAATTGCA ATATCTCGTT CCTTATTGAC

5221   CTTATAAGAG GGGAGAGCTC TTTTATCACA TTTATTAGGG TATTCTTTTT CAATGAAAGT

5281   AATAAAATCA AACTTCATTT GTCCCCGGTA CATGTGTGAA GCCAGCGTAT GAGCCCGATA

5341   ATTTAATGTT TTTGTATCAT TAAGGGAGTC AATTTTCAGC ATTACATTAC GGTCAAAATA

5401   AGATTCACCA TTATTGTTAT CTGCGGTAAC TGTTAAAAAT TTATACAATG ACCTTAATGC

5461   ATTAATAGAT CGATTGATTG AAGTAGGAGA ATTTAACCGT CCTTGTGCAT TGGTAGTATG

5521   CTGCAAATAA TCGATATACA ACATTACATC GCTACGCCGT AGATTCGCCA GTGTATCAAT

5581   TGGTAAGTCC TTATTAGAAT TAACAGAGAC GAGTCCACTT GACCGTAACC AATCAAAGAA

5641   TCGACGGATT TCAGTTAAGT ACTGATAGGT TGTTGTGACT GCATGGTTGG TCCCTAAATA

5701   ATACTCGTTA ACATAATCAG GAAGGTTCTG AAGCTCCTCT TGAATTAGCT TTAAATATTT

5761   ATCTGCTTCC ATTTTTATAT CCTCCTTGAT ACTAAAAAGA GTCGCTTGAA AGAAACTTT

5821   CAACGACTCT CTAAACCTAT CGGGAAAACA GGATTCGAAC CTGCGACCCC CTGGTCCCAA

5881   ACCAGGTGCT CTACCAAGCT GAGCTATTTC CCGTTAATAA CGAACAAATA TTATTCTACC

5941   AATTCTCAAT TAATTAGTAA AGGAATATTT TAATTTAAAG TGATTAATAG TTAATGATTA

6001   AATGACATAA TAGTAAAATT CCTATTAATT GCAAAAAAAT CATGATTAAC CGAAATCCTT

6061   TTCTAGCATC TAATGAAGAT GATAAATAAT TTTATTTTCG ACTAGTTATA AAAGATACCT

6121   TTCCGAAAAT AATTTGACAT TCAAAATACT TTTGAATATA ATTTGATTAT CGAATATTTT

6181   GATACTCGAA ATATTTTCCG AAGGCAGGTG AATCTTTTTG GCAATAATGA ATGCGCAGGA

6241   GATTATGGAA TTAATTCCTA ATCGATATCC GATTTGCTAT ATCGATTATG TAGATAAATT

6301   AGTTCCTGAA GAAAGATTA CCGCAACAAA AAATGTCACA ATTAATGAAT CATTTTTTCG

6361   CGGTCATTTT CCTAATAATC CTGTTATGCC TGGAGTTTTA ATTATCGAAA CATTGGCCCA
```

-continued

```
6421  AGCTGCTTCA ATTTTGATAT TAAAATCACC GCATTTTTAT AAGAAAACAG CTTATCTTGG

6481  CGCAATTCAT AAAGCAAGGT TTCGACAAAT GGTCCGTCCT GGTGATGTAT TAAAACTAAA

6541  CGTTGTTATG AAAAAAGTTC GATCATCAAT GGGGATTGTA GAAACACAAG CGCTTGTGAA

6601  CGGCAAATTA GCTTGTAGTG CGGAGCTTGT CTTTATCGTT GCTGAACGAG AAGAAAAGAT

6661  TTAGCACGGT GAATCATTAT CATTTATAAT ATATTTTGAT AATCAAATTA TTCGGGCTAT

6721  AGAATAAAAT TGAAGGGAAG AAATATATTA TGAGTAAAGA TAATGATTAC GAAAAAATTA

6781  ATAAAGGATT AATCAAAGTT TATTCCGGAA TTCTATGGAT TGAAGAAAAT GAATTGCGGA

6841  AAAGTACATT CAATGATTTA ACAATTAAAG AGATGCATGC AATTGATGCA ATTACGATGT

6901  ATAACCATCA AACAATTTCT CAAGTAGCAG AAAAGCTTCA TCTAACTCCA GGAACAATGA

6961  CTTCAATGGC TGATCGTTTA ATTCGAAAAG GATATGTGGA AAGAATTCGT GATAAAGATG

7021  ATCGCCGCAT TGTTCGGTTA TGTTTAACCA AAAGAGGCCG GGTACTATAT CGTGCGCACC

7081  GGGCCTTTCA TAACATGATG GTTGAACGTT TTCTTAAAGG AATGGATGAT GAAGAAATGA

7141  AGGTTGTTAA AAAAGCCTTG CAAAACTTAG AAGATTTTGT GGATGAGCAT GCTTAGAGAT

7201  AAGGATTGAC AAACATTGCA AAATTTAAGA ATTACTAGTA CTGCGAGTTA TCATCCACCC

7261  CTTAAAATTA CTAACCAGCA ATTATCAACT ATTATGAATA CTTCAGATGA GTGGATTAAG

7321  ACGCGGACTG GAATTCATCA ACGTTATATC AGCAACACTG AAAATACTTC AGACTTAGCT

7381  GTCAATGTTG GTACCCAGTT ATTGACTAAT GCCAATTTAA AGGCAACTGA ACTTGATTTA

7441  ATCATTATTG CAACGATGTC TCCTGATGCC TATACTCCTT CAACTGCTGC TATTGTTCAA

7501  GGAAGATTAG GTGCGAAAAA TGCAATTGCG TTTGATATCT CAGCAGCTTG TACTGGTTTT

7561  ATCTATGCCA TTAATACAGC TGAATTAATG TTGAAAAGCT CTCATTGGAA AAATGCAATG

7621  GTAATTGGTG CAGAAGTATT ATCAAAACTG ATTGATTGGC AAGATCGAAG TACTGCCGTA

7681  TTGTTCGGCG ATGGGCTGGC GGAGTGTTAC TTCAAAGAC AACTACAACA ACCCCTTTAA

7741  TTCTCGGCCG TGATCTCCAT ACATTTGGTG ACTTAGGAGA TAAAATTATT GCCGGAAAAA

7801  CAACGCCTAA AACTGGCTTC CCTAAACAAC TAACATCCCT TTCACCATTT ACGATGGCCG

7861  GCCGTGACGT ATACCGCTTT GCCACTCATG AAGTACCACG ATCAATCACT TCTGCCGTTC

7921  AACAAGCTAA TTTGAAATTA GACGATATCG ATTATTTTT ATTACATCAA GCAAATGAAC

7981  GGATAATTAC CCAAATTGCA AAGAGACTGG CGCAACCAAT TACAAAGTTT CCAATGAATA

8041  TTAGTGAATA TGGGAATACA GCTGCCGCTA GTGAACCAAT TTTATTGACT CAAGCTATTG

8101  CTCATGAATT GATTAAACCA GGTAACATTA TTGCAATGAG TGGCTTTGGT GGCGGGTTAA

8161  GTACAGGAAC AATAATTTTA AACTATTAAT AGAGAAAGAA GAATGGATAT GACTAAAGAG

8221  GAAATTTTTA ATACTGTAAA AACTATTACT GTTGATGAAT TAGATGTTGA CGAAAATCGT

8281  GTAACAATGG ATGCACGAAT CAAAGATGAT CTTGATGCTG ATAGTCTTGA TGTTTTTGAA

8341  ATTATGAATG AGCTTGAAGA TAAGTTTGAG ATTGAATTAG ATGCCGATGA AGGAATCGAG

8401  ACTATTAGTG ACGTTGTTGA TTTCGTAAAG AAACAGTTGG ATGAAAAATA ATGTACTACG

8461  GAATATTATT TAGCGGTCAA GGTGCACAGC GATCGGGAAT GGGAGTCGAG CTTATGGCCG

8521  ACTCCCTTTT TTCAAGGATT GTTAGTCAGG CAAGCGCTGT TTGTGAACTT GATTTGCTCA

8581  AAATTATGAA AAACGAGCAT AAGGAGTTGA ATAAAACAGC ATATGTTCAA CCAGCAATTG

8641  TAACAGTTAG TTATGGAATC TACCGAATGT TAAAACGGGA TTTACCTCAA CTACCAATTA

8701  AAGGGATGAT TGGCCTATCT TTAGGCGAGT ACGCTGCTTT AATTGCTAGT AATGCACTTT

8761  CATTTGAAGA AGGAATTAAA TTAGTTGCGG ACCGTGCTCA CTTTATGCAA CAAGACGCGG

8821  ATAGAGAAAT AAGTACATTA GCAGCTGTCC TTGATCCTCA ACTTCAAGAG ATAAAAGAAC
```

-continued

```
 8881  TAATCACCGC TCAACAAGAA AATGGTCAGC GAGTTTATAT TGCTAACTAT AATTCACCAC

8941  GACAAATCGT AGTGGGCGGG GCATTAAACG CTTTAAAGGC TACCCTTAAA AAGATTGAAG

9001  AGGACAAGCT TGCTAAAAGA ACGATCCTGC TCAAAGTTAA TGGTGCATTT CATACTCCCT

9061  TCTTTAACGG TGCACGTCAA CAGATGCATA ACCGGTTACA AGCAGTCGAC TTCCATGAGC

9121  CACAGATTGA AGTTATTAGC AATACTACTA ACAGCTTGTT TCATTGTGAG GATCTTCCAG

9181  GAATTCTTGA AAAACAATTA GCTGTTCCAA CACACTTTGG AGCTAATGTT AAGGAATTAG

9241  TCAAGCACGC GAAAATTGAC ACAATATTGG AAATTGGTCC TGGAAAGACG TTATCTCGCT

9301  TCGCTCACCA AGTTGACCAG CACTTAAATA CCCAACACAT TGAAAATCTT GCTGATTATG

9361  AAAAATTTAT AAAGGAGCAA AAAGATGGAA CTGACAGATA AAGTCGTTTT TATAAGCGGA

9421  AGCACACGCG GGATTGGGGC GGCTACTGCA TTAGAGTTTG CTAAGGCTGG TAGTCGGCTA

9481  ATCCTCAATG GGCGGCAGGA TAACTTACCA AAAACGTTTA AGAAAAGCT AGATCTACTA

9541  GGGGCGGATT ATCACTATCT TAAGGGCGAT ATTGCAAATG AAGAATCAGT TAGTGAATTA

9601  GCAGCAGCGG CTTGGCAAAT ATACGAGAAG ATCGACATTC TTATCAATAA CGCGGGAATC

9661  ACGAATGATA AGTTAATGAT GGGAATGAAA GCGAGCGATT TTGACCAGGT CATCAATGTT

9721  AATTTACGCG GAACATTTAT GTTAACGCAA CCTATTTTTA AGAAGATGCT CAAAAAAGA

9781  GTCGGTTGCA TTATCAACCT TGCTAGTATT GTGGGTCTCC ATGGTAATAC GGGACAAGCT

9841  AATTATGCGG CAAGCAAGGC AGGTATCATC GGCCTTACTA AATCTATTGC CCAAGAAGGA

9901  GCACGCCGTG GAATTCGTTG CAATGCGATT GCTCCCGGAA TGATTACTAG TGATATGACT

9961  GAAAAATTAT CTGAGCGAGT AAAAGAACAA ATTCTCAGTC GCATCCCCCT CAACCGCTTA

10021  GGACAGTCAG AAGAAGTTGC TAAGACCGCA AAATTTTTAG CAGAAAACGA TTATTTGACT

10081  GGTCAAACCA TTGTAGTTGA CGGTGGCATG ACAATTTAGG AGGAACTAAA TGACAAGAGT

10141  TGTAATAACA GGAATGGGTG CTGTTGCTCC TAATGGTAAC GGTATTCAAG AATTTATAAG

10201  TAATAGTTTT GCAGGCAAAG TTGGAATTAA AGCGATCAAG AAATTTGATG CCAAGTCGAC

10261  AGGAATTACC GTGGCAGGTG AAATTGACGA TTTTGACCCT AATGATGTCA TTGGAAGGAA

10321  AGCCGCGCGC CGAATGGATC TTTATTCTCA ATACGCCTTA CAAAGTGCGA TTGAAGCAAT

10381  GGAAATGGCG GAGATTAACG AAACAAATAC CAAGCCAGTC GACATGGGTG TTATCTATGG

10441  ATCTGGAATT GGCGGTTTGA CAACTATTCA AGAGCAAATT ATCAAAATGC ATGATAAGGG

10501  TCCTAGACGG GTATCACCAA TGTTTGTTCC AATGTCAATT GCTAACATGG CAGCCGGTAA

10561  TATTTCCATT CACTTTAATG CGCAAAATAT TTGTACATCG ATTGTGACTG CTTGTGCCAC

10621  TGGAACTAAT GCAATTGGTG AAGCCTTTCG TCAAGTTAAA GCAGGTCGCG CTAAAGTAAT

10681  GATCGCTGGT GGATCAGAGG CTTCGGTGAA TGAGATCGGG ATTGCTGGTT TTGCGGCATT

10741  AACAGCATTA TCACAAGCAA CTGATCCGCT TAAAGCTTCT TTGCCATTTG ATAAGGCACG

10801  TCAAGGATTT GTTTTGGGTG AAGGCGGTGC AACACTTGTT TTAGAGGATC TTGAGCATGC

10861  GCAAAAACGC AGTGCTAACA TTCTTGGTGA GATTGTCGGT TATGGTGCTA CCTCGGACGC

10921  TTACCATATT ACATCCCCTG ATCCAACTGG TGCAGGGGCG GCAAGAGCAA TGGAACTGGC

10981  AATTAAAGAA GCTGGAATTA GTCCTAGCGA AATTTCCTAT ATTAATGCCC ACGGAACCGC

11041  TACTCATGCT AATGATGAAG GCGAATCCAA AGCAATCAAT CAGGTATTTG GTTCCGATAG

11101  TAATGTTCGC GTTAGTTCAA CGAAGGGAAT GACCGGCCAT TTGCTTGGGG CTGCGGGCGC

11161  AATTGAGGCA GTCTTAACAG TAGCCGCTTT ACAAAAGGGA CAATTACCGT TGAATATAGG

11221  TTGCTTTAAT CAAGATCCAA AATGCTCGGT TAACCTTGTG ACGGCAGAAA ATAGGAACGC
```

-continued

```
11281  CTCAACCGCC CGTTACGCAA TAAGCAATTC TTTTGGTTTC GGTGGTCATA ATGCTGTTTT

11341  AGCCTTTAAG AAATGGGAGT GATCTATCTT GGAATTTAAA GAAATTCAAA CATTAATGCA

11401  AAATTTTGAA GATTCTGATA TTCGTGAATT AGAAATAAAT CAAGATTCCT TTCAGCTCTA

11461  TTTAAGCAAA AATAAGCAAA CCCACAAGCA TGAAATCTT ATAACAACCG AAAAAACAGA

11521  GCAAACGACT TCAGCTAAGA AAAAGCAAA CGAACAACTA ACTTTACCTT CGCAAAATAT

11581  AACTGCGCCC CTAGTCGGAA CAGTCTATCT CCAACCAACC CCCGATGCAG ATCCCTATGT

11641  TAAAAGTGGC GACCACGTAA AAAAGGGGGA TGTTGTTTGT GTGATTGAAG CAATGAAAAT

11701  GATGACAGAG ATAAAAAGCC CTTTTAACGG AACCATTACT TCAATTTGTG TAAGCAATGA

11761  AGAATTAGTT GAAGTAGAAC AACCGCTTTT CTCAGTTCAG GAGGATAAAG ACAATGCCTA

11821  ATAAAACTTT AGATATAACT GAAATTCAAA AAATCCTTCC GCATCGTTAC CCGATGTTGC

11881  TAATTGACCA AGTTGATGAA TTAATCCCTG GTAAGAAGGC CATTACACAC CGTAATGTCA

11941  CGATTAATGA AGAGGTTTTT AATGGTCATT TCCCCGAAAA TCCAGTTTTA CCAGGAGCAT

12001  TGATTGTTGA ATCATTGGCG CAAACAGGTG CCGTCGCTCT CTTATCTCAA GAAGAGTTCC

12061  AAGGGAAAAC AGCCTATTTT GGTGGAATTC GGTCAGCAGA ATTTCGTAAG GTAGTCCGTC

12121  CGGGCGATAC GTTAAGGTTA GAAGTCAGAC TAGAAAAAGT TCACAAAAAT ATTGGAATTG

12181  GTAAAGGCAT TGCAACGGTC GATGGCAAAA AAGCCTGTAC AGCCGAATTA ACTTTTATGA

12241  TTGGGTAGGT GGTTTAATGT TTTCCAAAGT ACTAGTGGCT AATCGTGGTG AAATTGCTGT

12301  CAGGATAATA CGGTCATTAC GGGAGCTAGG AATTAAGACA GTAGCTATCT ATTCAACTGC

12361  AGACCGCGAA AGTCTTCATG TTCAACTAGC GGATGAAGCT GTATGCGTTG GAACTGCCCG

12421  GGCCCAAGAT TCATATTTGA ATGCGAAAAA CATTTTAGAA GCTGCTCTTG GTACAGGTGC

12481  CCAGGCAATC CATCCTGGCT TTGGCTTTCT ATCAGAAAAT GCGGAATTTG CGACAATGTG

12541  TGAAGAATGC GGAATTACGT TCATCGGTCC CCAAGCCTCA GTGATTGACT TAATGGGAAA

12601  TAAGGAGCAT GCACGGGAGC AAATGAAAAA ATCAGGGGTG CCTGTGATTC CTGGAAGCGA

12661  TGACTATATT ACCAATGTTA ATGACGCTGT TGAGGTCGCA AACAAGATTG GGTATCCAAT

12721  TTTGTTAAAA GCAGCTGCTG GTGGTGGCGG TAAAGGGATC CGACGAATTA ACGATCATAA

12781  CCAGATGCGG CAAATATTTA GCGAGGCCCA AAACGAAGCC CGACTTTCGT TTAATGATGA

12841  CCGAATGTAC CTTGAAAAGA TTATGGAGAA TGTTAAACAC ATTGAGGTCC AAGTATTTCG

12901  TGATAATTTT GGCAATGCCG TTTTCTTTCC TGAACGTGAC TGCTCGATTC AACGGAATAA

12961  ACAAAAATTG ATTGAAGAAA GTCCTTGTGT CCTAGTAAAT GAACAAGAGC GAAAAACGCT

13021  AGGACAAATT GCAATGCGAG CCATTAATGC GATTAACTAC CATAATACGG GGACAATAGA

13081  ATTTCTAATG GACAAGGACC ATCACTTTTA CTTTATGGAA ATGAACACTC GTATCCAGGT

13141  TGAACATACA GTGACGGAGA TGGTAACTGG GATCGACTTA GTGAAGGCAC AGGTTATTGT

13201  CGCTGCGAAT GAACCACTTC CCTTTACCCA ACAGGATATT CAGGTTCATG GACATGCAAT

13261  TGAGTGTCGG ATAAATGCTG AAAATCCTAA ACAAAACTTT ATGCCAGTGA CTGGGACGAT

13321  TAATTACTTA TATCTTCCAG TCGGTAATTT GGGGATGCGC ATTGCACTG CTATTTATCC

13381  TGGCAGTAAG ATCACTCCTT ATTATGATTC AATGATCGCT AAGGTAATTG CCCTTGGTCA

13441  AGATCGCCAA GAAGCTATTG AAAAAATCAA ACGACTTTTA AATGAAATGG TAATTACGGG

13501  CGTAACGACC AATCAAAATT TCCATTTAGC AATCCTAAAC AATCCTAAAT TTTTGGCAGG

13561  AACAGCTTCA ACAACGTTTC TTGAAGACTT CTTCTTGCCA CAATGGAAAA AGGAGCTGAC

13621  AGCGTGAAAT TATATGATCA AAATAATACT TTAAGTGAAC GGCACATCAA AGCAGATAAA

13681  AATGCTGATG AAAGGGTCCC AGATCAAATG TGGTTAAGGT GTCCACATTG TCATCAATTA
```

-continued

```
13741  CTATTCGCCA AGCAGTTAAC ACAATATGCT GTTTGTCCCA ATTGTGACTA TGGATTACGA

13801  ATACCTGCCC GCCATCGACT CTCGTGGTTA GTAGATTCAT TTAAAGAATT CGATAAGGAT

13861  CTCCAGACAA AGAATCCGTT ACATTTTCCT GGATACCAAG AAAAAATCAG CAAACTTCAA

13921  AGACAAACTA AGCTGAATGA TTCAGTCCTA ACTGGTGAAG CTTCAATTAA TGATCAGCTA

13981  TTTTCACTAG GTATTATGGA TCCAACATTT ATTATGGGAT CCCTCGGAAC TGTTACCGGT

14041  GAAAAGATAA CGCGCTTATT TGAATATGCA ACTATCCATC GTCAAGCAGT AGTACTATTC

14101  ACTGCTTCAG GCGGGGCACG GATGCAAGAA GGAATTATGT CGCTAATGCA GATGGCGAAG

14161  ATTTCACAAG CAATAAATGA GCATGCTGCT GCCGGCCTTT TATACATTGT GATCTTAACC

14221  GATCCAACAA CTGGTGGAGT AACAGCTAGT TTCGCAATGG ACGGAGATAT TATTCTCGCT

14281  GAGCCCCATG CACTTGTTGG CTTTGCAGGC CGTCGAGTTA TTGAACAGAC GATTCATCAG

14341  CAAATTCCTG TTGATCTCCA ATCAGCTGAA AACATCCTGC ATCATGGATT TATTGATCGA

14401  ATTGTAAAAC GTCAAGATGA AAAAAAGCTG CTTGAATGGC TATTAAAAAC AGGGAGCGTT

14461  GCTAATGAAT GAACAATTAT CAGCAAGCGA GATTGTTAAA CGTGCTCGCA ATGACAATAA

14521  AATTACGGGG ATGGAGATTA TTCAAAATGT TTTCCCAGAT TTTGTTGAGT TGCACGGCGA

14581  CCGGGCAGGC GGGGATGATC CTGCAATCGT TGGTGGAATC GCTACTTTCC ATCAGCAAGC

14641  AGTTACCGTC ATTACCACTG ATCGAGGAAA AACAACAGAA GAAAAAATCA TAAAGCATTT

14701  TGGCTCACCA ATGCCTAGTG GTTATCGCAA GGCACTCCGC TTAATTAAGC AAGCAGTTAA

14761  ATTTAAGCGA CCTGTATTCT GTTTTGTTAA TACCGCAGGA GCATTCCTA GCAAGGAAGC

14821  CGAAGAAAAT GGGCAAGGAA GTGCGATTGC CCAAAACATT TTACAAATAA GTCAGCTTGC

14881  CATTCCAATT ATCACGATTA TTTATGGTGA AGGAGGTAGT GGGGGAGCCT TAGCATTGGC

14941  ATGTGGAGAT GAAGTATGGA TGTTAGAAAA CAGTACTTAT TCTATTTTAT CTCCTGAAGG

15001  GTTTGCCTCC ATCATGTGGA AAGATAGTAC GAAAGCAGAT AAAGCGGCAG AATTAATGCA

15061  AATGGTGCCG CAAGCTTTAT TAAAACAAGG GATTATCGAA GGAATTATTC CAGAAAGCGA

15121  AGAGCATCGT AAAACTTGCA AAAATATCGA GCAGGTTTTA CTAAAGCGAT TAAACAAGCT

15181  GCAAGAATTA CCGCCAAACC AACTTCTAGC AAACAGAAAA AAACGTTATC GAAAGTTTTA

15241  AGGAGGATAA TATGGGAAAT ATATTAACAG GAAAAAAGAT CGTTGTTATG GGAGTAGCTA

15301  ATAAGCGTTC TATTGCATGG GGATGTGCAC AAATGATGGC TGAACAAGGT GCCCAAGTTA

15361  TCTATACTTA TCAGAATTCC AGAATGAAAA AAAGCTTACA ACGGTTAGTA GATGATGAAG

15421  ATCAATTAAT TGAATGTGAT GTAGCAGATG ATGAAAGTAT TGACCAAGCC TTTACGATTA

15481  TCAAGGAACG TTTTACAAAA GTAGATGGAA TTGTACACGC AATTGCTTTT GCAAAAAGAG

15541  AAGAATTAGC TGGTTCAATC CTTGGTGCTA GTCGCAAAGG TTATGCAATT GCGCAAGATA

15601  TTTCGTCTTA CTCCCTTATT GCTGTCGCTA AGGTTGCTAA TGAGTTAAAT CTATTAAATA

15661  ATCCTGCAAG TATTGTTACC TTAACTTATT TTGGCTCAGA ACGTGCTATC CCTAACTATA

15721  ATGTAATGGG AATTGCTAAA GCTGCCCTTG AAGCTAGTGT TCGCTATTTA GCACGGGATT

15781  TAGGACAAAA ACGAATCCGT GTTAACGCAA TCTCTGCTGG CGCGGTTAAG ACATTAGCAG

15841  TTACAGGTAT TAAAGGTCAT GATGAACTTT TAAAGATGTC CCAAGCAAGA ACTGTTGACG

15901  GAGAAGATGT GACTATTAGC GAAATTGGGA ATGTGTGTGC ATTCTTAATG AGCGATTTAT

15961  CAACTGGAGT TACTGGCGAC ACCATTTATG TTGATAAGGG GGTACATTTG ATTTAAAAAT

16021  ATAAATTTTA AAGACTGAGA AATGAGTTTT TTTCAGTCTT TTTGCTGTCT TTTAGAAGGA

16081  AAACATAACA ATAGCAAGAA CTTTTTTTAA TTTTTTCTAA AAAGTTCTTG CTATTTTATA
```

-continued

```
16141   GCTCAGTTGG TATTATTAAT AACGTTGTGA AAGACGAGTT AATAATTTTG AGAAAAATTG

16201   TTTAATATAT TTAAAAATGG CCCGTTAGTC AAGTGGTTAA GACACCAGCC TTTCACGCTG

16261   GTATCGTGGG TTCAAATCCC GCACGGGTCA CTTTTGCGGA AGTAGTTCAG TGGTAGAACA

16321   TCACCTTGCC ATGGTGGGGG TCGCGGGTTC GAATCCCGTC TTCCGCTTAG CCAGTTCTAT

16381   TATGCCGGGG TGGCGGAATT GGCAGACGCA CAGGACTTAA AATCCTGCGG TTAGTGATAA

16441   CCGTACCGGT TCGATCCCGG TCCTCGGCAC TATTTCGGGA AATAGCTCAG CTTGGTAGAG

16501   CACCTGGTTT GGGACCAGGG GGTCGCAGGT TCGAATCCTG TTTTCCCGAT CTGGCTAAAC

16561   AGCTAAGAGG TAATCTTCTT AGCTGTTTTT TTGGATATCT GTCAACTGGT ATGGTTGACT

16621   AAAAATTTTT TTAGTGCGCC CGGCATGGGT ATTAGCTAGG TGGTGAAAGT CCGCTATGGG

16681   CCGTAGTAGT CGGAACCATG AGCTGAGGAC AAGGGTGTCC ACCGTGAGGT GGAATCTGAA

16741   GGAAGTCTAA GGCAAAGTAC TGCATCGATG AACAAGAAGT AGCTATAAGG CTGAAATTAA

16801   CTGGATAAGG CTGCTAGACA AGTTGAAGTC CAATACTACT CGAAGTTGGT CTCAGTAAAG

16861   CTAACGATGA CATGGTACGA AAGCTAATAT TCTTACCCGG GGAGATCTGG CCTACACGTT

16921   TCCGACAAGC AGTACTAACG CAGCCATTAA TTAGTTTTTT GAAATAAAAT AAACTTTTTT

16981   GAAAAAAGTA TTGCTTTTTA TAGGATAACT TGATAATATA ATATTCGTCG CTGATATGCG

17041   GGTATAGTTC AGTGGTAAAA CCACAGCCTT CCAAGCTGTT GTCGCGAGTT CGATTCTCGT

17101   TACCCGCTTT TAATTAATTT AATATGGCCC GTTAGTCAAG TGGTTAAGAC ACCAGCCTTT

17161   CACGCTGGTA TCGTGGGTTC AAATCCCGCA CGGGTCATTT TTGGAGGATT AGCTCAGTTG

17221   GGAGAGCATC TGCCTTACAA GCAGGGGGTC ACAGGTTCGA GCCCTGTATC CTCCATTGAA

17281   CAATTTTAAT AGTTGTTCAA CATTTTAATA TAATTGGGCT ATAGCCAAGC GGTAAGGCAA

17341   CGGTTTTTGG TACCGTCATG CGCTGGTTCG AATCCAGCTA GCCCAATTAG TCTAAAACAG

17401   TGAGTAAAAA TTACTCGCTG TTTTTTATTA GAAAAAATAG GCAATCTAAT AACGTAGGCT

17461   AAAAGCGAAC ATCATTGGAT TGCCCAATAA TTAGCATAAT TTATTCACGT CGTAACATAA

17521   TATGCCAGAC AAAGAAGCCG ACTCCAATAA TTAACGCCAA CCATGCCCAT AGTTGCAATG

17581   GAAGATAGAT AGTACACGTT AACAAGCCTA AAACCCAACT GATTAGCATC ATCGATAATC

17641   CAGCAATATC GCCACCTAAA CCATCAATAC CACAAGTAGC GATATAGACG ATTCCTGATG

17701   CCAGATATAA TAGCGAAACA ATTAATTCGG CTGTTCCGGC ATAAATAGGA ATTGCAGGAT

17761   TAGGATTCCC AAAACCTCCT CAAGTCTTAT TCTACCCGGA TGATTAGAAT TTATAAAGAA

17821   TTACAGTTTT TCTATTTACA AATAGAGCAG GGGGAACAAA AAATCAAACC AGAAATTATC

17881   TTCTGATTTG ATTGGATCTT ATTTAGTTGT ATCTTTTACT TTTTTCAAGG CTTCTAAAAA

17941   TACTTCATAA GGTTGTGCAC CAGTGATTGA ATACTTATTA TTAATCACAA ATAGCGGTGC

18001   ACTTGGCATT CCAATCATAA ATGCGCGCCG TTCATTTTTT CGAACTTCAT CTTCATACTG

18061   ATTAGATTCA AGAACTTTTT TAACATCAGC AACAGGTAGT CCGATTTCAT TCATTGCAAC

18121   AGTTAGAGCT TCATAGTCCG CGATTGATTC ATTATCATTA AAATAAAGTT GATAAAGACG

18181   TTTAACAGCC TTATTAAGTA ATGCTTGGTC ATTTAAACTC TCAATGTATT TTATTAAGCG

18241   ATGAGCAGCT AATGTATTAA CAGGAATCGC ATTTTCCATC TTAATTGGTA AATCAATATC

18301   GGCAGCAAGT TGATCAATTT TATGTATTTG TGTAACAGCT TCTTGCTTAG TTAGTTGATG

18361   AGTTTTTGCA TAATATTCTG TCATTGATAA ATCAGTTGTT GTTGGCAACG TTGGATCTAG

18421   TTGAAATGAC ATAAATTTTA ATGGTGTCTG ATCGGCAATC TTTAATTCTT TAAGCGCCCG

18481   TTGTAATTGT GTAATTCCCA TATAGCAATA TGGGCACGCA ATATCAGCCC AGTATTGAAT

18541   TTCCATAGAT GATCGCTCCT TATAAATATA TATTAATTTA ATCTAATCAT AAAATAAGCG
```

-continued

```
18601   AAGTTGCTAG TAAATACGTA AAGAGGGAAC GATTTATTTT AAAATTAACA TGTCATTAAA

18661   ATTATAGTTT TAATGCGACT GAATTTAAAA TTCCCCCCAG AATATCAATT TTTAGCTTTC

18721   TCAAAGAAT TTATTTAATG CTTATTTTTA ACTTTAATAA AACTTTTTCT AAACAAAACT

18781   AATACTTTTG ATTTATGTTT TAAAAGATTT ATGTAATACT ATTGATGAAG TCTATGTCAA

18841   AAGTATTTTA AAAGGAGTTT TTATCATGAA ACATACGCTT AAAGTTGATC AAGTACGTGA

18901   CGGTTTATGG CTAGATTCAG ATATTACGTA TACGCAAGTT CCTGGATGGC TTGGTAATAC

18961   AACGCGAGAT TTGAAGCTTT CAGTCATTCG GCATTTTCAA ACTAATGATG ATACACGTTA

19021   CCCAGTAATT TTTTGGTTTG CTGGTGGCGG CTGGATGGAT ACTGATCACA ATGTTCATCT

19081   GCCAAATTTG GTTGATTTTG CTCGGCATGG TTATATTGTT GTTGGTGTCG AATATCGTGA

19141   TAGCAATAAA GTTCAGTTTC CTGGGCAATT GGAAGATGCT AAGGCTGCTA TTCGTTATAT

19201   AAGAGCTAAT GCCAAGCGCT TTCAAGCTGA TCCTAATCGG TTTATTGCGA TGGGAGAATC

19261   AGCTGGTGGT CATATGGCAA GTATGTTAGG TGTTACTAAT GGTCTTAACC AATTCGACAA

19321   AGGTGCTAAT TTAGATTACT CCAGTGATGT TCAAGTAGCG GTTCCTTTTT ATGGTGTAGT

19381   TGATCCCTTA ACCGCTAAAA CAGGAAGTGC ATCAAACGAT TTTGATTTTG TTTACCGTAA

19441   CTTGCTTGGC GCTGAACCTG AAGCTGCAAA TCCCCTCACG TATGTAAATT CTACTTCTAC

19501   GCCCTTTCTT ATCTTTCATG GTACGGAGGA TGTCGTTGTT CCAATCAAAG ATAGTGAAAA

19561   GCTTTATGAT GTATTAGTTG AAAACAACGT TCCTACTGAA TTATACGAAA TTGAAGGTGC

19621   AAGTCACATG GATGTAAAAT TCCTTCAACC ACAGGTATTT AAAATTGTGA TGGACTTTTT

19681   AGATAAGTAT TTAACCCGGC CATAGATCAT TTCTTGCCTT TACTACTAAA AAGCAAACTA

19741   ATAACAATCC AACTTTCACA TTATTGCAAA AATCAAAAAG CACCATGAAA TTACTTTTTC

19801   ACGGTGCAAC TATTGTTAAT ATTTATCTAC TTGGCTTCCA TCAATGGAGA AATAGACAAC

19861   TTGATTTGCA AACCTAATCC AGCAGCATAT TTATTTAATG TAGGCAGCGT AGGGATTGAA

19921   TCTAAATTCT CGATTTTAGC CAATTGAGGT TGTGTCATAC CGATTTTTTT TGCAAATTCT

19981   GTTTGCGAAA TGCCCTGTTT AATTCTTTGT ACTTCTAAAA AAGACAAGGT ATCAACAATC

20041   GATAATTCTT CTTTTGTTGC AGCCGTCTGA TGCTTATCTA TATCTTCCCA TTTTCTCATT

20101   ATTTACCCTT CCTTTCGTAC CAATCGTCAA GTAGCGACAA GGCTCTTTCT ATCTGACGAG

20161   GATCTGTTTC ATCCTTTTTC TTAGCATAAT GATTAATAA TACAAAATTA TTTTTCTTCC

20221   ATACTCCATA AAATACTCTT TCTGGCATAG GTCGTAACTC CCATAGTTGA TGCCTATAAC

20281   CCTTTAATTT TTTTGCTTGT GGTGTATGCA ACACAGGACC AAGAGCTTGT AACATCTTAA

20341   TTTGATGGCG CATTTTTAAA TAAATTGCTT TATCTTGCTT TTGTTTACTT TGCGAAATTT

20401   TCTCGAAATA ATCACCAATT TCACTATTTC CATTTTTATC TTCGTAAAAA ACTACTTCAT

20461   ACATGCACTA TTTCCTTTAT TATAGCTTAT TTATTACTAA TTATAGCAAG ATTGCTATAG

20521   CTTTACTACT ATTAAAATAT ATTCCATAAT CAAAAATTTT TCTATTGAAA GCACCCGCAC

20581   ACTCAATTAA ATCAAATAAG TTTACGGCAA TGATTATTTT TGGTGCACAA AAATTGCCGA

20641   TGTTCCCCAG CTTTACAAAC TTTCACCATT TCATACCATT TTAACTAAAC AAAAGCTCCG

20701   GTAAAATGCC GTTATATCAG CATTTTATCG GAGCTTCTTT TTTATACAAT CTTAAAAAAA

20761   TGCGTCCCCC GAGCATAGAA GATTGTTGAT ATATCAACGT TTTGAAGGAG TTAGTGTGCC

20821   AAACGTGTGC GAACTTAACT AAAATAAAAA AGAGCGCCTA TCAGGGCGCC CCACGTTATA

20881   CCGGTACGGA TCAAGTAACG AACTGAATCC AATTTGCGTG CCGATACTTC TCATCTGATA

20941   TTTAAATTAT AACATAATTA TTTTATGATA CAATAATTAA TGCGTGTCGG GAGTAACGAC
```

-continued

```
21001   CCAAACTATC ACGCAAAAGG GGTGAATTCC CCGTGACATT TATACTTCTC ATTCTGATCG

21061   TGCCGAACGG GCTCGTCAAG CAACTGATGC ATTATGCAAA GGTTGTAATC AAAAAGGCTC

21121   TCAAACATCT AATTGATGAA TTACTTGGTT AATTCTGATA GGAAATGTGC GAGATGCTAT

21181   TTCAGCGGTA GTGTTTGCTA TCGCTGTTTT TTATTATACT TTAAGAATAT AGTCATGGTA

21241   TTTTTTTACC TTAGTAACTA TTCAGTTTAA TGTTACTCTA TTAAATTTTG AATTCCTTTA

21301   CATCCTTAAC CTCTATCATA TTACAATCTT TATCTTCAAC GTAGACGAAT TCTGACATAT

21361   CATCAATATC ATTGAAATCT TTATTAGCTG CGAGTTCTGC AGCATCCTTA AAAAAATTAG

21421   GCCTTTTTTC TTCTATTTTG TCCATCGGTA CTAAACATTT TAATATGTAA GTTTTGAAAT

21481   GCTCTTGTTC CCATCTTGTT TGAAGAGGCC CTTTTAATGG CCTACTTCTA ATATTATCTA

21541   ATTCATATAT GGCACTATCA AGGTACCTTA AAATTTCAGG ACACTTATAA ATGCAAGAAT

21601   AATCAAAATG ATATGGTATA AAAAAGCCAC TAATTCCGTT ATCATTTTCC AAACGTGCTG

21661   CAATATCATT CCAACTTCCA CCAGATTCAA TCAGGTATGA GTGCCCATTA TATGAAATAA

21721   AAGGATTATT ATTTTTACAG TAGAAACGAA TATTATTTTT TTCTAAAAAT GATCCTAACA

21781   AGGTACTAGA ATCTGTTATA ACTTTGCTAA GTGGTTTTAA TCCATCATAT AAATAGTTCC

21841   TTTGCTGTGA AGAACAAGTT GTAAAGTGGT AAAAATATGC ATTTTCAATT TCATCTTTTT

21901   TATATAGTTC TAATGATCTT TCAGCCATTT CATGAGTCGA TAAATCAAAT ATCTTGTATT

21961   TTTTCTTTTC AGACACCATG GTTTTCTCCT TTTTATGATA TATCTAATTT AGATTACTAT

22021   ATGACAAAAC ACCCTAGCAA CCATTAATCG GCTACTAGGG TGTTTATTAC TATAATTTTT

22081   CACTTAAATC TGAATTGTTT GACCAATGAA AATCATATTA GGATTTGCGA TGCCATTCTT

22141   TTGAGCTAAT GCTTGCCAGG TCTTGCCAAA CTTAGCCGCA ATTCCGCTTA GTGTGTCCCC

22201   TGCTTGGACA GTATAAGCAT TGGATTGTCC GTTGCCGGCT AAGTAGAGTT TTTGCCCAAC

22261   GTAGATCACA TTCGGGTTAG TAATGTGATT ACGGCTTACG AGGTCTGAGA CAGTGGTGCC

22321   GAATTTGGTG GCAATTCCGG ATAACGTATC GCCTGATTGA ACAAAGTAAG TATTTTCGTT

22381   TGATACTTTT CCGGTGACTT TGAGGACTTG GCCGACATTG ATCTGGTTTG GATTACCAAT

22441   ACCATTGATT GCTGCTAGGT TCTGATAAGT AGTCCCGTAT TTTTCTGCAA TTCCACTCAA

22501   TGTATCGCCC GGCTGAACAA TGTAGGTTCC AGTAGCTGGG TGACCAATAT GTTGAACCGG

22561   CTGTGGTGCT GGAATAACAG CTTGCGGAAC ATTGCCTGAT ACTAAACCAG TCGTAAAGGC

22621   ACCGTCAAAG TCATAACTAG TATCAATTCC CATGATGCTA TGATCAGAAT ATTGCCAAGC

22681   ACTTGCATTA TCAATCCCCA GTTCAGTCAC ACCATAGCCA GCAATCCAAA TCTTCCGGGA

22741   ATCAAAGCCA TGTGAATTAA GAATACCGCC AGTGAAGAAG GACTTCATGG AGTAAATCCC

22801   AGTATTCTTG TAACCAAGAG CTTCTACTTC TTGAAGAAAG GCTAAGGATA CTGATTGATA

22861   ATCTGCAGTT GAATGAACTT CCGCATCATC AATCATCAAA GTATCGTCAT ACATACCAAA

22921   TTGCTTAGCG ATTTTAACGA AGAATCGAGC TTCATTTTGT GCATCAGTCA CTGATGTATA

22981   ACGAGCAAAG TGGTAACAGG AAACGCGCAA GCCAACCGCT AAGGCATTAC GAATTTGAGC

23041   GGCCGCACGT GGATTAACAT AAGCCGAACC ATCTTCGGAC CCTTCCGTTA ACTTAACAAC

23101   GACCCCTAAT GCACCCTGAG CTTTAGCAGC TTGGAAAAAG GCAACAGTAT CTGGTTGATA

23161   ACTTGAAACA TCGATGAATT GATTACGCAT ATTATTCTTC CCCTTTCATT GGATCGATTG

23221   CTGGTGCTTG GCCGGCTGGA ATAGTAGCGG GTTTAGTTGG TTGTGATGTC GGATCAACGG

23281   TTGGTGTCAA TGCAGACTTT TCATAAGCTG ATTGCACAAG CGTTTCAATA GCGTTAAGGT

23341   CAATATTCTT AATACCCTGC TTTTGAAGTG CTTGTTGAAC AATACCTGTT GCTTGATGAA

23401   ATTTCTCATG ACCAGCCATG TCTTTGCCAA CTAAGGAAGC AACGGCATTA TCTGCAAGTC
```

-continued

```
23461   GTTCAGCACA AGACCAAGCA GCACGAGAAG TTTCTGTTTT GGCATGAGTG ACTTTAGCGT

23521   GAATAAATGT CTGGCTTTGC TTTAAGGCAA AATAAAAGAC CGTTGAGATA ACGGCCGTCA

23581   TGATATAGGT TGGAATTGCA TTAATGATTG TGCTCATGTT GTTTCTCTTC TTTCTCTACA

23641   TAATCTTTGC TGAGCTTGTA AATATGATTC TTTACCCAAG ATGGTAATGG TAGTCCCATT

23701   TGGCCCCAGT TTTCGATAAT CGAAACTAGG TAAAATAGGA AAAAGAAAAA GACAAGCGAG

23761   TCGCCTGCCT GTCCTAATCC GCATAATTCT AACATTGGAT AAACGGTTAA AGTCAAAATA

23821   ATAACTGCAG CATGTTTCAA AAGTCCACCC GTTCCTTTAC TAGAAGTTGT TCGGTGCGTA

23881   ATGATACTTT TGAAAAAACC TGTCACAATA TCAATCACAA TCGCCCAAAC TAACCATTCA

23941   ATGAGCACGT TGTCAATCAT GCTGGCAAAA TATTGAATGT ATAGAACGTG TTGTGGCGGT

24001   TGTGTCAGTA GTAAGTGCAT TTATAGTGGT CACCTCCTTA TAAGGGTAAA ATAAAAACGC

24061   CCTGTAGAGG ACGTTTAAAA TTATTTAATT TTTATTAAAA GATTCCCAAT TTCCATCTTC

24121   ATTATTATTG ATTTTAATTA TTAAGTCGTT AAGTTTATTA TCAATATCAT TAGCTAGCTT

24181   ATACGCACTT GAATCACCTC GTACTCTAGT AATTTCATAT ATTTTTCCTT GACGAAGTTC

24241   TTCAGTCAAA GATTTAATAT TATCTATTTC GTTAGAATAT TTCTGTTTGA GATTCACTTT

24301   ATCCCCATCT CCTTACCGCT AAAATAAAAG TGTTATATTA CGCTGTTACT AAATATGGAA

24361   TATTATTATC AGATAACCAT TGAACTGCAT TATTATTAAT TTTTACAACA TCATCTAAAA

24421   TTTTATCTAA ATTAAATGAA TAACCAAATA TAAAAAATTC ATGCTTATGA GGATCGTATA

24481   CTCTTAAAGT TTCATCTTTT GTAGGAGTGA ACACTTTGTC TCCAACTTTT ATAGTTTGAT

24541   ACAAATTACC AATTACTTGT TTTTCAACCA TTATGTGCTG ACGTCGGTTA AATTTAATAA

24601   GTCCTTCATC AATATGTTCT AAACTATTCC TGAGGCCTCT TAAATTTTCA TTTTCGACCC

24661   TATTAATATA GAAATCATCA GTTACATTCA AAATTTCCCT TACCTTTTTT CGATCATTAC

24721   TATTTTTAGA GTTAGAACCC CATAGAAGCT TAGCTATATC TGACGTATAC AATGCAATAT

24781   TTTGTAAATT ATACCAAATC ATATTATCTT TATAATATTT TTCATGTTTG GTATTATATA

24841   TATTTTTAAT AGCAATAATA GTAAAATTAC ATAACAGATA AGTTTCACTA ATTGCATACT

24901   CCTCGTCTTT ACTATTCATA GTATAATGTT GCATAATATT TACCATTCCC CTTATTAATT

24961   GTTTAGTAAT ATTATCGTAT CAGTAATTGA AATAATTATG ATATTATTAT GAAAAATTGA

25021   AGAAAAACCA AAGGCTAATA ATTAATTTAC AAAAGTATGG AATCAAAATT TTAATAAAAT

25081   GCCGCCCATA ATAAAAGCCC CGCTCGTTTG AGTGAGGCTT ATTTATGTAT TGTGTATTTC

25141   TAAGGCGACT ATAAGTAATT ACCGTTAAGC TAAGAATTCA TTTAATTATT AGCCATTTTC

25201   TTTAGCTTTT CTTTATCTTC AATCTGATAC AAGCGAATCT TAGTAATTAA TCCCTGATAC

25261   GCTTTTACTT CATTGGGAAA ATTATTAGCA GGAGTAAATT TATCATCTTC TTGGGACAAT

25321   TCAGAAACAT AGAATACATT TCGATAATAA CCTATATAAA GTTTATGGTT CAGTTTCCTA

25381   TATAATTTAT TTTTTTCAAT AATTTTTGCT TCTTTAGGAG TATAACCATC TTGTTTTCGG

25441   TCAAAATAGG CTTCCCATTT AATGCACTGT TCCTGTGAAT TAATCCGATT TGTTTTTAAA

25501   CCAAATGCTG CTAATGGATA CCCACCTAAT TTGGGATTGT TACACAATTC ATTATCATAT

25561   TCGTAAGCAG TATTAACAAT ATCTTCTAAT GATTTTGAAA TATTCAAGAT AACCACCTCT

25621   ATTTTATAGA GTATCACTAA TTTAGACTAC TAAACAATAA CTTAAATAAT TTTATTGTCA

25681   TGATTTATGC TCCTTGAATT TCGTAATTCT GACCGGTTAC CGTCTTATAT TCATCTTTAG

25741   TGATCGCTCC GCATCGTACA TAAACTTTGT AGAATTCTAA ATCATGGTTA CCCCAGTCAT

25801   TCCAAAACAT TTGAAGCATT TGTAATTGTG TCATCATTAT GCCGTTACCT CCTTAGATTT
```

-continued

```
25861   TTCGACTGCC TGTTGCTGAT TAACAGTCAT AAACATTTGT TGTAATTGCT TGATTTGAGT

25921   TGCTTGTTGA GCATTAGTAG CCTGCAATTT TGCATTTGAT TGGTTCTGTT GCATAATCAT

25981   TGCTTGCAAA ATAGTGATTT GTTGATTGGT ATTCCCGTTT GAATGCGAAA TAATCGTCAC

26041   AGGAATTTGA CTATCATTCA TAATAAAGCT CTCCTTAGTA TATTTTTGTT TGATAAAACA

26101   CTGTTACAGT TACCCCTGTA TTTTGTATAG CTGAGTTATC AATGTTTCTA ACGATTAATC

26161   CATCGCCGTT TCCAGCTTCT GAAACACTCA ATTGCCAGCG GTCGCCTTCT GCAACATAGT

26221   TAAGTATTTT CCCAGTAACT CCAAGTTCTT TATTGATAGC ATCCATTGGA AGTGTCTTGA

26281   CCTCTTGCGA ATTAAGTTGA TCAATAGCTA TAAATTTAGT AATCGTCTTT AAATTAGAAT

26341   TGTAATCTGT TTGATGATCT TGCAAACTCA TTCCTAGCGA TGTATTGCCT AAACTAATGA

26401   GCGAAGTTGG CGTTTTATCA GCATAAATTC TCCCAGCTTG AAAATGGGCT GAGTTTTGAT

26461   CGTAAAATTT AACTCCAGTA TTAAAAGCCT TTCCACCTAA CTTAAAGTGA TCCACATCTA

26521   GATATGTTCC AGTCGTACTA GGCCCAATAT ATAGCCCATT CATGCTTTCT CTTTCAGCTC

26581   CTAGCATAAT CTCGTTTGCT GTAAACTCAG CGTTAGTTTG CAGAGTGAGC AACTGATCGC

26641   ATTTTCCCCC AAGTGCAAGG TAATCAATGT GGCCCTTTGA TAGCATAATT TTTAGATTAG

26701   CTTGTCCACT TTTATTTGTA ACAAAATGGC TTTCCCAATG TTTGATAGTT AGATCGTAAG

26761   TTGAATCAAT CACTGATCCA ATAGCATTGT CTGCTATATC AAACGTTTCC TCCCACACAA

26821   AAGAATATTC ACCGAAACCG GATTGTTGCG ATACCGAATG CTGATACAAT GTTTGATAGC

26881   AATTATAGTT CCAAAGTTTG ATTTTGATCC CAATATTATG TGTGTTATCT GCATCTGTAC

26941   CAGTTACGTT TAATATACAT CCTCTGAAAT AATACCCTTT AATCGAAATA TTACTATGAA

27001   ACATGGTATC AAAAGAAACC CCATACTTAG CTGCACCTCG CTCTAGCATA ATTTGAATAT

27061   CATTTTGATT TCCATTTCTA AATTTGAATG CAATTTGATC CACGTTTAGT GCTGGTGTTA

27121   ACTTTAACCT CAACGAAATA TGAGACTGCT TCAAGTCAAT AGCTAATGGA CTTTCAATTA

27181   GATAACATCC ATTCCCATGA ACACTTTTAT TATTATCAAC TGCATAGGTT AGAATGCTTT

27241   GAAGGATTTG GTAATCATCA TTTTTACCAT CTCCATGTGC TCCCCATGTT TCAGGTATAA

27301   TTTCATTTTC AATAAGTTCC GCTAATAGTC CTGATGCTAA TTGTTCTGCA TGTTTAGTTG

27361   TTGTATCTGT GACATAAAAA AGCCCTCCTC CTCCATCATT TGGTTCATAA TAGCCAAGAG

27421   TTCTTGCGCA CATATCTTTG CTTAAAGCAC TATCAGCTTT CATGGCAGCT ACATTTGGAT

27481   ACACATGTGC ATAGTTAATC GCAATTGCCT TCATCATTTC CTGCTTAAAC GCCTCTGCTT

27541   CCGCCTGGGT AAACAAATTG TCTTGCTTAA TCTTAGCGTC TAGTGCATCT AAACCATTTT

27601   GAACAGTAAC GCCAAGAGCT TTGAGCGTGT TCATTGATTG GGTAAACTTA TCAATAAAGT

27661   CACTGGTCAT CTTGGTGAGC TTGTCGGTAC TGTCTTGGTA CTTGGCTTCG ATTTCGTTAA

27721   TTAACTCTTC GACGGGTGAA ATATATGTTC GTGGTACCAA GCCATCAATG ACCTTATCAG

27781   CAAGGACATC GAGGTCGAAT TCCAGGTAG TGATAGAGTT ACCGTCTTTG AGGATGCGAA

27841   AAAAGGCTTG GCGATAGGAA CCAGCGACTG TAAAGGCATG GCCGGGCATG TCGAAACGGA

27901   AACGTCCGGC GGTTGGGTCA AGGGCAACGT AGCCTTTATC ATCAATTACT CGGAAGTCGC

27961   CGGCGGAATT CTTAGGAAGT AATCCTTCAA ACCAGACGTT ACAGCCAGTT AAATCTAGTG

28021   GTGTCCCGTC TTCGTTCTTA ATATTGACAA AAACTTGACG CATACTTCGC TCATACTGAC

28081   GCGCTTGGAC CCAGTTAGTA TTACTGCCAT CAAAGTTAAC CTTGAAGTCT TGTACATTGT

28141   CAACATGCGG ACGCCGGTCT TGACCGATCA CATAAGTTAA AGTTTGTGAC ATTAAATCAT

28201   TCCTTTCTCT TTCAAAATCT GCATGACAGC TTGTTCAACC GTTTCATAGT CGGTCCCTAA

28261   AGCCACATGC TCAATTTTCT TTTTCCACGC TTCTTGAGCC TCTTTTAGTT CATCTCGCGT
```

-continued

```
28321  GGCTTTTTCT TGTTCGAGTT GGTCGAGACG AGTATTAATC TCCTCGAGTA GCCTAATCAA

28381  TTCTTTATAC TGCCTGTCAC GGAGATTATC GTCTTTGTTA TCCTCATTTT GAATTATCGT

28441  TAAATTATTT ATTAATTGCT GGCGGAATTT TCTTCCACTC TGCAAATCTA GATTAGTTTC

28501  TAAATCCAAA TGACCATCCC CCTCCTCACT TCAAACTACT CCAATCCGTC ACTCTGTAAC

28561  CTAGATTTAC CTGGGCCCGT GATACGTATG CTTTATCAGA TCCGGAAACA TTAAAAACCA

28621  GCCTTCCTTT AGTAGTGCCG GCTGGAATTT TAATGTTAAC TGTGCCGGCG GATTGCCAGG

28681  CGCCATTATT GACGATATAG ACAATATTCG ATTTGCCGGC AGAACTACCA TCGCTCTTCA

28741  AGAACTCGAC ATAAGTAGTA GCGGAACTTG AATTATCGGT CGCATTTAAC TTAGCCATGA

28801  GACGACTTGA GATGGAGGAG ACACCGTTGA GGTTAAATTC ATTGCTTCTG AGAGTGCCTT

28861  GCTCTACTTC AATTACTGGA CTGTCATTAT ATTTTTCGCT GGAAACAGTT CCGCCAGTCA

28921  TCATAGTTAC CAAATTATGC TGGCCATTTT GCATCCAGTA AATATTCTGG TCTACTGCTT

28981  CCATATTCTT ATCCGTCTCT TTCTTATCAT TCACGACTTG CGTTAATGAC TTGGATTGCT

29041  GATCCATGCT ATTTGCTAAT CCACTAATCC GGAGTCGTTG TTCTTCAAGA GCTTCTTGTA

29101  GACGTTTAGC TTTCTGATTT TGATAATCTA AAATAGTTGT TTTTGAATTA TTTAACGTTA

29161  TTTGATTATC TTGTCCCTTA GCTTCCGGAT ATATCGTATA ACCGACAGTC TTATAACTAC

29221  CTGAATATTT ATCTCGCGCA AGTACTCTTA AAATTTCACC AGCAACAGGT ACAAATGAAT

29281  TTCCCTGAAG CGTGACTTCA ATATTTAAAT CTGGATCAGG TTTAAGAGTA GTTAAGGCAT

29341  ATTTACGCAT TGCATCCGCA TCTTGAAATC TTTCATCAAC AAGATCAGGT CCAGGATGTT

29401  CTCCCCATTC GTCAATTGAC TTTTGATCAA CTACCATAAA CGGTTGAAAA TAATACTCTT

29461  CCTGTGATTC TGTGGTTGTA TCATTTCCGA CAGTATCATT GGTTTCTTTA CCACCGATAC

29521  CATCACGAAT AACTTGTAAG GGATCAAGCC AGGTTCCATC ATTTGACCAG GCACTTTTCA

29581  ATGCAGTCAT TAAATTCTTT TGCTTAGTAA TTCCAATATG AAGATGGCTA GTATCACGGT

29641  GGCCAATAAC ATCCCCCGTC TTAATTTCTT GGCCAACTTG AACAGTAATA TCTCCTCGAT

29701  TCAAAAATGC TTCTTGGTAG CAAATTAAAT AATCATTCGA CACAATAGTT ATATAGTTTT

29761  CCAGTCCAGC AATGTATCCA ATATCCTGGA CTTTCCCACC ATGAATCGCA TGAACATCGC

29821  GTCCAGGATG ATCGACAGAA CCAAAATCAA GGCCATCGTG AAAACCATTA GTTCGCCCCA

29881  CTCCATCTTG AGGGTGTGTT CCAAAAGTTT GCCCCAATGA AAAATGACCT TCTCCAACAT

29941  CTGGGAAAGG CCATCCCCAC GGATTAGGTG GTGAAATGAT CAATTTATCT TTCGTGATTG

30001  GGGCACCATG AGGACTCCAA CCAGTAACAC CATTAATTTG TCCTAGTGCA TTAGGAATAT

30061  TGAAGAACGC AATTAACTGG TCAAAACCCT TTAAGATATT TGTATAGGGC TCCCGACAAT

30121  AAGTATTAAA AGTTCCTCGC TTAAATTGAA GTAACCCAAG CGCCGGACCA GAACCATCGC

30181  CATCGGGATC AGTTCCTGGT TGCGGAATCG TCTCGTTTCC ACCTGATTCC AAATGAATTT

30241  GTGCCCGTAA AACATTAAGC TGCTGAGCAT TCGGTTTTAT TCCATAAAAG CTAGCAGCAT

30301  ACTGAATAAC TGGTGTCCAA TCACCGTTGA CTGGCTCAGT TGGTCCATTA GCATTAGTTC

30361  CACCTGTCCC GGTATAAACA GTGTGCTGAA CCTCATGCTT ACCACCAACA CAACGAATCA

30421  TATTAATAAT TGATTGACTG TCCCGAGTAG TTTTAACTGA CTTTGCATCC CTTGGAAAAT

30481  CAATCACTCG ACCATTATCC TTATAGAACT CATCTTCTGA ATAAACTCGT ATCTTCTTGT

30541  TATCCGGATA TATAACTGCA CTTGGCCATA ACTCAGTAAT CTTACTAAGC ATCTCTTTAC

30601  CACTGCCGCT ATCGAACTTA GAAGTTGACT GCTTATCAAA ATTACCATGA ACTTCATAGC

30661  TAAAGCCTAG CTTATTTCCA TCAATCCAAG CCTTTAGTAA GTCCTCAACT CCATAAGACT
```

-continued

```
30721  GATCCTTACT AGCATTACTA TCCTGATTGT TATTTAAGGT AAGGTCACTT CGTTTATAAA

30781  TTCGACTAAT CTCATTATAG ACATGCCAAG CAGTGATATT TTTCGTATTA GTATCAAAGT

30841  TTTCAACACA ATTTTTTACA ATATATTCCT GTCCCTCAAG CACAATCGAA CTTTCAACAT

30901  CTAATGGATC ATACAATGCT GAATCGTAAT CAAATACTGA AAAAGTCAAT TGAAAGGTCG

30961  AATTCTTAGA CCACTCGCTT TGCATTGTTG GCCAGAGAAT AATGTCTCCG ATTGGCTCCT

31021  TAGTTGTCTC TTTATGAGGT GTCATCAATA CTAAACTAAT TGTCCTCACC TCCTAACCAA

31081  GATACATAAA TGGGAAACTG AATGTAATTT CCAAATCATC TGCACCAGTA ACTTCAAAGT

31141  CATTCTTTCC AGGCGCTAAA GTAATATACC CATAATCGGT ATTGGCACTG TCTGGGTTAT

31201  TATTCTTAAA TGTTCGCCGT CCCTTTAGCA AGAGAGTATC GTTTCCAGAT AGATTTTGAT

31261  TGTACGTCCA AGAAGTATTA GTAGTTGTAT TCTTTACTGT GAATTTTCCA CCATTATGCT

31321  TAATAGTAAT TTTTAGATCA TGACGCTGTT CAACAGGATC GATTGTAATA TCACTATCGT

31381  TAAGGATAGA AAACTTATTC TGGCCTTTGA AATGGTATGA AGGAGTTTCC TCATCCATGT

31441  TCATATTCAA GTCTAAGAAA TCCTCATCTT TCATCTCATC CGTATGCAAT TTACTAAATC

31501  GCATTCCGCT TGGATTTTCA AAAGGCACTT CAAACGTACA ATAGTTAACT TCTTCTGGTT

31561  CGCTTTTAAT CTCAAAGGAA CTAGCCCGAC AGTAACGGAC AATATCCGGC TCAACTCCTG

31621  TTCTTAACCT AAAGATTCCT TTTTGTGCAA AAACGCGATA AATCTCATGC TTTGCCATCT

31681  TAAAATCTTT TCGATCAAAG AACTGCAATA AGAACTTAGC GGTGATCGTC GTTTGGCCAT

31741  AACGGGAATA ACTCCAAATT TGACCATCTT GTTGGGAATC ATCACGATAA TTATTAATAA

31801  CACTAGGCGA TTCAGTTAAG CCAAGAAAAG TTAAGTGGTC AGTAATATCT GTGCTGGCCA

31861  CTTCTTTTTG ATCATCAATT TTAATGTAAA GAATGTTTAC AGCGATTACG ACCACCTCCT

31921  AAAGATGTTG ATTATCAAAT AATGCTTGAT CAGTTCCTTC AATCCCATAA AACTGGTTCT

31981  TGTCAAAGGC GCCGGCTTTA ATTGCAGAAA GTTGAGCTGC ATTTAAGCCC AGCATTGTCC

32041  CAAAGCGGTT GAGCATCTGG TCCATCCGAT CTAACATCTC TTTTTGCATT CCATTATTAC

32101  TTTGGCCACC GTTATTATAA TTATTTACAA CTTGGGTGCT TTGCATATTG GGCTTAAAGT

32161  TAGTTAATAC CGAAACAGCA TCATCAGTAC CATTAGCATA TTGTGGTAAG TGCTTAAACA

32221  TCTTAGCAGT ATCGCTAGCT TTAACAACTT TTGTTCCTCG TGGTGCTGGA AAGACTACAT

32281  TACGCCCATA AGGAATAAAT GGTGTTTCAC CTGGGAATTG AACTAACTCA CGAAAGACGG

32341  GGCCAGGTTG ATCATTAACT TCCATCAATC CACCTTTATG GTAATTAGTT CCCTGAGCAT

32401  GCTTTGATTT ATGAAAAATA ACATTAACTG TTTTCTCAAT AGTATTAGGT ATACTCATAA

32461  AATTATGGAT TGCATCAAGT GCTGTTTTAA TTGGCCCAGA AGCTTTATCA TTAGCTTTTG

32521  CAATTTTTGC TGGTCCCGTA TTTGATCCAG CAAAAGCATT TACACCATTG CGAGCACTAT

32581  ACATTGGTCC ACTAGCATTA TCAACGGCTA AAGCATTTTT AGGAGCGCCA GGATTTGAAC

32641  TAGCAAAAAC ATCGACACCA CCAGTAGCAT TTCTCATCGG ACCACTAGCA TTGTCAATTG

32701  CCAGTGCATT CTTTGGTTCT CCCGGATTAG CATGACGCCA AGATTGAAGG GCATCGTTAG

32761  CAGCTTTTAG ATTTCCACTA GCTTTATCAT CAGCAATGAT TTGTTTTGCA GCACTAACCG

32821  GCATCCCCTT CCACAGCCCA TAATCAGTGA TCAGTTGCTG TAGTTCGGGT CCACCCTTAG

32881  CATTTACGAT TGCTTGCTGT TGCTTAGGAC TAAGTTGATT CCAGCGACCA ATTTTATTGA

32941  GCGCATCCAT TAATCGACCA GCACCCTGAG TAGTAACCAA AGCACGTTGT TGCTTAAACG

33001  AAAGACTATT CCAAACACCA GCCTGCACTA ATGCATCAAC TAATTGTGGA GTTCCTTTAG

33061  CGTCAATAAT CGCTTCCTGT TGTTTTTAAGG TTAAATTATT CCACTGTCCG GAACTTTGCA

33121  AGGCTTCATA AATTGGCTTA GTTGCCTTAT TAGTAATTAC TGCTTCCTGT TGTTTTAATG
```

-continued

```
33181   ACAAGGAATT CCATGCACCG GATTCAAGCA GAATGTCGGC CATTTCTTGC TTACCTTTAG

33241   CCTTAACAAT TGCTTCTTTG GTCTTAAGAT CAAGATTATT CCATTCTCCC GACTTCTCTA

33301   AAGCTTGAAC AATTGTTTCA CTAAAGCCGT CTTTCAACCA AGCTTTCTGC TCTTTCCAAC

33361   TCATGCTATC CCATTTACCA TTTTCGATTA ATGCAGCTGC CACCATTTGT TGAGCATTGG

33421   TACTTAACTT ACCTTCCTTT TTCAGAAGTT TAATTTGGTT CCATTGATCT TTAGAATTAA

33481   CAGCCTTATT AACTTCCTCC TGGGCATTAG TCCGAACTTT ACCAGTTTTG GGATCGAAAA

33541   CTAAGTCATT CCACATATCA GCGGCTTTTT TAGCTTTTCC ACTTAATTTA GTAGTATTTA

33601   CCGCTAAGCT TTGTAGGTTT GTTTCGGCAG CTTTGGATTG CCGCTTAATC TCATCAGTGC

33661   CATCTTTATA ACTAAGTCCC ATACTTTTTA GGTCATTCTT AATTAATTTA GTACTTTCAC

33721   CATTAGCACG GGCCAGGCGA ATATATTCGG CAGCTGCTTT ATTCGTGTAA TCTGTTAATG

33781   CTTTCTTATT AGCACGCATA CCGACCTTAT ACAGTTCAGA ATCTTTTCCG TAGCGTTTAG

33841   CAAGCATTGA AGACTGCTTC TTGTATTGGT TTTCCATTTC AGCAGTTTCA CTGGTTATAT

33901   CTCCCATTTT TGTTGAGCGT TGTTGCATAG ACATATGCTT AATATCGTTA TTAAGGACAG

33961   CCATTGCTTT AGCACGCTTA CTTCCACTTA ATTTAAGAAT TTTCATCTCA TCGTTAAGCA

34021   TTTCCTGCTG GTTGTTCTTT AACATGACTC GCTGAGTATC ATTTAATTGT GAAACTTTTT

34081   TATTGTGGTC AGATAGAATT GTTTGAACAC GCTGATTGGC ATTATCTGCA TCATTCACAT

34141   ATGAATTATA TTGTTTTTTC TCCTTTTCTA ACTCATCGTC AATAGCTTTA GATATTTCTG

34201   GAGACAGACC TTTTTCTGCC TTTTTGGCAT TAGCAAAATG TTGTTTTGCA CTATTTTCAA

34261   TATTAGTAAA CTCACGGTCA AAATCAGCAG CTAATTTCTT TGTTGAAGTT GAGGCAGCAA

34321   CATCCATATC TGACAGAGTG TTCTGAATTC CTTGAGAAGT CGACTGCATT TTTGATAAAG

34381   CCTTATCAGC AGCTGCACCA ACATCAGATC CCCAACGATT CGTTCGTTGT GATGATTCGA

34441   CAGCTTTCTT ACCCCAAAGC TCCCAAACAG TAATTCCACC GGCAATGGCT AAAGTAGCAA

34501   CTCCAGCAAC AGCGGCAACT GTTCCTAAAG ATACTCCAGC CGCAGCAGTA GCAGCACCTG

34561   CTTCACCTGC AGCTACACCG GTACCTTGTA AAGCGACAGT CGCAGCACCA ACACCGTTAG

34621   CAGCTTGAAC CGCCCGACCA CCTGCACCAG TCATGGTTGT TCCAAACTTT GCAGCTTGAA

34681   ATGTTGATTT TGAAAAAGCT GAGCCAATAA CGTCTAACCC ACTGGCTCCT AGTTTCATTG

34741   CAGTTTGTAC ACGGCCGATT CCGGAAGCAA TTTTTCCAAA GGCAAGAACT GTCTTCCCAG

34801   CACCACTAGT CAGTTTACCC AATGCTAGGA ACAACGGGCC TGCACCAGCA GTGAACAGGG

34861   TAGTTGTTAC AATTGCCTTC TGGACAGCTG GTGATAAATC ACCAAAGCCA TGTGCAAGTC

34921   TGGAAAGGCC TTGAACCATT GGAATAATAG ATGGTAAGAC GTACTTTGCC ATATCCATTC

34981   CAGCGTTAGT TAAAGATTCC TTGAAGATTG CTAATTGTGC TTTAGGAGAT TGAAGGTTTT

35041   TCTGTGACAA GTCGCCGATA TAATCCCGCT TGGCAGAGTT TTGAACTTCT TTATTAAGTT

35101   CACGTAACCG ATTAGCGTTT TCGGTTAAAA TTGCCCCAGC TTGTTGTCCA GTTGTTCCAA

35161   ATAACGCATG AAAAATATCA TTCTTTTGGT GACCAGATAA GCCTTTCATA TGGTCATTTA

35221   ACGTCTTAAA AATAGACGAC ATTGATTTTA ACTTTCCACT CTTAGTAAGA AAATCTTTAG

35281   TACTTAAATT AATACTTGCT AAAGCTTTTT GACCATTAGC GGTTGGCGTA ATTAGTGAAT

35341   TGATAACCTT TCGTAGACCG GTACCAGCTT TGTCTGCTTC TAGACCATTA TTAGACAAGA

35401   TCCCCATTGC ACTAGCAGTT TCTGAGAGAC TAAAACCTGC TTGATGAGCA GTTGAGCCAA

35461   CATATGACAT TCCCACACCA AGTGATTGAA AATCAGTTGA TGTGGCATCG GCAGCATAGG

35521   CTAACTCATT TAATGTTTTA GTAGATCTAC GCTGCATGAC TGTAGCATTC TTGATTGGAC
```

-continued

```
35581  GTCCTGCTTT ATCAGTAGCC AGTCCAAAAG ATTCCATTGT CTGCGAAGCA ACTTTGATTA

35641  CATCATTAAA GTCATCCCCA GTGGCCACAG ATGCTTTAAG TTCGTTCCGC ATTACTCCAA

35701  TTGCTGCTTT AGATGTATAA CCACGCTTTA CTAGATCTTG ATACCCGGCA GCAATCTTTT

35761  GCTGACTAAC ACCGTACTCG TCAGAATACT TTCGGGCATC TGCAGTCATC GTTTTATATG

35821  CGGCATTCGT TTCTGCAGCT GATTCTCCGG AAGTTCGAAT AACGTTCTTG ACCTTTGTCA

35881  TTTGATCTTG GAAGTCAACG AGTTTCTTAG CGGAATATGT TAACCCTGCC GCAATTGGAG

35941  CTGTTAAATA AGTCGACATC CCTCGACCGA CACCTGATAT TTTAGAACCA ACATTGGTGG

36001  CCACATTTCC AAAATGTTGA GTGCGATTAG CAAGTTGTGT CCACTTATTC GACTGCAATT

36061  CAATATCACG ATTAAGAGCT TGCATTCGTC CACGTAATTG TTCAATTTGC GCAGACGTTT

36121  TATTATATTG GGTTGCTGCC TTAGTTCGTG ACTGCTCGCT CCTGGTAGTA TCATCCATTG

36181  CTTTCTTAGC ATTCTGGAGT TGCGCATTAT AATTGCGCAT TTGTTGACTC ATAGTCGCAT

36241  AAGCAGCACG CATATTATTA ATACTTCCAC CGGATGCTTT CAGTGCCGCT TCTTGCGCAC

36301  GCAAAGCATT GGCTGTTGAT TTAATTTGCG CTTTTAAAAC ACCATTAGCC GCTTTAAACG

36361  GATCAATATC CAAACTAACA GTTGCTGCCA AATGTCCTAA TGATTGGGTC ATTATTTAAC

36421  CTCCTTTCCT AGAATAAGAA TGGGAATGCT TTATCAATGG TTGTCTGCTT TTCTTCAAAG

36481  ACGTAATTCA TTAATTTCAA ATCTGAAAGT GTTAGCTTAC TGACCTCATT CCATTTATAT

36541  CCATCGCGCA TTTTATTTTT AATGAAATCT GTGAGACTCT TGATTGAATC ATCAATCATC

36601  TCAACAGTTA TTTTTTTGGC TTTTCGTTAT CCTTTTTCTC TTCTAAGTCA TCTTCACTTA

36661  GAGGAGAACC GAGAGTTTCA TTAATTGCAT TAACAATGCT AATTAACCCT TCTATAGCCG

36721  TAACTCCTGA AAGAACATCC TTTTTAGTCA ATCCATTCTT CCAAAAATTA GCAGCAAACT

36781  CAGCCCGTAA ACTTAATAAT CGTTCATTAT CTTTATCTGT TGGCAATTTT TTGGGATCAG

36841  AGTACATCAC TATTTCTTGA CGTTGAACCT TTAATGCATC TAATAGATTT TCAAGCATTG

36901  GGGCTTCTTT TCGTTCATAG ATTGTTTCTT TGCCATCTGT TTTTACTTTT AATTTATATG

36961  GCATTTCCAT ATCCTCCTCA TCGTCTCACT TAACTCGTCT CTGTCTGATT AATTAGTTAC

37021  CCTTTATCAA CAACAGTTTC TGGTTTAGTA TCTTTTGTAT TGGTTGGATC AGTTACTGGA

37081  GCTTCTTCCC CAAAGACCAT TGCATGGAAC TTAGCAAAAT CAAATCCTTC ATTATCTTCC

37141  CGACCGATTA AAAGGATGGT TCCAGTATCC GCATCCCCAC GCGGAACGAA ATTACCTTCA

37201  ATTTCATCTG CTTCTGGGTC TGGAGCACCG TCCTGAGTCT TGATTGAAAT ACCTGGTAAG

37261  GAGAACATCC CCTTGGTTAA ACCAACCCAA CAATGCTTCC CGTTTGAAAG CTTTGTCCGG

37321  AACATAGTAG CAACATAATT TGGTACAAGA TTCTTAGTAT AAACTTCTGT ACCGTTCTGA

37381  ATATCAATTC CATACAAGTC TTTCTTCATG ATGGAATCAA TATCATAAAG GTTGATGGTT

37441  TCCTTAGCTT CGGTAATTCC ACCAGAAAGA ACCAAGTAAG GGCCGTCATC GGCTGCTAAC

37501  GTCTTTAATT CGTTAGTCAG CTCCAGCTTA ACTTCACTTA ACCCGCTCAT CTTTCGGGTA

37561  TCTTTAATCT TTTCGTTCTC GTCTAGCACC CCATATTCAA AATTAGAGGC CCCAAACTTA

37621  GCAACTTTTG CATTTGGTGT TCCCATTAAA TATCATTCCT TTCTTCAAAC CCTTCAAAGT

37681  TAGCTGTGAC CATTATGCAA TTATCCAAGT CCGGATCCGG ATAAGAATTC TTGTAGTAAC

37741  GTTCAAAGCC ATGACTGTGG AGGGTTTCAT ATATTCGTTC TTGAATATCC ATTAGCCGGT

37801  CATCATTCTC TTCACGAATC CAAAAATCAA CTTGTACACG TGGGTATTCA AAAAAGCGAG

37861  CATTGTCACT GTAAATTGCA TCATCCCCAG GTAGGGGGGT GATCCGAATC CACGGTGCTG

37921  AACTCGCTTT AATAAATGGA TCATCAGGCG TACTAGTAAA AATTGGAACA TATGATAATT

37981  TATCTTGTCG CAACTCATCC ATCATCACGA CTAGGCACTC ATCATTCGTT AGATAATCGG
```

-continued

```
38041   CTACTTGCAT CTCTGGAGTT TTCATACTTT CAAGTCCTCA ATAAATTTAG CCAATATTTT

38101   CTTCTTAGCA GCATTTCTTG AATCTTCAAC AAAGTGTTGT GGATCTTGCT TAGCAGTTCC

38161   AGCATCGGGG AAGTGAGCAA TCCATCCTTT ATCTTTGTCA TAACCAACAT CGACAGAATA

38221   ATCTCCACCG TTAGTCTTGA GATTACCGTG TTTAGTATGA TCTTTTAAAG GAGTCTTGCC

38281   TGAATGATCA GAGCCTTTAG AAGCCACAGG CGTCCATTTT CTTAATTCTT CTTGAAAGAC

38341   TTTAGCACCA TCACGGGTTG CTTTTCGTGC CTTCTTTTCT TCCGTCTTTT CAAGTTTAGT

38401   TAAGTTAGCA ATCAGCTCTG CTTCACCGGT CACTGCCATT TTGGACAACC TCCTGGGCGG

38461   TAATTTTTGT TAGATCTCGC TTTGCATAAT CAGGATCCAT TCCCGTGATT TCATACCATT

38521   TTCCTCGCCA GTTAATTAAC CAATTCGATT GAATTTCCTT ACGAGTTTTG AAAGCAATTA

38581   AAAACGTGGG TGATTCTTTT CTGAACCCCA CGTTTGAACT GTTTTGGACA AATTCACGGA

38641   CTGACAGCTT AGGAACTTCT GCCCACACGG TAAATTCCTT AACTTTCTGA TCCTTGATCG

38701   GTCGATGAGT TTCCGGATTG ATCCCCATTT GGACTGAGTA AAATGTTATC CGTTCCGTCA

38761   TGTTCCGTAG TTTCATCGGT ATTCACCTCA CTACTTATTT GATTAATAAG GCCATCAATT

38821   CCTGATGAAA GAACTGGTCG GTAACTATCT GCAGTAATTC CTCGCTCGTA GAAGTCTTCT

38881   TTCACCTGCT TCATAAGTGC AATTTTGAAT CGCGGTTCGT CAGAGTAGTC AGCAGGCTTA

38941   CTCTCCCATT TAATTGCCCT TGCAATCATC AATGCGGCAG CATCAACAAT TATTTTAAGA

39001   ATTTCATCAT CAAAGTCCTG GTCAATTTTG CAGTAGTTTT TTAGATTGGC AAAGAATTGT

39061   TCATCACTCG AGAAAGTGTG GTCTGTTTCC ATCCTACTCA CCTAGCTTTG CTAACAGTTG

39121   ATCCTTAGTA TCGGTTGAAG TATAGGCAAT TCCATGATCA TCTAAGTACT TTTTGATTGT

39181   GTCTACCGTA TCAGCACTAG TCGGTTTAAC GTCCGCCCCG TTGTCGGACG GCGTTATTTT

39241   GACGCTGCTG ATGGACCAGT AACAAAGTAA CCAGCGTTTT CATCGGCCTT CTTCACATCT

39301   AAACGAAGAA CCGCTTGGAG ATATTGACCA TAAATGTCAT TATCAACCCA CCGTACCTGG

39361   AGATCTTTTC GATTTGCTAA AATAATTGCA CGGTATGGAT CACCAACAAA GGCATGAGCT

39421   TCACCCTTTG CTCCAAATAA GTCATCTTCA ATTACAGCAA CGTTGATTCC AGAGACCGCT

39481   TTACCAGACG GACTAGAAAT ACTATCTTGA AGTAAGTAAC GTCCATTCTT ATCTTTCAAT

39541   GTATCAAGCC AGTTGTAGAA GCTTTGGCTG GCAATAATCA TCTTATTGTA AGCCACATCT

39601   AAATCGACAT TCCAAATTTT CTTTAGGTCA TCGATTGCAT TAGAGCCATC AACGGTCTTA

39661   GCTGAAAATC CCTTAAAAAT TGTAGCAATA GCCGCATTCT TTGTATTTAA GGATTGTTCT

39721   TTTGCGTTTC GAGCAACTAA TCCAGTTAAA TCAATTGCTG AATCATCAAT CGATTCTTGT

39781   GAAATAGGAA TTGCTCCACG ATAGGTCTCA ATTTGCCATG CTACCTTAAG AAATTCAGGT

39841   TTTTGAAGAT CAGGATTCTT TGCAAGTTCT TCAACAGTAT GCATTTGAGC AGTTGCCTTT

39901   TTAAGAATTG GATAACTACC AGAAGCAGTT GTGGCGTTAA ATACTTGAAC AAATTGGCTA

39961   AGATCAGTTA CTGTTTTAAT TTCATTTTCA GGATTGTAAA TGATTGATTC AGGAATAGTA

40021   ACGCTTGCGT CTGAAGAAGT AATTCCAGTA GTACCATCAC GATGTTCTTG GTGAAGATAT

40081   GCGTTGAAAT TACGTTTTTC TTCATTTTCG TCCTCGTTAT TTTGAGAACG CTTATGAGGA

40141   TCTGGAGCTG GATTACCCTT AGCTGCTTTA CGGTAAAGCT TAAGGTCATC TTCAATACTC

40201   CGAACTTCCT TTTCAGCAGC TTCAATTTCA GAACGTAATG ACTTAGCTCG TGTTAAGTCT

40261   TCATCAGTTG CGTCTTCATT TGAGAGCAGT TGGCGCATTT CATTAGTTTT TTCGTTAATT

40321   AATGCTCGCT TACCTTCTTT TTGAGCAAGC AATTCTTTAA TTTTTTCGCG AAACATTTAA

40381   TTTCCTCCTT CGAGTGTCTT CAATAATTCT TGTCGTTCTA ATTCACGTAA CATCTTTTTA
```

-continued

```
40441   CGTTTCTGAT CAGTAGCATC TCTATTTTCT TGGCTCTGCA TTTGCTTAAC CATATTGATC

40501   GAACGCTGAC CGACCTGAAC TTCTGTATCC GGATAAGCAG GTGTTGTAAC TACTGATACA

40561   TCGAACAAAC GATCAATTTG TCGAATGGTT CGTTCATAAT CAACTCCATC CTGGTCAGAT

40621   TCTTCCCAAT CTTGGGCCTC ATCTGTGTTG GCCACCGTAA AAGCAAAGCT GCATTGATTA

40681   ATAACGCCTG CCTTGATATT GGCGATCAAA TCACGCGCAA ATGATGTATC AGTTGGCTTA

40741   ACAGTGAATT TCAAGCCAAT TGCATCAGAA GATAAAGTCA TGTTCACCCC TGATCGTCCC

40801   AGTACCTGGT TAGGATCGTG ATTGATCGTC GCTACTACAT TTGACATATC AGCGTCATCG

40861   AACGCTCCTG GAGCAATTTG CTCAATAAAG CGAGTAAAGC CACCCAAAAC TTCGGATGGC

40921   TTATTGTATT TGGCTGCATA ACCTTCAATT ACTGGTTCAT CATCTTCATC AGTTGCCGTT

40981   CTCATCTGAA TTGGCATCAT TAACTGTCGA GTTTCCAAGT CGCTTGTCAT CGATTCCACC

41041   TCCCTTCGCT GTTGATTGTT TCTGATACTC TTCTTTTTTA TCAAGGAAGA CAGTATTCAA

41101   GGTTGATTGG AAACGGTCTA AGTCTGGATT GTCAGATTTG ACTAACCCCA TCCGAACTCG

41161   TCCTTCATTA GGAGTAATGA CGTTATTTGT AACTCCCTTT TGTACATCGT CCATTGACAT

41221   CCCTGTTTCT TTGCGTGTAT CAAATTCGAT GTGGCAGTTA TGACGTTGCC GATCAGTCAG

41281   CATTGTCATT TCCAAATTAC TTGCAATCGG CTTGAAGTAA TAAGGTAAAT CAGAAGTAAT

41341   AAAGTCTTCA TTTAATTGTT TAATCGATTG GTTAGGACTA TTAACTGCTA ATTTATATGC

41401   TGGAATATGC AACGCTTTGG CAATTTGAGC AGTTGAATAG TTGTTGCTGT TAATTAGTTG

41461   CAAAACATTG GTATCAATCT CAATTGGCGA GTAATCGAAT GTATCATCAG TAACGATTGG

41521   GCTACCGGCA TTGCTATTAG CTTGTGCATA TTCAAACGCC TTTCTAGTTT TAAGACGCGC

41581   TTCCGGACTT AACTTACCTT TAGCCTTTAG TAATCCACCT TTAAGACCTG ACTTAAAGAA

41641   CCGCCGTAAA GTCTTAATTC CATCATCCTG TAATCCAATC TCATCAGCCA AAGACAACAA

41701   CGGCGACCGG CCATGAATAC CATCGTAGGT AAAGAACATA AAATGAATTA CATCTTCAGC

41761   CGGCACAACG ATTGTTTGAC CACCGCCTTT TTGATTGATA GGTGTAAATT CGTATTTAAT

41821   ATTCGTTACA TCAGAATCAT CAATATAGGT TTGCGATGGT GGAAAATATT GTATTTCTAA

41881   CGGTGCTTTT GTATGAGGAT CACGAATTAT TCTTGAAAAA CCATCCCCAG TTAAAATTGC

41941   GTTAACTGTC ATTAGGAAAC GCCAATGATA AGCAGATAAC ATATCGTTTG GGTGCTTATT

42001   CAGCAAATAA TCAACACTTT TGATATTCTT TACTGCATTT TTACCATCAT CCAAAATGAC

42061   AATCGGAAAT CGAGCTACAT TACTAGCAAC ATGAGAGACT GCAGTCAGCA CATCAGAGTT

42121   TCTAAGAGCA CCGATTCCAC TATAAGATGG CATATTGCTA AACCCCGGAA GAATCCCCTG

42181   GTCAATATAA TCTTGTGCCC ATTCGCGTTT CTCGGTATGA AATAACACTC AGCTTCACCC

42241   CCTTTCATAA GAGATAAAAG CCATTACGAA TAATTCAATT GAAATAATTA GTAAGCCAAT

42301   CTTCGTGGAA AATAAAAAGC CTGTAACTGC TAAACAGATA CAAGCTAATA TGAACAGCAA

42361   AACCGGTTCG TTTAGTTTCC AGAATTTCAT GGCATCACCC GGAGAAGAAA TTTCAAGTCT

42421   TCATCCGTAA TCTCAAATTT CTCAATATAC GGGGCAAGCT TTCTCAGTCG TTCCAATCGT

42481   CCCTTGATTT CATTAAGTGC GGGAGTTACA TCAATCTTCA TTCCTTCTTC ACCGTCGTAT

42541   AGATACTTAG CCATGTCTAT TCCTCCTCGA TTCCTTTGAT AAATTCAATT GCTTCCTTAG

42601   TTAAGGCCAA TGGATGGAAA TATTCTCCAT CTGAACAGTC ATTGATGATC TTCCCTTTTA

42661   ATAGGTGCTC CACATCATTT TTAGTGATAA AGGTGGTCCA GTTGCTATCG TTGCCATATT

42721   CATCTAGTTG CTTAATATCA TGGCTAAATT TATCTTTTTC AGAAACCAAA GTCATCATTA

42781   AACACATCCT CATCTGTTAA ATAATCATCA ATATTTTCAC GGAAACAAAT TGCATATGCG

42841   TCTAGCAATG CATCGGCAGC ATCAATCTTA TTTGAATAAC GGTTCTTATC AATCCGGACA
```

-continued

```
42901   CCATTGTTAT CTGATTTAAG GATCGCGTTA GCCATTGCGC CAGTTAAAAT TTCATTGTCA

42961   GAATGTCGAA CTCGCTTATC TAAAATATCA TCCCTAAATT GCTTGGTTGG CATTGAAAGA

43021   GTTAGTGTTC CTTGACGAAC AGATATCTGT TGCCATTCCG GATGACCTTT TTCAATCTGA

43081   GTTAACAAGG TTCCATATTG TGCGGGGTCA TAACAAATTG CCTGAACATC AAGATTGTGT

43141   TCTCTGACAA AGCCATCCAG CCATTCATAT ACCCGTTCAA CATCAATAAC TCCAGATTCA

43201   AGCTTCGTAA TTTCACACTG GCCCATCCCT TGCAACCGGA CATAATCTAA CCGGTCTGCT

43261   TTAATCTTTG CTTCCAAACC ATATTTAGTA CCGACAAACG CATAAGAATC CGCATACCAA

43321   TACCCCTCTT GAGGAATTAA CCAACTAATT GCATAAAGGT CAGATGATTT ACCAACGTCA

43381   ATCCCAAACC AAACTCGTTG ACCATCAATG TCAATTGGAT CAATTTGAGC TGCATTCCAA

43441   GTATCAATAT CCATATAACT ATCCTCTTCG GCTTGTCGCC ACATATTAAA GTTCTTAACT

43501   AGAACAGAAT TCTTTGTCCC TTTCTGTTTA GCTTCTTTCC ACCGCTTTGC CAAATATCCA

43561   TATACCTGGT CTTGCAAAGC CGGGACACTC AGAATTGGAT TGGATTTAAT CCAGGTACTT

43621   TTATCATCAA CTTCTGATAC ATTATCTTGT TCAGCAATGT AGGCAAAATA AGTATCATCA

43681   GTAATTTCAC CTTTCAAAAC CTTCGTTGCA TAGGGATATT CAATTGTATG CATTGGAACA

43741   TTCAAATCAA AGCCGGCTGT TGAAATAATC ATGATAAGTG AGTTATGAAG TAAGGCCTGA

43801   CCGGATTCTA GTAATTCCAT CATTTCAGTG GTCTTACTTG CAGCATACTC GTCTAGGATT

43861   CCAACATGAG GTTCAAAACC ATCAACCGTT CCCGTTTCCT TGGAAAGAGA CCGAACATAA

43921   GAATAATCAT CAAGGTTACT AATTAAATCA CGATTAACTT TTGTCCCACG TTTTGTATCA

43981   CCATCACTGG AACGTAGAGC ATTGAGGCGT TTCTTAATCA TATTAAAAAC GATGTTCGCT

44041   TGCTTTTTAT CGTTAGCGGT ACAAAATATT TGCCGGGAGA ATTCAGGTGA GTTACCCATC

44101   AAGAACTCAT ACAATGCAAT TCCGGAAATA AGGATCGACT TACCATTTTT TCGTGCCATT

44161   GATAACATTC CTTTTCGGAA GCGCCGTTCA GATGGCTTGT CTTTTTTCCA CCAGCCATAC

44221   ATATTAGCAA TAATGAAACG CTGAAAATCT GCTAAAGGAT ACGCCCGCAT CGTTTTTGGA

44281   TCCGGAAGTA TTTCCATGAA TTGAATAACC TTATTAGCAC GTTCATTATC ATAAAAATAT

44341   TCAAAGTCAT CGTTATCCGC CTTTTTAAGA TCATTTAAGT ACCTTTTTGC AGCTAAAATC

44401   ACCTTTTTAC CAGCAACTAT TTTGCCGGCC ACGACCTTTT CAGCATAATC TTTAGCGTAA

44461   TTCATCATGA AATCCTAAAC TTATCACGCA AGGATTGATG CTCTTCCTTG TCAGTTTGTG

44521   GCATGTTCAT CTGCAGCCGC GAATTAACAT TAAGCCCAAG ATCAGATGCA AGACCCTTTA

44581   TTGCCCTGGT TGCTTTATCA ATTGTCTTAA TTGCGTTATT GATTTTAGCA ATGTTCTTTC

44641   TTTTCTTGGA CTGTTCCTTA TTTAATTGAA CGGAAGCATC TTTATAAATG CTGTACCAGG

44701   TACAATACAA TTCCAATTCG CTCCGGTCCA AGTTACGCAA TGGCAGCTTT CCGATAGAAC

44761   CAATAATTCG CCGATATTCC GCTTTGGCCA CCTTATCTAA ATGTGCCGGC GGAGTCTTTT

44821   GCAACTCAGG TAAACCATCG GCAGCCATAA ATTCTGCCTT ATATTTTGCT TCTTGTTCAA

44881   CCACTCTAAG GTGGCCTGTT GACTGCGATA ATAATTTTTG CTTTCTTGCC AA.
```

Bacteriophage loci 3 has a sequence of:

(SEQ ID NO: 12)
```
  1   CTATACAAGC GCCCGCAATT GTTGAATCAT GCTTAACACT TGGTAAGGGG TATTTGACAT

61   GTCAATACCT CTATTTTGAT ACCAAAATTG CGCCAACATC TGAACAGCGA ACGTATATTG

121   TTCATACTGG GTTAAGTCTG CTGTGGGGTT TACAGCGTTT TGTACATAAG CCTTAGCGTT

181   CTTTAGATAA TCCTTGATTA ATTGGTCTTC TTCTTCACCG TCAAGATATA AGGCTTGCTT
```

-continued

```
 241  AAAGTTGTCT ACTTCCCACT GCTCTACATC AAATTTCATT AATTTCACCT TCTTTTAGAA

301  CACATCTAGG TCTAACTTTT TAGCAACATC TACTATAAAT TGATCACGTA ACTTGTACGC

361  TTTTGTAGTG CTACACCATA TATCGCCAGT TGCTACTAGG TTCTTTATCG TCTTATGATT

421  AGGGTTAAAA TAGCATTCTT TAATTATCTT CTGGGTACAG TCCCCAGCGT CTTGTAATGC

481  TAAGTCAATA GCTTCTTTCT CACGTTTTAA GCGGTGCATA TATCTATCTT GGTCAATGGT

541  TATTAACATA TCATCGTAAT AAGTCCATGG TCGATTGATA GCACGTCCAC CACCTACATT

601  TTCATCTCTT TTGCGGATAG GGTGCATTAG TTCAAACTTA CGGCTTTTTA GTTTCTTATT

661  AATTGAAGGA TAATCTTTCA GTATTACTAT TACTAGACTT TTTACTTCTT TTCGCATTAA

721  TACACCTCAT AAAAAAGAG TGGGCGATAT TGCCCACCCT GTGCTAGTAG CTATTATTTA

781  CTTTCGGTCG CCTTAGTTGT GGTTAAAGAG AGATTAAAAG CAGCGTCATT ACTAATTGGT

841  TGGTAGTCAT TACGGACGAT AACAGATAAA CCTTGACTGT AACTGTCGAA CTTGTCCCAT

901  TGGGCTGTAA CTTGATTACG CCGGAATACT GCTACCGCTT CTGAAATATC ACCTAAAATC

961  ATTGGATGTG AACCGTCTGT GTTATCTGGT AAGAACTTAT TACTAATCTT AACAACGGGT

1021  TGGCCAAGTA AAGAAAATCC ACTAGGAGCG GTTACATCTG GTTGTAATAA GTAACGTCCT

1081  TCATTGTCTT TCAAAGTATC TAATACTTGG AAAGCTGATT GATTTACTAA CCATGTAGAA

1141  GTACTTTGTA AGGCTGGGTC AAGGTCAACG TTGAATACTT GCTTCAAGTC GTCAACATTA

1201  GCTACGGTTT TCTTAGTAAA GTTATCGCCT TGTAATACCT TGATAATTTC AGCGTTATCA

1261  GTGTTATCAA CTAACTTTTG AAGTTGGTTC TTTACTTCAG ATACAATATC AACTTCTGAA

1321  TCGTCAACAA CTTCATTTGA TAGTGCAATC TTACCGGCAC GGGTCTTTAC ATCAAACTTC

1381  ACATCTTCAA ACATATTAGC GTCTACATCA GCAATTTCTG CTTGTTCTTC CTTAGTAGTA

1441  AGTACCGCTG TGTTGTAACG GGTAGCGATT GGATAATGAC CGGAACCAGT CCCTACAGTC

1501  TTTACAGTAG CGTACTTTGC TAAGTTATAA GCACTGTTCT TTAAGTCTAG GACTGGAGTA

1561  ACAACTTCTT CTGGAATAAC GGCTTCTGCC CCCTTAGTTG TTAATCCGTC ACGGGTTTCA

1621  CCACGTGAAC GAATGAAGCT TTCAAAGGCG TTAGCTGGTT GTTCTGTATT GTTTTTGGGG

1681  TCTAAGATTG TGTGTTGCAT TTTATTATGT TCCTCACTTT CGATAAATTG GTTGTAACTA

1741  CGAATGCTTG TTTTATCTAC ATCAACATTT GTCTGATCAT ATGAAGGCAC TGTAACGGTT

1801  GAAACCTCAA ATAAATCTTT AATCTGATTA ACGGTGCGTG TAATTTGTCC GTTGTCGTCA

1861  CGTGTCCAAC TGTCAGAACC ATCATCAACA TCAAAACGGA AAGACATAGA ATTAATGTTC

1921  CCATTCTTAA CATTATTAAG AGTGTCACTT GCGTAACTTA CACTTGGGTC AATAGTTGCC

1981  TTGAAGTGAA GCCCCTTATC GTCCACATCA AGTTGTAATG AACCAGCCTT AACGCTTGCT

2041  AGTGGCTTAG TGTAGTCGTG TTGATCAAGC ATAACTACAT TGGATAGGTC TACGTTATCA

2101  AGGGCGCTAG GGTCAATCAC TTCAACAAAA CCGCCTAAGT CCTTGCTGGG TTGATTAAAG

2161  AGTAACGCAT AGCCTTCAAC TGTATTAGGC TGTGAGGCTT GCGTTTCATC TTGGTTATCT

2221  TGCTGGTCTT TTGTTGGGTC TTCTTTAGGG CTTACCGTTT GTAAACCTGC GTTAGTTGTT

2281  AGTCGTTTCT CCATTGGCTG TAACTCCTCC TTCTTTTTCA ATAAAATTAT CTCCATTAGT

2341  TACCGGCACT AAATTAAGTA AGGCTCGGGC TTCATTGCGT GTGTAGATAC CGTTAACATA

2401  ACCATCAACT GCCATCTGCT GTTGAGCGGA CGGGTCAAGG CTTAATAGCT TGCTATTATC

2461  AAAGCTAAAA TCTTGCCCTA GCTTGTAGTT CAATTCAGAA GTAAAGCAAT CTTCATAGTG

2521  CTGTAAAGTA CCTTGTAAAT ACTGAACGTT ACTTTGTTGT TGGTTGCTAT GCTCGTTTTC

2581  TACACCTAAA CGCTCGGGTG GTAGTCCGAA CGCTTTCGCA ATTTGACGGG TATTCCAGTC
```

```
                                    -continued
2641   ATTAGAATTT ACTAGCTTTA ACACGTCTGT ATTAAGTGGT AGGCTTTTAA CGTCCATACC

2701   ATCATCAGTA ACAATTGTGT TAAGTGAATT ATTGCCGGTA GTTGCCTCAT CAAATTGTTT

2761   TCTAATGTTC TCTTTACCAT CCGAACTAAG ATCAGCTTGG TGGACTTGGA CAACTGTTGT

2821   GCCATGAATT CCATTATTAA AGAATCCAGT CATTAACCTG TTTCCAGCCG CCTGTATCTT

2881   CATTTCATCT TTTAGCGCAT ACAGTGGCGA TAGTCCGACT AAACCATCAC GGGTAAAATA

2941   CTTAAAATGT AAGATGTTAG AAGAGGCAAT TACTCGCTTA ATACGTCCAT CTGGGCTGTA

3001   TGTGTAAGTC AGCTTTTGCG TTACATCATC TTGCTGGACA GTTAATTTAT TGTTAGGAAT

3061   AAAATTTAGC GTGTGTGAAC TTAAATCAAT TTCGGCAAAC GCATTACCAT TTAATAGCAT

3121   TTCAACCGCT AGGGCGTACT TGAAACTTCT GCCGTCCATT AACTCGTTAG GATGATCATT

3181   AATCATCTTG TTATATAGGC TAGAACTAGA CTTAATCGGA TTACTGGCAA GATCACCAGC

3241   GATAGAACTA ATTGCAGCAA ATATATCACT ATTACGTAAA GCCGAAGCAC TAACGTAACT

3301   ATTAGGGTCA TTACTAGAAA GACTTACTAG AGCGTCTAGA AAGGGGTCTT GTGCGCTTGT

3361   AGTCGTTGTT CTCTTACTAA ATAGGCCCAT TATCTACCCT CCTTTACTTG TGATTATCAG

3421   AATAGTTAAT CATGAAAGCT AGAACAATCA TTTCAATACC AAGAAAGCCA ATCCCAAACA

3481   ACCAACCGGT TAATCCTATA GCACTGATCT CCATTAGAAC GCCTCCGGTG ATCAACAAAA

3541   CCGGTTTAAT ATAGCTAGAA AAGATTTTTA GCAGTTTCAT AGTATTCATT TGTACGTTCT

3601   TGCTCCTTTC TCTTAGTGAA GTAATCATAA CCAGCCGCCC AAGCATCCAT AAGAGCAGCA

3661   AGGCAATCTA TTTTATTTTG CTTTCTAGTC TTGTCTAATA ACGCTTGACC ATTAAAGTTA

3721   TATTTCAATA TTGCATTTCC TACGTTGTAA GCTAACATCT GATTGTTAGT GTGAAGAATG

3781   TTACCAGCAA TTAATTCTTC CTTAAAAGTC CCAATTGGTA CCGATAAATT CTTATAGGAT

3841   TGTGTTAATT GAAGTTGTGG TAGTCCTGCC CGTTCAAAAC GATTAACAAG ATCAGCCCAT

3901   TTATAAGGGT CAAATACTAA GAATTTAACA TTTAGATTAT ACTTACCGAT TAGGTCCATC

3961   ACGAAATCAT ATACGGAATC ATAATCAATC AAGCCACTTT CTAATGAACT GATTGAACAT

4021   TCTCCACGTT TAGCAGCCAT TTCATAATCA ATTCCATCAC GTTTTGATTT AGTAACAATT

4081   CCACCATAAC GAGATACAAA GGCGTGGGAA TCAGCGTAAA ACTTTCCATC TTCTAACGGA

4141   ACTAACCAAC TAATCGCCGT TAAATCTCGG CTTTTTGATA GATCAGCACC AATATAAACA

4201   TCTCTATTAC TAATATCTGG AGCTTTTTCA ATCAATCCAT GTTCCCAATC TTGCGTACTA

4261   ATATATGAAT TTTCATTCTG CTGTACAAAC ATATTCATAT TCTTTACAAG TACGTTATTA

4321   ATATTATTTT GTTTTGTGGC TACATCTAAA TCATTTTGAA TGTGTTCCCT CATTGTCTTA

4381   GCAATCTTAG GATTACTCAT CAAAGGATTA GCTTTAATCC ACATTGTGGG GTCGAATATT

4441   TCTTCTTTTT TATCAAGACA ATACATAACC GCAAAGTAAC GATCATTCTT AATTTTGCCG

4501   TTGAGTATAT CGGCTGCATA GTCCCATTCA TTTTTGAAGG GTGAATTAAG ATTAAAACCA

4561   GCAGTAGAAA TAATCGCTAG AATACCATTG TCTTGTTGAG CCATACCTGA ATTCAAGGCG

4621   TTTAGAATAG TGTTATCTTT AGCTTGGTGA TATTCATCGA CTACGCCCAG TGTCGGGTTA

4681   TAACCGTCCG TACTGTGGGT ATCAGTAGAT AGTGGAATTG CGAAGCTACC TGTCTTTTTG

4741   TCAGTCACCC GTTGTTTATT GATTTTCACT CGTTGCCTTA AATACTTTGA ATTACGCCGT

4801   AAGTTTTCTA GTTGGTCACT CATAATATCA AACGCAAGGT GTGCCTGCTG GGAACTGTTA

4861   GCAGTAAATA GTATTTGTCG ATTACGGGCT GGTTGCTTTT CCATAAGAAG AGACACAACG

4921   CCAATCGCTG CCAGTAAGAA GCTCTTTCCA TTTTTACGGG CTTCACTTAA TAGAATCCGA

4981   TTGAAGCGCA ATGAATTATC GTCTACCTGT CGCCAACCAT AGATATTAGA TAAGATAAAC

5041   ACTTCAAATG GCTCTAGCTT CAATGGTTCA CCGTTTGTTT GTGGTAAGCT CTCAACAAAT
```

-continued

```
5101  TTAATAACCT TACCAGCATA CGTTTCAGAA TAATAATAAG GAAAGTCATC GGTCTTTTGC

5161  TTTTTCATGT CGTCTAAGAA GCGCTGGCAA GCATGAATAA CTAACTTACC GGCGATTAAC

5221  TCACCTTTAA CAACTGAATT AGCATACTGA ATAGCTCTAT CCATTATGAC AACATCTCTT

5281  CAAACTCATC AGTAGGAGCT TCTTCACTCA TTGCCTTGTG GACTTCTAGG CGTACCCGTG

5341  ATTGTGGGCT AAGTGCCATT TGACTATCAA TTGACTTCAT TTCTTTAATA GCCTTATCAC

5401  GTGCCATGTA GTAAGGTGAC TGCTGTAATC CTCGTTTTGT ATCAATAACT ACCCCAGTAC

5461  GATCAATCTC TTTAGTACAT TTGATAATTG TTGAATACAA AGTACAGTGA GTAGCGATTA

5521  AACTAACATC TAGTTCGCTA ATAGGGGCAC TCTTCTTTAA GAGTGGGACA ATTCTACGCC

5581  ATTCCTTTTT TGCTACATCA TCAAGCCATT TAGGGGCGTG AGATGTTAAG TTTGGGTATT

5641  CTGCCAATGC TTTTTCAGCG TCTTCACGTT GTGCTTTTTC TGCCTTAGTA ATATGACCTT

5701  CTGGACGGGT CTTCATTGGT TGAGCCAACT ATTTAACCTC CTTCTATTTA TTTGGTGACA

5761  CCATGTCACT ATTTGTTTAA AAAAATAAAA AAAACATCAT TTCATATTCA ATTATCGTAT

5821  TATTTAACCC TTATTATACC ATATTTGAAT AGTTTGTTAA GTTCAATGCC TAAAAGTTAT

5881  AATAAAAAAT CCTTGACATT TGAGGCTCTA AATTATTTAA TAAAGTTGAA AAGAAAACCA

5941  TACAAAATAA AAAGAAACGT CTTGAAATCT TCGGATTTTA AGGCGTTTTT TTGTAAAGGG

6001  AGAATTTTTT TAAAAGAAAC CCCCACCATT ACGGCTCCTA CCGGTCTATA CCAATAGCGG

6061  GGGTATTAAA ATTATTTCAG CTATTCATAT TTATTTTCCT TTCTCGTTGA TGATCTTTTC

6121  TTGTCTTTTC TCGGTGACAA CGATAGCAAA GTGATTGTAG ATTAGTTGAA TCCAATCTTT

6181  TACTCCAATC TTCACGTATA GGTACAATGT GGTCAACTAA ATCAGCTTTT TTTACTATTC

6241  CCTTTCGTAA ACACATAACA CAAACTGGGC TTTTCTGGAG CGTTTGACGG CTTAATTTAA

6301  CCCACTTACT CGTTTTGTAG AATCTATTAT AGTCATGAGG AGCTTTGGCG CTTCTTTCCA

6361  TTCGCTTTTT GTATACTTTT CTATTGTATT CATGTTTCTG TTCTTTGGTC ATCTTTTTAT

6421  AGTTATCTCG TTGCCAATGT TTACGCTTGT CTTCATATTC TTTTTGTAGA TATTGATGTT

6481  TTTTACAAAA ATATTGACCT ACTGGAATCA CCTCTCGACA ACCAGCAGCA CTACAAAACC

6541  TTACTACACT CATTTGATAA CCTCCTATGA AAAAAGGGCA TCGCATAACA CGACACCCTT

6601  AGCACTTACT TATTAATTAA TTCCATTGCC TTACTATATG CTTCAAGCCT GCTTATGTGC

6661  CAGCTTTTAA CATCGTTAAC CGTTCTCTTA ATGCAAGCTT CAAGCTCCAT TGTATCGGCG

6721  CTGTAAGGGT CACACTCGCT TAGTCTATAC CTTGCCATCA TCACCCAGTC TTGGCGACTT

6781  TCCTCTGCGT CCTTGCATAC TGCCACTTGT GCAATACACT TTACTAGCTC TTGGTTGTCT

6841  GGTAGTCCTA GATCAATCGC TAATGGTAAT GGACTGCCAT TTACTGAGAC TAATTTTAAA

6901  CTATAAAGCG TAGTATACAT ATGATAATTA GAAGGATCAT CACCGCTTGC CTCAATCATT

6961  ACATTAATAA AGTTGTTATA CTCTGGGTGC GTGTTGACTG TTAATTTACT CATCCCCATT

7021  TCACCTCTTA TTTATGACTA TCAAGCTTGC GTAAGGTTAC AATATCATAC GCCAATAACT

7081  CATCATCAAT TGACCAACCA GCAACTTTAT AGATACTGCC ATTGTATTGT GCTTCTGGAT

7141  ATTTCTTCAT GTCCGTTAAA TCTTTCTTGT GACGAACTAC CAATATAACA TCATCAGTAA

7201  TTGAACTACC TGCCTCACTA ATAGCTTGAC TAGCACTGAT TGAATAGTTA CCACAATGTA

7261  CTGTCACATC TCCTACAAAA CCTGTCATGA TCATACCAGT ATTCGGGTTA CGTTTCCCCG

7321  TACCACCTTC ATGACCGAAT GTGACCTTAT GCTTTAATCG TGTAATTGCG TATTTATTAC

7381  TTCGCATTTA ATTATTCCTT TCTGCCTGTA CTTGCAGATA CAAGCAATAG TAGAACGTTT

7441  GCAGCCGTTC TAGTGAAATC TACTGTTACT TTATTTTTAA CTCCTTAATA GGCTTTTCAC
```

-continued

```
7501  CTATCCGGTG GTATGTGGTC ACTGCCTCAA AATAAAAGTA CGGTAAAAGC AGTTTTAATT

7561  GTTAATTTTC ATCTCTTCAA TTGAAAATAG TTTTTACTTT TATCGGTTAC CCCGTTTCAA

7621  GTACCCACAA TCGCCTTTAT ATCAACATTT ATATGGTAAC CGATAGGATA TAAAGGTAAC

7681  CGATACATTG CAGTTACTTA ATATAGTAAC CCGAAACTAT CGGTTACCTC AAAATGCTTT

7741  CGGTTACCTT TAAATAGCTT TATATCAAGC TTTATAAGAA CTTCTGCAAA GGTAACCGAT

7801  AAATATAAAA CTATAACTAA TTTTTAAGAG CAATTCCTTT ATAACCTTTA ACATTTTTAC

7861  CGTTAATCTT AACTGTAGTG TGTTTGTATC CTCGTGCTAT TAGCTCTTTC GCAAACTTAC

7921  GATTACTAAG ACAAGGAACA GCAGTATTTT TACAATACTC TTTGTAATTA TCATATAGAT

7981  ATACTGATTT TTCTTTATCT TTCTCATTTG TAGTACAGCA ATCATTAATC CAATTACCGA

8041  TATTGTCATT AGCATTTACC CAGCTTCGCT TTTGCTGTTC CATGTATTCA GTCACTGGAA

8101  ACTTACCAGA ATCAAGTGCT TTTTTATAAG ATTTTAAGCA TTCATAGGCA AATGCTGGCA

8161  TTTCTCTTTT AAAGTCTTGC TCTTTGAATT GCTCTTTAAA ATGTTTAATC TTATGGAACG

8221  TTACAATAAT TGGTCGTCTT TTAAATCCGT CTGTAAAATC ATTGAAGGCT GGTAAATCAT

8281  TAGCGCTAAA AATCAATTTA GCTTCATTTT CAAGTTTAAA TGGATCTTTA TATTTAAATT

8341  GAGCTGTTGT AGTGTCGTCA CCAGTTAATG TTTTAATAAT ATTAGTCTGT TCCATAAATT

8401  TGGGGCTTAT ATCAGCAAAA ACATTAGCAG CTTTATGATA CAGCTGAGAA GTAGCAAATT

8461  TAGCTTCTTT TTGGTCGGAT AATGCTTCTA AAGAAACGTT TGAAACGTTA GGCTTCCCTA

8521  TTAACTCCAT TAGTTTATTT AGAAATGTAG ATTTACCATC CCCACCCAAC CCGTATAGAA

8581  TCATATAAAT TTGAAAGTCC TTAAAACTAC CTGCTAAAGC AAAACCAATA AAGGCTTTTA

8641  CTGTTTCAAT TGCTGTTAGG TCATATTCAT CTTGTAGTTT TCCAGTATCA TCACGGATTT

8701  CTTTAGTTGA GGGTACTAAT GATTGTTTTA ACCATTTATT CCACGTTGTA GCTTTTCCTT

8761  TTGTTTCTAA TTCATATGGT CTATTTTGTA AAAGATAGTT CTCTGGTGAA TTATCTTCTA

8821  AAGTGTCCGT CATCAAGTTG TAAGTGTGTT TACCAAACAC TGCTTTATAA GGTGCTGGTT

8881  GATCAAATGG ATTGTCTTCT ACAATTTCTT GTGAATCTAA GGCAATTAAT TTAGAAACCG

8941  ATGCTAATAA GTTCGTTCTC CATATTCCAT GAGGTACAAT TTCATTTTTG ATTGATTTTT

9001  CAATGACTGA ATCAGCGTAA TTTTTCCATT GTCTACTTTT AGGATCGAAC CAATAGCCGT

9061  GTTCTATAAA TTGGTTGGAT GTAAAGTGAT ACTTTTTTTC TAAATATTTA GCCAACTTAA

9121  TTTCATCAAC CAGTTTATTT CCTTTATCAC TTACAGTTAA CCATTCTGGA AAACTATTGT

9181  TATTTACTAA GTCATCAATA TTAGCCATAT TTTTCCTCTC TTTACATGGT AATTTAGCGT

9241  TTGTATTTAA GACTGATAAT CTCTACTTCG CCTTTTGTTT TGATATATTC AAAGCTTTTC

9301  CCGTCTAAAC TTGTTTCTTC GTATATATTG TCCCAATCGA CTATTGATTG ATCTTCGTTT

9361  TGACTAGCAT TATTCCAATA CTTAAAGAGT GGTGTACGGT GCAGTATTCG GTTAACTTGT

9421  TTAACGTCAT CCCCTGTGTA GTAGAGAAGA TAAAAACACA TTGCACCAAT AGCAGGTTTA

9481  ACGCTATGAT ATTTATTTAG GTAGTAGGAA ATTATTTCCT CATTATTTTT ATAAAGAGCA

9541  ATAAATTTTC TACTACTTTT ACTACTAACA GCTCGTTCTA TAACCTTGTA ATCATCGTTA

9601  TAGTATTCAA GTGCTTTCTG AAACTGTTTC TTTGCGTACT CATTAAGGGG ATGTGACGTT

9661  GAATTAATAA TTTTTTCCAT CTTGTCACTA TCTAATAAAG GATTAACGGA TAGTTTTTCT

9721  TCAAAACTTA ACACTATTAA TCACGTCCCA CCTATTGCAA TTGATCATGA ATTTGATCTA

9781  ACTTATCCAA CAAAATACTA GATAGTGCTA ACAATGCTTT CTTACGTGAT ACTACTGTTT

9841  GAGCAACCGT AGACACTTGT TCATCACTCA TTGCTGCATA ATTGTCTACT CGTACAATTG

9901  GAGCAAAAAC ATCATTTAAC TGATCATACA GTGCTTGGGC TATTCCGGTT GTTTCTTCAA
```

-continued

```
 9961 CATTGGAATC TGCTTCCCAC AACTGATTTT CAAACGCTAG TTCTTGGTTC TTATCTTTTT

10021 CCATTGTTTA AACCCTCCAC TCATGTTAGA ATGAAAGAGA ATTAAATATT AGTAATTCGT

10081 CCAACATCCC CCGTAAAGAT TGTTGGCTTT TTTATTAGCT AAATTTAATT CTCTAAGTTT

10141 TATTTAGTCG TTGTTAGTGT CTGAATTGGC GTTCTCACTA TCAACGGCTT TTTTATTACC

10201 ATCCATAAAG TCGTTTTCAA AATCAGTTAA AGTTTTATAT TGAATTGCTA AATCTTTAAT

10261 TTCTTTAGCG ACCTTAATAA TTTCATCTGC TGAGGAAATC GGATCATCTG CAATTATTTC

10321 TCCATTTTCT TTAGTGATAG TACCTTCAAA ACAATCTTCA GTAATTGAAT TTATATAACT

10381 GCCAGCTTTA ACAATCCTGT CTTCTATATC AATAATTCTT TTACTTAATA TTTCTTATTC

10441 AAATTTTTTA GTGTATAAAC TCATTTCTTA TTACTCCTTA AAATAAGTTA CTAATTGCAA

10501 CAACAATACC CAGCAATGGT AAAAACGTTG CTAGATAAGC CCAAAGGCGT TGGTCTGGTG

10561 AAGTCCACCA GTAAGCTAAA ATCTTACCAT CAATTTTTTG TAACATATGT CTCACCTCCT

10621 CCTATTTATT TCTCTACAAT CACTTGCCAG CCAGCTGTGC GATTATTACT TAGAATTTTC

10681 TTTTACCCAA CGGTCAACAT CTTCACGTTT ATATACATAT TTTCCTCCAA CCTTTGATGA

10741 TGGAAAATTT CGGGTCTTAA TCCAACGATC AATAGTTGTT CGAGAAACAC TTAGATAATC

10801 CGCAGTTTGG CCCTTATTCA TAAACTCTGG TTCGGTTTTA ACAGTCTTAG CATCTTGTAA

10861 CTTATTGTTC TCTAGCTTTT TAGCCACAGC TTCAGCTAAC TGATCAATGA ACTGATCTAA

10921 AATAGCTGTA CTCATTATTA TCACCTCTTT ATTTCATATC GTAATTACAA TATATAACAT

10981 AATGAAATAT TATGCAACAA CAAAATAAAA TATATTGTGT TTTGTATTGT TATTTTCGGT

11041 TATGTATAAT ATATTAACTA TACAAGGAGG AATTAATGTG AAAGAAATTT CATCTGACCA

11101 GAAAATAGGT TCTAACATTG CACTAATTCG TAAAGCTAAA AAGATGACTC AAAAAGACTT

11161 AGCAAGAAAA ATTGGAATAT CACAACCAGC CTTGGGGAAT TATGAACGTG GCCAGCGGAT

11221 TATACCTGCT TCGATTTTTC ACAGTTTACC TCAAATATTA GATGTTCCTC TAGATTTTCT

11281 AGTCTATGGA ATTCCCAACA ATATTACCTT TCATGATTTA GCAACGCTCG ATTCCGTATC

11341 TCTCAAAAAG AAAGCTGCTC ATATTGAAAA TGATAGAAGT ATTATTGAAC GTGGGTTAGG

11401 GCGTGACGAC ATAAAAAGAC ATTTATTAGC TGCTGTTTTG CTTGATAATT ATGGTTATCT

11461 TGTGTACCCA GATGAATCTA GCAATGACAA AGAACATGAA CAACTTAAAA AATTTGTTTG

11521 GAATACATTA GATGGATTAC TTACCGGCGT ACCAATTACC AATGAAATAA ATTTTAAACA

11581 AATTAATGAA CAATTTGAAT TACTTGCAAA TACGTATTTA AGCCTAATTA TTGACGAAGA

11641 GGCAAATCGC TATCCTGCTT TCCGCAAGGA TTTACCACCC TTCAAAGAAA AACTTACACA

11701 GTTTTTAAAT GATAACGGAT ATTTTAAAAT TTTAAAAAAA TAATTTTAAA CCTTTCTCTA

11761 CAATCTCTTG CCAGCCAGCT GTGCGATTGT AGGAGGAAAG TAAAAATGTC AGTATACAAG

11821 GATAAAGAA ATGGTACGTG GTATGTTAAA TACCGCATTA ATGGTAAATC AACCAGTAAG

11881 CGAGGTTTCA AATTAAAATC GGACGCTGTA GCGTGGGAAC AAGAAAAAGC TGTGGAGCTT

11941 AAAAAATATG GTCAAATGAA TAACCATAAC ATGACCGTTG AAGAGCTATC AAAAAAATGG

12001 TTGCCAGTAT ATGAACAGAC TGGGATAGAA AATTCTACTA TTCATAAAAC AAAACAAATC

12061 ATTAAAAATC ATATTCTACC CCGCATTGGA AACTATAAAG TTGCTGATCT TAGCATTGAG

12121 TTATTAACTG AAGTTGCTGC TAAATGGAAA GAAGAATTAG TAAAGAGTGA CCCTTTTAAC

12181 TATACTAAGC GAATGTTAGA CTACGCAGTA CAATTAAGAG CGATCCCAAC TAATCCAATG

12241 AATTCTGTAG TAAAGCCTCG TAAAAAACAT GACAAAACAT TTACTAACAA TAATTTCTTT

12301 AATGAAAAGC AACTTCACAA TTTTATCAAG TGTATAAAAA AAGACTACGA AGAAAAAAAT
```

-continued

```
12361  CCTCGTGCTT TCATGGTTCT ATGGTTAGCC CTTTTTACTG GCATGAGAAA ACAAGAACTT

12421  CAAGCCTTGA CGTGGCAAGA TGTTAAATTT ACAAAAAGCG GTGGAATAAT CCATATTAAC

12481  AAGGCTATTA AGAACGCAAA ACATCCCTAT CTTGGTGGCC CTAAAACCGC TAACTCTTAT

12541  CGCTGGATTT CAATAGATAA AAAAACTGCT TCCTATCTAA AAAGATGGAA ACAGCAACAG

12601  ATAGATATTT TAACTAAACT AGGTTTTAAT CCACACCAAA AAGAGCAATT GATTTTCTCT

12661  ACCTACACTA AAAATAAAAT TGTTTTAGGT GCAGAATTGG ACAAGCCGTT AAATAAAGTA

12721  ATTGTTAGAA ATAATCTAAA GAAAGTTACA TTCCATGGAT TACGTCATAC CCATGCTACA

12781  CATTTGGCTT CTATTGGTAC CCAGCCAAAA TTAATAGCAG ATAGATTAGG CGATACAATG

12841  GAAACTGTTC TTGAAGTTTA TATTAATGCA GATACTGAAC CAGAACAAGG AATCGCCGAC

12901  AAGTTCGCCG ATAGTTTAGT ATAA.
```

Bacteriophage loci 6 has a sequence of:

```
                                                            (SEQ ID NO: 13)
   1   TTAAAATTGA CTAAGTGCCT GGACGATTTT GTCATCAGTT TTACTTTTAT ATTCATCAAT

61   CAAGTAGGCG TATGTGTTCA TTGTGGTTGT GATATCATTA TGTCCAAGTC TCTTGCTAAT

121   TGCATAAATA TCTATTCCGT TACTTAACAG TAAAGCAACG TGACTATGAC GTAAACTATG

181   GAAATGAAAA TTCTTCTTTG ATAATTTTGT ATCACTCATA ATTTGTCGAA GCGTTTTATT

241   TAATGCTGTA CTAGTAGGGA TAGTATTAAA TTGATCCATA AAAACAAGGT TACTTGATGA

301   ATTATTGCGC AATTGTTTAA GTAGTAATAG TAGTTTTTCA TTAACTTTTA TTTTACGTGT

361   AGATGATTCA TTCTTGGTGG GTTTAAAGCG ATGTGTATTA AAATGTTCGT CTGTTTCGTC

421   TCTTCCTTTT ACCTCTCTCC ATGCTTTATC AATATTAATG GTATGATGAA TGAAATCAAT

481   ATCATTCCAG GTAAGAGCTT GAATTTCTTC TTTTCTCATT CCAGTATATA TCGCAGTGAC

541   TATCATATAA CGGCTTGTAT ATCTTCTATT AGTAATTCCA TTGATTGTAG TAGTTAATAA

601   TTTCCTTATT TCAGTTACAT TAGGGTATTC TACCTTCATT GTTTTGCTAG TATTGGCAGC

661   TAAAGTAACA CCTTTAGTAA AATCTTTAAG CAGATAATCA TCAAGGATAG CAGATTGTAC

721   GCAAGACCGT ATTATTGAAT TAAGCTTCTT TACACTTGCT ATAGCATGAG TTGCTCCATA

781   CTTGTTAATA AATTCTTGAT ATTTAGAACG GTTAATTTCT TTAATAGAAG CTTCTTTGAA

841   ATAATCATTA ATTAGATTAC CGATTATAAT ATAACGATTC AGAGTTACAC TTGATATTTT

901   AGGTTGCTTA TAAGTATTAA CCCATTCTTC GTAATAATCA CTAAAAGCAA TTTTTTTCTC

961   AATGTGTATT CCGCGATTAA GATTAGTTTC CATTTCAGCT GCCCACTTTT TAGCTAGTGC

1021   TTTTGTTGCA AAACCAGCTT TGGACTTTGA AAAACGTTTT CCTTCAGTAT CTTTCCACTG

1081   AATTCTTACA GACCATTTTC CGCTTCTTTT ATATATTTGA GCCATACTTG TCCCTCCATT

1141   ATTAAATTGT GTATAATGAA AGGGTTGATA GAATTTGTTT GGACGCAATT AATATCAACC

1201   CTTGGTCCAC TGACAGTTGC CGCTGTCGGT GGGCTTTTTT AGTTAAATA GCTTTTTACG

1261   TCATCAATTT AGTTGGACGA GAAATTTAGC TTTTGTTTAG CTTCTTTAAT TGATTAATAA

1321   TTTCTTGATT TTGCTTAATT GTTATCCAAT TTTGCTGTTT GATTATTCTT AATTCATGAA

1381   AAAGGGCTTT TGTATCATTA CTTGTAAAAG TAGGATAGGC ACCTGTTAAT TTTTCGGCAA

1441   CTGCTATATC TTTTACAGAT TCGAGAATTT CGTCATCTAA ACTTTCTAAA CGATTTTCTT

1501   TAATATATTT ATCTTTGTCT TTAGCAAATC CATCTTTACC ATTGAAAATA CTCATTTTTA

1561   GCTTTCTCCT ATCTTTTTAA TTTTTACATT GTAAAGAGCG TTATTTAAAT CATTACAGTT

1621   CCTAAGATAG GAAAAAGCGT TTTTTAAAAG TTTATTCATC CTTTGACTCC TTATATTCCT
```

-continued

```
1681  AAAATTTGTT TCTTTTTAGC ATCAAATTCT TCTTTGTTAA TGATTCCATC ATCAAGTAGT

1741  TGTTTTAATT CTCTTAATTG CGAAAGGTCA TTACTAGAAT TGGATTGTGC TGATGTCTGC

1801  TTAAAATCTG CAGCTGCCTG TTTAATAGTC TCAGCCATCT TTTTAGCAGG GTAGGGTTGC

1861  ATATTTTCTA TTTGAGTTGT AATAGCTCCG TTGGTTACTG CAATAGATCC CAACATTAAA

1921  CCTTTAGAAT ATGAAACGCC ATTAATCATA TCAAGGGGAA TGTCAGTTGA TTTACTACCA

1981  TAAATCAGGC CGTGGTCAAG AAAAATTACG CGCTTATTAG TACAAACCGC AAGAATGGAA

2041  TTAGTTTCAA CGAAAGCATT AGCAGCATAA AGTATTTTTT CTCCACCATC GACATCTATT

2101  ATGTCTGGCA AGGCTTTGAT TTCCTTTTTA GTACCGAATA GATTTTCTAC ATTGGCATCC

2161  TTTAACTGTT GCTTAATAAC ATCCAATTTT TCTTGTTCGC CTTTGTTGAT TTCGTCAATT

2221  GCTGCTTGTA AAGTATCAGC TTTTTTACCA GCGCTATCAG CAATTGAATC AAGTTTCTCA

2281  GTTACTTTAG ATAGCTTTGA TTTATACAAA TCAGGATGTT CTTTGTAAGG TACGGTAGAA

2341  TGAATCCCTA ATAAACTTTC AATTTCACTA GCGGTATGGG AACTAATGAA ATTGCTAAGT

2401  TTAATTGGAA CACGGTAAGT ATTTGCTGGA CGTTTGGGAT CAAGTCTGTT GGCATCTTTG

2461  CCACAAATTA AATATCCATC TTTGGTAATG CAAGAAGCCT TTAACATTCC CAGGGCATCA

2521  TTACATATGA AGCATCTCTT TTTACTCATT TGGATCACCT TATTCCATTG TCACTGAATA

2581  TTTAACTAAT TTACCAACAA TTCGACCTGG ATGCTCTTCA TCAAGAATTA TTGGATCATA

2641  GTTTTTATTA TCTGGCATTA GCATAACTAA ATTGCCTTGA TGCTTAATAC GTTTTAAAGT

2701  AGCTTCGTTA TCATCGTCAA CAAGAACTGC AGCTATCTCA CCATCTTCAA CTTCAGGTTG

2761  CTCTCTAATA ATGGCTAATG CGCCATTAGG AATGGTAGGC TCCATGCTAT CACCTTTACA

2821  ACGAAGACCA AAAAGTGTTC CACTAGGAAC TGGTTTTTCA AAGATTTCAT CAGTATAACC

2881  TTCGATATTT TCTTCAGCAG TAATCGGATC GCCACAAGCA ATTTCACCAA TGATTGGAAT

2941  TGAAACAACT TCTAATCCTT CTTTAGGATA AATAATATTA GAAGGTTTCT TTTCTCTGGT

3001  AGGGAAAAAG TCATCAACAT TTACATTAAA AATTTCAGCT AATTTAAATA AAACATCTTG

3061  ATTTGCCTTT CTAGATCCTA ACTCATATCT AGTCACAGTT GCTCTTGTCG TATCAAGTTT

3121  GTCTGCAAGT TGTTCTACTG AAAGGCCACG TTGTTCACGA AAATTTCTGA TTTTTTTGACC

3181  AATGAATTTA CTTAGTTCCA TTTTATGTAC CTCTCTTATG TAACTAATTA TATAACTTGC

3241  GTTACCGAAA TGGAATATTT TTTATCTTTT TCGAAAAAAA TAGTTGCATT TGTTCCAGAA

3301  TGGTTTTAAT ATATAATTGT TCCAAATTGG AACGGAAAGG AGAGATAATA TGCAGTCAAG

3361  ATTATATGAT TTACGAAAAC ATGTTAAAGG AATGACTCAA CAACAAATGG CTGATTATCT

3421  AAATATTAGT GTCAAAGCTT ATCGTGATAA GGAAAATGGT AAAAATCAAT TTACTCAAGA

3481  TGAAATGTTT GCTATTAGTA AATTATTTGA TCTTAATATT GACACTATTT TTTTGCCTCG

3541  TAAGTTCCAT ATTGGAACAA AGGGCTAAGA GAGGTGACAC AAAATGCAAG CATCGCTAGA

3601  TGAACAAGAT TACCAAGTAA TTACTAATGA GGTTCTCAGG CGTATTAAGG AATGTTACAA

3661  CTTAGTGCCT AAACAAGATG TCCAAACTGA CAAATGGGTC GGTATCAAGG AATTCACGAG

3721  TAAGTTGCCC GTTATAAAGG ACAAGGAATG GGTCAGAATG TTTCTCCTTA CACTTCCAGT

3781  CTTTAAGAAC TGGGTTATCA ATTTGAATGC AGGTCAAGGT CATCGAACTA AGGTAAATGT

3841  GACCAAGGCA TTGCCTTGGA TTATGTCTCA TCAAGCTGAT ATTGATTGGA ACCAGTCATT

3901  GCCACGTTAG GAGGTGAACA GATGGCACAA CCGATATTTG TAAAAGGAAT TTTTGGAAGA

3961  CGAATTATAG TTTCTCAATT TGAACAAACG TCTGATTTTA TTTTGCAAAA GAAAAACGCT

4021  GACCTAATAA AAGAAGCCAG CGGATTTTCA AAAAACAAGA AATTGTTTAC TCGTTATCAA

4081  GGTAAAGACT TTCAAATTAT GGAGCAATTA AAGTGGCAAC CCAGTGTTCT TTTTGATGAT
```

-continued

```
4141  GCCAGTAAGA ACCGTAGTAG CCACAGATTT AAGGACACCA ATGGAAACTG ACTTTAGAGT

4201  GTTAGTAGCT TTCTTTGTTT GTTTCCAAAC CTCATCATCT CGAATGGAAT CAAGTAGTTC

4261  ATGCCCAGAC CAAGTGATGT CATAGACAGT TAATTGGCGA ACCATTTTAT TAATAAATGG

4321  TTTGGCACTA ATGAAACCGC CTGAGTAGAG CTGATAAAGG GTATAAACAA TATCATTTTT

4381  ATCAAAGGTC TCATTAGCAA TAACATTTGC AATTTGAGAA TCTGTAAAAC CTTGGTAAAG

4441  CATTTGCAAT TGCTGTTTTT CTAATGATAA AAGAACATAC CTAACACAGT CTTGCTTCAA

4501  TTTCACAATT TTCACCACCT TTATTTTGAA TTAATCAAAG TATAGCAGAA AGGGAGAGCA

4561  GTTAAATGGC GTTGGTAATT GGATTACCAA TATTAATTAT TGCAATGTGT TTGTTATATG

4621  CATTGGTGTA CAGCTTATTG TATGAGCGGA ATAAACCATT GCTATTGAAA GAAAAGTATC

4681  GGAAGAAACA TTGAAAGGAG GTGATATGAA CTTTGGTAAA TTTATTTCTT TTGTTGTTTT

4741  TTATCTTTGT TATAATGCCG CTTTTGTATC AATTTTTGAA TTACATCAGA AGGCAAATTG

4801  AAAATTTCTT TTGGAAAAAA AGCCATAAAA ATAAGAACGA ATGAAATGAA AGTAGCTGTA

4861  AATTCAAATT GTTCTTTGGT CTGAGTTATT AATAGCCCAG TAATAGTAGA AAGAATAATT

4921  GCTATTTTTG AAAGATCATC CAAGTATTTT TCGCTTATTT GAAATCCTAA AGTTTCTGTA

4981  AGCCAGCCAA GGATAAACAA TGGAAAAGAA AAGAAGCCAG TTAGAAAAAG AATAGTAATT

5041  AAGCAATCAA ATATTCTGAG TTTTTGGAAT TCAAAAATTA CAGCATCTGG ATTAGCAGCA

5101  TATGTAATAT GTAGAGCTAA ATAAGTAAAA CAGATGAGGC AGAAGATACA AACCATAAAG

5161  TCGGTTAGTT TCTTACTATA GTAATTAAAT TTGGTTAAAA ACTTAAAAAT TTTACGCATA

5221  ATGATTTTCC TTTTGTACTG AGTTAATCAA AGTATAGCAA ATGAAAGGAT GGTAGTTTAA

5281  TGAGTAAATT AATTGCGCTA ATCGTTGGTG CTTGGATCAT GTATTGTTCA ATGATTGGCT

5341  CTTATGATGG AGCGATGGCG ATCCTAGCAG TTTATCTTCT GCTAGTGGTT CTTGATCCAC

5401  TAAATAAAAA AGGTACGACT GCCGCAAACA GTCGTACCGA TAAATAAATA ATCTACGAGG

5461  TAATTATATA TGAATGAGTT TAATTTATCA AAATTAAATG CCAGGGTTGG CGATAATTGT

5521  GTATTTGTAT CGAATTTGGC AGTTCGCTAT CAAAGCGCTG CTACTCCTGA AGAGCGAATG

5581  GCAATGGCCA TCAAAATGGA GAATGCTGCT ACGATGTTAC GCATTTCAGC TGAGCGTTTG

5641  GCCACTGAAA CTAAGAATGT TTACGGAGGT AAGAACAATG ACTAACGAAG AAAAGATTAA

5701  GGCAATTAAA CAAATTCTTG GACCAGAATA CGAGGAGGTA GCCATTTTCG CTGCTAAAAA

5761  ATCAGAAATT CGTGACGAAC GTACTAATTC ATTAGTTGAT GCGGATCCCG GAACGGTAGC

5821  AGCCATGATT ATGAATTGGT TACATACTAA TCCGATAGCA GCTTCAATTG TCAAAGCAAC

5881  TATTGATACT TTGGAAACTG ATCCAACTGC TGATTTATTT GCACAGATTT TTCTAGGAGG

5941  TAAGAACTAA TGAATTTATT TGAATTAAAC GACAACTACA AAACACTTGC TAGTCGGGAT

6001  GACTTAGATC CAACTATTCT AAAGGATACA TTGGAATCAA TTAAGGATGA TCGGAAGACC

6061  AAATTGGACA ATCTTGCTTC ATGGGCAGAT CATTTGAAGT CAGAAATTGA TTTTATGACC

6121  GACAAAAAGA AGTCATGGGA AGAAGAAATT ACTTACCGAA AAAATAAACT TACTTGGATC

6181  AAGAAATATA TTACTGAAGT TCTTGATGAT GCCGGTATTA AGAAAATAAC TACTGAAAAT

6241  CACTTACTTA GTGCCCGGAA CTTTAAGGCC TCAACCATTA TTGATAGTGA TAAGAAGCTT

6301  CCGGATAAGT TCAAAATTAC TGAGACGACT ACTAAGCCAG ATAAGCAGGC CATTTACCAA

6361  GCACTCAAAG CTGGAGAAGA AGTACCAGGA GCACATTTAA AAGCTAACCG TAACACGGTG

6421  ATTAAATAAT GTTTGAACTC CGTGATTATC AGCAAGAAAC GATTGATAAC ATCATGAATT

6481  CTATAAGTGC TGGTCACCGT TCTATCATGG TTCAACAGCC GCCACGAACG GGGAAGACAG
```

-continued

```
6541  TTATTATGGC CGAGATTGCT AGACGAGCAA CGGCAAAGGG TAACCGTATC TTGTTCGTGG

6601  TTCATCGGCA AGAAATTGTC CAGCAGGTTA TCAAGACTTT CAAAGCTAAT GATGTAAATA

6661  TGGATTTAGC TAAAATCGGC ATGGTTCAAA CGATTACCCG ACACGTTAAT AATTTGGACC

6721  CACCGGCGAT AATTTTTGTT GATGAGGCCC ATCATGTTCT GGCTAAATCA TATCGAAGGA

6781  TTCTTGATGC TTTTCCGAAA GCTTATAAGT TACTGTTTAC CGCTACTCCT TATCGGTTAG

6841  GTGGACAGGG TTTTACTGAT GTGGCTGATG ATTTAATTAT TGGCAAATCA GTCCCCTGGT

6901  TAATTGACCA TCACTTTTTA GCACCAGTTG ATTATTACGC TCCTTCTTAC ATTGATACTG

6961  CCAAGTTAAA AGTAAAACGA ACTGGTGAAT ATGACACTGA TTCAATCAAA AAAGCCATGA

7021  AGCCTAAAAT CTACGGGAAT GCGGTTAAGC ACTATTTGAA ACTTGCTACG GGAATGCAAG

7081  CCATTGCCTA TACCTATAAC GTTGATAGTG CAATTAAGTT AGCCAATGCA TTTAATGGCT

7141  ATGGGATAAC TGCAAGCGCC GTTTCCGGAA AAACGCCCAA AGAAGAACGG AATAAAATCA

7201  TTGAGGACTA TCGCCAAGGA AAAATTCAAA TTGTAACCAA TGCAGAATTA TTTACAGAGG

7261  GCCTAGATTT ACCAAATGTT GATTGTGTCA TTATGTTACG GCCAACTCAA TCATTATCGT

7321  TGTACTTACA ATTTGCAATG CGCTCAATGA ATCCACGGGA AGGTAAGACT GCAATAATTA

7381  TCGATCACGT GGGAAATGTT GAACGATTCG GGCTGCCGAC TGATGAGCGG CAATGGACAT

7441  TAGAAGGTAG CGGAAAAAAT AAACAACAAC CAGGAACAAC GCTTAAACCT GTATCAGTAT

7501  GTCCGATATG TTTTGCTTCG TTTTATCGTA CAAGTGATAT TTGCCCTTAT TGCGGGGCGG

7561  CATTAGGAGA AGAAAAAGAA ATTGAAGTCG TTGATGATGT TCAACTAAAA AAAGTTACTA

7621  AGTCACGGCT AGCGATTATT AAGAAAATTC AATCGTCAGC AATTATGAAT AATGTTGCTG

7681  GCAAGCGTCC AAACGAATTG AAGAATCTGA AAGAAATACA AGCCTATGCC AAATTAAAAG

7741  GTTACAAACC AGGCTGGGCT TACCACTACG CTAAACAGCG TGGATTTATT AAGAAGTGAG

7801  GTTGATATTA TGAGTATTTT GCCACCAAAT AAGCCACAGA AGGCACGGCG AGTTCCAAGA

7861  AATTACTTTA TCTACGGAGA TACAATGTCC GGAAAGTCAT ATCTAGCTGA ACGTTTTCCA

7921  AGTCCGCTAT TTCTTAACAC CGATGGTAAT AGTGAGATGA ACACCGCACC AAGTATTCAA

7981  TTAAAGAATG TCCGAAAGAG CGATGGAAGC TTGAAAGAGT CAGTGATTGA TCAACTAGAC

8041  AAGATTATTC TTGCTCTTGG TACTGAAAAT CATGGTTACA AAACAGTAGT TATTGATGTG

8101  ATTGATGATG TAGTAACACT AATTGAACAG GCCATCTGTT ATGACAATGG AGTAGAAACG

8161  CTGGGGGATG TTCCTTACGG CAAGGGATAT GCACAATTTA ATACCGTCTT TCAAGCATTT

8221  GTCACTGAGC TAAAAGCCTT ACCACTGAAT ACGGTTTACA TTAGCCGGTT AATGATGCTA

8281  ACTGATGAAT CTTCTGGCCA CACCGAAGAC CGACCATCAC TAAAACAGAA ATATTACAAC

8341  GTGGTTAACG GAAATTGTGA TTTAGTGATT GAAACTAAGC GCTATGGTGA CCGTTATATC

8401  CGGATGGTTA AGATCGACG AATTCATTAT GTCAAAGATG ATATTACTGA TCCGGCAATC

8461  TTACGGGTAC TTGAACATGT AAATGGCGTC TTTGATAAGC CAAAGCAGAC TACTACAAAA

8521  GAGCAGAATG AAATTGTTAA CAAAATTAAA AAGCAAAATG TAAAGGAAGG TTAATGAATT

8581  ATGAGTTTAC GAGATGCAAT GAATAAAGCT ACTGAAGGTT TTGATCCAAA GAATGATTCA

8641  GTTAATAAAT TTAAGGGACT GGAAAGTGGT AAATATACCG TTGTAGTTGC AAAAGTAGAA

8701  AACCATGAAA CTCCTTGGAA TGCTGAACAG CTTAACTTTG AGTTAGAAGT TGTCGATGGA

8761  GAATCAGCCG GCCAAAAAGA ATTCTTACAA ATTGGATTAG ATGAATTAAC TTCTAAGGGT

8821  AATCCCAATC CAATGCTAGA AACTAATTTA CGATTGGTTT CTAAGTTAGC AGCAATTCTA

8881  GGTGTTGAAA TTCCCGATGA AGTTTGGGAT GACGATACTT TAATCTACGA GAACTTGGCT

8941  AAAGCATTTG CACCGGCAGT AGGAAAGACC ATGATTATGG ATTTGAAGGT TCGACCAAAC
```

-continued

```
 9001 AAGAAGAACC CCCAATATCC ATACCGTAAT TATGACTTTG ATGAAGCGGA ACAGCCGGAA

9061 ACGCCAGAAG TTACAGATGA TGAAATGCCC TTTTAAGTAA ATATTTGAGT CAGTGAACTT

9121 ATAACACCGT ATGGCTGGGA GGCCATTAAG GAGGAAAAAT GAAAAATCTA GTTAATTACG

9181 CCTTAGCCTA TCAAGCAAAG GGTTTAAGCG TCCTCCCAAT TGCTGGCAAG CGTCCACTAA

9241 TTAAGTTTGC TGATCGTGAT CCACTTACCG CCGAAGAAAT AAAGACCATC TGGATAGAAC

9301 ATCCATATGC TCAAATTGCG TTGCGGACTG ATAAGTTCTT CGTTGTTGAT ATAGACCGCA

9361 ACCATGCTGA TAACATTGAT GGTTTTGAAT CAATTAAGCA ATTACCAGCG GAATATTTTC

9421 CGGAAACTTT AACCCAAACC ACCAAGCATG GTGGCCGACA GTTATTTTAT TTGAAACGTT

9481 CAGATATGCG AGTTAATCAG TTAATTGGTT ATTTACCAGG TGTTGATGTA AAGGCCCACC

9541 AAAATAATTA TGTTGTGGTT GCGCCATCAG AAGGTTACCA ATGGCTGAAT AAGAAGCCGA

9601 TTGTTACGGC TCCTAAGTCG TTAGTAGTGA ATATTAACCA AATGCGAGCC AGTAACCGGC

9661 GAAGTTCTCC AGATGATTTA GTTTTTAAAC CACGTGAACG CAACTCAACT ACTGACTTAC

9721 TTGAGACCAT CGCAAATGGA TTGGGAGATA AAGGAATAAG AAATAAAAAC TTAGCTGGAA

9781 TGATTGGTGC TTTATTGTTT CGGGGAGTAG AACCAAAGTC TGCTTATCAA TTAGCGATGA

9841 TTTGTAATGA GAATACGCCC GATCCACTAC CAGAAGAAGA AGTGAACCGG ACATTTCAAT

9901 CAATGCTAAG ACGTGATTTG AGAAACGGGG GTGAAATACG TGGCGGATAA TATAATTCGC

9961 AAACCAATTG AATTTGAATT AAATACTCAA GGCAATCCTA AAACTAATAG TTTGAAGAAT

10021 ATTGGTTTAA TCCTTGATGG CGATCCACTA CTGCATGGCA CCTTCAAATA TAACGAGTTT

10081 GCTTATTCAA TTGATGTTGT TAAGGACATT CCACAGCTAT TTATTGAAAA GGGGCAACTT

10141 GATGATAGCT ATTCAGCAAT TATGCTCCGT TACATTGAGG ATGAGTATGG GGTGATGTTT

10201 CAAGAAAAAT TGTTAAATAT GGCAATCACT GTTGAAGCAA AAGCCACCC ATATAATCCG

10261 GTTAAAGAGT ATATGGAAAA GTGCTATAAG AATTGGGACC ACAAAGAACG AATCAAAGAC

10321 TTCCTACCAG TCTATTTAGG AGTACCCAGT GGTGAAGTAA CAACGCTGCA GACAAAATTA

10381 TTCTTAGTCG GAGCGGTGAT GAAAGTCTAT AAGCCGGAAA GTAAATTTGA TTGGGTGTTT

10441 GATTTAGTTG GTGGCCAAGG CGTTGGTAAA ACTACTTTAC TTAAAAAGTT AGCCCATGGT

10501 TGGTATACAG ACCAATTTAC GGACTTCAAA GACAAGGATA ATTTTGCCAA TATGCTGCGG

10561 GCATTGATTG TTAATGACGA TGAAATGACG GCCACAAATA ATTCTGACTT TGAAAATTTG

10621 AAGAAATTTA TCTCAGCTGA AGAATTAGAG TTCCGGCCAC CATATGGACG ACATACAATC

10681 CGCCGGCCAA AGAATTTTGT TATGGCCCGG ACTACTAACG AATCAACCTA TTTGAAAGAT

10741 AAAACCGGTG AGCGGCGTTT CTTACCTAAC ATGGCTGATA AGTCCCAAGC AATGGCTAAT

10801 CCGGTAACTG ATCTTGATGA TACGATGGTC AATCACATTT GGGGTGAAGC TGTTGGCCTC

10861 TACAAAGAAG GCTTTTCTTT CATATTGACG AAGGAGCAGC AGAAGCTCAT TGAGGATAAT

10921 CGAAAGATAT TTATGTACAT TGATGAAACT GAAAATCAAA TTGAACGGGT TCTCAGTACT

10981 TGGGACGATG ACTGGATTGA AAGCTCAGAA ATTGCTCATC AATTAGGTGA AGATAATCTG

11041 GTTAAGAATC GTTCATTAGC CAAAAAGATT AAGTATGTAA TGGATAACCG GCATGATTGG

11101 AAAGCAGGAC AACGGCGAAT TAAAGGAATT AGTCATCGTG GTTATAGAAA AGTGCATACA

11161 GATAATACAC TATGAATATA GTTAAGTGTA TGCAGAAAAA ACCTATTACA TCAACGTTTA

11221 TTAAGGTTTG CATACACTAC TACACTATTT TAATAATAAA AAATAAATAT ATATAAATAC

11281 TATATATGCG TTATAAAAAG TTGAAAGTTA GTGTATGCGT GTATGCAGTA ACTAAATCCG

11341 TTGAGAGAGT AAGAATTAAG CTGTATACAC TACTGTATGC ATAGTGTATG CAAGGAGGAA
```

-continued

```
11401  AATATGAATG AATTAAAAAA CATCAGCACA TCAGAATTAC TTGATGAACT GATTGAACGT

11461  AATGCATTAT TTCGTGTAGA TTGTGGTCTT TATCGGAATT GGGAGTTGAA GGGAAAATAT

11521  CAATTTAGCG ATATTAAATT GCCTAGCGCA TATCCTATTT ATGTAGGAAA TTCAATTATT

11581  GACCGCATGA TTAAGTGGGA GTGTGAGCAT TGACGAGTGA ACATAAAATT CAAAACGATA

11641  TCCGGGTTGC ACTATCAAAA CATCAGTGTA CAGTGTTCCG GGTAAATGTC GGTTCGGTAA

11701  AAACACCAGA TGGAAGATTT TTTTCAGCTG GTGTACCTAG TGGTCACCCG GACTTATATG

11761  GATTTCGTTG GTCGGATCAT CAAGTATTTT ATATTGAAGT GAAAAACGAA AAAGGTAAGC

11821  CTAGAGCGGA TCAAATTAGA TTTCATGAAA TGCTAACTAA ACGAGAAATT ATTCATGGAA

11881  TCGCTAGGTC TGCTGGAGAT GCAGTAAAAA TTGTTGAGGA AGGATTGATT GGTTATGGAT

11941  ATGAAAATAA AAAAGAACCA CCACAACAAG TAAAATTAGT TGAAGTAATT CAGGTTATAA

12001  CCTCTCGTGG AGCTGGAACA AAGGAGGATC CGATAAGAAA GATTATTCAG TATTGGAGCA

12061  AAGAAGGCAC ATTATTAGCA GAAAGTTTTG GAAACTAATT TTTCTTTGAG TCACGTTTCT

12121  CTATGTGCTT TAGTTGTTTT TCAGGAAGAC TATTATAAAA CTTATCAATT TGATTTGGCT

12181  GTGTTATTAA ATTGTCTGTA ATTATATTTA ACAGATTTAA AAGACTTTTC GCCATTTCTT

12241  GGTTATCAGT TAAGTCTATC TCACCAGGAT GAACAGCATT ATTTCCAACA ATTCTTACAA

12301  TATCAAACGC TTGTTGTAAT TTAGCCGGAA GTCCCTTAGA TACTAGATCA CCAATACGAT

12361  TATCTAATGA ATGTTTATTG GAAAATTCTT TTGTTAGTTT ATCTATTGCC AGACGAGACA

12421  AAGCAGCAGA TGCTCTTGGT GAATCTCTAA GTACTTTTGC CGCTTCAATA TAAATTTGTT

12481  TAATATCATC GGGCATATCT GGATTAGGAG CTGTTAATTT TAAAGGAAAA CTAGGAAAGA

12541  TAAGTATATC TTCATTGGAT TGCCGATTAT GAAACCAAAT AGAATCTAAA TAACATGAAG

12601  TGCATTTTGC AACTATTAAA TTATATTCGT ATTGTTTTGA TTTTATTTTT TCTGCATATT

12661  TCCAATCAAA TTGAGCATAT ACATGACAAT AAGGACAAAT AATAGGAGCT TTCCCTGTAA

12721  AATCATTACT AAAATATTTA GTCATTAAAT TCACCTCAAA TAAGATTATA GCGTAAAGGA

12781  GTAGATGTAA TGCTACACAA ATATAGAAAG TTACCAATTG TGGAAGCTGA ACAGTTTGAT

12841  GGGTCAGATG AAATGATTGA AAGGTATTCA GTGCATGTAT TTAATCCTAA TTTAGCTAAA

12901  AACATCTTCT TTATAGGTAT GAACGTTCTA GCTATTGGTG ATTGGATTGT TAAGGATGAA

12961  TATGGGAATT ATCAAGTGGT AGCTGATGAT ATATTCCGTA AAAGTTATGA GAGGTGCGAC

13021  TAATGCACAT TTATGAAGTA ATCGTTGTAG CTGTATTTGG CACAGATATT AGCCACTTTG

13081  TTGTTGCTAA GAATGCCGAT AATGCTAAGA AAATTATTCT TGATTATTAC AGCACTCGTG

13141  ATGATGGTAT CAGGCCAACT GTGACAATGT ATGACCTAAC AACAAAATTA ATCAATCTTA

13201  ATAACTACAT TGATGAGGTG ATGCTTGGAT GAGATTAAGT GACAAAATTA TTATGACTTC

13261  CTTTTTACTG TTATTAATTG TTTCAGTCGT CTTATCAATA GTTACGGGAA GTAAAGTCTG

13321  GATATGGATT TTTCTTTTTC TGATGACACT TGAGATGCTT TACAAAATTT GGCGTTAGGA

13381  GCGTGACTAA TGAAAGCAAG ATGTGGCGAT TGGAGTACTG ATGTTTATCC AGTTGAACCG

13441  TTTGTTTATG AAGTAGCAGC TGATGGTAAG AAAGAATTTT ATCAATCAGC ATGGGATGCT

13501  TTTAGTTCTG AATTGCATAT GAAAAATGTG ACGGCGAAGA TTATCAAAAT ACCAGTTGTT

13561  CCAATGAGTA ATGATGAAAT TAAAGCAGAG AGTGTTGCAT TTGAATTAGG CGAAAAAAGG

13621  CATTATCCAC ATGTGGAAGA ATTCACTAAT AGTAAACCGA GGAGGAAAGT TACATTTCTT

13681  CAGGTTGCGG AAGCTTTTGC AATTATAACG TGGATTATTT TAATAATTCT TATAATAAGT

13741  ACGGCGTTTA TGTAGGAGGT AAGTTACTAA TGACATTTGA AGAGGCGTTA AAACATGAAG

13801  AAAATAATGT GCCAGTATTC TATAGCGATC GAAAATATTA TGTAATCGGG CACAATGAGT
```

-continued

```
13861 TAACCGAACA ATTTACAATT CGTGAGCTAA GTGGTAATCC GTTATTTACG GTGCCGGTTG

13921 ATGTACAAGC GGAGGAATTG TCATGAGTAT TAAAATTAAT GCGCAAACAG TTGTATTTAA

13981 GGGACAAAGT TTTATTCCTA GCAAAAGTAA CTGTGAGTAT TGTCAATTTC CATTTAAGAA

14041 GTTAATGGTT ACTAAAGCAT CTCCAGATCC ATCAGTTAAG ACAGAAGTAC CAATCAAAGT

14101 TGACGGTGAG GTATTTAATT ATTGTCCTCA TTGTGGACGG AATTTACAAG GGTGAGGCAA

14161 TGTTACTTTT AATTGTATTA ATGATGATTG TCTTTATTGC TGGGTTCCTA TTGGGTAAGA

14221 AAAATCCATG ACGAAAAAAG GACCCACCGT AAAAGATGTG TCCTCACTAA AAATATTTAA

14281 CCATAATTAT TATATCAGAT AGCGAGGGTA CGTCATGCAA ACAAGTTTGA ATTTAGATAT

14341 TGATTGTCTG AAAACTGCAA GAAAGGTTAC TGACTTTCTT GATAAGAAGC TGGATCGCTA

14401 TCTGGCTTTA TCGGGGAAGC AACGTTTTGA TTTGAAGTCA CCAGGGATGG ACGGAATGCC

14461 TAAAGCTCCC AGCCATGGTA ACGGTAGTGA AAATCGAATG CTGAATATCT GGTTGGCAGA

14521 AGAGGTTGTT GATTGTGTGG GTTGCGCTAT GCGGAATATG ACAAAGGAAT CACAACGGAT

14581 TTTACTAAAT CGGTATTCGG ATCAGATGTT AACGTATAAC ATTGCTAGGG AGCTAAGTAT

14641 TAGTTCAGCA ACGTATAGTC GAAAGCAGGA AAAAGCGCTG TGTGAGTTTG CGGACCGGTT

14701 TGAATTTCAG TTAGTTAAGC ACGGTATTCA TACTGAAATT GATGATCTAC ACGTTTATCT

14761 TGACGAGGAA GATTGATAAA TTGATGATAG ATTATTGAGC GAGCAATTCA TGATAGAAAT

14821 GTGATAATAG TATTGTCGAA TGATTCGATA TTCATATAAT AATCTTCCCA AATGAAGTCT

14881 AGCTATTATG GCTAGGCTTT TGTATTATGT TTAATTGGGT GATTTTTATA TGATTGAATA

14941 CTTAAAAACA TTTTTGGAGG CTTTGAGTAT GAAGCCAAAA ACTAAATTTG TTGGAGTTAT

15001 TTTTGGAATA GTACTTTTAT GCTTAAAACC ATTTTTAATT CAATATAATA TGAAATGGTT

15061 TTACAATAAG TTTTCTTGGA TTATTATTTT AATTACTTTA TTTTTTGTAG CCTCATTAAT

15121 AATTGAAGTA ATAGTTGAAG TATACGAATG GGGTAGAAAC AAGTATAACA AACATAAAGT

15181 TGAAAGAGAT TACGAAAAAT ATATCTTAGG CTTGTCTGAT AAAAAGTTGG CAATTGTAAA

15241 GAAACTTTAC GCTAATGAAC ATCACCAAGG ATATTTAAGA CAAAACGATA CTAATGTTAT

15301 TGAATTGGTT AATATGTACG TAATTATGCA ACTTAATAAT GAAATTATAG TAAGAGAAAG

15361 CCAAGTTGAA GATATAAACG ATCCTGAATT TCTTTTTGTA TTACAGCCAC CGGCTTTACA

15421 CATCATAGAA AAGAATTCAG AAAAATTTAA ATAAATTTAA TTAGTTTAGC TTAACGGCTG

15481 ACTTTTTACT TTTTAGGAGG TGAGTAGCAT TACTCAAAAA TTAACACAGA AGCAACAACG

15541 ATTTGTCGAT GAGTACATTA TTTCGGGTAA TGCTACTCAG GCGGCAATTA AAGCTGGATA

15601 TTCTAAGAAG ACAGCTAAGC AGTCTGGTGC TGAAAACCTA GCAAAACCTT ACTTAAAAGC

15661 TGCAATCGAA AAACGCAATG CTGAAATTCA ATCCGAGAAA ACAGCTGATA TGACAGAGGT

15721 GATGGAATAT CTTACTTCAG TTATGCGTGG TGAGCAAACA GAATCGGTTG CTACTGCTAA

15781 GGGTATTTAT GAAGACGTTG AAGTGTCGGC AAAAGATCGT ATTAAAGCTG CTGAATTAAT

15841 TGGAAAGCGT CACGGCGCCT GGACTGATAA AAAGGTTATT CTGGTGATG TTCAGATTGA

15901 TGTGGGAATG GGGGATTATG ATGATGAAGA GTGAAGAACA ATGGAGAAAA ATCAAAGATC

15961 ATCCTCATTA CTTGGTTAGC AATAAAGGTA ATGTTTACAG TGAGTATAAA GGCGGCTTGC

16021 TTAAACAGAT GAAAGATGCT TATGGATATT CTCAGGTTAA TTTAAACCGC CGCTCCAAAA

16081 AGGTGCATCG TTTAGTAGCG GAAGCTTTTA TCCCAAACCC AGACAAATTG CCTGAAGTTA

16141 ATCATAAAGA CGAAGATAAA AATAATAACC AGGTGGATAA CTTGGAATGG TGTACTAGCA

16201 AGTACAACAT GAATTATGGT GACGTGGAGA AAAGGTCAAT TCTTTCACAA CAAAGCCATA
```

-continued

```
16261 GTACTTGGAA AATTTATCAA TATGATTTAA ACGGTAATTT GGTAAAAGTA TGGAATTCAG

16321 CGAGAGAAGC CGACAGACAT GGATTCAACC GTAGAAGTGT GTATCGCTGT TGTGATGGGG

16381 AAATAAAATC TTTCAAAGGA TACATATGGT CAAGACAAAA GAAGGTGATA CCATGCCAAA

16441 CATCAAACTA AATTTTCCTA AACCATACAA CGTTTTCAAT AAACAAATTT TTGATAACTT

16501 GTTTGATTAC AGTCATTTCG TTGAGGTTTG GTACTGACTT ATGGCGGTGC ATCTTCTGGT

16561 AAATCGCATG GTGTGGTACA GAAAGTTGTA CTTAAATCAC TCCAACACTG GAAACATCCC

16621 CGCAAAGTGC TATGGCTGCG GAAAGTTGAT CGAACAATTC AAGAATCTAT CTTCGCTGAC

16681 GTAATTGACT GTTTATCAAA TTGGCAATTG TTATCGTTAT GTAGAGTAAA TAAATCAAAC

16741 CGTACTGTTC ATTTACCGAA CGGTGCGGTT TTCCTGTTTA AGGGTATGGA TGACCCAGAA

16801 AAGATTAAGT CAATCAAAGG GTTATCTGAT GTGGTAATGG AAGAAGCTTC CGAATTTACA

16861 CAGGACGACT TCACGCAGCT TACCCTACGT CTCCGTGAAC CTAAGCATAA GAAACGACAA

16921 TTGTTTTGTA TGTTTAATCC AGTTAGCAAA TTGAACTGGA CTTATAAGCA ATGGTTTGAT

16981 CCGAAAGTGA AAGTTAATCC GGAACGAGTA TCAATTCACC AATCAACTTA CAAGGATAAT

17041 CACTTTTTGG ACGCTGATAA CATTGCAACG ATTGAGAACT TAAAACAAAC CAACCCGGCC

17101 TACTATAAAA TCTATACGCT GGGCGAGTTT GCTACATTGG ATAAGCTGGT CTTTCCAGAG

17161 TTTGAAAAAC GTCGGTTAAG TATTCGAACC TTATCACAGC TTCCCTCGTA CTTCGGCTTG

17221 GACTTTGGGT ACACTAACGA TGAAACAGCC TTTATGCACG TTAAAGTGGA TGAGAGTACC

17281 CGTAAAATTT ACGTGATGGA AGAGTACGCT AAGCACGGTA TGTTGAACGA TGATATTGCC

17341 CGAATAATTA AACAAATGGG TTATAGCAAG GAAGTTATTA CTGCTGATGC TGCTGAGCCT

17401 AAATCGATTG CTGAAATTAA ACGCGATGGT ATCTCGCGGA TTCGTCCAGC TAAAAAGGGG

17461 AAGGACAGCA TTATACAGGG ACTTTCATTT ATGCAGCAAT ATCACTTAGT CGTTGATGAC

17521 CGGTGTGTGA AAACGATTGA GGAATTGGAA AATTATACAT ACAAGAAGGA CAAACAAACT

17581 GGTGAATACA CCAATGAGCC TGTCGATAGT TACAACCACG AAATCGATGC TATCAGGTAT

17641 GCTTTATCTG AAATCAACGG AATGGCTAGT CCAAAGGCAA CTGTAATGAA AAATATTTAT

17701 ATTTAGGTGG TGATTGAATG GAAACAGTAA ACGGTAAAGG ACAAATTTTA GATGGCCATA

17761 TTTTTATCTA TCCAGCTGAT GAAGAAGAAC TTGATCCGCA TGATTTACTG TCGTTCATGA

17821 GAAGAAATAT TCAGTATGCT AAGGATTACA AGCATAATAT GCAAATGTAT CTAGGTAATC

17881 ACGATATCTT AGATCAACAG CGGCGGATGT ATGGGCCAGA TAATCGGCTA GTAGCAAATT

17941 TACCGCATTA TATTGTTGAT ACTTATAATG GATTCTTTAC TGGAATCCCA CCTAAGATTA

18001 CTTTAGATGA TAAGAATGAG AACGAAGCAT TACAGCAATG GAATGACACT AATTCGTTCC

18061 AGGACAAATT GAGTGAAATT AGTAAGCAAA CGGATATCTA CGGACGTTCG TTTGCTTTTA

18121 TTTATCAAGA TGAGAACGCA GACACTTGTA TTGCTTATGC TTCTCCTACA GATGCCTTCA

18181 TGGTTTACGA TGATACGGTT GCTAGAAAAC CTTTTGCTTT TGTTCGTTAC TGGAAAGATA

18241 CTGAAAGCGG ATTATGGACC GGAATGGTTT ATTACGCTAA TAAAATTAAA ACCTTTAAAG

18301 GTAGTGTTGT TGAAGATTCA GATCAAAATA ATATGTATAA TTTAGTGCCA GCAGTTGAAT

18361 TTTATGGAAA TGAAGAGCGG CAAGGTGTTT TTGATAATGT GAAAACCTTA ATCGACGAAT

18421 TAGACAGAGT GTTATCACAG AAAGCTAACC AAGTGGAATA TTTTGATAAT GCTTACCTTA

18481 AAATTCTTGG TCTTGATTTA GATGAGGATG GTGATGGTAG ACCGGATGCT AATTTAATTG

18541 GTAATCAAAT GATTTATTCG CCTAATGCTG ATGCTGCTAA TGCCGATGTC GAATTCATTT

18601 CAAAACCAGA TGGTGATAAT ATGCAAGAAC ATATTATTGA CCGGCTTGTT TCAATGATTT

18661 ACCAGGTAAG TATGGTTGCT AACCTTAATG ATGAAGCGTT TGCTGGTAAT AGTTCTGGGG
```

-continued

```
18721  TGGCTTTGCA ATATAAGTTA CTTCCAATGC GAAATATGGC AGCTAATAAA GAGCGTAAAT

18781  TTACTCAGGC ACTCCGGAAG TTATATCGAA TAGTGTTTAG TGCTGATCAA GTAGTCAAAG

18841  ATAAGGAAGC CTGGCAAGAC TTGCTCTTTG ATTTCAAACA AAACTTACCG ATTGATGTTT

18901  CTGAAGAAGC TGATACTTTA CAAAAACTAT CAGGGGTTGT GTCAAAAGAA ACTGCATTCC

18961  GAAATAGTCG TTTAATTGAT GATCCTAAAA AAGAAGTTGA GCGTATGCAA AAAGAGAAGC

19021  AGGAAGAAAT AAACCAAGCG CTTCAACATT CTGCTTCTGC TACAGATCAA ATGCTAATGG

19081  ATGATCAAAA AGAAAATGAT AAAGAGATAG TTGGTTTCCG GAAGAACGGT GAATCCGATG

19141  ACGAAGAAGA ATAATTATTG GGCTGATCGT ATTGCTCGGG AACGTAAATG GCAAGAAGAG

19201  CAATTAAGTA AAGATGCTCA ATTTAATCAG CGCCTTCAAC AGTATTATGA TCAAGCAATT

19261  GTCCAGATTA ATAAAGACAT TGAAGATCAG ATAAATTCTT TAGCTGTCCG GAATAAAGTT

19321  TCTTATGCTG AAGCTCAAAA AGAAGTGTCC ACTACCGATA TTGCTGATTA TGAAACAGAA

19381  GCTAAGAAGG TAGTTCAGGA AGCTAATCGT TTAAGAGCAC AAGGGAAGCA TGTTACTTAC

19441  AATGATTTCT CTGATGAAGT TAATGAACGA TTGAGGAATT ATAATACGGC GATGCGATAT

19501  AACCGATTGA ATTTATTGAA ATCTAAAATT GGTTTATCGA TGGTTGAAGC CGGAATGAAT

19561  ATTGATGCTG ATATGCAAGC TAAAATTGGT AAAGATTATA CTGATGAGCT AAAACGTCAG

19621  TCTGGTATTC TAGATCATTC TACCGAAAAT AGTTCGTTTT GGACTTCTAA AGATGTTGCG

19681  AAACAAGTAA TGAAGCAAAT TAATGGAGCA ACTTTTAGTC AACGAATTTG GGCTAATCAA

19741  GATACTTTGA AAGCTCAACT TGATACGGTT ATCACCAACG GAATTTTAAC TGGTAAGAAT

19801  CCGCGAGTTG TAGCAAGACA ATTAAGAGAT AAAGTAAAAG TCACTGTTAA AAATCACAGT

19861  TATGTTACTG AACGTATTGC CAGGACAGAA TCAGCACGGG TTCAGTATTC TGCTCAGATT

19921  GAATTAATCA AAAAGAATGG TTATCAATTT GTCCACTGGA TTGCGGAGCC AAGAGCCTGT

19981  GATGAGTGTC GAAAGATTGC GACGCAAGAT AATGGCTTTG GTGATGGTAT TTATCGAATT

20041  AATAAAGTTC CTAAAATACC AGACGATACT CATCCTAATT GTCGCTGTTC AATTAGTGAG

20101  ACATGGGTCG ATGGTCAACG CAATATAGCA TTATCTGATG ATGAACAGGC GGCATTGAAT

20161  AATTATATTA GTTCAGATTC ATATAAGATT AATGATGATT TGAGGCGTAA TAAGATTTCT

20221  AAAAATAAGA AACAATTTAT TGAAAACTTA GATGCCGCAT TGGCTAAAAT GCCAATTTAT

20281  CATAGTAGCA AGCCACTCCA GCGTGATTAT TTCTTTGATA AACAAGAAGC ATTGGATGAT

20341  TTTATTAGTA ATTTTGAAAT TGGTGGAGTC TTCACTGATT CATCATACAT TTCAACTTCT

20401  AAAATTTATT ATGGACAGGG CAAAGAGACA ATTCATGTTA TTATTAAATC AAGTAAGACA

20461  GGAAGAGATA TCTCTGAGTT TAATTTTAAT GAGCAGGAAG TATTATTCCC CAGAAATAGT

20521  AAGTTTAGGA TTGATGATGC ATACGTTGAT GATAACGGGA AGATGACAAT GGTTTGGAGT

20581  GAATTAGATG AGTAACAAGC CTTTTACTGA TAAACGTTGG CGAGATAATT CTTTGGAAGG

20641  CGTTAAATTT GATAATTCAA AAGTAACGTC AGAACAAAAG AAGAAGACAG AAGAATTCCA

20701  TGAGTTATTC AAAAAGACGT TTGCTAAACA ATTAAAAGAA AAACACTCAC ATAAAAAGTA

20761  GGTGATCCAA TGGGAAATAA TGATTTCTTT ACGGTAACGT ACAAAATACT AAGTTATCTT

20821  AAGTATTGTT ATGAAAATGG AATTAATCCT GATCCTAATA TTCTTAATGC TGATACATTT

20881  AATATTAGTA AAGTTCAATT TGGAAGAACT CTACAAATGT TAAGCGAGCA TGGTTATATT

20941  TCAGGAGTGA GATTTACACA AGCCAAAATC GAAGGTACTG TTGTTGGTGG ACTCCACAAT

21001  ACGTCAATAA CGGTTGAAGG TCTGCAATAT TTAGCTGAAA ACTCAATGAT GAAAAAAGCA

21061  TATCGAATTT TTAAAGAAGT CAGAGATTGG CTTCCGGGTT TCTAAGCATT CACAAATTAG
```

-continued

```
21121  TGAGTGCTTT  TTGTTTTGGA  CTTTTTACTT  GTTGCAGTCG  TTAAAGAACA  ACCCGGATAT

21181  TACAGTCCAC  CGGACTATAA  ACGAGGTGTA  TTTATGTTTG  AAAAATTACC  AATGCGTTTA

21241  CAATTCTTTG  CTGAAGATCC  AACGCCAGAT  CCAGATAATG  ATGGTGCACC  TGAAGGAACT

21301  GATGATGGAG  ATAACGGTAA  AAGTGAAAAG  ACATTTACTC  AAGCAGAATT  AAACGATATT

21361  GTCAAAGCCC  GAGTCAATCG  AGCCTTGAAG  AATAAGCAAG  AGGAAATTGA  CCAGGCTAAG

21421  AGTGAAGCTA  CTAAACTTGC  CAAGATGAAT  AAGGATCAAA  AGCAAGAATA  TAAGCTTCAA

21481  CAAACTGAAA  AACGTGCCCA  AGATGCTGAA  GCAGAATTGG  CCCGTTATAA  AATGCGTGAT

21541  ACAGCGAAGC  AACAATTAAT  TGATGGCGGT  TATGACAATC  CAACTGATGA  AGATATCGAT

21601  TTAATTGTTA  CTGATAAAGC  AGAAACAACT  AAAGAACGTG  GTGAAGCATT  TCTTAAAGCT

21661  TATAACCGAA  TTAAAGAAAA  TGTTCGTCAA  GAACTATTAA  AGGGAAAGTC  ACCACGAATT

21721  AATGGTGCTC  CTGCTACTGC  AATGACTAAA  GAACAAATTG  CAAAGATCAA  GGATCCCGTC

21781  AAACGGGTCC  AAGCCATTCG  GGATAACTTA  TCCCAATATG  AAAAATAAAA  GGAGGAATAT

21841  AAAATGGCTG  AAACTAATTT  AACGACAAGT  ACAGACCTAG  TTGCACAATC  TATCGACTTT

21901  GTAGAACAAT  TCTCTGGAGG  AATCCAAACT  TTATTGAATG  CATTGGGAGT  TATTCGTATG

21961  CAGCCAATGA  CTACTGGTTC  ACAGATTAAG  ATTTACAAGT  CAGAAGTAAC  TAAGGTCGAT

22021  GGTAATGTTG  CTGAAGGGGA  AGTTATTCCG  TTAAGTAAGG  TTACTCGCAA  GCTAGCTAAT

22081  ACTTTGACAT  TAGGATTTAA  AAAGTATCGT  AAGGTAACTA  CCATTGAAGC  TATTCAGTCA

22141  GCTGGTGGTG  CTACACCTGC  TATCGTGGAT  ACTGATAATA  AGCTACTTCG  AGAAATTCAA

22201  AAGGATGTTA  AGAAGGACTT  ATTTAATTAC  ATTACCAAGT  CTGATGCAAA  CAAGACTACC

22261  GCCTCTGGTG  ACGATTTTCA  AAAGGCAATG  GCGGCAGCTT  TAGGACAACT  TTCAGTTAAG

22321  TGGGAAGACT  ACGACACACA  AACTGTCGCC  TTTGCTAATC  CGCTTGATCT  ATATGCATGG

22381  TTAGGTAACC  AAAACTCTTAC  TGTTCAATCT  GCCTTTGGTT  TGCAATACAT  TCAGAATTTC

22441  CTTGGCTTTG  ACACTATTAT  TCTAAGTGCT  GAAGTACCAC  AGGGAACGAT  TGCTACAACA

22501  GTTGCAGATA  ATATCAATTA  CTTCTACGCT  CCAATTTCAT  CCGTTGGTCA  GTTATTTAAC

22561  ATGACTTCTG  ATGAAACTGG  TTTAATTGGT  GTAACTCATG  ATGCAGTTAA  TAACAATTTG

22621  TCATACGAAA  CTGTTGTAAC  AATGGCTAAT  GTATTGACTA  CAGAACGTTT  GGACGGCATT

22681  GTATTGTCAA  CAATCAGTGG  TGCTAAGTCT  GCTGGTAAGT  AGGTGATTGA  ATGGACCAGA

22741  ATACGGTTTT  GCAAAACTTA  AAAGTAATGC  TTGAAATTAA  AAATGATGAC  CGTGATGCTT

22801  TGCTGAAACT  AATCATTGAT  AATACAGACC  AAGCATTGCG  ATTTAAGCTA  GAACTAACTG

22861  AAGACGAAAA  TTTACCTGGA  GAACTAGGTT  ATATTGAATT  AGAAGTTTCA  GTTCGACGAT

22921  TCAATCGACT  GCAAAACGAA  GGGATGAGTC  AATATAGTCA  AGAAGGGGAA  AGTATTACTT

22981  TTAATTCTTC  AGATTTTGAT  GATTCCTTG  ATGATATTGA  TTTGTGGAAA  CGACGACACC

23041  AGAAAGATGT  TAAATCTTTA  GGTGCCGTTT  CTTTTATTAA  TCCTTATGCG  GGGATGAGTA

23101  AAAATGCGAA  AAACACAGAT  AATTAAGTTT  TATTTTCAAG  ATGAAAATGG  CTATAATCCA

23161  TATGCAGAAG  AAGACACGAT  TACTAGTCCT  AAGCTAGTAG  CACAACGGTA  TGCCAATGTT

23221  ACTGATGTAG  GGACAAATCG  CCTAGTTGAA  TTATTTAGCA  GGCTAGATCA  GAACGCCAAG

23281  GTAATTCGAT  TGGAGTCTCC  AGTAAATGAC  TCTTGGTCAT  ATCTGACTAT  TGATGATTGT

23341  CCTATCAAGT  ATCGTCTTGA  AACCTGTCGG  AAACCATTAA  AAGGCACAAC  GCTGATTGTA

23401  GGTGAAGCCA  GTGGCTAATT  CTTTTAAGGT  TGATGTTAAA  GGTACTAAAG  AACTAGCGAA

23461  TTTCTTAAAG  AAGAATAAAG  ATTTGACTCC  AGTTAAACGG  ATAGTCGCAA  AACATGGAGC

23521  AGGTCTCAAA  AAGCAAACGC  AGCAAAATAT  GAACAATTTG  TATAAGGGCC  ACTACGAATG
```

-continued

```
23581  GAAGAAGGGG GCTGGGCTAA CAATGGTTAG CCCTACCGGG AATACTAGAC GGTCCGTAAC

23641  AAATACAATT TCTAATAATG GTTTAACAGC AACGGTTGCT CCACAAACTG AATATTTCCC

23701  ATATCTTGAA TATGGAACTC GCTTTATGGC AGCACGACCG ACATTACATC CAGCGTTTGC

23761  AATTGAGTCT ATGAAATTTG CTAATGATTT GAATAAGTTA TTTAAGTAGG TGAGAAAATG

23821  TCACCAAGTA TTGAAATTTA TGATGCAGTT TTTGCTCAGG TCCAAAAGCA TTATCAGACC

23881  TACGATCACC CACCGCAGTT AAATGAACCA GTTACCTATC CATTCGTGGT TGTTGATGAT

23941  AGCCAGTCGA TTTTGACGAA CTATAAAACA GCCACAGGAA TGCGGGTAAC TTTAATAGTC

24001  CATGTGTGGG GGAAGTCTAA CCAACGTAAG ACTGTTACTA AGATGGTTGA TGAAATTAGT

24061  CGTCTGGGGA TGCAAGCAGT TCGGACGAAA CATTATGCTT GGCAAGGACG ACCTAATGAG

24121  CAAGAACAAC AATTATTAAC TGATACGAGT GTTCCGAATA CTGTGTTAAA GCACGGTTAT

24181  TTAACACTCG TTTTTGATTT GAAATAAAGG AGGATAAATA TGGCAACATA TCCAGTATTG

24241  GAAGGGAAGA ATGCAGTTCT TTTTGAACGA CTATTAGAAA ATGCAAGGAA AGAGCCGGCA

24301  CAATTGATCC CGTATCAAAC ATCACTAAGT TATGATCCTA AACGGGATAC TGATTCAACA

24361  ACTACGAAGA TGGGGAATGT TCCTACTGCT TCTAATATTG AAACAGATTT AGAAGTAGAG

24421  TTCCTAAATG CAATTTCCAA AGCTGCAGAT GATGTTTATG ATTCTTTGTA CTTTAATAAG

24481  AAGATTGAAG TATGGAAGGT TCATATTGAT CGAGTCCGGT CAGATGGCAA AGTTTATGCC

24541  GAATATATGC AAGGAATTGT GTCAGAAGAC TCTAATGATA ACGACCCAGA CGATCATTCA

24601  ACTCGGGATG TGACCTTTAC GATTGATGGC GTGGCCAAAC GTGGGTGGGT CACTCTACCG

24661  CCAGAAATCA AGGAAGAAAT TGACTATGTA TTCCGTGGCT TGGCACAGCT TAAAGGCGAT

24721  GACGACAACG GTGAAGGTGA AGCTTTTGCT GATGGCGATC GTGGTGCTGG TGCAAATGAA

24781  GCAGTAACAA CTGAATAGGA GGAAGATTAT GAAGTTAAAA ATTAATGGTC AAGACCAATC

24841  ATTTGTATTC GGAGTTAAGT TTTTTGCGAAA ACTTGATGCT TATCGGGGCC CTGAACAAGA

24901  AATCCAAGGA GTTAAGGTTA AGCTAGGAAT GGGGCTAGCC ATGATGCTTC CCCAATTAAT

24961  GACTAAGGAT GCGGCCGCTT TGGCAGACGT GTTGTACTGT GCGGCTAAGT CTAGCATTAA

25021  GTTAGATACA ATTGATGATT ATATTGATAA TTGCAAGGAC TTGGATTCAT TATTTAATCG

25081  GGTAATGAAT GAAATTAAGG CAAGTAATGC CGCTAAGCCG ATTGCAAAAA ATCTAAAAGC

25141  CTAGATGGTC CTGAGCTTAG TTCAGAACAA AGCTATCACG AAATTCTTTT GAATTCGTTG

25201  GCTTATCTAG GCTTTCATAA TATTTCAGAA ATTGAAGAAA TGGGATTGGC TGAATATCAG

25261  CTCCGGATGG AAGCCTATAA CCTCCAACGG GTTAGCCAGG AACGAGACTT AGCATTGCAA

25321  GCTTTCCTTA ATCAGTCGGT ACAAGCGACG AAAGGGAGCG AAAAGCACCC AATTCCGAAG

25381  TATAAGAAGT TTAGCCAATT TTTTGATTAT GATAAATTTG TTGATGATGT TCGTGGGCAC

25441  TATGAGCCTG ACTATCAGCC AACAAGCAAG GCCAGCCTTG AAAAGAAACG AAATGATCTA

25501  ATCGTCAAGC GGTGGCGTGA ATTCCGGAAG ATGAAACAAA AACAGAGAGG AGGTAATGGC

25561  TAGTGTCACA ATCAATGAGA GTTGAAGCGG TATTATCAGC ATACGATGAG AGTTTTAGCG

25621  CAACCTTAGA TAAGGCGCTT AAATCGATTA ATAATTTAGG CCGTGAAACC CAGTCAACCT

25681  CTCAAACTGT TAGTGCAGGT GGTTCTAGTA TTTCCAGTAC CTTTAAATCG ATGGCTGGAG

25741  CAATGGGTGT AGTTGCGATT GCTGGTAAAG CATGGGACGT TGTTAAAGAT TCAATGAGTG

25801  GCGCCATTAA CCGGTTTGAT ACATTAAACA AGTATCCGGT AGTAATGAAG GCTTTGAATT

25861  ATTCAACTAA GGATGTTGCA AAGTCAACCG CTATCTTATC TAAGGGAATT GATGGATTAC

25921  CTACTTCTTT GCAAGACGTT ACAAGTGTTG CCCAACAATT AGCGCCATTA ACTGGTAGTG
```

-continued

```
25981  CAACTAAGGC TTCTAAGTCG GCGATTGCCT TGAATAATGC CTTCCTTGCC TCCGGTGCTA

26041  GTGTTGCCGA TACCTCTCGT GGACTTCAAC AATACACACA AATGCTTTCA ACTGGTAAAG

26101  TCGATTTAAT GTCTTATCGA ACATTGATGG AAACCATGCC AATTGCATTA CGTAAAGTCG

26161  CCAATTCATT TGGTTTTACT GGTAAGTCTG CTGAACAAGA CCTTTATAAA GCTTTGCAGT

26221  CAGGACAAAT TACGGTAGAT CAGTTGAATG ATCGTTTTAT CAAGCTGAAT GGTGGAGTTA

26281  ATGGTTTTGC TCAATTAGCA AAGAAAAATA GTGAAGGTAT CGGTACATCT TTTGCAAACT

26341  TAAAAAATGC CGTTGTCAAA AATCTGGCAA ATATGTTATC GGCAATTGAC AATGGTTTTA

26401  AGCAAGCGGG CTTTGGAAGT ATTGCACAAG TCCTAGACAA CATGAAGGGT AGTATTAATT

26461  CTGCTTTTCA AGTTATTGGA CCAGTTGTTA CTAATGCTAC TGTTGTAGTT CTTAATTTTG

26521  CAAAGGTTAT AGGCGGAGCG CTTAAATCTG CTTTCAGTAA TGATATTTTT AAAACAGCAG

26581  TTGTGGGAAT ATTAGGCTTT GTGGGTGCAG TTATGGCAGC CCATAAGGTT ATTTCAATAT

26641  TTACAACATT AAGATCTGCA ATAGTTGGTT TAAGTGTGAT TACAAAAGCT GGTAATTTGG

26701  CAATGGCGTT TAGTGAAGCA ATGTCAACAC TTGCTAAAAC TTCTAAGATT GCTGGTGGAG

26761  CGATGAAAGC ATTCAGTGCG GTGGCCTCAT TAGGTCCCTG GGGAATTATT GCTGTTGCAA

26821  TTGCAGCTGT GGTTGCAGCC TTAACTTATT TCTTTACCCA AACGAAAACC GGTAGGGCTT

26881  TATGGCAAAG TTTTTACTACG TGGTTATCTG GAGTATGGCA GAGTTTGGTT GGAGTGGCTA

26941  CTACTGTTTG GAATGCAATT GGTAATGCTA TTAATGCAGT AGTTAATTTT ATTAAACCTT

27001  ATTGGCAAGG ATTATTAACA TTCTTTACCG GAATCTGGAC ATCAATTGTG GCGGGTGTTG

27061  CTCCAATTTG GCAAGGGTTA GTTAATGTCT TTAATAGCAT TATCAGTGCA ATTTTAGCCG

27121  TTTGGCAGGC TTTAGCTCCA ATTATTGTTC CGATTGTAGC TGGTGTAGTT GCTATCATTG

27181  GGGCAACCCT AATTACGATT GTTACCGTCT TTCAAACTGT GTGTAATATG CTTGTACCCA

27241  TTGTTCAAGT TGTATGGCAA TTAATTTCAA CAGTTGTATC TACTGCTATT ACGATGCTAG

27301  GTACAATAAT CCAAACAGGC TTGGCAATTA TCGTTGCTAT TTGGAATGTG GTCTGGAATA

27361  CATTCAGTAT TGTTGTAAGT ACGGTATGGA ACGTTATTAC TACTATTATA TCTACCGTGC

27421  TGAACGTTAT TGCGGGAATA ATTCAAGCTA TCACTGCTGC AATACAAGGC GATTGGTCAG

27481  GAGCTTGGAA TGCAATTCAG AATGTTGTAT CAACTGTTTG GAATGCAATT GCCAGTATTA

27541  CTTCTAGTGT ATTGAATGGA ATAAAAGGAA TCTTTGATGG TGTAATGAAT GGTTTAAAGA

27601  GTATTACTTC TAGTAGTTGG AATGGTATTA AATCGCTATT CAGTGAAGGT GTTAATTTCA

27661  TTAAATCAGT TGTTCATATA GATTTAGGTG CTGCTGGTAG AGCTATCATG AATTCACTTT

27721  GGAATGGAAT GAAATCCATT TGGAATAGTA TTAAGAATTG GGTTAGCGGT ATTGCTGATT

27781  GGATTAAAGA ACATAAAGGA CCAATCAGTT ATGACCGTAA GTTACTTATT CCAGCTGGGC

27841  AAGCAATTAT GAATGGTCTT AATAACGGAT TGATTAATGG ATTCAGTGAA GTTCAATCAA

27901  ACGTTAGTGA TATGGCTAAT CAAATTCAGC AAGCTATTAC TAATCCAGGC TTTGATATTG

27961  GAGCAAGTAT TGGTAACTTG GGTTCAATTA ATTCAAATTA TACTGGTAGC CTGGCAATTC

28021  AAGATAGTCA GTTACAAATG CAGAATAATG CTTTGCTTCG TCAATTACTT AATAAAGACA

28081  CGACAATGGT TCTTGACGAT GGCACTCTTG TTGGCTATAC AGCGGATCAA TACGATTATC

28141  GCTTGGGTCA AAATACAGCA TTGAAGGATA GGTGGAGCCG ATGAAATTCT TAAATAATGA

28201  CTATTCTTTT CGTGGATTAG GACCCACAAA GGATGATCCA GAATACTTAG AAAATGCAGA

28261  ATATATCGAC TTTGCCGGTT TTAATTCTTC TGATTATGAT TGGTGGTTGA TTGATCGAAC

28321  AGCAACTACG CCAGAAGAAC AAGAAATTAC AGAAAGCGTC CCTTACATGC AAGGAGAATA

28381  TGATTTCTCA ATGTATGATC AGGAACGTTT TTTTAAGACC CGTGAGTTGA CTTATAAGTT
```

-continued

```
28441  TGTATATTTT GGTGAAGTTT ATCAGGATCG TAAAGCTTAC GAAGAGGAGC TTAAACGGCA

28501  ATTACTGCCA CATGGTTTCA CTAAACTAAT TGATTCTCAT GATCCTGTTT ACTACTGGTC

28561  AGCTAAGTGT ACTAGTGTTG AGGTTGAGGA TGACCAAGAA AAGGGAATGC TCACAGCAAC

28621  TATTACTTTC AAGGCTTATC CTTTTGCTTA TACTAATCAT AACGAGGGCA CCGATTATTG

28681  GGATGATGTC GCATTTGATC ATTGGATTTG GCAACCAGTT AAAATTCAATG TTAACGGTGA

28741  TCAGGATGTT AATGTTAAGA ATATCGGCTC ACGACCAGTC GAATGCTCAT TTCAATTGAC

28801  AGGGTCCATA ACTTTGAAGA ACGATTCAAT TGGTGAAGTA GGTTTAACTC AAGACAATTT

28861  TAAAACAACC ACGATTGTAT TAGAGATGGG TGACAATAAA ATGCATCTAT CCGGAAACGG

28921  GACAATTGAA TTTCAATTTA AGCGTGAGGA GATGATTTAG TGTACCGAAT TATTGGTTAT

28981  AATGAACCAA CAGATAAAGC AGGATTTATT GTACTGGATC CCCGAGTTAA TCGTCATATT

29041  AGTTCGGGAA AACTCACGCT TAAAGAATCT AATATTGATG ATTTGACTAT TACGGTTAAT

29101  CAAGCAAGTC CATTATGGGA CAACGTAAGG CCTTATCATA CTCATGTTAA CGTTTATGAT

29161  GATAATGAAC TTATTTTTCG TGGACGAGCT ATCAAACCTA AAAAGTCGAT GGAAGAAAGC

29221  GGACAATTCA TTCGTGAATA TGTTTTTGAA GATATTGAAG CATATCTCAT GGATAGCACC

29281  CAAAGATTTT ATGAAGGTGT TGGTCAAACG CCCAAAGAAT TTTTACAAAC TTTAATCGAT

29341  GTTCATAATT CACAGGTTCC TGACTATAAA AAGTTTCAAG TCCGGAATGT AAATGTCACT

29401  AATAATAAGG ATGACCAATA TCGACAAATT GATTATCCCA AAACTAGCGA TGCTATTAAT

29461  GATAAATTAG TTAAATCTCT TGGTGGTTAT ATTGTGACTA CTTACAACGC TAACGGAATA

29521  AACTACATTG ACTACTTAAC GGATATTGGG GTTGATCATA AGATGATAC TCCTATTCAG

29581  TTAGCTAAAA ATATGAAGTC TGCAAGTATG CAAATTGATC CTACTAAGGT GATTACAAGA

29641  CTGATTCCAC TGGGAAAGAC ACTAGAACCA TCAAAAGTTG ATGTAAGTGA TGATGATGGA

29701  GAGGGCGGTT CTGGATCATT AGATAGCCCT GAAGAATTTT GTAAATCAGA AATTAATGCT

29761  ACTTGGGGTA GTGATATTAA TAATATGAAA CAAGATTTTG CCGCTCGTTC TTCGAGAGTT

29821  CGGGCTTGGG GAGTGGACGT TAATCGTTTA TATGATGTGG TGAAAAATGC TGGAGTAAGT

29881  CCTGAATGGT TCTTTGCTTA TGAACTTCAA GAACAAGGAA CTTACTATGG ATGGCTTAAC

29941  CATACTTATC GACACGGTGA TGCGTATAGT GATGCGCAAT CTGTTTGTGA GTGGATTAAA

30001  AATTGTTCAA ATAGTAATTC CATTAATCCA GCATGGAGCG CACCGGAAGG ATCAATGGCG

30061  CCGAATCAAG CATTAGCGGA TAAATGGAAT CAAGAGTTTG GAAAAGGTAC TATTGGCCGC

30121  GTTTATTTAC AAGGGACTGC CGCTGCTGTT TGGGATTTAG CTGGTCAAAC GCCTAATCCA

30181  GCTATTGGAA AGCCAATTAG TGGATGCATT TCTTGTATTA AACGTTGGGG TGGTCATTCT

30241  AATGCAGCTG GTGGTACATG GGGATGGCCT TTTCCTGATG TTGGGGAAGG TCATTTTTCT

30301  CAAGTTCAGA GTTTCGGAAA TGATGGCGGA TATCGTCAAA ATAGTTATCA CGATGGTGTG

30361  GATTTTGGAT CAATAGATCA TCCTGGTAGA GAAGTGCATT GTATTCATGG TGGAACGGTA

30421  ACTATCAAAT CAGCTATGGG TGGCTTAGGT AATTTTGTGG TTATTCATAC GCCGGAAGGA

30481  TTCAATATCG TTATCAAGA AGCTTTTAGT TCTCCCTCTA ATATTATTGT TAGTGTTGGG

30541  CAAAAAGTAA AAACTGGTGA TGTAATTGGA TATCGTGATA CAGACCATGT TCATATTGGC

30601  GTAACTAAGC AAGATTTTTA TCAAGCAGTT CGAAATTCTT TTTCTCCTGC AGGTGGTTGG

30661  CTAGATCCAG TAAAACTAAT TAAAGAAGGT GGCGATGGGT CTAAACCACA AGAAGGAAAG

30721  AAAGATCAAA CTGTTGATAA TAGTAATGCT GCACGTCCTA AATTAACCAT TACTACTGTC

30781  AATAACGGTA GAGACTATAT TGATATTCCT GATTTACAAA AAGAATTCGG TATTATTGAG
```

-continued

```
30841  GGAACTGTTG AATTTGATAA TGTAGATGAT CCGAATGTTT TAATGCAACA AGCTCAAACA

30901  TGGATAAAGG CTCAAAGAAT ACCTCAAAGT TGGGAAGTTA CAGCTTTAGA ATTACATATG

30961  ACAAACTTCA AATCTTTTAA GGTTGCTGAT AGGTACATGT TTATTAATCC AAATGTTGCA

31021  AAACCCCAAT TATTACGAAT TACTCAAAAA GAAATTGATT TACTAAAGCC CCATGCGTCT

31081  TCATTAACGA TTGGTGATAA GACGATGGGG CTTACTGATT ATCAGTTAGA AAATCAAGTC

31141  AATTTTCAAC AATTTAAGGA AATTCGAGTG ATGGTTAATC AGGTTGTCCA AACCCAAGAG

31201  CAATCTGCTA ATAACAATAA TAAGGTTATG CAAAATTTTG CTAGTAGTGC TGATCTTGCA

31261  CAAATGAGAC AGGATCTAAG AAATCTTCAA GATGATAACG ATCGTGCTCG CAAAGGAATG

31321  GTTTCCTTAG AAGAATTCAA TAAACTAAAG GAACAAGTAG AAAAACTAAC AACAGGAGGC

31381  GATGATAATG GCAAGTGAAA CCTATGATTA TGAGTCATTT GATAATACGG ATCATACTAT

31441  GAAACAAATC GCTGACGCTA TTCGTCACAA GGGTTATGGA AAAGATGTGC GTGAGGCAAT

31501  TGCACAGGGC TTCGAAAACT TAGATAAACA TTTAAGTAGT ATTGAAGAAG AACTGAAACA

31561  ACAAGAAAAG AAAAAGTCAT CGTCTATGGA TGATATTTTT AATTCTTTTG GTAAGAAGGA

31621  GTGATGATAA ATGGCAAAAG AGATTAGTAA TCTGATTACC TTTAACACCT ACAAATTTGA

31681  ACGAGGCGGC CTTTTGGTTG ATATGTTTAA CCAATTTAAT GCTCGTGTAG GAGATCAAGG

31741  AACGGAATTA GCCATCCAGT GGGAAACTAG TAAGACTGAA ACTAAAATTA ATTTAAAAGA

31801  ACGAGGATTA CATTTCTTTG GGACAGGTTC AGTTGGACAG TACCTTGAAA AATTAGAAGA

31861  TGGAACTGGC TTTAAGATGT CTGCAGATGC ATCTACCGTT GAATGGGAAG ATAAAGATGA

31921  AGCTGGTAGT TTAGACGATG GAATTACGGT TGTTAAGTTG CCAAAACAAT TTTTCCCTCA

31981  AAAAGGTATT TTCTTTGGTT ACTTTGGCCT AAAAGATAGA CAAGGTAATA TCTTTACTAG

32041  TGTTAATGTT TGGTTCCGTG TTCTTGGCGG TGTTCCAACG ATGGGGGCTG CTATTCCTTA

32101  CTTTGTTACT GAATTTGATG AAGTATTAGA GCGATGCAAT GGTAAGATTA TTGACGCTTT

32161  AGCAGAATTA CGTGAAAAGT ACCAGGCAGA AGTTAAGAAG AATGAGGATA TGTCTGCGGA

32221  AACAAGAGCA GCGTTGAGTA AACTTGCTGA TGCTGTTGGT GCAATTCAAG CGCAGATTGA

32281  TGCAGGTAAT GTAATTACAC GTAAAGAATA TAATAATCTT GCTAATCAGA TTGATAATCG

32341  CCTTAGTAAA ATGACACAGA ACATTGAGAG TTTTTCATCA CTCGATGACT TAAAAGCTCA

32401  ATATCCTAAT GGAAAAGATG GACTCTTTGT TACTAATGAC AATAATCATA AGTATCAATA

32461  CAAGAATGGA TCATGGGTAG ATGAAGGTAT ATGGACAGTT ACTACCTTTG ATCCAGAAAC

32521  GCGACGACGC CTTACATACC TTGATACATC TAATTCTATT TTGCAAAAAT CACTCAGTGA

32581  ATTGACTAAA GAAGTCGTTG ATATAAATTG GTTTTTAGGC GAAATTGATG CAAATACTGG

32641  TAAAATTACA CCTCACGAAA GTTTTAATCG TGCATACTCA TCACTCAAAG TAATTGGTAA

32701  ATCACATGCT TTTGAATTTT TGCTTAATAC TGATTATTTG CAATATATTA GTATTTTTGA

32761  ATTCAATTCA AATGGGGAGA TTATTAAGCA CGATAGTGTT GGCGATAAAG CGATATATAC

32821  ATTTGAAAAG GATACGACTG CGGTAAGGTT TCAGATTACT AGTACTGCTG CTACTATGAA

32881  GCAAAATGAT TTACGCGATA CTATTCAAAA TAGTGGGCTA AAAATTATCG ATCGAGGACA

32941  CCGTTCAGTA ATTAATGATA TTGATCATTT ATATATCCGT GAACATTTAA TGCCGATTGA

33001  AGCAATTGAA GGCTATACAA TTAACACTAA TGTTGATTAT GGTGAAACTG TTGATGTATC

33061  ACATCCAATA GTAACGTCTG CGTTTCAATA TATTAATCAA GTATGTAAGC CGGGCGATAT

33121  TTTCGTAATT AATAATCTAT CTGGAGGCTT TAACGCAATG GCTTGGGCCT TTATTGATAG

33181  CGAGAACCGG TTAATTCAAA AATCTGAAGT AAACTTATCT CAATCTCAGG TTACTTTATA

33241  TGCGCCAAGT AATGCTGCAA AATTAATTAT CAATAATATG GATAGTAACT GTACAGCATA
```

-continued

```
33301 TAGATATACT CCGGATAAAG AACATTTAGC TAAAATTAAT ATTGCTTTAA CTACCAATAT

33361 TCATCGAAAT ATCAAGTTAG CTTATCAAAC AGGAGAAACA GTCTCATTAA TTCCTGAAAA

33421 AGTAAGTAAT TACAAATATA TTATATTAGA TTGTAATTTT AATGATGCTT TCAGAATAAA

33481 GGGTTATGGT GGATTGAATC CACGATTATA TGGATTTATT TCTGAGCAAA ACACATTAAT

33541 GAATGTTGCG CCTGCAAATG TTAATGATCA ATTAACTGAT GTCTTTATCA AAACGCCAAA

33601 AGGCGCCAAA AAATTAGTAG TTAATTTCAA TCTTGATCAA CAAGTAAATC CCAAACAAAT

33661 TGCTGAACTT TATAAGCTTC CAGACATTAA TGTTATTACT GAGCAAAAAA TAAAAAGAA

33721 TTTATTGAAT CAACAAACAG TCGATACATT AATTTCTAGT TATATGAATG GTATATTACT

33781 TGGTAAAGAT TTAGCCAATC ATCTTGCGGA TTTTGCTAAA AGCGGCGATA AAATGGTTCA

33841 TGTATCAACG TTTTATAAAG TTAACGATAC TCTTTTTATG TCTTATTATG CTAATACAAG

33901 ATCGGCTTAC GAAGATCCAA CCCAGCATAC AGCACGATTA GTTTATGCAC CGTTTGAGAA

33961 TCTAAATCAA CAAACGTACA TCGATGTAGC CGACATTGGA CAAGAATATA ATGGTCAAAA

34021 GATTGAAGCA ATATACGATT CTTTGCTTCT TAAAACAAGT GATGATTCAT ATATGATCTA

34081 TGCCTTTACT GCTAAGGTAG GTGGTAAGTT CTATATGCTT TACCGTCGTT TTGATCCTAA

34141 GACTAAGCTG TTGAGCGATA TTCATACAAT GAATTTTAAA GTTGGAGTAA TGACGTCGAC

34201 ATTTGATACA GTAAGCGTTC ATGATTTGTT AGCTAAGGCA GGAATTGACT ATGATTATGA

34261 AGATCGTGAT ATTTCCTTTG TCCAAAAATT AAGTCCACGG ATTGAAGATG GCGTAGTGCA

34321 ATACTATGCA GGTATCGGAA TCTTACATTT TTGCTTTGTA GTAAAATCAA GCGACTTAAT

34381 CAACTGGACT TTTGTCAGTA CTCCAGACTT TATGTACAAG CCAGAATTTG AACCTTCTGT

34441 ATATGTTAAG GGAGACAATG TTTATTATTT TTGTCGTCAG CGAGGGACAG AAGGTAATGC

34501 AGTTTTAGCT AAGTATAATA TCCCTAATGG TCAATGGTCG AATCCGATTC TTGTACCAGA

34561 TACTCAATCA CGCTATGACT TTTTCGAGAA TAATAGTCAG TTGTACCTTG TTCATTCACC

34621 GCTAGACCGT AATCATATTA GTTTGATGCA GATTGATCAG AATGTTCTGG AAAAGAGCTA

34681 TGAAGTAGCA ACAGCAGTAG TACAAGATTG CTTCTACCCA TTTACTCAAA ATATTGATGG

34741 TCAGATGTAT ATGAGCTTTA CACAAGTAG GCAACATATT TGGCTAAATA AATTTAATCC

34801 CCACAGTCTG CTAGATAGTG ATGTAGCAAC TATTTTCAGT AATTTAATTG AGTAGCAAAA

34861 CATAGTCGCC TTATAAATAC ACAATACATA GAAAGTTGCA TTGCTTAAAT GGAAACTTAA

34921 TGGGCGGCTT ATAGACTTTT ATTATTTAAA AGAGTATACT GGAATTATTC TTTTTATTGG

34981 GAGGAAATAT AAAAGTGACA ACTAAAGTGA GAGATAAATC GCTTGATATT ATCCGGGGGA

35041 GCATCCTTCT AGTTGTCTTG GGTCATATAT CTGGGATACC TTTTGAGTTA AAAAAGTACA

35101 TATATTCTTT TCATATACCA CTGTTCTTTT TTGTTTCGGG ATATTTGTTC AACTTTGCTA

35161 AATACAGGTA TTTTTCTTAT AAAGAGTTTA TAAAATATAA AGCTAAAAAA TATATCCTAC

35221 CTTATTTCAG AATGGGGTTG ATATGTTTGC TTCTATTTGG CATAGTTTAT CCACTATTTG

35281 CTGAAGGGTT TAGTAAACAG TATATGCTTC AATCTACAAA ATATGTTTTA GGTTTACTAT

35341 ACTCGCGTGG AGGTCCTAAT TATATGGCCT GGAGTTCGCC ACTTTGGTTT CTAACAGCCT

35401 TATTTATTGC AGAGATTATT TTTTTTGTGG TTCTAAAATT TAATTTTAAA TATCCATTAA

35461 TAGTGTTTGG AATCTTAGCT ATATTGAGTT ATATTTACTC GATTACAATT AAAAATTCCGT

35521 TACCGTGGAA TATTGATGTT GCAATGTTTG CAGTGTTATT CATGTACCTA GGCTTTATTA

35581 CACACAAATA TAATTTAACT AAGCACATTA ACTTACCGGT TTTCTTACTT TTGATTGTTA

35641 TTTTTGTATT ATCTGTAGCT TACAATAATG AGATTGACAT GAATTTAAGA AACTATGGCA
```

```
                         -continued
35701  ATGGATTTTT AACAATTATT AGTGGAACAA TAGGTACTGT TATATGCTTG CAAATTGCGC

35761  GATTGTTAAA AGAGAATAAG ATATTAGAGT TTTATGGTAA AAACACATTA TTTATCATGG

35821  GCTACACGTA TGCTGTGTTT AATTGTATTT TGGCTTTAAG CAGCCATTTT AGTACTGTAA

35881  AGAATGTTGT AGCTTCGTTT TTGATTCAAA TTATAATTTT AACTTTATTA ATAGTACTGA

35941  AGAATTTATT CAAACAAATA AAAAGCCCA  TTTATGCATA TACTAGGAAA ATTAACAATT

36001  AAAAAAACTA ATACGTCCTA CTCAGGGCGT TTTTATTTTA CCTTCAAAGG AGATGATCAA

36061  CATTGCCCTA TCATTTATTT ATGCTGCACC AAATGCAGAC ATTAGTTGAT GATAAACTAA

36121  TGTGGGCTTT TACAATCGTG ATGATTGTAG ATTTAATTAC GGGAATGATT AAACCGTATT

36181  ATGCAAAGAA AACAATTAAG AAAACTAATA GTTCAGTTGG AATCCCTGGG ATAATTAAAC

36241  ACACAGTAAT TTATTTAGTG GTAGTAATTG CTTATCCATA TCTTTATACG ATTGGAGCAA

36301  GCACGATGGC TACCACTTTT TTAATTGCTT GGATTTATCA ATATTTAATT TCAATTGTAG

36361  AAAATTGGAC AGAGATGGGG TGGTGGTTGC CTAAACCAAT CATGGATTTC TTTGAAGCCA

36421  AATTAGCTAA GGATCAAGAA GATTATGACC CATCTAAGTA CAATTTTCTT GGTAAATATA

36481  AAGGAGGTAA AAAGTAA.
```

Example 4. Selection of *L. reuteri* Promoters and Transcription Terminators

Global proteomics analysis of *L. reuteri* 3632 pellets and culture supernatants is performed to identify potential strong promoters and secretion signals, respectively. The proteins in the pellets and supernatants are ranked by their expression level, and the promoters and secretion signals from highly expressed and secreted proteins are identified by whole-genome sequencing (Example 2). The genetic elements are selected for use in expression cassettes that can be used to generate a genetically-modified bacterium which deliver the desired biomolecules to host animals in need thereof. Expression cassettes would comprise a suitable promoter, a heterologous coding sequence encoding a desired biomolecule, and a transcription terminator. The heterologous coding sequence could comprise a signal sequence for secretion, a cell-wall anchor sequence, and/or a detectable peptide tag.

Six suitable promoters are identified through analysis of the global proteomics data. Those promoter sequences are:

```
Xylulose-5-phosphate phosphoketolase promoter
                                                      (SEQ ID NO: 14)
    1    TTAAAGTATT AAAATAGATG TAAAATTTAT TTTTTTCAAA AGAAATTTTA ATTGTACACT

61    GTTGGTATTG AACGGGGTTA AACAAAGGTA AATTAGCATT TCTGCGGATT AAGATAAATA

121    GAAAAATGTT AAAGAACACC TTAAAAAGAT TAATTTTTTA TAATTGGACC GTATCAATTT

181    GTAAAAAGGT TGACTTTTTG AAAAAAAAGT TTATCATTAA CATTGTAAAT TTAATGATTT

241    ACGTTATGTT GTTATAGAGC ACAGGACGTA TTGATTTATA TAGAAGGAGT GTTTATTAGA;

Elongation factor TU promoter
                                                      (SEQ ID NO: 15)
    1    ATGAATGGAC AGATGTTTTA ATCGCTAGAA TAGAAGGAAA GAAAGTCGCA ACAAATACGG

61    TTTCTAGTAC GTGGCAGGAA CGACTAGGTA AGCAGATTGA CGAATTAATA GAAAAACATT

121    AGTCAAATAC ATTTACAAAT GAACAGATAG TTGATATTAT ATTTAAGAAT TCTTCTTCAG

181    AGCCTAAGAT TAAAGCTTTC AATTGGCGAA AAGAAGTTGT ACAATATGTA TAAAGGTATG

241    TCAGTCACCG AATCAGATGA TCTGGCATTA TACTTGTAAA TTATCAGGAG GTTTTCATTA;

Glyceraldehyde-3-phosphate dehydrogenase promoter
                                                      (SEQ ID NO: 16)
    1    ATCTCACGTG CGATCCATTA CACTAAGGGC GCGTCAACAA ATATTATACT ATCTTAAATA

61    AGAATGAATT GCAAGCATTA TTTGAAAATT TTAATTAAAA TAACGCTTAC ATCAGAAAAA

121    TGTTGTGATT GAATAGACAA TTTTTTTGAA GATGGTATCA TAAGTATCGT AGGAGTTGTA

181    TTATTGCTTA GACCTTACCA CTGCGTCACT TACAATGGTT GAGAGTTGCG ATGCTGATGT

241    AATGTGATAA ACTAAGCAAG TACACTAATT ATGTTTTTTC CTAAAGGAGG AATTTGCAGT;
```

-continued

Glucose-6-phosphate dehydrogenase promoter (SEQ ID NO: 17)

```
  1    TTGTTTAAGA TATCTTTCAA AGCTGCGGAA TTTTTCCCAG CTTTTTTAGT TAGTTTTGTT

61    TTCATAAGCT ATAATTTTAA CCGATTCCAA ATTTCTTTTA AAAGTTTTTT TGATCTAGAC

121    CATTAATTGA TAAACGCTTA CCAAAGACTA ATCAACAAGC CATTTAGCGG TAGTGGTCCA

181    TTTTAACTTT CTAAGACATC TTCTCAGAAA ACGTTTCCTT TGATAGTGCA GATTGTGCTT

241    TAAGAGTATA TAATTGTCAC GGTATAAGAA TTTTCTGAAA TTTCAGAAGG AGTGAACATT;
```

L-lactate dehydrogenase promoter (SEQ ID NO: 18)

```
  1    CTCCTCTATT ATTATTCCTG ATCAATTTTA AATTAATCTC CCTAGATAGG TATATTTTAG

61    CACAGGTCAC CAACGTTCCA AAGTTTAATC TATGTTTAAA CTTTAATTTT CAAAAAAATG

121    CTATACTATG TTCACGATAC TTTAAGGAAA GGTGATTACA ATAGTGAGTC TCTTAATTGC

181    TATTCTTATC TGCTGGTTGC TATGGAAGAT TGGGGGTTTA ACGGTTAAGT TCATTGGTCT

241    AATCCTTCTT ATTCTATTAA TCGGGACATT AATTCATGTT TTACTTTGGC CAGCGATCCT

301    TTTAGCAGTT ATTATCTTAG GAGCAGGTTT ATTCACTAAC TAATTTATCT ATAAAATCTT

361    ATAGTAATTT TTCTGCGGAA TGTTATAATC ATTACTGTGA GAGAAATCTC AAATAATGTA

421    TACATAAGAT GAAAGGGAGA CTGTTTATT;
and
``` tuf promoter (SEQ ID NO: 19)

```
  1    ACAAATACGG TTTCTAGTAC GTGGCAGGAA CGACTAGGTA AGCAGATTGA CGAATTAATA

61    GAAAAACATT AGTCAAATAC ATTTACAAAT GAACAGATAG TTGATATTAT ATTTAAGAAT

121    TCTTCTTCAG AGCCTAAGAT TAAAGCTTTC AATTGGCGAA AAGAAGTTGT ACAATATGTA

181    TAAAGGTATG TCAGTCACCG AATCAGATGA TCTGGCATTA TACTTGTAAA TTATCAGGAG

241    GTTTTCATTA.
```

The underlined regions of the above sequences denote the ribosomal binding sites.

Four suitable secretion signal peptides are also identified through analysis of the global proteomics data. Those secretion signal sequences can be derived from the following proteins:

C protein alpha-antigen precursor (SEQ ID NO: 20)

```
  1    MVSKNNHQFY QQKHAERKQR WGIRKLSVGV ASVLLGTTFM LYGNHAVLAD TVTSPSDDVT

61    RSTTTQGGNK DKVTEGTTEG TTSTPQTSGD STDKQANGQN VNQQVPTTDT EEATNHQDTP

121    QGQDTTQNTT NVDKKDTEVT PANDATTPTT QKITAKFTTA KFTTAKFTAA KFKVLAARPV

181    MKVAGTASLP ISNQDIKLDS QPMLTEIINK PTDNWVYNNL KWYQDTSTEK IKEILQNHTA

241    NDESGRYYFA GVANYNEHYH AIYLLARSNN LNDNSLYVTI LHTGLGKNIQ EAVVAPGESK

301    KVEYSGTTHT PIFTNYDGTS ASIDLDGIEK GDNIYGMVVG FAYGHNTGIK GDPASMGNGF

361    VMTPIPTKMT TTIHYIDQAT GDEIAVPKSF EGVAYQKYTI TGEAPTIDGY TLKKSPETTG

421    YISPYKVGES YDFRLDKHVV IKQTVIDAQG LVRVTAYYDG EVLNNTTRYL GNKLNVNDRM

481    SFISHGKWYT YINQITSTND GIVYYYAKDG SEDKSEVRVH YIDVTGSKNS IFVPGDGEEV

541    ATDKISGKLG ENYNYDVNLP TDYNLATNQA NTVNGTYTID HHDEYVYVVK KTSAELDPTV

601    PAKTKVDNPT SLTADEKKTI EDKIVEANKD KFPEGTGVTV ANDGKATITY PDKSVDTIEG

661    NQLVEEKTSA EKLDPTVPAK TKVDNPTSLT ADEKKTIEDK IVEANKDKFP EGTGVTVAND
```

-continued

```
 721    GKATITYPDK SVDTIEGNQL VEEKTSAEKL DPTVPAKTKV DNPTSLTADE KKTIEDKIVE

781    ANKDKFPEGT GVTVANDGKA TITYPDKSVD TIEGNQLVEE KTSAEKLDPT VPAKTKVDNP

841    TSLTADEKKT IEDKIVEANK DKFPEGTGVT VANDGKATIT YPDKSVDTIE GNQLVEEKTS

901    AEKLDPTVPA KTKVDNPTSL TADEKKTIED KIVEANKDKF PEGTGVTVAN DGKATITYPD

961    KSVDTIEGNQ LVEEKTSAEK LDPTVPAKTK VDNPTSLTAD EKKTIEDKIV EANKDKFPEG

1021    TGVTVANDGK ATITYPDKSV DTIEGNQLVE EKTSAEKLDP TVPAKTKVDN PTSLTADEKK

1081    TIEDKIVEAN KDKFPEGTGV TVANDGKATI TYPDKSVDTI EGNQLVEEKT SAEKLDPTVP

1141    AKTKVDNPTS LTADEKKTIE DKIVEANKDK FPEGTGVTVA NDGKATITYP DKSVDTIEGN

1201    QLVEEKTSAE KLDPTVPAKT KVDNPTSLTA DEKKTIEDKI VEANKDKFPE GTGVTVANDG

1261    KATITYPDKS VDTIEGNQLV EEKTSAEKLD PTVPAKTKVD NPTSLTADEK KTIEDKIVEA

1321    NKDKFPEGTG VTVANDGKAT ITYPDKSVDT IEGNQLVEEK TSAEKLDPTV PAKTKVDNPT

1381    SLTADEKKTI EDKIVEANKD KFPEGTGVTV ANDGKATITY PDKSVDTIEG NQLVEEKTSA

1441    EKLDPTVPAK TKVDNPTSLT ADEKKTIEDK IVEANKDKFP EGTGVTVAND GKATITYPDK

1501    SVDTIEGNQL VEEKTSAEKL DPTVPAKTKV DNPTSLTADE KKTIEDKIVE ANKDKFPEGT

1561    GVTVANDGKA TITYPDKSVD TIEGNQLVEE KTSAEKLDPT VPAKTKVDNP TSLTADEKKT

1621    IEDKIVEANK DKFPEGTGVT VANDGKATIT YPDKSVDTIE GNQLVEEKTS AEKLDPTVPA

1681    KTKVDNPTSL TADEKKTIED KIVEANKDKF PEGTGVTVAN DGKATITYPD KSVDTIEGNQ

1741    LVEEKTSAEK LDPTVPAKTK VDNPTSLTAD EKKTIEDKIV EANKDKFPEG TGVTVANDGK

1801    ATITYPDKSV DTIEGNQLVE EKTSAEKLDP TVPAKTKVDN PTSLTADEKK TIEDKIVEAN

1861    KDKFPEGTGV TVANDGKATI TYPDKSVDTI EGNQLVEEKT SAEKLDPTVP AKTKVDNPTS

1921    LTADEKKTIE DKIVEANKDK FPEGTGVTVA NDGKATITYP DKSVDTIEGN QLVEEKTSAE

1981    KLDPTVPAKT KVDNPTSLTA DEKKTIEDKI VEANKDKFPE GTGVTVANDG KATITYPDKS

2041    VDTIEGNQLV EEKTSAEKLD PTVPAKTKVD NPTSLTADEK KTIEDKIVEA NKDKFPEGTG

2101    VTVANDGKAT ITYPDKSVDT IEGNQLVEEK TSAEKLDPTV PAKTKVDNPT SLTADEKKTI

2161    EDKIVEANKD KFPEGTGVTV ANDGKATITY PDKSVDTIEG NQLVEEKTSA EKLDPTVPAK

2221    TKVDDPTKLT NDEKKEVEDN IRDHNTGLPE GTKIAVGDNG DTTITYPDKS VDTIEGNQLV

2281    EEKTSAEKLD PTVPAKTKVD DPTKLTNDEK KEVEDNIRDH NTGLPEGTKI AVGDNGDTTI

2341    TYPDNSVDTI PGDKVVEGKS DAAKNEPKVP GDKVKVDDPN KLTEDEKSEV VKAVEDANKD

2401    ENGKSTLPEG SKVTVGDNGD VTVTYPDGSK DTIPGDKVVE GKGTEGQTDA DKNEPKVPGD

2461    KVKVDDPNKL TEDEKSEVVK AVEDANKDEN GKSTLPEGSK VTVGDNGDVT VTYPDGSKDT

2521    IPGDKVVEGK GTEGQTDADK NEPKVPGDKV KVDDPNKLTE DEKSEVVKAV EDANKDENGK

2581    STLPEGSKVT VGDNGDVTVT YPDGSKDTIP GDKVVEGRGT EGQTDADKNE PKVPGDKVKV

2641    DDPTKLTEDE KSDVEQAIKD ANKDENGKST LPEGSKVTVG DNDDVTVTYP DGSKDTIPGD

2701    KVVEGKGTEG QTDADKNEPK VPGDKVKVDD PNKLMEDEKS DVEQAIKDAN KDENGKSTLP

2761    EGSKVTVSDN GDVTITYPDG SKDTIPGDQV IEGKSDADKN TPNVPGGDKV KVDDPTKLTD

2821    NEKNAVKDKV DEANSNLPDG TKVTVGDDGT TTITYPDGST NTISGHDLVT GKTDADKYPL

2881    NPGQAVNVVD PNHLTQAEQD QVKEAIQTTN PTAPIATITV DTAGNVQVTF ADGSTTTLQA

2941    NLHKHVTEAT TGSAIKPGVG TNGGQTKGAT STNQTATKQQ AQQHLPQTGD QPATWAMLSG

3001    LGVAFLGLLG LKKKRED;
```

-continued

Arabinogalactan endo-1, 4-beta-galactosidase  precursor (SEQ ID NO: 21)

```
   1    MEIKKHFKLY KDGKKWCCAA IATTVLGIGL AIGSPSVLAD ADTITSTSDA NNSLVKNDNT

61    SDTDSNSEST FTDTNKNSTN EKEINENKNI DSSQQINQEQ TKSNNSEEQT TPVNVKAENT

121    DIKDSIPEKS TPNSFKEING STYYYGENGD LYRNQFYNNW GRTYYFQANG ARLDNGFYNN

181    WGRTYYFGSD GARWDNRFYN NWGRTYYFQN DGSRLDNSFY NNWGRTYYFG VDGARWDNRY

241    MVKWGRAYYF GNDGALLQNQ LKSINGINYW INNEGIIPLK NQFLTANENQ LFYFDGNGSL

301    VVNKFYHNWG HTYYFGSDGA RYTDQFLNRD GKVYYFDNQG IMYQDQYYKN WGHTYYFGSD

361    GARYTDQFLN RDGKVYYFDN QGIMYQDQYY KNWGHTYYFG SDGARYTDQF LNRDGKVYYF

421    DNQGIMYQDQ YYKNWGHTYY FGSDGARYTD QFLNRDGKVY YFDNQGIMVT NQVRVIDGKG

481    YEFNDNGEAT ETSDMGQTRD TVAKEVAQAL TNQGIKGVKY DWRNTNNDYQ ELALHDIAQE

541    VAQGDTNPDK NVIEKKLQAN NLLSGKVLVV YSTDFTNDDP QKITNTFMNS YDFTNADNSV

601    LGVGADLNKN KLVIILFKPG EKAEQPQATS TISASISDIF KKAGVNVDVD NGLTKGSVVN

661    SADLGNALTN GTAELLKGDK GTIISQEVLK AIFAAFAGNT SAVEGTKNYY NGNDAYHYEF

721    WLEGQSADDK LNNFLALNKG AKYGDQLKVN YTATLVFGQE TGTNSNESKV PASERTDEQL

781    DLAYKTGTDT GLRYDSVKVE KIPGMTDDMV RGVDVSSYQA LINAGVKFYD FNGQESNLFK

841    ILKDSGVNWV RLRVWNDPYN AQGQPYAGGD NNEENLIKMA KEASDNGLKL LIDFQYSDFW

901    TDPAQQILPK AWRNLSHGEM SQEVYLYTSK ILNDLQKAGA SVKMVQIGNE ITNGAFGLYT

961    GRNGGGNWAS LWETSDGDQV AKYIQAGSSA VRRIDPTIKV AIQLETPEIN KYRGIMNVLK

1021    KNNVDYDYLG TSYYPFWSTT QGNGWYDNVD LGYGANTPVN LEAIEKMAWN EFGKRTVILE

1081    SGWLNNTNDA DGTHNSVGEN NETTNIDRYS ADPQGQVDEI EDMYNAIIAQ KGLGAFYWEP

1141    AWIPVKAGWN NWQYNKLMSN IYGSGWASQY AKGYAPDSVL YYDGKEAWGG SSWDNISLFD

1201    DHGHPLQSLN VYNGMLNGYE SPKNVKSSLS TQLVKIWNET DVIPNDGLTE GTKLSTDLFG

1261    TTQLSGNDGQ SIGNAELTKL AGRLKDGISS KVYTAANGAR YHYIYWLEGG NNKVNTFVSA

1321    NKDAKYGQPL IANYSATVVV DSEPGTQVAT SPLQIKISQV WNTVNNEEIK IDNPLKQGDL

1381    ITDKSDNAFS GILNSKDIKE ALTGEKGKDV SESTVNDVKS LLPKEVKGSK TYTTADGNQY

1441    YYDFWLASVE TSNVNYGEPI IVNYTASLKW LG;
```

Chromosome segregation protein (SEQ ID NO: 22)

```
   1    MEKTMKKKAL VATTAVAGIT LVGEVTTVHA ADNVQQPVNE QNVNQSSQEE KQAAQNLQNA

61    QSDVNTATEA NSNAQDNLAS ANNNLSNAKK AVSDQAAKVA DATKAQSDAS TKVDNDNKVV

121    ADAQQKADQA TPANIENAKQ AIEGQNKVID QDNENIKYSN TDQDKAQNTL NNAQSNEDKA

181    NATLSNKKSS QASAQNNVKQ AEDALNGTHL VEAQNAFNQA QSNVENAQSK YDQANNQLSD

241    AQKKVTTNQN DLTAKNKALD NINNQVDTDQ NNVNSNQATA DSASSATQVA QNAVDQTKQS

301    LDKVIEELNG FSENTIKVPA GAQEAYEAFI DAVDNNADQS QLDSLAKKMY DTLHQGQGTN

361    GINHFNSSKY DQNQLVDVDH LTTDQLNELT QFAADMINSA RKAWGSDKNA GTLIPTQGVS

421    EMAQQIAKGY VSDNWHISQG HDVKRVTAAA GLIGLNDAGQ FYEDASEGYV HAWPWEKDSY

481    TMDNLKEAVY DSILGMLFAD DNSGNGHMTD LLGLHVNRKE DHQYFGLSTN MCPGSYMGQL

541    HFIIVENDPA YIKDPQTFNA KGGTTKIEYI DPKVQLNQQK DILTTTLSTQ QADLATKQDA

601    LNKANQNLAN AKKQLSEDQD LQTVAQQNRD SAQKALNDAT AKVSNLQATV NSLSQDLNSA

661    KATLDQAKKT LESYTADHKA KLDNYNNAKA ALDDANKAVA EAQSAVDTAV NETKIAQNNL

721    DQKKQAVTDA QNKLANDQEY LATLKQNLAD LQNAPQNLQK AKDQLAKDQI ALDNANKDLQ
```

-continued

```
 781    NQKDSLDELN KKLEDAQVKV NEAQSAANVT KATLDQAQAK LSDAEATWKE LHNDAHRYGN

841    VVKVTPITME AGTSLPDPVI ENGFTVNTGT NQLFVSLAAI DSSNNNIPQG TKASWANRSK

901    ALTDSQNAGS YSEDILITFP DNSTVTVPVD LTVTAKKITE DQKATEGGYH IVNGSVVDKQ

961    NNLVSGWTVK NGQMVDPEGN VIKTTMSTAQ GVTIEKNNSK SGNTKTNMIQ TSLTIANNKA

1021    TTNKDNQLPQ TGNYNNNTKV LGLAGIALAS ALTMFGYKKR QHN;
```

D-gamma-glutamyl-meso-diaminopimelic acid endopeptidase CwlS precursor
(SEQ ID NO: 23)

```
   1    MKSTTKKILA SSLGVAGAMA MGTVTAKADT TVTVNAGDSL NGIAQKYNVS ADDIATANHL

61    QNKELIFVGQ KLTIPTKDKN ETPANNAEKK DQASKNSQSL QDSVNKAMSY LGTPYVWGGN

121    KPGGFDCSGL VQYCYGIPQR TTYEQQALGP HIHDNVLNAP YGALVFYGSD DAPYHVAISL

181    GDGRIIQAPN ENETVKITDQ QYFPGNYYVV MH,
```
and

Chromosome Partition Protein Smc
(SEQ ID NO: 40)

```
   1    MNKANQKVAD DTTAVNNKQT DVNNAAEAKK NADEALKNAN DAQTSAQKNK DAKQAIADEA

61    SVALADANTA VKDAQAKVDA INDKLANFNT ITLPAGYKDD LIAYYNYFGN SNYNQDEANN

121    LAQDLLKYRD QAMSQNKFKD NLSDDRVVDI DNLNSTDRAE LSQFVASLIN QVRTQMGTNL

181    VISSPAADDY AEQVSQNYNK DNWNSADNGK HDQSALNNAT DQLNISWNGE NMGLDQSIFT

241    TDYTVLTDGT KLPTGNKQTI NDLKHLIYDD FISMMFDDAD SAWGHATNFA GIDNFAAEKQ

301    AVGFSLDKFY NTHYDLVEAN QKVEENSYTL PSINALTQKL ADAKDDLSIK QTDQASKQKA

361    NDDAQNALSS ANQVLVAAQN DVKDKTATAQ EANDNLTTAQ NDLATLQNQL SADQANQKQA

421    QTTFDSFDAD LATKQANLQK ATDSLKAEQG RLAIAQADLD NANKALSDAN NNLAQKKQVV

481    ENDNETLKVD NDKLVQLQNN LSDLQNAPKL LAAAKEQVAT AQKALADAQE AYNVANDKLT

541    SLKQTAAGTT TNVSKAQQAL AEAKNNEDAA KEVLDQAQQA LTELRQKEAL AKQVAEEQAK

601    LAAEKEAKDN GYHIENNQVV DAKGNSVNGW TVKGNQIVSP TNATVDPAVS VTTNVNVDSK

661    GQVQPQTSVT ANSVKTVAAT ESANPVATTT VQTREQYKQQ LKSNNQLPQT GNNDSAVLSL

721    AGVALAAMLS LFGIKKREY.
```

A person of skill in the art would recognize that, because of the redundancy of the genetic code, multiple nucleic acid sequences could encode the above peptides.

Example 5. Expression Cassettes

Based on the information provided in the previous examples, expression cassettes that produce high levels of secreted target biomolecules can be designed. For example, one of these expression cassettes (CwlS_C2; SEQ ID NO: 23) has evolved to deliver endopeptidase (cell wall hydrolase) to the cell wall. That endopeptidase plays an important role in cell division and separation. Replacing the endopeptidase with a heterologous coding region would result in the secretion of desired target biomolecules, such as anti-infective biomolecules that target pathogenic bacteria. A specific example is that the novel mersacidins disclosed herein could be expressed at high levels by exchanging the native mersacidin promoter with a strong promoter (Example 4; SEQ ID Nos: 14-19) and optionally a strong secretion signal (Example 4; SEQ ID Nos: 20-23).

Expression vectors are designed and synthesized with different combinations of some or all of the following components: an origin of replication for replication in *L. reuteri* (e.g. from the high copy number plasmid; SEQ ID NO: 8), an origin of replication for replication in *E. coli*, a drug resistance marker for selection, a strong promoter for expression in *Lactobacillus*, a signal sequence for secretion, a heterologous coding region encoding a desired biomolecule, an expressed peptide tag for detection, a cell-wall anchor for secretion, and terminators for transcription termination.

Figure 3A:
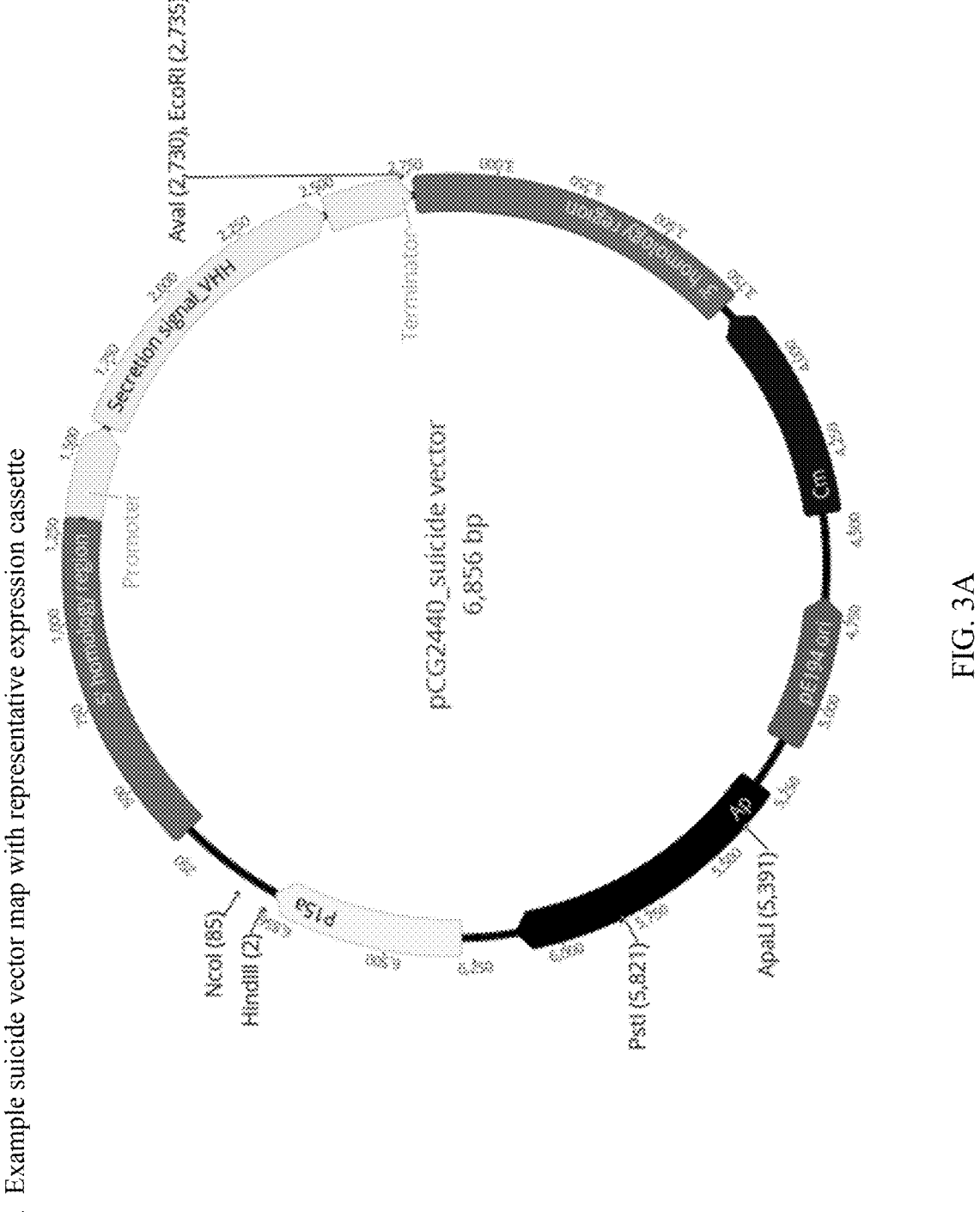
FIG. 3A and 3B. Chromosomal integration of an expression cassette. A. A non-limiting example of a suicide vector map with a representative expression cassette. B. A map of possible chromosomal integration sites.

Alternatively, a heterologous coding region encoding a desired biomolecule could be integrated into the chromosome of the genetically-modified microorganism. Chromosomal integration of the expression cassette (a strong promoter for expression in *Lactobacillus*, a signal sequence for secretion, a heterologous coding region encoding a desired biomolecule, terminators for transcription termination, and optionally an expressed peptide tag for detection and a cell-wall anchor for secretion) is accomplished with a suicide vector. The suicide vector comprises an origin of replication for replication in *E. coli*, a drug resistance marker for selection, and an expression cassette flanked by nucleic acids homologous to a specific region of the chromosome. An example of such a suicide vector is presented in FIG. 3A.

Figure 3B:
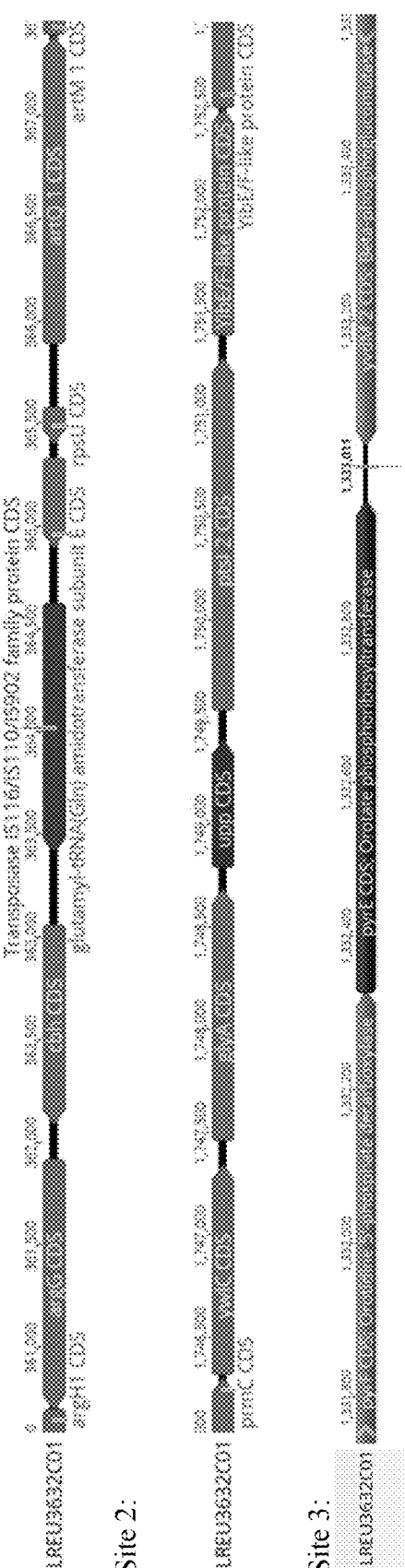

For chromosomal integration, *L. reuteri* genes may be interrupted by the insertion of the expression cassette. Maps of these chromosomal loci are presented in FIG. 3B. Two genes which may be interrupted are Transposase and Uracil phosphoribosyl (UPP) transferase. Chromosomal integration may also be accomplished within the pyrE gene locus, and pyrE deletion and subsequent re-insertion may serve as a selection marker for integration (Sakaguchi et al., *Biosci-*

*ence of Microbiota, Food and Health*, 32: 59-68 (2013)). A modified pyrE gene may also be used for biocontainment of recombinant bacteria, as the recombinant bacteria cannot survive in an environment absent metabolic supplements.

Example 6. Enzymatic Genes for Inclusion in Expression Cassettes

An expression cassette would comprise a heterologous coding region encoding a desired biomolecule. The desired biomolecule may be a biomolecule with anti-infective activity. The anti-infective activity could be lysis of pathogenic bacteria by a lytic enzyme, for example from a bacteriophage, with specificity to a certain genus of pathogenic bacteria.

Lytic enzymes may include PlyCM, a lytic enzyme targeting *Clostridium perfringens*, encoded by a sequence of:

```
                                                        (SEQ ID NO: 24)
   1    ATGGAAAGCC GTAATAACAA TAACCTGAAG GGCATCGATG TGAGCAACTG GAAGGGCAAC

61    ATCAATTTTC AAAGCGTCAA AAATGACGGT GTTGAAGTTG TTTACATTAA GGCAACCGAA

121    GGCAACTACT TCAAAGACAA ATATGCTAAG CAAAACTACG AGCGCGCTAA AGAACAGGGT

181    CTGCGTGTGG GCTTCTACCA CTTTTTCCGC GCAAACAAAG GTGCCAAAGA TCAGGCGAAC

241    TTCTTCGTGA ATTACCTGAA CGAAATCGGT GCGGTCAATT ATGACTGTAA ACTGGCACTG

301    GACATCGAGA CTACCGAAGG CGTCGGTGCG CGTGACCTGA CCTCTATGTG CATCGAGTTC

361    CTGGAAGAGG TGAAGCGTAT TACGGGTAAG GAAGTTGTCG TGTACACCTA TACCAGCTTC

421    GCGAACAATA ATCTGGATTC CCGTCTGTCT AGCTATCCGG TGTGGATTGC GCACTATGGC

481    GTCAACACCC CGGGTGCGAA CAATATCTGG AGCGAGTGGG TGGGTTTCCA GTACAGCGAG

541    AATGGCTCCG TCGCCGGTGT CAGCGGTGGC TGCGATATGA ACGAATTTAC CAATGGTATC

601    TTTATTGACT CGAACAATTT CACGTTGGAC AATGCAACGA CCAAAAATGT TAGCATTAAG

661    CTGAACATTC GCGCCAAGGG TACGACCAAC AGCAAAGTTA TTGGTAGCAT TCCGGCGAAC

721    GAAAAGTTTA AGATCAAATG GGTTGATGAA GATTACCTGG GTTGGTATTA CGTTGAGTAT

781    AACGGTATCG TGGGTTACGT TAACGCCGAT TACGTCGAGA AACTGCAAAT GGCGACCACG

841    CATAATGTTA GCACCTTTCT GAATGTACGC GAGGAGGGTT CCTTGAATAG CCGTATTGTG

901    GACAAGATCA ACACTGGCGA CATCTTTCGT ATTGACTGGG TTGATAGCGA TTTCATTGGT

961    TGGTATCGTG TGACGACGAA AAACGGCAAG GTCGGCTTTG TTAATGCAGA GTTTGTGAAA

1021    AAGTTGTAA;
```

PlySS2, a lytic enzyme targeting *Streptococcus suis* and *Staphylococcus aureus*, encoded by a sequence of:

```
                                                        (SEQ ID NO: 25)
   1    ATGACAACAG TAAATGAAGC ATTAAATAAT GTAAGAGCTC AGGTTGGGTC CGGTGCGTCT

61    GTTGGCAACG GCGAATGCTA CGCTTTGGCT AGTTGGTACG AGCGCATGAT TAGTCCGGAT

121    GCAACTGTCG GACTTGGCGC TGGTGTGGGC TGGGTCAGCG GTGCAATCGG CGATACAATC

181    TCTGCCAAAA ACATCGGCTC ATCATACAAC TGGCAAGCTA ACGGCTGGAC AGTTTCCACA

241    TCTGGTCCAT TTAAAGCAGG TCAGATTGTG ACGCTTGGGG CAACACCAGG AAACCCTTAC

301    GGACATGTGG TAATCGTCGA AGCAGTGGAC GGCGATAGAT TGACTATTTT GGAGCAAAAC

361    TACGGCGGGA AACGTTATCC CGTCCGTAAT TATTACAGCG CTGCAAGCTA TCGTCAACAG

421    GTCGTGCATT ACATCACACC GCCTGGCACG GTCGCACAGT CAGCACCCAA CCTTGCAGGC

481    TCTCGTTCCT ATCGCGAGAC GGGCACTATG ACTGTCACGG TCGATGCTCT CAATGTTCGC

541    AGGGCGCCAA ATACTTCAGG CGAGATTGTA GCAGTATACA AGCGTGGTGA ATCATTTGAC

601    TATGATACTG TCATCATCGA TGTCAATGGC TATGTCTGGG TGTCTTACAT AGGCGGCAGC

661    GGCAAACGTA ACTACGTTGC GACGGGCGCT ACCAAAGACG GTAAGCGTTT CGGCAATGCT

721    TGGGGTACAT TTAAATAA;
``` and CP025C, a lytic enzyme targeting *Clostridium perfringens*, encoded by a sequence of:

```
                                              (SEQ ID NO: 26)
  1 ATGTCGAAGA TTTTTGGTTT AGATGCGGGT CATTGTACGA GCGGCGCAGA TACGGGTGCG

61 CAGGGCAATG GTTACAAAGA ACAAGACTTG ACCCGTCAAGT TGTTACCTA TCTGAGCGAA

121 TACTTGGAGA AAGAGGGCCA CACTACCAAG TACTGCCATT GCAATAGCGC GAGCACGGTT

181 AACGAATCCC TGCGCTATCG TGTGAACAAA GCCAACTCCA TCGGTGTCGA CTACTTCGTG

241 AGCATCCACC TGAACGCCGG TGGCGGCGTT GGTACCGAAA CGTACATCTG CGCGCGTGGC

301 GGCGAGGCCG AGCGCGTGGC GAAACGCGTC AATTCTAAAC TGGTGCAGTA CGGTTATCGT

361 GACCGTGGTG TCAAGGTTGG TAATCTGTAT GTGATTAAGA ACACCAATGC ACCGGCTATC

421 CTGGTTGAGA TCTGTTTCAT TGACAGCAGC AGCGATGTGG CAAAGTTTAA CGCGAAGGCA

481 ATCGCGAAAG CGATTGCTGA GGGTCTGCTG GATAAAACCA TTGGTGAAGT CGAGAATAAG

541 TAA.
```

Additionally, two of the three productive prophages found in *L. reuteri* strain 3632 contain putative lytic enzymes. These lytic enzymes may be used to target pathogenic bacteria or to control environmental spreading of genetically-modified *Lactobacillus*. These two lytic enzymes are: an N-acetylmuramoyl-L-alanine amidase sle1 precursor from prophage locus 1 with a nucleic acid sequence of:

```
                                                    (SEQ ID NO: 27)
   1    ATGCGTAATC AATTCATCGA TGTTTCAAGT TATCAACCAG ATACTGTTGC CTTTTTCCAA

61    GCTGCTAAAG CTCAGGGTGC ATTAGGGGTC GTTGTTAAGT TAACGGAAGG GTCCGAAGAT

121    GGTTCGGCTT ATGTTAATCC ACGTGCGGCC GCTCAAATTC GTAATGCCTT AGCGGTTGGC

181    TTGCGCGTTT CCTGTTACCA CTTTGCTCGT TATACATCAG TGACTGATGC ACAAAATGAA

241    GCTCGATTCT TCGTTAAAAT CGCTAAGCAA TTTGGTATGT ATGACGATAC TTTGATGATT

301    GATGATGCGG AAGTTCATTC AACTGCAGAT TATCAATCAG TATCCTTAGC CTTTCTTCAA

361    GAAGTAGAAG CTCTTGGTTA CAAGAATACT GGGATTTACT CCATGAAGTC CTTCTTCACT

421    GGCGGTATTC TTAATTCACA TGGCTTTGAT TCCCGGAAGA TTTGGATTGC TGGCTATGGT

481    GTGACTGAAC TGGGGATTGA TAATGCAAGT GCTTGGCAAT ATTCTGATCA TAGCATCATG

541    GGAATTGATA CTAGTTATGA CTTTGACGGT GCCTTTACGA CTGGTTTAGT ATCAGGCAAT

601    GTTCCGCAAG CTGTTATTCC AGCACCACAG CCGGTTCAAC ATATTGGTCA CCCAGCTACT

661    GGAACCTACA TTGTTCAGCC GGGCGATACA TTGAGTGGAA TTGCAGAAAA ATACGGGACT

721    ACTTATCAGA ACCTAGCAGC AATCAATGGT ATTGGTAATC CAAACCAGAT CAATGTCGGC

781    CAAGTCCTCA AAGTCACCGG AAAAGTATCA AACGAAAATA CTTACTTTGT TCAATCAGGC

841    GATACGTTAT CCGGAATTGC CACCAAATTC GGCACCACTG TCTCAGACCT CGTAAGCCGT

901    AATCACATTA CTAACCCGAA TGTGATCTAC GTTGGGCAAA AACTCTACTT AGCCGGCAAC

961    GGACAATCCA ATGCTTATAC TGTCCAAGCA GGGGACACAC TAAGCGGAAT TGCGGCTAAG

1021    TTTGGCAAGA CCTGGCAAGC ATTAGCTCAA AAGAATGGCA TCGCAAATCC TAATATGATT

1081    TTCATTGGTC AAACAATTCA GATTTAA,
``` and a Peptidase family M23 from prophage locus 6 with a nucleic acid sequence of:

```
                                                (SEQ ID NO: 28)
  1 GTGTACCGAA TTATTGGTTA TAATGAACCA ACAGATAAAG CAGGATTTAT TGTACTGGAT

61 CCCCGAGTTA ATCGTCATAT TAGTTCGGGA AAACTCACGC TTAAAGAATC TAATATTGAT
```

-continued

```
 121 GATTTGACTA TTACGGTTAA TCAAGCAAGT CCATTATGGG ACAACGTAAG GCCTTATCAT

181 ACTCATGTTA ACGTTTATGA TGATAATGAA CTTATTTTTC GTGGACGAGC TATCAAACCT

241 AAAAAGTCGA TGGAAGAAAG CGGACAATTC ATTCGTGAAT ATGTTTTTGA AGATATTGAA

301 GCATATCTCA TGGATAGCAC CCAAAGATTT TATGAAGGTG TTGGTCAAAC GCCCAAAGAA

361 TTTTTACAAA CTTTAATCGA TGTTCATAAT TCACAGGTTC CTGACTATAA AAAGTTTCAA

421 GTCCGGAATG TAAATGTCAC TAATAATAAG GATGACCAAT ATCGACAAAT TGATTATCCC

481 AAAACTAGCG ATGCTATTAA TGATAAATTA GTTAAATCTC TTGGTGGTTA TATTGTGACT

541 ACTTACAACG CTAACGGAAT AAACTACATT GACTACTTAA CGGATATTGG GGTTGATCAT

601 AAAGATGATA CTCCTATTCA GTTAGCTAAA AATATGAAGT CTGCAAGTAT GCAAATTGAT

661 CCTACTAAGG TGATTACAAG ACTGATTCCA CTGGGAAAGA CACTAGAACC ATCAAAAGTT

721 GATGTAAGTG ATGATGATGG AGAGGGCGGT TCTGGATCAT TAGATAGCCC TGAAGAATTT

781 TGTAAATCAG AAATTAATGC TACTTGGGGT AGTGATATTA ATAATATGAA ACAAGATTTT

841 GCCGCTCGTT CTTCGAGAGT TCGGGCTTGG GGAGTGGACG TTAATCGTTT ATATGATGTG

901 GTGAAAAATG CTGGAGTAAG TCCTGAATGG TTCTTTGCTT ATGAACTTCA AGAACAAGGA

961 ACTTACTATG GATGGCTTAA CCATACTTAT CGACACGGTG ATGCGTATAG TGATGCGCAA

1021 TCTGTTTGTG AGTGGATTAA AAATTGTTCA AATAGTAATT CCATTAATCC AGCATGGAGC

1081 GCACCGGAAG GATCAATGGC GCCGAATCAA GCATTAGCGG ATAAATGGAA TCAAGAGTTT

1141 GGAAAAGGTA CTATTGGCCG CGTTTATTTA CAAGGGACTG CCGCTGCTGT TTGGGATTTA

1201 GCTGGTCAAA CGCCTAATCC AGCTATTGGA AAGCCAATTA GTGGATGCAT TTCTTGTATT

1261 AAACGTTGGG GTGGTCATTC TAATGCAGCT GGTGGTACAT GGGGATGGCC TTTTCCTGAT

1321 GTTGGGGAAG GTCATTTTTC TCAAGTTCAG AGTTTCGGAA ATGATGGCGG ATATCGTCAA

1381 AATAGTTATC ACGATGGTGT GGATTTTGGA TCAATAGATC ATCCTGGTAG AGAAGTGCAT

1441 TGTATTCATG GTGGAACGGT AACTATCAAA TCAGCTATGG GTGGCTTAGG TAATTTTGTG

1501 GTTATTCATA CGCCGGAAGG ATTCAATATC GTTTATCAAG AAGCTTTTAG TTCTCCCTCT

1561 AATATTATTG TTAGTGTTGG GCAAAAAGTA AAAACTGGTG ATGTAATTGG ATATCGTGAT

1621 ACAGACCATG TTCATATTGG CGTAACTAAG CAAGATTTTT ATCAAGCAGT TCGAAATTCT

1681 TTTTCTCCTG CAGGTGGTTG GCTAGATCCA GTAAAACTAA TTAAAGAAGG TGGCGATGGG

1741 TCTAAACCAC AAGAAGGAAA GAAAGATCAA ACTGTTGATA ATAGTAATGC TGCACGTCCT

1801 AAATTAACCA TTACTACTGT CAATAACGGT AGAGACTATA TTGATATTCC TGATTTACAA

1861 AAAGAATTCG GTATTATTGA GGGAACTGTT GAATTTGATA ATGTAGATGA TCCGAATGTT

1921 TTAATGCAAC AAGCTCAAAC ATGGATAAAG GCTCAAAGAA TACCTCAAAG TTGGGAAGTT

1981 ACAGCTTTAG AATTACATAT GACAAACTTC AAATCTTTTA AGGTTGCTGA TAGGTACATG

2041 TTTATTAATC CAAATGTTGC AAAACCCCAA TTATTACGAA TTACTCAAAA AGAAATTGAT

2101 TTACTAAAGC CCCATGCGTC TTCATTAACG ATTGGTGATA AGACGATGGG GCTTACTGAT

2161 TATCAGTTAG AAAATCAAGT CAATTTTCAA CAATTTAAGG AAATTCGAGT GATGGTTAAT

2221 CAGGTTGTCC AAACCCAAGA GCAATCTGCT AATAACAATA ATAAGGTTAT GCAAAATTTT

2281 GCTAGTAGTG CTGATCTTGC ACAAATGAGA CAGGATCTAA GAAATCTTCA AGATGATAAC

2341 GATCGTGCTC GCAAAGGAAT GGTTTCCTTA GAAGAATTCA ATAAACTAAA GGAACAAGTA

2401 GAAAAACTAA CAACAGGAGG CGATGATAAT GGCAAGTGA.
```

Example 7. Single Chain Antibodies and their Activity

An expression cassette would comprise a heterologous coding region encoding a desired biomolecule. The desired biomolecule may be a biomolecule with anti-infective activity. The anti-infective activity could be inhibition or neutralization of toxins produced by pathogens. The inhibition or neutralization could be accomplished with single chain antibodies. *Lactobacillus* has been described as an expression system for single chain antibodies directed against host attachment factors. WO2012/019054. Toxins to be targeted by single chain antibodies include *C. perfringens* alpha toxin and NetB.

Camelid heavy-chain only (VHH) antibodies against *C. perfringens* alpha toxin and NetB are prepared by QVQ Holding BV (Utrecht, NL). Briefly, two llama calves each are immunized with either recombinant alpha toxin or NetB variant W262A. Neither of these immunogens are haemolytic. The immunized llamas are boosted twice with toxin peptides. On days 44 and 72 after the primary immunization, blood samples are taken and RNA isolated for phage library construction. Phage libraries are screened for binding activity towards each of the two toxins. The candidate antibodies are sequenced and further screened in bioassays as described below.

Alpha toxin causes membrane damage to a variety of erythrocytes and cultured cells. It is preferentially active towards phosphatidylcholine (PC or lecithin) and sphingomyelin (SM), two major components of the outer leaflet of eukaryotic cell membranes. The N-terminal domain possesses full activity towards phosphatidylcholine but lacks the sphingomyelinase activity and is not haemolytic or cytotoxic. The C-terminal domain is devoid of enzymatic activity, but interaction between the N- and C-terminal domain is essential to confer sphingomyelinase activity, haemolytic activity and cytotoxicity to the toxin. Although alpha toxin is a potent haemolysin, the lysis of erythrocytes is only seen after intravenous administration of toxin in experimental animals or in cases of clostridial septicaemia.

The inhibitory capacity of the VHH antibodies directed towards alpha toxin on the alpha toxin lecithinase activity is determined by measuring its effect on egg yolk lipoproteins. Fresh egg yolk is centrifuged (10,000×g for 20 min at 4° C.) and diluted 1:10 in PBS. The ability of the VHHs to neutralize the alpha toxin activity is assessed by pre-incubating a two-fold dilution series of the VHHs (two wells per dilution, 5 µM starting concentration) with a constant amount of alpha toxin (either 5 µg/ml recombinant alpha toxin or $3.33 \times 10^{-4}$ U/µl alpha toxin from Sigma, P7633) for 30 minutes at 37° C. prior to the addition of 10% egg yolk emulsion. As a positive control, serum from calves immunized with the recombinant alpha toxin is used, starting from a 1:4 dilution. After incubation at 37° C. for 1 hour, the absorbance at 650 nm ($A_{650}$) was determined. Alpha toxin activity is indicated by the development of turbidity which results in an increase in absorbance.

The control serum is able to neutralize the lecithinase activity of both the commercial and the recombinant alpha toxin. An eight-fold dilution of the antiserum (corresponding to 3.12% serum) is able to completely neutralize the alpha toxin lecithinase activity of the recombinant alpha toxin, whereas only the highest dilution of the antiserum (corresponding to 25% serum) is able to completely neutralize the lecithinase activity of the commercial alpha toxin. Considerable difference in inhibitory capacity is observed between five candidate VHH antibodies. VHH EAT-1F3 had no effect on the lecithinase activity of either of the alpha toxins. The neutralizing capacity of EAT-1A2 and EAT-1C8 is very similar and is the same for both the recombinant and commercial alpha toxin. The maximal inhibitory capacity is preserved until a 32-fold dilution (0.16 µM VHH) of the VHHs. However, both EAT-1A2 and EAT-1C8 are unable to completely neutralize the lecithinase activity, resulting in 40% to 50% residual lecithinase activity. Two other VHHs, EAT-1F2 and EAT-1G4 show a difference in neutralizing capacity towards the recombinant and the commercial alpha toxin. EAT-1F2 has a high neutralizing capacity towards the recombinant alpha toxin but is unable to completely neutralize the commercial alpha toxin, resulting in about 25% residual lecithinase activity. In contrast to EAT-1F2, EAT-1G4 neutralizes 100% of the lecithinase activity of the commercial alpha toxin, but is less capable of neutralizing the recombinant alpha toxin.

Neutralization of the alpha toxin haemolytic activity by the VHH antibodies directed towards alpha toxin is determined by measuring its effect on sheep erythrocytes. Similar to the inhibition of the alpha toxin lecithinase activity, the ability to neutralize the haemolytic activity is assessed by pre-incubating a two-fold dilution series of the VHH antibodies (two wells per dilution, 5 µM starting concentration) with a constant amount of alpha toxin ($6.25 \times 10^{-5}$ U/µl alpha toxin from Sigma, P7633) for 30 minutes at 37° C. prior to the addition of 1% sheep erythrocytes. As a positive control, serum from calves immunized with the recombinant alpha toxin is used, starting from a 1:4 dilution. After incubation at 37° C. for 1 hour, the plates are centrifuged to pellet intact red blood cells. The supernatant is transferred to a new 96 well plate and the $A_{550}$ is determined. Alpha toxin activity is indicated by the increase in absorbance due to release of haemoglobin from the erythrocytes.

The inhibitory capacity of the VHH antibodies towards the alpha toxin haemolytic activity is determined using the commercial alpha toxin only, as the recombinant alpha toxin shows no haemolytic activity. Up to a 16-fold dilution of the control serum (corresponding to 1.56% serum) completely inhibits the alpha toxin haemolysis. To the contrary, none of the candidate VHHs has an effect on the haemolytic activity of alpha toxin. Because the control serum contains polyclonal antibodies, whereas the VHHs are monoclonal, the combined effect of all 5 VHHs towards alpha toxin is determined (1 µM of each VHH in the highest dilution, corresponding to 5 µM VHHs in total). Combining the VHHs has no effect on the alpha toxin haemolysis.

Based on the above results, EAT-1F2 and EAT-1G4 are selected for further characterization. The peptide sequence of EAT-1F2 is:

```
                                     (SEQ ID NO: 29)
EVQLVESGGGLVQAGGSLRLSCAGSGRTGSLYSMGWFRQAPGKEREFVA

AITWRPSSTYYADSVKGRFTISRDDAKNTVYLQMNSLKPEDTAVYFCAA

RPRGGLSPTPQAYDYWGQGTQVTVSSAAASGSLEQKLISEEDLNGAAHH

HHHHGAA,
``` and the peptide sequence of EAT-1G4 is:

```
                                     (SEQ ID NO: 30)
EVQLVESGGGLVQPGGSLRLSCAASGSIATINDMGWFRQAPGKQRDWVAT

IVSDGSTAYADSVKGRFTISRDNAKNTVYLQMNSLKPEDTAVYYCSARRH

YGQGTQVTVSSAAASGSLEQKLISEEDLNGAAHHHHHHGAA.
```

An R27H mutant of EAT-1F2 (SEQ ID NO: 49) may also be generated to improve protease resistance of the antibody.

A person of skill in the art would recognize that, because of the redundancy of the genetic code, multiple nucleic acid sequences could encode the above peptides. However, an exemplary sequence encoding EAT-1F2 could be:

```
                                            (SEQ ID NO: 31)
  1    GAGGTGCAGC TCGTGGAAAG TGGCGGAGGT CTTGTTCAGG CTGGGGGATC GCTCCGTCTG

61    AGCTGTGCGG GGTCTGGCAG AACAGGTAGT CTCTATTCCA TGGGTTGGTT TCGGCAGGCC

121    CCGGGTAAGG AGCGGGAGTT CGTTGCAGCG ATTACGTGGA GGCCCAGCTC TACCTACTAC

181    GCGGACAGCG TAAAGGGACG ATTCACCATT AGTAGAGACG ACGCAAAGAA TACTGTATAT

241    TTGCAGATGA ATTCGTTGAA GCCTGAGGAC ACCGCTGTCT ATTTTTGCGC GGCGCGACCG

301    AGGGGCGGTC TCTCCCCGAC ACCTCAAGCA TATGATTACT GGGGACAAGG GACCCAAGTC

361    ACTGTATCCA GTGCGGCCGC GAGCGGCAGC CTTGAACAAA AGCTGATAAG CGAGGAGGAT

421    CTCAATGGTG CTGCACATCA TCATCACCAT CACGGGGCAG CG,
``` and an exemplary sequence encoding EAT-1G4 could be:

```
                                            (SEQ ID NO: 32)
  1 GAAGTTCAGC TTGTAGAGTC CGGTGGGGGT CTTGTACAGC CCGGCGGGAG CTTGCGACTC

61 TCATGCGCTG CTTCCGGAAG CATTGCGACA ATAAATGATA TGGGTTGGTT TAGACAAGCC

121 CCCGGGAAGC AGCGTGACTG GGTCGCGACT ATTGTGAGTG ACGGCAGCAC GGCTTATGCG

181 GACTCAGTGA AAGGGAGATT TACGATTTCG CGAGATAACG CGAAAAACAC TGTATACCTG

241 CAGATGAATT CACTCAAGCC GGAAGATACA GCTGTGTATT ATTGTTCTGC CCGACGGCAC

301 TACGGACAGG GGACCCAGGT CACAGTCTCG AGCGCTGCCG CCAGTGGGTC ACTCGAGCAG

361 AAGCTGATAT CAGAGGAGGA CCTTAACGGT GCGGCGCACC ATCACCACCA TCATGGTGCG

421 GCG.
```

NetB is a heptameric beta-pore-forming toxin that forms single channels in planar phospholipid bilayers. The NetB activity is influenced by membrane fluidity and by cholesterol, which enhances the oligomerization of NetB and plays an important role in pore formation. NetB has high haemolytic activity towards avian red blood cells.

Neutralization of the NetB haemolytic activity by camelid VHH antibodies directed towards NetB is determined by measuring NetB-mediated lysis of chicken erythrocytes. The ability to neutralize the NetB haemolytic activity is assessed by pre-incubating a two-fold dilution series of the VHH antibodies (two wells per dilution, 5 μM starting concentration) with a constant amount of NetB toxin (20 μg recombinant NetB) for 30 minutes at 37° C. prior to the addition of 1% chicken erythrocytes. The non-toxic NetB variant W262A is included as a negative control as this variant displays no haemolytic activity. Positive control serum from rabbits immunized with the recombinant NetB (wild type NetB) is used, starting from a 1:4 dilution. After incubation at 37° C. for 1 hour, the plates are centrifuged to pellet intact red blood cells. The supernatants are transferred to a new 96 well plate and the $A_{550}$ is determined. NetB activity is indicated by the increase in absorbance due to release of haemoglobin from the erythrocytes. The control serum is able to neutralize the haemolytic activity of NetB. VHH antibodies ENB-1F4 and ENB-1F10 have no effect on the NetB haemolysis. ENB-1B9 has intermediate inhibitory capacity, while ENB-1D11 and ENB-1A4 are able to neutralize the NetB haemolysis up to a 4- to 8-fold dilution (1.25 μM-0.625 μM VHHs).

Based on the above results, ENB-1A4 and ENB-1D11 are selected for further characterization. The peptide sequence of ENB-1A4 is:

```
                                            (SEQ ID NO: 33)
EVQLVESGGGLVQAGGSLRLSCAASGSIFSTNVMGWYRQAPGKQREFVAG

ITIGGTARYPDSVKGRFTISRDNTQNTVYLQMNNLKPEDTAVYYCNAVLP

SDQRRWSWGQGTQVTVSSAAASGSLEQKLISEEDLNGAAHHHHHHGAA,
``` and the peptide sequence of ENB-1D11 is:

```
                                            (SEQ ID NO: 34)
EVQLVESGGGLVQTGGSLRLSCTASGTIDMTYGLIWYRQAPGKERELVAS

IRRDGRTNYADSVKGRFTISIDNAKNSIHLQMNSLKPDDTARYYCNSPYH

ALWGQGTQVTVSSAAASGSLEQKLISEEDLNGAAHHHEIHHGAA.
```

An R56H mutant of ENB-1D11 (SEQ ID NO: 50) may also be generated to improve protease resistance of the antibody.

A person of skill in the art would recognize that, because of the redundancy of the genetic code, multiple nucleic acid sequences could encode the above peptides.

However, an exemplary sequence encoding ENB-1A4 could be:

(SEQ ID NO: 35)
```
  1    GAGGTACAAC TGGTTGAGAG TGGGGGTGGT TTGGTGCAAG CCGGAGGTTC CTTACGTTTG

61    TCTTGCGCGG CTAGTGGGAG CATCTTTTCA ACAAACGTAA TGGGGTGGTA CCGCCAAGCC

121    CCAGGTAAGC AGCGGGAATT TGTGGCCGGG ATAACGATCG GAGGAACTGC GAGGTATCCT

181    GATAGTGTGA AAGGGCGTTT CACAATTAGT CGAGATAATA CACAGAATAC TGTCTATCTC

241    CAAATGAATA ATCTCAAGCC CGAAGACACA GCAGTTTATT ATTGTAATGC CGTTCTCCCC

301    TCTGATCAGC GTCGATGGAG CTGGGGACAA GGCACCCAGG TTACGGTTAG CAGCGCGGCA

361    GCGTCTGGTT CGCTCGAGCA AAAGCTCATA TCTGAGGAGG ACCTGAACGG GGCAGCCCAC

421    CATCACCACC ATCACGGAGC AGCT,
``` and an exemplary sequence encoding ENB-1G4 could be:

(SEQ ID NO: 36)
```
  1GAGGTACAGC TGGTGGAGTC CGGCGGTGGT TTGGTGCAAA CCGGGGGTAG TCTGCGGCTT

61AGTTGCACGG CGTCTGGGAC AATAGACATG ACTTATGGTC TCATATGGTA CAGGCAAGCG

121CCTGGGAAAG AGAGGGAACT CGTTGCGAGT ATCAGAAGGG ACGGCCGCAC AAATTACGCT

181GATTCAGTGA AAGGGCGCTT CACTATCTCG ATCGATAATG CGAAAAACAG TATTCACCTT

241CAAATGAACT CCCTTAAGCC CGATGATACC GCCAGGTATT ATTGCAACAG CCCATATCAC

301GCACTTTGGG GTCAGGGTAC GCAGGTAACA GTGTCTAGTG CGGCAGCCTC TGGTAGTTTG

361GAGCAAAAGT TGATAAGTGA GGAGGACTTA AATGGGGCGG CACATCACCA CCACCATCAT

421GGGGCGGCT.
```

Example 8 Multifactorial Expression Cassettes

Expression cassettes may be designed and synthesized with different combination of the following components: promoter for expression, signal sequence for secretion, cell-wall anchor for secretion, at least one heterologous coding region encoding a desired biomolecule, and terminators for transcription termination. An expression cassette may contain multiple heterologous coding regions.

One representative expression cassette for the expression of camelid antibodies is:

(SEQ ID NO: 37)
```
  1    AAATTAAAAG GCTGGATTTT TTCGGCCTTT TTTTAGTGCA AATAATTATT TTTTACGTAT

61    TTATATTATA GGGCTAATCA CTAAACTAAT AATTAGTGGT TGAAGCGCTG AAAATTTTCT

121    GCTATTTTAT TAATAGTTTG ATAATAAAAT AATGATATTT AATATAAAGA GGGATAAACG

181    AAATAATGAA ATCAACAACA AAGAAAATTC TTGCATCGTC GTTAGGGGTA GCTGGCGCAA

241    TGGCAATGGG CACGGTAACT GCAAAGGCTG ATACGACCGT TACGGTCAAT GCTGGCGATA

301    GTTTGAATGG GATTGCTCAA AAGTATAATG TTAGTGCGGA TGATATTGCA ACCGCTAATC

361    ACTTGCAAAA TAAAGAGTTG ATTTTTGTGG GACAAAAGTT GACAATTCCA ACCAAAGATA

421    AAAATGAAAC AGAAGTTCAA TTAGTTGAAA GTGGTGGTGG TTTAGTTCAA CCAGGTGGTA

481    GTTTACGTTT ATCATGTGCT GCAAGTGGTT CAATTGCAAC TATTAATGAT ATGGGTTGGT

541    TTCGTCAAGC ACCAGGAAAG CAACGTGATT GGGTTGCTAC TATTGTTAGT GATGGTTCAA

601    CTGCTTATGC TGATAGTGTT AAAGGTCGTT TTACTATTTC ACGTGATAAT GCTAAGAATA

661    CTGTTTACCT TCAAATGAAT AGTCTTAAGC CAGAAGATAC TGCAGTTTAC TATTGTTCAG

721    CTCGTCGTCA TTATGGTCAA GGTACTCAAG TTACTGTTAG TTCAGCTGCA GCTAGTGGTT

781    CATTAGAACA AAAAATTAATT TCAGAAGAAG ATTTAAATGG TGCAGCTCAT CATCATCATC
```

```
                              -continued
841    ATCATGGTGC AGCTTACTTC CCTGGAAATT ACTATGTTGT GATGCATTAA TATTCCCTTT

901    CACCTCACCT TTAATAATTT AAATTAGTAA TTATCTTGCG CATCACAAAA GAGTGCTATA

961    TACTATTTCA GATTAGAAAG TTTTATGAGG GAGACAAATT G;
``` where nucleotides 1 to 185 represent a promoter sequence from the Cwls endopeptidase (SEQ ID NO: 41), nucleotides 186 to 262 encode the Cwls endopeptidase secretion signal (SEQ ID NO: 23), nucleotides 263 to 407 encode a LysM domain for attachment to extracellular polysaccharides, nucleotides 408 to 431 are a spacer sequence, nucleotides 432 to 854 encode VHH EAT-1G4 (SEQ ID NO: 30) and nucleotides 855 to 890 are another spacer sequence ending in a stop codon for translation termination.

A second representative expression cassette for the expression of camelid antibodies is:

where nucleotides 1 to 275 represent a promoter sequence from chromosome segregation protein (SEQ ID NO: 42), nucleotides 276 to 383 encode a secretion signal from the chromosome segregation protein (SEQ ID NO: 22), nucleotides 384 to 806 encode VHH EAT-1G4 (SEQ ID NO: 30), nucleotides 807 to 1190 encode the cell wall anchor sequence from the chromosome segregation protein (SEQ ID NO: 22), and nucleotides 1191 to 1193 are a stop codon for translation termination.

A third representative expression cassette for the expression of camelid antibodies is:

```
                                                        (SEQ ID NO: 38)
   1    GAAGTACAAA GTTACTTTAA CTATAATGAA AAACAAGACA ATATAAAGAA AACAACATAT

61    AAGGTTCAGT TCATAACTGA TTAGATTTAT AATAAATATT GTAAATCGGA CAAAAATAAA

121    TTAATTTTCA ATTAATTCAA AAAAACCATA TTTTTTTCGT TTTGGCATAT TTGGATTTGC

181    TACACTAAAG ATGATCAAGA AAGGGGAAAA GATAATCTTC AATCTTGTGT ACTTAGTTTG

241    TTAATTAATT TATAAATTTA GGGAGGAAAC CTATCATGGA AAAGACTATG AAAAAGAAAG

301    CTTTAGTTGC AACTACTGCT GTAGCCGGTA TTACTTTAGT AGGAGAGGTT ACTACTGTTC

361    ATGCCGCTGA CAATGTACAA CAAGAAGTTC AATTAGTTGA AAGTGGTGGT GGTTTAGTTC

421    AACCAGGTGG TAGTTTACGT TTATCATGTG CTGCAAGTGG TTCAATTGCA ACTATTAATG

481    ATATGGGTTG GTTTCGTCAA GCACCAGGAA AGCAACGTGA TTGGGTTGCT ACTATTGTTA

541    GTGATGGTTC AACTGCTTAT GCTGATAGTG TTAAAGGTCG TTTTACTATT TCACGTGATA

601    ATGCTAAGAA TACTGTTTAC CTTCAAATGA ATAGTCTTAA GCCAGAAGAT ACTGCAGTTT

661    ACTATTGTTC AGCTCGTCGT CATTATGGTC AAGGTACTCA AGTTACTGTT AGTTCAGCTG

721    CAGCTAGTGG TTCATTAGAA CAAAAATTAA TTTCAGAAGA AGATTTAAAT GGTGCAGCTC

781    ATCATCATCA TCATCATGGT GCAGCTAAGA AGATTACAGA AGATCAAAAA GCAACAGAAG

841    GCGGTTATCA TATTGTTAAT GGATCTGTTG TAGATAAGCA GAATAACTTG GTTAGTGGTT

901    GGACTGTTAA GAATGGTCAA ATGGTTGATC CTGAAGGTAA CGTTATCAAA ACAACAATGT

961    CTACAGCCCA AGGTGTTACT ATTGAAAAAA ATAATAGCAA GTCCGGGAAT ACAAAGACAA

1021    ACATGATTCA AACTTCTTTA ACTATTGCTA ACAACAAGGC AACAACAAAC AAAGACAACC

1081    AGTTACCACA AACTGGCAAT TACAACAACA ATACAAAGGT ATTAGGATTA GCTGGTATTG

1141    CACTTGCATC TGCTTTAACT ATGTTTGGAT ACAAGAAGCG CCAACATAAC TAATTTTCTT

1201    ACTTGATGGG TTTCTAAATA AAAAATGGAC TACTTCAGCT CAAGGTAGCC CATTTTTATT

1261    ATTATAGTGA AGCAGTTATT CTTACGTATA ACCAGACTAA AATATAATAA AAATCTATTA

1321    TATATTAATC AACATCTCGG TTTAATCGTT AAAACTCCTC TGAGAGCTAA TTGTTAATAT

1381    TGAGTTGTAT AGT,
```

(SEQ ID NO: 39)

```
   1    GCAATGCACA AGATGCTGAA ACAAAGGCAC AACAAAATGC AGATCAAGCT TCACCAGCTA

61    ATATTCAAAA GGCACAAGAT GCTATTGCTA ATCAAGAAAC TCAAATTAGT AAAGACACCG

121    ATGCTATTAA TGACGCTAAC AAAGCCGTTA GCGATGCACA AAGCACAGTT GATGCAGCGC

181    AAAAAAAGTT AATGATGCAA CTACTGCTCG TGACAATCAA CAAAAGAATG TTGATACTGC

241    TAGTGATGCA GTTAAGAATG CTCAAGCTAT TCTTGACAAC AGTGATCAGG CTAAAAAGGA

301    AGCCCAAGAT GCTTTGAACA AGGCTAACCA AAAAGTTGCT GATGATACTA CTGCCGTTAA

361    CAACAAACAA ACTGATGTTA ACAATGCAGC AGAAGCTAAG AAGAATGCAG ATGAGGCATT

421    GAAGAACGCC AATGATGCGC AAACTTCTGC ACAAAAGAAT AAAGATGCTA AGCAAGCAAT

481    TGCTGATGAG GCAAGTGTAG AAGTTCAATT AGTTGAAAGT GGTGGTGGTT TAGTTCAACC

541    AGGTGGTAGT TTACGTTTAT CATGTGCTGC AAGTGGTTCA ATTGCAACTA TTAATGATAT

601    GGGTTGGTTT CGTCAAGCAC CAGGAAAGCA ACGTGATTGG GTTGCTACTA TTGTTAGTGA

661    TGGTTCAACT GCTTATGCTG ATAGTGTTAA AGGTCGTTTT ACTATTTCAC GTGATAATGC

721    TAAGAATACT GTTTACCTTC AAATGAATAG TCTTAAGCCA GAAGATACTG CAGTTTACTA

781    TTGTTCAGCT CGTCGTCATT ATGGTCAAGG TACTCAAGTT ACTGTTAGTT CAGCTGCAGC

841    TAGTGGTTCA TTAGAACAAA AATTAATTTC AGAAGAAGAT TTAAATGGTG CAGCTCATCA

901    TCATCATCAT CATGGTGCAG CTGCTGAAAA GGAAGCTAAA GATAATGGCT ACCATATCGA

961    AAATAACCAA GTTGTTGACG CTAAAGGTAA TAGTGTCAAT GGCTGGACAG TTAAGGGCAA

1021    CCAAATTGTT AGTCCAACTA ATGCTACTGT AGATCCCGCT GTTTCTGTAA CCACCAATGT

1081    CAATGTTGAT AGTAAAGGTC AAGTACAACC ACAAACTAGT GTTACTGCTA ATAGTGTTAA

1141    GACTGTAGCT GCAACTGAAT CAGCAAATCC AGTAGCAACT ACTACTGTGC AAACCCGCGA

1201    ACAATACAAG CAACAATTGA AGAGCAATAA TCAATTACCA CAAACTGGTA ATAATGATAG

1261    TGCTGTTCTT TCACTTGCTG GAGTAGCACT TGCAGCAATG TTGAGTTTGT TCGGTATTAA

1321    GAAACGTGAA TACTAATTTA GAAAATGTAA GTATTATTAT GTAAAAAGGT TCAACCAAAT

1381    TGGCTGAACC TTTTTGTCTA AAATTTAAGG AGAAGTTTT,
``` where nucleotides 1 to 313 represent a promoter sequence from Chromosome Partition Protein Smc (SEQ ID NO: 43), nucleotides 314 to 499 encode a secretion signal from Chromosome Partition Protein Smc (SEQ ID NO: 40), nucleotides 500 to 922 encode VHH EAT-1G4 (SEQ ID NO: 30), nucleotides 923 to 1333 encode the cell wall anchor sequence from Chromosome Partition Protein Smc (SEQ ID NO: 40), and nucleotides 1334 to 1336 are a stop codon for translation termination.

Many other combinations of the disclosed expression cassette elements are also possible.

Example 9: Anti-infective Molecules Derived from *Bacillus*

Certain *Bacillus* strains may also be used as DFM, for example for poultry. Over one hundred *Bacillus* isolates are collected from chicken cecum. The chickens are sourced with the state of Indiana, USA. Isolated strains are selected to withstand 100° C. for 10 minutes for development as pellet-stable products. The isolated strains are confirmed to be *Bacillus* using 16S rRNA sequencing. The isolates are tested for antimicrobial activity against various poultry pathogens such as *Salmonella Enteritidis*, avian pathogenic *E. coli*, *Clostridium perfringens*, *Enterococcus cecorum* and *Campylobacter jejuni*. Different isolates display different antimicrobial activities against these pathogens. Of all the isolates, five isolates are cytotoxic for all the pathogens tested. All 5 isolates are isolated from samples collected from the same study, suggesting that they may potentially be clonal.—Two isolates, D24 and D72, are selected for further characterization.

The two selected isolates (D24 and D72) are sequenced by ILLUMINA® sequencing and determined to most likely be *Bacillus velezensis*. The genomic sequences are analyzed for potential bacteriocins, antimicrobial peptides and digestive enzymes. The isolates contain several full loci potentially encoding for antimicrobial peptides and bacteriocins. Considering the feasibility of engineering these antimicrobial peptides and bacteriocins into an *L. reuteri* expression system, five ribosomal bacteriocins are selected for further study. Based on the sequence homology, the five *Bacillus* bacteriocins are identified to be Antimicrobial Peptide LCI: AIKPVPSPNGIFAASFELNGTTWIFKYKYYDSS-KGYWVGIYESVDK (SEQ ID NO: 44); Circularin A: LASTLGISTAAAKKAIDIIDAASTIASIISLIGIVTGA-GAISYAIVATAKTMIKKYGKK YAAAW (SEQ ID NO: 45); Lanthipeptide 3 (Plantaricin C): EFSGGGGAEQR-GISQGNDGKLCTLTWECGLCPTHTCWC (SEQ ID NO: 46); Lanthipeptide 5 (Lichenicidin A2): SDATPMTVTPT- TITIPISLAGCPTTKCASIVSPCN (SEQ ID NO: 47); and Lanthipeptide 6: SEATPMTVTPTTITIPISLAGCPTTKCA-SIVSPCND (SEQ ID NO: 47). These bacteriocins have been previously shown to kill various Gram-negative and Gram-positive pathogens.

These *Bacillus*-derived anti-infective peptides may be incorporated into an expression cassette and expressed recombinantly. Recombinant *Bacillus*-derived anti-infective peptides may be expressed alone or (without limitation) one or more of the other anti-infective peptides or phage disclosed in Example 2, the lytic enzymes disclosed in Example 6, or antibodies such as those disclosed in Example 7.

Example 10: In Vivo Effects of *L. reuteri*

An identified strain can effectively function as a direct feed microbial only if the strain is able colonize the host gastrointestinal tract. The ability of *L. reuteri* strains to colonize chickens is assessed following different routes of administration.

*L. reuteri* is administered orally to 10-day old chicks. At various times post inoculation, chicks are sacrificed and the presence of *L. reuteri* is measured in the crop, small intestine, and cecum. Strain 3632 is able to colonize all three tissues and remain detectable for at least 18 days.

*L. reuteri* is administered by in ovo inoculation (i.e. injection into the egg) 3 days before hatching. Strain 3632 is found in the tissues of chicks at 3 and 7 days post hatching, while colonization of a control strain declines after day 3.

*L. reuteri* is administered in ovo by spraying a liquid containing bacteria onto the egg surface. Again, Strains 3630 and 3632 are able to colonize and remain present in chicks 3 and 7 days post hatching. Inoculation by spray is just as efficient as in ovo injection but requires less manipulation of the incubating egg.

Recombinants strains 3630 and 3632 carrying expression cassettes comprising one of the antibodies of Example 7 or the PlyCM lytic enzyme are administered by in ovo inoculation. The recombinant strains are able to efficiently colonize chicken gastrointestinal tracts at comparable levels to unmodified parental strains. Thus, genetic manipulation as contemplated herein does not alter the ability of the modified strains to act as DFM.

Chicks carrying *L. reuteri* strains or modified strains are assessed for their susceptibility to necrotic enteritis. Chicks are inoculated with *L. reuteri* live expression systems wherein the expression cassettes contain either a single chain antibody or a lytic enzyme. Inoculation is done orally by providing chicks drinking water containing $10^8$ recombinant *L. reuteri*.

An experiment is performed as given in Table 2, with 40 one-day-old chicks placed in each of ten groups. Group 1 chicks served as the untreated and unchallenged controls. Group 2 chicks served as untreated challenge controls. Group 3 represents challenged chicks given standard antibiotic therapy. Groups 2-10 each received $2\times10^8$ CFU of *C. perfringens* on each of days 17 and 18. Groups 4-9 each received prophylactic inoculation with *L. reuteri* continuously from day 1. Group 10 received only therapeutic doses of *L. reuteri* on days 18-21. On day 21 chicks are sacrificed and small intestinal tissues are examined for the presence of lesions. Survival of chicks within each treatment group is also recorded.

As shown in Table 2, the four antibodies can each ameliorate disease to some degree. A combination of strains may be more effective than any single strain.

TABLE 2

Antibodies produced by recombinant *L. reuteri* can treat necrotic enteritis.

| Group | Strain | Ab | Challenge | Lesion score (avg) | reduction in lesions | Mortality (avg) | Reduction in mortality |
|---|---|---|---|---|---|---|---|
| 1 | none | none | none | 0 | n/a | 0 | n/a |
| 2 | none | none | Yes | 1.80 | n/a | 27.5 | n/a |
| 3 | none | none | Yes[a] | 0.375 | 79.17% | 2.5 | 90.91% |
| 4 | 3630 | 1G4 1F2 1D11 1A4 | Yes | 1.35 | 25.00% | 22.5 | 18.18% |
| 5 | 3630 | 1G4 | Yes | 0.5 | 72.22% | 10 | 63.64% |
| 6 | 3630 | 1F2 | Yes | 0.95 | 47.22% | 20 | 27.27% |
| 7 | 3630 | 1D11 | Yes | 1.25 | 30.56% | 25 | 9.09% |
| 8 | 3630 | 1A4 | Yes | 1.45 | 19.44% | 22.5 | 18.18% |
| 9 | 3630 3632 | 1D11 1D11 | Yes | 0.675 | 62.50% | 0 | 100.0% |
| 10 | 3630 | 1G4 1F2 1D11 1A4 | Yes | 1.275 | 29.17% | 17.5 | 36.36% |

[a]Treated with BMD. Bacitracin methylene disalicylate

What is claimed is:

1. An expression cassette comprising a promoter for transcriptional expression and at least one heterologous coding region encoding a biomolecule;
   wherein the biomolecule is a bacterial peptide, an enzyme, a lysin, or a single chain antibody and wherein:
   (a) the bacterial peptide is selected from mersacidin-E1 and E-2 molecules comprising sequences of SEQ ID NO: 2 and SEQ ID NO: 4, or Bacillus bacteriocin comprising a sequence selected from SEQ ID NO: 44, SEQ ID NO: 45, SEQ ID NO: 46, SEQ ID NO:47, and SEQ ID NO: 48;
   (b) the enzyme is selected from SEQ ID NO: 5 or SEQ ID NO: 6;
   (c) the lysin is selected from SEQ ID NO: 24, SEQ ID NO: 25, SEQ ID NO: 26, SEQ ID NO: 27, and SEQ ID NO: 28; or
   (d) the single chain antibody is directed against pathogenic bacterium Clostridium perfringens, specifically recognizes the bacterial protein C. perfringens alpha toxin or C. perfringens NetB toxin, and selected from SEQ ID NO: 29, SEQ ID NO: 49, SEQ ID NO: 30, SEQ ID NO: 33, SEQ ID NO: 34, and SEQ ID NO: 50;
   wherein the promoter comprises the sequence of SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42 or SEQ ID NO: 43.

2. The expression cassette of claim 1, wherein the cassette comprises an origin of replication comprising the sequence of SEQ ID NO: 8.

3. The expression cassette of claim 1, wherein the expression cassette is located on a plasmid or suicide vector or is located on or integrated into a bacterial chromosome.

4. The expression cassette of claim 3, wherein the expression cassette is integrated into a bacterial chromosome and is inserted into a transposase locus an Uracil phosphoribosyl (URP) transferase locus, or a pyrE locus of a bacterial chromosome.

5. The expression cassette of claim 1, wherein the single chain antibody directed against pathogenic bacterium Clostridium perfringens comprises one or more sequence selected from SEQ ID NO: 29, SEQ ID NO: 30, SEQ ID NO: 33, SEQ ID NO: 34, SEQ ID NO: 49, and SEQ ID NO: 50.

6. The expression cassette of claim 1, wherein the promoter comprises the sequence of SEQ ID NO: 41, SEQ ID NO: 42 or SEQ ID NO: 43.

7. The expression cassette of claim 1, wherein the expression cassette further comprises a nucleic acid sequence encoding a signal sequence for secretion.

8. The expression cassette of claim 1, wherein the biomolecule is a single chain antibody directed against pathogenic bacterium Clostridium perfringens and comprises the sequence of SEQ ID NO: 29, SEQ ID NO: 49, SEQ ID NO:30, SEQ ID NO: 33, SEQ ID NO: 34 or SEQ ID NO: 50 and wherein the promoter comprises the sequence of SEQ ID NO: 41, SEQ ID NO: 42 or SEQ ID NO: 43.

9. The expression cassette of claim 8, wherein the expression cassette is selected from the expression cassette of SEQ ID NO: 37, SEQ ID NO: 38 and SEQ ID NO: 39.

10. A genetically-modified microorganism comprising the expression cassette of claim 1, wherein the genetically-modified microorganism is a bacterium selected from the group consisting of Bacillus, Lactobacillus, Lactococcus, and Entercoccus.

11. The genetically-modified microorganism of claim 10, wherein the genetically-modified microorganism is a Lactobacillus reuteri strain.

12. The genetically-modified microorganism of claim 11, wherein the expression cassette is integrated into a Lactobacillus reuteri strain bacterial chromosome.

13. The genetically-modified microorganism of claim 12, wherein the expression cassette is inserted into a transposase locus.32, an Uracil phosphoribosyl (URP) transferase locus, or a pyrE locus.

14. The genetically-modified microorganism of claim 11, wherein the Lactobacillus reuteri strain is selected from strain 3632 ATCC PTA-126788 and strain 3630 ATCC PTA-126787.

15. The genetically-modified microorganism of claim 10, wherein the genetically-modified microorganism is a Lactobacillus bacterium and wherein the microorganism comprises an expression cassette wherein the biomolecule is a single chain antibody directed against pathogenic bacterium Clostridium perfringens and comprises the sequence SEQ ID NO: 29, SEQ ID NO: 49, SEQ ID NO: 30, SEQ ID NO: 33, SEQ ID NO: 34, or SEQ ID NO: 50, and wherein the promoter comprises the sequence SEQ ID NO: 41, SEQ ID NO: 42, or SEQ ID NO: 43.

16. The genetically-modified microorganism of claim 15, wherein the Lactobacillus bacterium is a Lactobacillus reuteri strain and is selected from strain 3632 ATCC PTA-126788 and strain 3630 ATCC PTA-126787.

17. A method of reducing colonization of an animal by a pathogenic bacterium, the method comprising treating an animal with the genetically-modified microorganism of claim 14.

18. The method of claim 17, wherein the pathogenic bacterium is selected from the group consisting of Salmo-

*nella, Clostridium, Campylobacter, Staphylococcus, Streptococcus*, and an *E. coli* bacterium.

19. The method of claim 17, wherein the animal is a bird, a human, or a non-human animal.

\* \* \* \* \*

SEQUENCE LISTING

<160> NUMBER OF SEQ ID NOS: 50

<210> SEQ ID NO 1
<211> LENGTH: 231
<212> TYPE: DNA
<213> ORGANISM: Artificial Sequence
<220> FEATURE:

<223> OTHER INFORMATION: Based on Lactobacillus reuteri sequence

<400> SEQUENCE: 1
atggacaaag aagaattaga aaaaattgta ggtaataact ttgaggaaat gagtttacaa      60
aaaatgacag aaattcaagg tatgggtgaa taccaagtgg attcaacacc agcagcttct     120
gcgatttcac gggcaacaat tcaagtatca cgtgcatctt ctggaaaatg tctaagttgg     180
ggtagtggtg cagcatttag tgcttatttt actcataaaa gatggtgcta g             231

<210> SEQ ID NO 2
<211> LENGTH: 76
<212> TYPE: PRT
<213> ORGANISM: Artificial Sequence
<220> FEATURE:
<223> OTHER INFORMATION: Based on Lactobacillus reuteri sequence

<400> SEQUENCE: 2

Met Asp Lys Glu Glu Leu Glu Lys Ile Val Gly Asn Asn Phe Glu Glu
1               5                   10                  15

Met Ser Leu Gln Lys Met Thr Glu Ile Gln Gly Met Gly Glu Tyr Gln
            20                  25                  30

Val Asp Ser Thr Pro Ala Ala Ser Ala Ile Ser Arg Ala Thr Ile Gln
        35                  40                  45

Val Ser Arg Ala Ser Ser Gly Lys Cys Leu Ser Trp Gly Ser Gly Ala
    50                  55                  60

Ala Phe Ser Ala Tyr Phe Thr His Lys Arg Trp Cys
65                  70                  75

<210> SEQ ID NO 3
<211> LENGTH: 186
<212> TYPE: DNA
<213> ORGANISM: Artificial Sequence
<220> FEATURE:
<223> OTHER INFORMATION: Based on Lactobacillus reuteri sequence

<400> SEQUENCE: 3
atggaagaaa aagaattaga aggtgtaata gggaattcgt ttgaaagtat gactgtagag      60
gaaatgacaa aaattcaagg tatgggtgaa tatcaagtag attcgacgcc tggatatttt     120
atggaaagtg ctgccttttc agctcttaca gccaatataa caagacatgc tatgcatcat     180
cattaa                                                               186

<210> SEQ ID NO 4
<211> LENGTH: 61
<212> TYPE: PRT
<213> ORGANISM: Artificial Sequence
<220> FEATURE:
<223> OTHER INFORMATION: Based on Lactobacillus reuteri sequence

<400> SEQUENCE: 4

Met Glu Glu Lys Glu Leu Glu Gly Val Ile Gly Asn Ser Phe Glu Ser
1               5                   10                  15

Met Thr Val Glu Glu Met Thr Lys Ile Gln Gly Met Gly Glu Tyr Gln
            20                  25                  30

Val Asp Ser Thr Pro Gly Tyr Phe Met Glu Ser Ala Ala Phe Ser Ala
        35                  40                  45

Leu Thr Ala Asn Ile Thr Arg His Ala Met His His His
    50                  55                  60

<210> SEQ ID NO 5

```
<211> LENGTH: 373
<212> TYPE: PRT
<213> ORGANISM: Artificial Sequence
<220> FEATURE:
<223> OTHER INFORMATION: Based on Lactobacillus reuteri sequence

<400> SEQUENCE: 5

Met Val Glu Ile Ala His Phe Gly Val Glu Ala Trp Leu Asn Lys Trp
1               5                   10                  15

Glu Lys Ser Ala Thr Tyr Asp Ile Ser Gln Ser Thr Ile Ala Ser Leu
            20                  25                  30

Ser Met His Asp Leu Leu Asn Leu Asp Gly Asn Asn Gly Glu Glu Phe
        35                  40                  45

Tyr Glu Met Leu Asp Lys Gln Gln Met Asn Tyr Gly Trp Ile Glu Gly
    50                  55                  60

Ser Pro Glu Phe Lys Glu Glu Val Ala Lys Leu Tyr His His Val Asp
65                  70                  75                  80

Pro Glu Asn Ile Leu Gln Thr Asn Gly Ala Thr Gly Ala Asn Ile Leu
                85                  90                  95

Ala Leu Tyr Ala Leu Ile Asn Pro Gly Asp His Val Ile Ala Glu Tyr
            100                 105                 110

Pro Ser Tyr Gln Gln Leu Tyr Asp Ile Pro Lys Ser Leu Gly Ala Asp
            115                 120                 125

Val Asp Tyr Trp His Ile His Glu Glu Asp Asn Trp Tyr Pro Arg Ile
    130                 135                 140

Asp Asp Leu Lys Ala Met Val Lys Pro Asn Thr Lys Met Ile Cys Leu
145                 150                 155                 160

Asn Asn Ala Asn Asn Pro Thr Gly Thr Val Leu Asp Lys Glu Phe Leu
            165                 170                 175

Glu Gln Val Val Glu Ile Ala Lys Ser Val Asp Ala Tyr Val Leu Val
            180                 185                 190

Asp Glu Val Tyr Leu Pro Leu Asp His Pro Glu Lys Phe Ala Gln Ile
            195                 200                 205

Ile Asp Leu Tyr Asp Lys Gly Ile Ser Thr Asn Ser Leu Ser Lys Thr
    210                 215                 220

Tyr Ser Val Pro Gly Val Arg Ile Gly Trp Thr Ala Thr Asn Ala Glu
225                 230                 235                 240

Val Ala Asp Ile Phe Arg Lys Phe Arg Asp Tyr Thr Met Ile Cys Gly
            245                 250                 255

Gly Val Phe Asn Asp Gln Leu Ala Thr Tyr Val Leu Arg His Arg Asp
            260                 265                 270

Gln Val Leu Ala Arg Asn Arg Lys Leu Val Leu Gly Asn Leu Ala Ile
            275                 280                 285

Tyr Lys Asp Trp Ile Asp His Glu Asp Arg Ala Ser Val Ile Met Pro
    290                 295                 300

Gln Ala Val Ser Thr Ser Phe Pro Lys Leu Asp Val Pro Val Asp Ile
305                 310                 315                 320

His Thr Phe Cys Glu Asn Leu Leu His Asp Glu Gly Val Leu Leu Val
            325                 330                 335

Pro Gly Asp Ala Phe Asp Thr Pro Gly His Val Arg Leu Gly Tyr Cys
            340                 345                 350

Ala Pro Glu Ala Thr Leu Lys Glu Gly Leu Lys Arg Leu Ser Lys Tyr
            355                 360                 365

Met His Gln Tyr Asp
    370
```

-continued

```
<210> SEQ ID NO 6
<211> LENGTH: 178
<212> TYPE: PRT
<213> ORGANISM: Artificial Sequence
<220> FEATURE:
<223> OTHER INFORMATION: Based on Lactobacillus reuteri sequence

<400> SEQUENCE: 6

Met Ile Leu Thr Thr Phe Ile Ile Leu Ile Leu Met Gly Cys Phe Ile
1               5                   10                  15

Asn Gly His Arg Arg Gly Leu Leu Thr Met Thr Leu Met Leu Gly Thr
                20                  25                  30

Tyr Ile Val Ala Trp Ile Val Ala Arg Gln Gly Ala Gln Leu Ile Gly
            35                  40                  45

Gly Trp Leu Lys Ser Leu Leu Pro Ser Ile Gly Thr Pro Ala Thr Phe
        50                  55                  60

Ser Glu Ser Leu Leu Ala Asn Val Asn Ser Asn Leu Phe Phe Tyr Asn
65                  70                  75                  80

Gly Ile Ala Phe Met Ile Ile Phe Thr Ile Val Ser Ile Leu Cys His
                85                  90                  95

Trp Gly Ile Arg Gln Leu Asn Trp Ile Lys Arg Ile Pro Val Val Gly
                100                 105                 110

Thr Val Asp Lys Ile Ala Gly Gly Leu Ile Ser Phe Leu Ile Gly Tyr
            115                 120                 125

Leu Ile Ile Tyr Val Val Leu Leu Ile Met Gln Leu Phe Pro Ala Gly
        130                 135                 140

Trp Trp Gln Met Gln Ile Ala Asn Ser Glu Leu Ala Arg Phe Met Ile
145                 150                 155                 160

Asn Gln Thr Pro Gly Ile Ala His Leu Val Ile Asp Thr Leu Val Gln
                165                 170                 175

Gly Gly

<210> SEQ ID NO 7
<211> LENGTH: 4653
<212> TYPE: DNA
<213> ORGANISM: Artificial Sequence
<220> FEATURE:
<223> OTHER INFORMATION: Based on Lactobacillus reuteri sequence

<400> SEQUENCE: 7
ttggcaatct ttcacctatc agcaaaaatc attagtcgag gaaaagggca atcagcaatt        60
gcctcggctg cttatcgttc agggaacaaa cttcacgatg aacgatacga cgaaacacaa       120
gattacacaa acaaacgttt catcgaacac tcagaaatcc aacttccaga gaatgcccca       180
gctaagtatc aagatagggc aacccctttgg aacagcgtag aaaaggcaga aaaagctaag       240
aattcgcagt tagctagaga aattgaaata gccttaccac gagagctaac accagaacaa       300
cgagttaaat tagtccacga ttacgttcag aaaacctttg tcgataaggg aatggtagcc       360
gattggtcta ttcacaaccc acaaccagat aaggataatc cagaaaagcc agcaaacccg       420
cacgctcata tcatgctcac actgcgtagc ttgcgttcta acggctcttg ggcaccaaag       480
aagacaagtc actatgaact agacgaaaac ggccagaagg tgcctgtaat cgatcctgag       540
acaggcaaac agaagttagg ggcgaaaaac caaaaaatct ggaaacgagt aattccccca       600
actaatgact ggaataaccc caaaaacgtt gaaaatggc gggctgaatg ggcgaagact       660
tgtaataagt acttggctcc tgaccaccag attgaccacc gcagttataa acggcagggc       720
```

-continued

```
aaaaaacaaa ttccaacaat ccatgagggc tatgttgctc gtaaaatgga acgagaagcc      780
acaggaagct cagagagggc ttctttaac caaatcgtaa aatatatcaa caacgagtta      840 aaaatcgctta gaaagcaaat taggggcatt atacgcgaaa tacggaatct agaaaaagga      900
cgtgaccaag atgagaaagt tcgacttcag caagacaccc gagcaaatca aacaagaaca      960
agcagagatc aagcgctggg aggaggagtt caacgcacga ttacagacaa tcgggagcaa     1020
tccggaaacg gtagagccaa cggaactgcc gaagaagccc aacgaacaga tcctaatcaa     1080
cttcatcaac agtctttcgg agaaacagca agaagaattt tccgagattt ccggctattt     1140
gcggagcgtc aacgagaagc tcgacagcga caacgccgac ttagccaagg cttacaacat     1200
catcaagaaa cagaaaaacg acttgaagca gggcaacaac aacttactcg aacaaaacat     1260
acagctgacg aacgaaaaca acagcttaca gaacgacaaa ttcgagttag aaaagctttt     1320
agcgacgctt ctaagtccaa agtcttggaa cgatactaca ctcacttccg tcaaacaaaa     1380
actcaagcaa atcatgcaaa aggattagac taccaaggac caattctggg acattcccga     1440
ggacgctcaa ggtagttatg ctagaatgat taagccgtcc gtggcaactc ctacgtaaag     1500
gaggtggcaa catggcacat atactcctct cagcagtttt gagccttctg ggttccttga     1560
taactgcact gttcgctgat tggcttcgtc ggcgaaaata gtttttgacg gcatgaagcg     1620
caaattaaaa gccactcaac tattcgcact agttgggtgg cttttttgca acgtggcaat     1680
atacttctct cggttaaatt ataacatggt tgttccagaa gtgcattagg taggcggttt     1740 gtccccccc atgggttttg gcttcgaaaa tcaatcgttg aagtgaccag cgaagctcag     1800
ctgatggagc cctcatattc aagaagcagg tcaacgaatg ccaattccaa catgagggcc     1860
atgacttagg ccactgatac tcgcaaatga ctgtcacacc aacggtatta gccattctga     1920
taagcgagtc taacgacttt tgacgcataa tcgaccacct accttatttt caaagcgcct     1980
cagagctaat tagagtattc ttcaaggagc ttagcgagga ttatagacgc ttggcggact     2040
tcactttcgg cttgattgac ccgtttagcg atcttgtcat catggcgagc cacctttttcc     2100 aagtcatgga gattatcagc gatttggtca gtcatgacgg agtagttctt aatacccgac     2160
agcaggcttt caacgttagt attctcaagg ttttcgttga atatcatggt tattcctcct     2220
tatcctcaaa cttagtcatc ttctgtctcc tgttttagag aattttcaat catgtctaat     2280
aatgttgaca tgtcaatgtt aaatgaatca aggctaccat accgcttgat ttgagtttta     2340
acactatcca atccatattc ttcaagtaat gcttttaatt taccagtaac tttttcacct     2400
aaatgcccaa aatactgaag ccagctctta agtaattctc ggtactggtc aaattttttct     2460 ttttcagtaa gctgtttctc aacttcttct tggtcctcag aaccgttaac tactttccag     2520
aggtcagggt cagtagtacc caacttataa ccaagtaccc gatcatatgc tctggccttt     2580
tcctttggag tcaaatcagg attaaggtca atattatcta gcttcatacg ttggtcagca     2640
taacgacctt tttcaaagtc atcggcattc ttggcttcag gttgccaagt gaactcatag     2700
ccaacaacag gacgtcctct accagctcct cgaatagttt ttacggttaa gccacgaata     2760 acagggggtta gctcttcttt aattggacgt aacactcttt ttcttacgtt accctggtct     2820
ttcttgtagc tcttgggtag atctagttgc ttaaataatt cgtcactggt taacttcaac     2880
cgccctactg ttcgatattg tttaattaac actctttttc ttacgttacc ctggtctttc     2940
ttgtagctct tgggtagatc tagttgctta ataattcgt cactggttaa cttcaaccgc     3000
cctactgttc gatattgttt aatcaagcga aacatgttct tagcataagc agattgaaga     3060
```

-continued

```
ctattaaact gagctagttg aaatcttgtc caatgactta aatcattgaa tagcttctga      3120
aatagagggt taacttgaac agtcagaatc tgtttactcc tctgaatctg aaatacattc      3180
caacaagcaa attgagtaat ggtgtctcca tcatcggtgt aggcattaat ctctaatagc      3240
tttttattag ttttcatcaa atcttttaca aaattagatg tactccgttc atacttacta      3300
agactttgta gttgcgtaaa tgaaaacttt aatttctgag tacccttttg atacgactgc      3360
tgaactagtg taataaatag atttagctca ttagagttca gtcggccaag tggaatagta      3420
ttaagccgat tactatactt cacaatttca ttactcaatt ttctcacctc aaatatatta      3480
taacatttta tcgtacacaa tcaagagtac gtacttatag cacacgtaca gtattagcgc      3540
gtatattaag acaaaaattt agacaaaatg taccttataa cggacaaaat gtaccttata      3600
aaccggacaa aatgtacctt ataacggaca aaatgtacct tataaaaaac gaaactctta      3660
ctctcccaag gagtttcaaa cccctaaaga gtatttaaag aatatatata aagatattta      3720
aagaggcacc atacggaaaa tctcctttct gatttcaatt tcagagagga gattatcact      3780
aaatttcaaa attcaatttt tcgccaaaaa cttttttagt agttttcggt aactagcaaa      3840
atcaacttcg ttgattattt tgactatttc gaaattcatc aaaaactgaa tgcccgtctt      3900
tatagtgaat ttgtttagtg aagttcacta actgcttcag catattcagt tgaccacgta      3960
accattgttc actatcagca ggactaattt gttctgataa ttgctctttt tggtggttat      4020
aagccttata agcctgatat ttagcataac cttgtgggtc atctgattta gccactctag      4080
ccactttagg tactttttcta agcccccttag cttgagcttg aatatcttct aaaaccgccc      4140
ctttttcgat gagacgctta tttcgttgct ttctcttttc agtattgatg cgagccattt      4200
gacgctctcg acgagcctta aacactgctt cctttttcttg aaggcgttca agttctgctt      4260
tcattttttc aatatcagcc ataacaaatc ctcctaatgt gaataatgtt ttctgaaatt      4320
caaatgttat ctagattata tgatgttaca attgatttaa ccactacgtt tggtctccct      4380
gttaagggcg cacttataca cattcaaaga atgtaattac gcctgacggc gacgtgcgct      4440
ctccgagggg acttacccag tcggggcgac ttcatcgaga ccatgtcatg gagattcagt      4500
ttcaccgaaa cggaccacta accccgtgga ggggagaagt ttcacttcta gggaccattc      4560
catggagggt cgcttttttac aaaagcaacg caaaacaaaa gactagctcc caagcttacg      4620
caaggtcgtt agtccctaag gaggcagcac aga      4653
```

```
<210> SEQ ID NO 8
<211> LENGTH: 1026
<212> TYPE: DNA
<213> ORGANISM: Artificial Sequence
<220> FEATURE:
<223> OTHER INFORMATION: Based on Lactobacillus reuteri sequence

<400> SEQUENCE: 8
ttagtcatct tctgtctcct gtttttagaga attttcaatc atgtctaata atgttgacat      60
gtcaatgtta aatgaatcaa ggctaccata ccgcttgatt tgagtttttaa cactatccaa      120 tccatattct tcaagtaatg cttttaattt accagtaact ttttcaccta aatgcccaaa      180
atactgaagc cagctcttaa gtaattctcg gtactggtca aatttttctt tttcagtaag      240
ctgtttctca acttcttctt ggtcctcaga accgttaact actttccaga ggtcagggtc      300
agtagtaccc aacttataac caagtacccg atcatatgct ctggcctttt cctttggagt      360
caaatcagga ttaaggtcaa tattatctag cttcatacgt tggtcagcat aacgaccttt      420
ttcaaagtca tcggcattct tggcttcagg ttgccaagtg aactcatagc caacaacagg      480
```

-continued

```
acgtcctcta ccagctcctc gaatagtttt tacggttaag ccacgaataa caggggttag       540
ctcttcttta attggacgta acactctttt tcttacgtta ccctggtctt tcttgtagct       600
cttgggtaga tctagttgct taaataattc gtcactggtt aacttcaacc gccctactgt       660
tcgatattgt ttaattaaca ctcttttct tacgttaccc tggtctttct tgtagctctt       720
gggtagatct agttgcttaa ataattcgtc actggttaac ttcaaccgcc ctactgttcg       780
atattgttta tcaagcgaa acatgttctt agcataagca gattgaagac tattaaactg       840
agctagttga aatcttgtcc aatgacttaa atcattgaat agcttctgaa atagagggtt       900
aacttgaaca gtcagaatct gtttactcct ctgaatctga aatacattcc aacaagcaaa       960
ttgagtaatg gtgtctccat catcggtgta ggcattaatc tctaatagct ttttattagt      1020
tttcat                                                                   1026
```

<210> SEQ ID NO 9
<211> LENGTH: 332
<212> TYPE: PRT
<213> ORGANISM: Artificial Sequence
<220> FEATURE:
<223> OTHER INFORMATION: Based on Lactobacillus reuteri sequence

<400> SEQUENCE: 9

```
Met Asn Glu Tyr Asn Ala Glu Met Ala Lys Leu Asn Gln Gly Ala Asn
1               5                   10                  15

Ala Pro Val Ile Thr Thr Asn Ser Val Asn Gln Ala Leu Ser Leu Lys
            20                  25                  30

Pro Glu Asn Asn Ala Thr Val Asp Ile Glu Ala Leu Asn Pro Arg Ile
        35                  40                  45

Thr Phe Lys Arg Val Glu Glu Gly Thr Lys Tyr Ala Gly Tyr Gln Ile
    50                  55                  60

Phe Asp Lys Asn Asn Ala Tyr Val Asn Asn Ile Asp Gly Glu Phe Leu
65                  70                  75                  80

Arg Val Thr Tyr Thr Asn Leu Lys Asn Ser Thr Tyr Lys Gly Ser Lys
                85                  90                  95

Ile Ser Lys Ile Val Val Thr Tyr Ser Asp Ser Thr Pro Thr Gly Asn
            100                 105                 110

Arg Ile Thr Gln Ser Gly Leu Asn Ala Val Thr Glu Gly Ala Asn Asp
        115                 120                 125

Asn Phe Leu Val Val Phe Glu Asp Pro Val Arg Gly Asp Met His Ser
    130                 135                 140

Thr Thr Val Thr Ala Thr Tyr Gln Tyr Tyr Asp Ala Asn Gly Asn Leu
145                 150                 155                 160

Ile Asp Phe Ser Gly Thr Asn Asn Ala Trp Leu Ser Val Gly Ser Leu
                165                 170                 175

Asn Phe Asp Gln Gly Asn Asp Tyr Gln Gly Gly Lys Asn Glu Gly Asn
            180                 185                 190

Pro Thr Ser Gly Ile Ser Glu Gly Val Lys Leu Ile Ser Gly Ala Gln
        195                 200                 205

Ile Lys Gln Leu Ala Gly Ser Ser Ile Ser Val His Asp Asp Gly Trp
    210                 215                 220

Ala Tyr Ala Gly Phe Asn Asn Tyr Ser Gly Thr Gly Met Asn Asn Gly
225                 230                 235                 240

Ile Asn Thr Asp Asn Gly Gly Ser Gly Trp Asp Met Asp Gly Ser Pro
                245                 250                 255
```

-continued

```
Asn Ala Tyr Tyr Gly Ala Ile Val Phe Gln Leu Thr Gly Ser Ser Val
            260                 265                 270

Ser Leu Arg Gln Gly Leu Val Ser Trp Gly Gly Ala Asp Ile Ala Ser
            275                 280                 285

Gln Tyr Asn Asn Gln Phe Leu Asn Asn Ala Trp Phe Thr Ala Gly Thr
    290                 295                 300

Thr Leu Pro Glu Thr Gln Ile Lys Gln Pro Ile Arg Lys Thr Ser Glu
305                 310                 315                 320

Thr His Tyr His Tyr Asn Pro Ser Val Ile Arg Leu
                325                 330

<210> SEQ ID NO 10
<211> LENGTH: 2059
<212> TYPE: PRT
<213> ORGANISM: Artificial Sequence
<220> FEATURE:
<223> OTHER INFORMATION: Based on Lactobacillus reuteri sequence

<400> SEQUENCE: 10

Met Ala Gln Lys Leu Met Ser Ala Asn Ser Thr Asp Lys Asn Phe Lys
1               5                   10                  15

Met Tyr Lys Ser Lys Lys Ser Trp Val Phe Ala Tyr Ser Thr Thr Leu
            20                  25                  30

Ala Leu Ala Ala Val Ala Gly Ile Thr Leu Ser Thr Thr Asn Val His
            35                  40                  45

Ala Asp Thr Thr Asn Gly Gly Asp Asn Gln Val Asn Ala Thr Ala Val
    50                  55                  60

Thr Gln Asn Thr Thr Ser Asn Thr Val Asp Gln Ile Ala Ala Asn Thr
65                  70                  75                  80

Ala Gln Thr Asp Asn Thr Ser Thr Ser Ile Asn Ile Arg Ser Leu Met
            85                  90                  95

Asp Asp Leu Ala Ser Gly Asp Asp Thr Ser Ser Ser Gln Asn Gly Gln
            100                 105                 110

Glu Gln Ser Gln Asn Tyr Ala Ser Ser Asn Gln Asn Ser Gln Thr Gln
            115                 120                 125

Gln Glu Asn Gly Thr Thr Gly Gln Ser Thr Ala Ser Gln Asn Gly Thr
    130                 135                 140

Thr Ser Asp Gln Thr Asn Ser Asp Gln Ser Asp Lys Asn Tyr Tyr Val
145                 150                 155                 160

Ile Ser Thr Arg Asp Leu Asp Lys Asn Gly Asn Val Asn Tyr Leu Thr
            165                 170                 175

Gln Lys Asn Tyr Thr Ser Ile Lys Gly Gln Glu Val Ala Asp Gly Thr
            180                 185                 190

Val Val Thr Trp Pro Leu Ser Val Ser Ala Leu Pro Ala Asn Arg Ala
            195                 200                 205

Gln Asp Leu Lys Ser His Val Ile Ser Glu Thr Leu Asp Pro His Leu
    210                 215                 220

Glu Tyr Leu His Tyr Arg Ala Tyr Leu Thr Asn Thr Asp Gly Thr Val
225                 230                 235                 240

Thr Asp Val Thr Asn His Val Asn Leu Asn Arg Ser Gly Gln Thr Leu
            245                 250                 255

Ile Phe Thr Asp Asp Asn Tyr Leu Leu Ser Ile Tyr Asn Asn Asn Arg
            260                 265                 270

Tyr Arg Val Gln Asn Leu Pro Val Ile Lys Leu Val Thr Lys Ala Asn
            275                 280                 285
```

-continued

```
Gly Asn Gly Tyr Ile Ile Pro Asn Ala Phe Lys Ser Ser Tyr Val Phe
    290             295             300

Asn Asp Gly Ser His Asp Val Ser Phe Thr Thr Thr Ser Asn Asn Val
305             310             315             320

Gln Ile Lys Thr Phe Asn Pro Gly Asn Ser Lys Asp Val Glu Ile Gly
            325             330             335

Gly Asn Val Gln Gly Asp Pro Ser Gly Thr Ile Asn Gly Gln Val Val
            340             345             350

Ala Asp Gly Ser Val Val Thr Trp Pro Met Ser Val Gly Asp Leu Pro
            355             360             365

Ala Asn Arg Ala Gln Asp Val Leu Ser His Ile Glu Thr Asp Thr Leu
    370             375             380

Tyr Asn Gly Leu Asn Tyr Glu Gly Tyr His Ala Tyr Leu Pro Gln Ala
385             390             395             400

Asp Gly Ser Phe Gln Asp Val Ser Ser His Ile Asn Val Gln Gln Asn
            405             410             415

Gly Gln Asp Leu Thr Phe Ile Ala Asp Asp Tyr Leu Ile Gly Leu Tyr
            420             425             430

Asn Gln Asp Lys Ser Thr Ala Phe Lys Met Pro Ile Ile Asp Leu Ile
            435             440             445

Thr Ser Val His Gly Thr Ser Ile Ile Ala Pro Asn Lys Phe Asn Ser
    450             455             460

Gln Leu Ala Phe Lys Asp Gly Asn Gly Gln Thr Val Ile Asn Asn Thr
465             470             475             480

Ser Asn Gln Val Gln Ile Ser Thr Tyr His Pro Thr Asn Thr Lys Asp
            485             490             495

Val Glu Leu Gly Gly Asn Val Gln Gly Asp Thr Pro Asn Ser Ile Asn
            500             505             510

Asp Lys Val Val Ala Asn Gly Ala Ile Val Thr Trp Pro Met Ala Ser
    515             520             525

Ser Glu Leu Pro Ala Asn Arg Val Gln Asp Leu Gln Ser Arg Val Ile
    530             535             540

Ser Glu Thr Leu Asp Ser His Leu Gln Tyr Gln Gly Tyr Lys Ala Trp
545             550             555             560

Leu Gln Asn Ala Asp Gly Lys Tyr Thr Asp Val Thr Ser His Val Lys
            565             570             575

Leu Thr Gln Asp Gly Gln Asn Leu Thr Phe Ala Asp Asp Glu Tyr Leu
            580             585             590

Leu Asn Leu Tyr Asn Ser Asn Lys Gly Thr Ala Tyr Lys Leu Pro Ile
            595             600             605

Ile Asp Leu Val Thr Lys Val Asn Gly Ala Gly Ile Thr Ala Pro Asn
    610             615             620

Ser Tyr Thr Thr Lys Tyr Val Tyr Ser Asp Gly Asp Gly Asn Thr Thr
625             630             635             640

Ile Asn Val Thr Ser Asn Thr Val Lys Ile Ser Thr Phe Asn Pro Thr
            645             650             655

Thr Asn Lys Asp Val Glu Leu Gly Asp Asn Ile His Gly Asp Thr Glu
            660             665             670

Ser Ser Ile Ala Gly Lys Leu Val Ser Glu Gly Thr Ile Val Thr Trp
            675             680             685

Pro Leu Ser Thr Ser Asp Leu Pro Ala Asn Arg Ala Gln Asp Val Val
    690             695             700

Ser His Thr Ala Val Asp Ala Leu Glu Pro Thr Leu Gln Tyr Ile Ser
```

-continued

```
705                 710                 715                 720

Tyr Thr Ala Trp Leu Pro Asp Ser Asn Gly Gln Leu Gln Asp Val Thr
                725                 730                 735

Ser His Val Lys Met Thr Arg Asp Gly Gln Lys Leu Thr Phe Thr Asp
                740                 745                 750

Asp Asp Tyr Leu Ile Gly Leu Tyr Asn Gln Asn Lys Asp Ile Ala Leu
                755                 760                 765

Lys Met Pro Ile Ile Asp Leu Val Thr Lys Ala Thr Gly Asn Thr Lys
        770                 775                 780

Leu Leu Pro Asn Ser Phe Asp Ser Gln Phe Val Tyr Asn Asp Val Asp
785                 790                 795                 800

Gly Asn Thr Ile Ile Asn Val Ser Ser Asn Lys Pro Thr Val Glu Thr
                805                 810                 815

Phe Asp Pro Thr Val His Lys Asp Val Glu Leu Gly Gly Asn Asn Val
                820                 825                 830

Gln Gly Asp Thr Pro Asn Ser Ile Asp Gly Lys Ile Val Ala Gln Gly
        835                 840                 845

Thr Val Val Thr Trp Pro Met Ser Thr Ser Asp Leu Pro Ala Asn Arg
        850                 855                 860

Thr Gln Asp Val Val Ser His Ser Thr Ser Glu Thr Leu Asn Gln Asn
865                 870                 875                 880

Leu Gln Tyr Val Gly Tyr His Ala Tyr Met Pro Asp Ala Asn Gly Lys
                885                 890                 895

Leu Gln Asp Val Thr Ser His Val Gln Leu Gln Gln Asn Gly Gln Asn
                900                 905                 910

Leu Val Phe Thr Asp Asp Ser Tyr Leu Ile Asn Leu Tyr Asn Gln Asp
                915                 920                 925

Lys Ser Ile Ala Phe Lys Met Pro Ile Ile Asp Leu Met Thr Lys Ala
        930                 935                 940

Ile Ser Asp Ser Ala Thr Ile Pro Asn Thr Phe Glu Ser Gln Tyr Val
945                 950                 955                 960

Phe Asn Asp Gly Asn Gly Asn Thr Thr Phe Lys Ser Thr Ser Asn Thr
                965                 970                 975

Val Gln Ile Ile Thr Tyr Lys Pro Lys Thr Thr Lys Asp Val Glu Leu
                980                 985                 990

Gly Asp Asn Ile His Gly Asp Thr  Asn Ala Ser Ile Ala  Gly Gln Met
        995                 1000                1005

Ile Thr  Asp Gly Thr Val Val  Thr Trp Pro Met Ser  Thr Ser Asp
    1010                1015                1020

Leu Pro  Ala Asn Arg Thr Gln  Asp Leu Gln Gln His  Val Val Thr
    1025                1030                1035

Asp Asn  Leu Asn Asp Asn Leu  Ile Phe Gln Gly Tyr  Thr Ala Trp
    1040                1045                1050

Leu Pro  Thr Ala Asn Gly Leu  Val Asp Val Thr Asn  His Ile Glu
    1055                1060                1065

Leu Thr  Arg Asp Gly Gln Asn  Leu Thr Phe Thr Asp  Asp Ala Tyr
    1070                1075                1080

Leu Leu  Asn Leu Tyr Asn Gln  Asn Lys Asp Thr Ala  Tyr Lys Leu
    1085                1090                1095

Pro Ile  Ile Asp Leu Val Thr  Lys Ala Asn Gly Asn  Thr Lys Leu
    1100                1105                1110

Ile Pro  Asn Asn Phe Asp Ser  Met Phe Val Tyr Asn  Asp Gly Asp
    1115                1120                1125
```

-continued

```
Gln Gln Thr Thr Val Asn Val  Thr Ser Asn Thr Val  Asn Ile Ser
    1130            1135             1140

Thr Tyr Asp Pro Thr Ala Thr  Lys Asp Val Glu Leu  Gly Asp Asp
    1145            1150             1155

Ile Glu Gly Asp Thr Ala Asp  Thr Ile Asn Asn Leu  Met Val Gln
    1160            1165             1170

Ile Gly Thr Lys Met Thr Tyr  Pro Leu Thr Val Ser  Asp Leu Pro
    1175            1180             1185

Ala Asn Arg Ala Asp Glu Ile  Thr Ala His Gln Ser  Val Asp Thr
    1190            1195             1200

Leu Ser Asp Tyr Leu Glu Tyr  Gln Gly Tyr Lys Ala  Tyr Leu Pro
    1205            1210             1215

Asp Ala Asp Gly Lys Leu Gln  Asp Ile Thr Glu His  Val Asn Leu
    1220            1225             1230

Lys Arg Glu Gly Gln Lys Leu  Ser Phe Asn Asp Asp  Asp Tyr Leu
    1235            1240             1245

Ile Asn Leu Tyr Asn Asn Ser  Lys Ala Thr Lys Gln  Ala Leu Pro
    1250            1255             1260

Val Ile Asp Leu Val Ala Lys  Val Thr Gly Ser Asn  Asp Gly Lys
    1265            1270             1275

Lys Val His Ile Ile Pro Asn  His Phe Asp Ser Thr  Ile Thr Thr
    1280            1285             1290

Lys Asp Gly Lys Ile Asn Thr  Thr Ser Asn Thr Val  Val Ile Asn
    1295            1300             1305

Ser Asn Asp Pro Glu Ala Val  Lys Asp Val Glu Leu  Gly Asp Asn
    1310            1315             1320

Val Val Gly Asp Thr Pro Asn  Ser Val Thr Gly Thr  Thr Val Ala
    1325            1330             1335

Asp Gly Thr Ile Val Thr Trp  Pro Met Ser Val Gly  Ser Leu Gly
    1340            1345             1350

Ala Asn Arg Ala Gln Asn Val  Ile Lys His Thr Glu  Thr Glu Asn
    1355            1360             1365

Leu Asp Ser Gly Leu Thr Tyr  Leu Ser Phe Lys Ala  Tyr Leu Pro
    1370            1375             1380

Asp Ala Asp Gly Lys Met Gln  Asp Ile Thr Glu His  Ile Asn Ile
    1385            1390             1395

Gln Gln Asp Gly Gln Lys Leu  Val Phe Thr Asp Asp  Asp Tyr Leu
    1400            1405             1410

Ile Ser Leu Tyr Asn Lys Asp  Lys Ser Gln Arg Phe  Ala Leu Pro
    1415            1420             1425

Val Ile Asp Leu Val Thr Arg  Val Asn Gly Asp Asn  Lys Ile Ile
    1430            1435             1440

Pro Asn Thr Phe Val Ser Gln  Phe Thr Phe Asn Asp  Gly Lys Gly
    1445            1450             1455

Asn Thr Ile Thr Ser Val Thr  Ser Asn Gln Val Asn  Val Ser Thr
    1460            1465             1470

Phe Lys Ser Asn Pro Glu Lys  His Val Thr Leu Gly  Thr Asp Ile
    1475            1480             1485

Glu Gly Asp Asp Ala Glu Asn  Ala Asp Gly Thr Val  Val Ala Gln
    1490            1495             1500

Gly Ser Glu Val Thr Trp Pro  Leu Ser Asp Lys Ser  Pro Leu Pro
    1505            1510             1515
```

-continued

```
Ala Asn  Arg Ser Gln Asp Val  Lys Ser His Thr  Leu  Val Asp Lys
    1520             1525              1530

Leu Asp  Asp Asn Leu Gln Tyr  Asn Ser Tyr Lys Ala  Tyr Leu Lys
    1535             1540              1545

Gly Thr  Asp Gly Lys Leu Gln  Asp Val Thr Asp His  Ile Lys Leu
    1550             1555              1560

Thr Arg  Asp Gly Gln Asn Leu  Thr Phe Ile Asp Asp  Asp Tyr Leu
    1565             1570              1575

Leu Asp  Leu Tyr Asn Lys Asp  Lys Ser Thr Ala Phe  Asn Leu Pro
    1580             1585              1590

Ile Ile  Asp Leu Val Thr Thr  Val Val Gly Asn Asp  Lys Leu Ile
    1595             1600              1605

Pro Asn  Lys Phe Asp Ser Asn  Phe Val Phe Ser Asp  Gly Asn Lys
    1610             1615              1620

Asp Thr  Ser Met Lys Thr Thr  Ser Asn Glu Val Ser  Ile Ser Thr
    1625             1630              1635

Tyr Thr  Pro Val Thr Asn Lys  Asp Ala Glu Leu Gly  Asp Asn Val
    1640             1645              1650

Val Gly  Asp Thr Ser Asp Ser  Ile Ala Asn Glu Thr  Val Pro Asp
    1655             1660              1665

Gly Thr  Ile Val Thr Trp Pro  Leu Ser Val Ser Ser  Leu Pro Ala
    1670             1675              1680

Asn Arg  Ser Gln Asp Val Phe  Lys His Val Ile Glu  Asp Ile Leu
    1685             1690              1695

Asp Gly  Asn Leu Thr Tyr Asn  Ser Phe Lys Ala Tyr  Leu Lys Asp
    1700             1705              1710

Ala Ala  Gly Asn Leu Gln Glu  Val Thr Asp His Val  Lys Leu Ala
    1715             1720              1725

Gln Glu  Gly Gln His Leu Thr  Phe Thr Asp Asp Asp  Tyr Leu Ile
    1730             1735              1740

Asn Leu  Tyr Asn Ser Ser Lys  Asn Lys Glu Gln Ser  Leu Pro Ile
    1745             1750              1755

Ile Asp  Leu Val Thr Thr Val  His Gly Asp Ser Lys  Leu Ile Pro
    1760             1765              1770

Asn Glu  Phe Asp Asn Val Phe  Val Phe Lys Asp Gly  Lys Gly Gln
    1775             1780              1785

Thr Thr  Val Lys Thr Thr Ser  Asn Lys Val Thr Ile  Lys Thr Ala
    1790             1795              1800

Ser Leu  Pro Thr Pro Thr Lys  Glu Glu Thr Asp Asp  Gln Gly Asn
    1805             1810              1815

Asn Ile  Asn Gly Asn Glu Val  Lys Ala Gly Glu His  Val Asn Tyr
    1820             1825              1830

Thr Leu  Asn Trp Asp Leu Ser  Asn Asp Lys Asp Val  Lys Ala Thr
    1835             1840              1845

Pro Glu  Met Ile Lys Lys Gly  Phe Phe Phe Ile Asp  Pro Ile Asp
    1850             1855              1860

Ser Arg  Ala Leu Ser Val Asp  Asp Leu Ser Lys Ala  Lys Val Val
    1865             1870              1875

Asp Gln  Asn Gly Asn Lys Val  Asp Gly Ile Ser Phe  His Leu Tyr
    1880             1885              1890

Asn Ser  Leu Ser Glu Val Pro  Glu Phe Ile Gln Glu  Gln Val Lys
    1895             1900              1905

Ala Asn  Asn Leu Gln Asp Lys  Ile Thr Gly Pro Phe  Val Val Ala
```

```
          1910            1915            1920

Gln Ala  Asp Asp Leu Gln Ala  Phe Phe Asp Lys Tyr  Val Lys Thr
     1925             1930             1935

Gly Ala  Lys Leu Lys Val Thr  Ile Pro Thr Ile Val  Lys Ser Gly
     1940             1945             1950

Phe Thr  Gly Glu Phe Ser Asn  Thr Ala Tyr Gln Phe  Gly Phe Gly
     1955             1960             1965

Lys Ala  Thr Pro Thr Asn Thr  Val Thr Asn Tyr Val  Lys Pro Met
     1970             1975             1980

His Lys  Pro Ala Ser Pro Glu  Thr Pro Ala Ala Ile  Ala Pro Gln
     1985             1990             1995

Val Ile  Ser Ala Thr Ala Gln  Pro Met Thr Ser Asp  Ala Pro Val
     2000             2005             2010

Thr Pro  Ser Glu Lys Thr Ala  Lys Leu Pro Gln Thr  Gly Asn Ala
     2015             2020             2025

Asp Glu  Gly Ala Leu Leu Gly  Leu Ala Ala Val Ser  Leu Val Gly
     2030             2035             2040

Ser Leu  Gly Leu Ala Ala Leu  Gly Leu Lys Gln Asn  Arg Asn Asp
     2045             2050             2055

Asp
```

```
<210> SEQ ID NO 11
<211> LENGTH: 44932
<212> TYPE: DNA
<213> ORGANISM: Artificial Sequence
<220> FEATURE:
<223> OTHER INFORMATION: Based on Lactobacillus reuteri sequence

<400> SEQUENCE: 11
ctattcaaat ttgaaatttt gaacaacttt atcaaggtct tcttgttcaa tccctagata     60
gtggcgcgta tttcgttcag aggagtgatt aaataactgc gaaatgattt caacgttaac    120
acctttctta tagagttgtc gaccaaaagt ttttctaaaa gagtgtgttc caattttagc    180
aacgatttta ttattttccg tttttctagc cattcgttgc aacatttcgt aaaagccatg    240
tactgaaaaa tgaccttctt gtttcccagg gaaaagataa tcattctcgt ctttataatt    300
caagtcatta agataatcaa taatttcggc aagacaatta ttccaaaaga gcgttttagc    360
cttacctgtt ttttgctcaa taacacgggt tttagtttta tttagaacat gaccaaccct    420
taacgttaca acgtctgatg ctcgcaatcc gttattaagg gcaattgcaa ttagtaatag    480
gtttcggtta accaattcag gacgcgaatg cagcttaatt gtctcacgta actgatcata    540
ttcttcgaga gtcaagaatt aacattttc tacccatatt ttccgtttac ccttgatttg    600
accattagtt ttattttttgg gaatataaac tcgttttta gttgacataa tatttcttcc    660
tttgttaatt tgcgaggtaa tcaactaaag cagggacgat ttcctctcct tctttccgcc    720
cagtttcata aagtgctcga attttcttaa tatttccttc aatccgctta attttaattg    780
gtttagaggg agcaatatta aagatctttc cttcacaaga caaacgatta atttcagcag    840
tctgttggtt gtagagaagg ggacgatcaa tccccgcttt agcaaattcg ggataatctt    900 tataccat gtcgtacaac ttctttacag cagaactaga tggcttcttt cggtagttaa    960
tatccctggt ccgtacaaca acaatcttgt catagccttg tcgttgtgca atatcaaatg   1020
gaattgaatc tgtgatccca ccatcaaggc aaggcccttg agaagtttcc tgtggatctg   1080
aaagaaatgg cattgatgag gaagctttga gggcattggt tagctcctca ccaacaggat   1140
```

-continued

```
ccgtaaataa aactgttttt cctgtttttca cagaagtagc aactgctgtg aaatgagatg   1200
ctgaccgtcg atatgcagct tcattaaaat tctgccaaga atatccgtga tcttcaaaaa   1260
gataatcaag attaattatt tgcttttttaa atacgcgagc catcgagata tattggcgat   1320
cgtgccgatg atcaatatta atattggcag cgcgtccgta ttgcttagag acgaaattaa   1380
ctccacaaag tgaaccagca gaaacgccaa ttacacttcg aaattcaata tggtgagcga   1440
gaaatgtatc aacaattccg gcagtatatt gtccacggaa tgcgccacct tctaaaacta   1500
atgctgcatt atataacata aaatgaaata actcctttt gtccgccaaa aatagcaaaa   1560
atgacctaat ttttagtgag acactttttc aataaaatta tacaacagtc tcacacgaaa   1620
atataggatt ttaaaagctt gttatatcaa cgtttattct cggttaccgt aagactcttt   1680
tatcaaaaga gtcttactga ttttgaaata acgcaaaagt aggggcaaaa acggatttttg   1740 cctctcagac gaactgaaat tcattttgat gagtagtagg tcgttacaat tcgtctcaga   1800
agaaaaacgc atattgatat caaaaaatga gtaaatagac agtaaatatt taaatatgaa   1860 cttttttatga agaaactatt gataatttaa gataatcata ataaaatagt gcacagttaa   1920
ttgttaaacg tttagcaaaa aaggtaaaga aacggggtta tttctatgct agaacgcaag   1980
gaacataaga aaatgtataa aagtggtaaa aattgggcag ttgttacact ttctacggct   2040
gcactggtgt ttggtgtaac aactgtaaac gcatccgcag acacgaatac tgaaaacaat   2100
gattcttcta ctgtacaggt tacaacaggg gataatgata ttgctgttaa aagtgtgaca   2160
cttggtagtg gtcaggttag tgcagctagt gatgcgacta aaaattctgc taatgcaaat   2220
agtgcttctt ctgccgctaa tacacaaaat tctaacagtc aagtagcaag ttctgctgca   2280
acagcttcat ctacaagttc agcatcttca tcaactaaca cagatagtaa agcagctaca   2340
gaaaatacta atgtagccaa agaggatgat acacaaaaag ctgcacccgc taacgaatcc   2400
tctgaagcca aaaagaacc agctgtaaac actaatgatt cttcagctgc caaaaacgat   2460
gatcaacaat ccagtaaaaa gaatactgcc gctaagttaa acaaggatgc tgaaaacgtt   2520
gtaaaaaagg cgtggattga tcctaatagt ttaactgatg accagattaa agcattacat   2580
taaataagat gaacttctcg aaagctgcaa agtctggtac acaaatgact tataatgacc   2640
ttaaaaagat tggtgaggct ttagttgatc aagatcctaa atacgctatt ccttatttta   2700
atgcaagtca aataaagaat atgcccgctg catatactag ggatgctgaa acaggtgaat   2760
atgctgattt agatatttgg gattcatggc cagttcaaga tccagtgact ggttatgttt   2820
ctaattggaa tggctatcaa cttgtgatcg ctatgatggg acggcctcat cacgaagata   2880
atcatattta tttactttat aataagtatg gtgataatga tttttcacac tggcgaaatg   2940
caggatctat atttggatat aatgaatctc cactaacaca agaatggtcc gggtctgcta   3000
ttgttaattc tgacaactct attcaactct tttatactat caatgataca aataatgcta   3060
ttaaccatca aaaattagca agtgctacta tgtacttaac agccgacaat gatggtgtcc   3120
atattaataa tgtagagaat aatcatgtgg tatttgcagg tgatggttat cattaccaaa   3180
cttatgatca atggaaagct gcaaatagtt ttgctgacaa ctacactttg cgggatggac   3240
atgttgtaca aatgccaaat ggtgatcggt atttagtatt tgaaggaaat actggaactg   3300
aaaattatca aggtgaagat caattatata attggtcaaa ttatggtggt aacgatcgct   3360
ttaatattga aagcttgttt catcttttaa gtagtgatgt tgattataaa aaagctatct   3420
ttgctaacgg ggcacttgga attattaaac taacgaatga tgaaaagaac ccgcaagtag   3480
aagaagtata tactccatta gttacatcaa atatggttag tgatgaactt gaacgtccta   3540
```

-continued

```
atgttgttaa acttggagat aagtattatc tattctcggc tacacgttta agcagaggaa    3600
ctaatatcga tactcttaat aaagctaata aagttgtcgg agataatgtt gcaatgattg    3660
gttacgtagc cgatagtctt acaggtccat ataaaccatt aaatggttca ggggttgtag    3720
tgacagcttc tgttcctgcc aattggcgta ccgctactta ttcttactat gctgttccag    3780
tagaaggaaa agaaaatcaa ttactcatta cttcgtatat gacaaataga ggcgaagttg    3840
ctggaaaagg tatgaattca acatgggcac caagttttat tgtgcaaatt aatcctgatg    3900
atacaactat ggtattagct aaagtaacta accaagggga ttggatttgg gacgaatcaa    3960
gtaacaataa taatatgtta ggaaacattc aaacagctgc tttacctggg gaatttggta    4020
aaccaattga ttgggatttta attggtggtt atggattaaa accgcatgat cctgctacac    4080
caaatgatcc tgaaacgcca actacaccag aaacccctga gacacctaat actcccgaaa    4140
caccaaagac tcctgaaaat cctgggacac ctcaaactcc cgatacacct aatactccgg    4200
aagttccttt aactccagaa acgcctaagc aacctgaaac ccaaactaat aatcgtttac    4260
cacaaactgg aaataacgcc aataaagcca tgattggcct aggtatggga acattgctta    4320
gtatgtttgg tcttgcagga attaacaaac gtcgagttaa ctaaatactt taaaataaaa    4380
ccgctaagcc ttaaattcag cttaacggtt ttttattttg aaagtttta ttatcgaaaa    4440 aaacaaatcc tcgttaatcc tttaatgcaa ttgttgtaaa accttgcgac agtaataaca    4500
gtggatttgc ccatctttgt cagctaactt ccgtgcatgc attgcagaaa aagtatagtg    4560
ctcatgacaa aatggacaaa catattgctt tttcccaaat agtgaggtaa taaagcccaa    4620
aattttctcc tccataaaaa aattatacac cccttaacat tatagcgaag attatcttta    4680
tagaaaaggc ttttattcat ttgtttttttt atatgaagtt tcactaattt cttttaagagc    4740 atcacgctgc tgtttctggt caacgtgagt atataaatcg gtagcagatg ttcctttttg    4800
tcccaactgt tgggccacta atacttgatc tttcgttacc tcatacattt cagaagcaag    4860
ggtgtgccgt aatttatggg gagtaagagg atggccaaat gcggttgaat acttttttgac    4920 cattttttca attgcattag ctgtcatccg tcgagtttgc ttgtgataaa cggttaggaa    4980
gaaagcagta tccttttttta aagcgtggta tcgttgtgca cgaatcgctt ggtaagtttg    5040
gatataagta atagcccaag gagcaattgg taccgaatcc ctctggccac cttttcttgt    5100
tacatctagc agcgattgtt ttaagtttaa atcaccaagg tttacatttg ccgcctcgga    5160
tacccggacg cctgttccta aaataagagc aataattgca atatctcgtt ccttattgac    5220
cttataagag gggagagctc ttttatcaca tttattaggg tattctttttt caatgaaagt    5280 aataaaatca aacttcattt gtccccggta catgtgtgaa gccagcgtat gagcccgata    5340
atttaatgtt tttgtatcat taagggagtc aatttttcagc attacattac ggtcaaaata    5400
agattcacca ttattgttat ctgcggtaac tgttaaaaat ttatacaatg accttaatgc    5460
attaatagat cgattgattg aagtaggaga atttaaccgt ccttgtgcat tggtagtatg    5520
ctgcaaataa tcgatataca acattacatc gctacgccgt agattcgcca gtgtatcaat    5580
tggtaagtcc ttattagaat taacagagac gagtccactt gaccgtaacc aatcaaagaa    5640
tcgacggatt tcagttaagt actgataggt tgttgtgact gcatggttgg tccctaaata    5700
atactcgtta acataatcag gaaggttctg aagctcctct tgaattagct ttaaatattt    5760
atctgcttcc atttttatat cctccttgat actaaaaaga gtcgcttgaa agaaaacttt    5820
caacgactct ctaaacctat cgggaaaaca ggattcgaac ctgcgacccc ctggtcccaa    5880
```

-continued

```
accaggtgct ctaccaagct gagctatttc ccgttaataa cgaacaaata ttattctacc   5940
aattctcaat taattagtaa aggaatattt taatttaaag tgattaatag ttaatgatta   6000
aatgacataa tagtaaaatt cctattaatt gcaaaaaaat catgattaac cgaaatcctt   6060
ttctagcatc taatgaagat gataaataat tttattttcg actagttata aaagatacct   6120
ttccgaaaat aatttgacat tcaaaatact tttgaatata atttgattat cgaatatttt   6180
gatactcgaa atattttccg aaggcaggtg aatctttttg gcaataatga atgcgcagga   6240
gattatggaa ttaattccta atcgatatcc gatttgctat atcgattatg tagataaatt   6300
agttcctgaa gaaaagatta ccgcaacaaa aaatgtcaca attaatgaat cattttttcg   6360
cggtcatttt cctaataatc ctgttatgcc tggagtttta attatcgaaa cattggccca   6420
agctgcttca attttgatat taaaatcacc gcattttat aagaaaacag cttatcttgg   6480
cgcaattcat aaagcaaggt ttcgacaaat ggtccgtcct ggtgatgtat taaaactaaa   6540
cgttgttatg aaaaaagttc gatcatcaat ggggattgta gaaacacaag cgcttgtgaa   6600
cggcaaatta gcttgtagtg cggagcttgt ctttatcgtt gctgaacgag aagaaaagat   6660
ttagcacggt gaatcattat catttataat atattttgat aatcaaatta ttcgggctat   6720
agaataaaat tgaagggaag aaatatatta tgagtaaaga taatgattac gaaaaaatta   6780
ataaaggatt aatcaaagtt tattccggaa ttctatggat tgaagaaaat gaattgcgga   6840
aaagtacatt caatgattta acaattaaag agatgcatgc aattgatgca attacgatgt   6900
ataaccatca aacaatttct caagtagcag aaaagcttca tctaactcca ggaacaatga   6960
cttcaatggc tgatcgttta attcgaaaag gatatgtgga aagaattcgt gataaagatg   7020
atcgccgcat tgttcggtta tgtttaacca aaagaggccg ggtactatat cgtgcgcacc   7080
gggcctttca taacatgatg gttgaacgtt ttcttaaagg aatggatgat gaagaaatga   7140
aggttgttaa aaaagccttg caaaacttag aagatttttgt ggatgagcat gcttagagat   7200
aaggattgac aaacattgca aaatttaaga attactagta ctgcgagtta tcatccaccc   7260
cttaaaatta ctaaccagca attatcaact attatgaata cttcagatga gtggattaag   7320
acgcggactg gaattcatca acgttatatc agcaacactg aaaatacttc agacttagct   7380
gtcaatgttg gtacccagtt attgactaat gccaatttaa aggcaactga acttgattta   7440
atcattattg caacgatgtc tcctgatgcc tatactcctt caactgctgc tattgttcaa   7500
ggaagattag gtgcgaaaaa tgcaattgcg tttgatatct cagcagcttg tactggtttt   7560
atctatgcca ttaatacagc tgaattaatg ttgaaaagct ctcattggaa aaatgcaatg   7620
gtaattggtg cagaagtatt atcaaaactg attgattggc aagatcgaag tactgccgta   7680
ttgttcggcg atgggctggc ggagtgttac ttcaaaagac aactacaaca acccctttaa   7740
ttctcggccg tgatctccat acatttggtg acttaggaga taaaattatt gccggaaaaa   7800
caacgcctaa aactggcttc cctaaacaac taacatccct ttcaccattt acgatggccg   7860
gccgtgacgt ataccgcttt gccactcatg aagtaccacg atcaatcact tctgccgttc   7920
aacaagctaa tttgaaatta gacgatatcg attatttttt attacatcaa gcaaatgaac   7980
ggataattac ccaaattgca aagagactgg cgcaaccaat tacaaagttt ccaatgaata   8040
ttagtgaata tgggaataca gctgccgcta gtgaaccaat tttattgact caagctattg   8100
ctcatgaatt gattaaacca ggtaacatta ttgcaatgag tggctttggt ggcgggttaa   8160
gtacaggaac aataattta aactattaat agagaaagaa gaatggatat gactaaagag   8220
gaaattttta atactgtaaa aactattact gttgatgaat tagatgttga cgaaaatcgt   8280
```

-continued

```
gtaacaatgg atgcacgaat caaagatgat cttgatgctg atagtcttga tgtttttgaa   8340
attatgaatg agcttgaaga taagtttgag attgaattag atgccgatga aggaatcgag   8400
actattagtg acgttgttga tttcgtaaag aaacagttgg atgaaaaata atgtactacg   8460
gaatattatt tagcggtcaa ggtgcacagc gatcgggaat gggagtcgag cttatggccg   8520
actccctttt ttcaaggatt gttagtcagg caagcgctgt ttgtgaactt gatttgctca   8580
aaattatgaa aaacgagcat aaggagttga ataaaacagc atatgttcaa ccagcaattg   8640
taacagttag ttatggaatc taccgaatgt taaaacggga tttacctcaa ctaccaatta   8700
aagggatgat tggcctatct ttaggcgagt acgctgcttt aattgctagt aatgcacttt   8760
catttgaaga aggaattaaa ttagttgcgg accgtgctca ctttatgcaa caagacgcgg   8820
atagagaaat aagtacatta gcagctgtcc ttgatcctca acttcaagag ataaaagaac   8880
taatcaccgc tcaacaagaa aatggtcagc gagtttatat tgctaactat aattcaccac   8940
gacaaatcgt agtgggcggg gcattaaacg ctttaaaggc tacccttaaa aagattgaag   9000
aggacaagct tgctaaaaga acgatcctgc tcaaagttaa tggtgcattt catactccct   9060
tctttaacgg tgcacgtcaa cagatgcata accggttaca agcagtcgac ttccatgagc   9120
cacagattga agttattagc aatactacta acagcttgtt tcattgtgag gatcttccag   9180
gaattcttga aaaacaatta gctgttccaa cacactttgg agctaatgtt aaggaattag   9240
tcaagcacgc gaaaattgac acaatattgg aaattggtcc tggaaagacg ttatctcgct   9300
tcgctcacca agttgaccag cacttaaata cccaacacat tgaaaatctt gctgattatg   9360
aaaaatttat aaaggagcaa aaagatggaa ctgacagata aagtcgtttt tataagcgga   9420
agcacacgcg ggattggggc ggctactgca ttagagtttg ctaaggctgg tagtcggcta   9480
atcctcaatg ggcggcagga taacttacca aaaacgttta aagaaaagct agatctacta   9540
ggggcggatt atcactatct taagggcgat attgcaaatg aagaatcagt tagtgaatta   9600
gcagcagcgg cttggcaaat atacgagaag atcgacattc ttatcaataa cgcgggaatc   9660
acgaatgata agttaatgat gggaatgaaa gcgagcgatt ttgaccaggt catcaatgtt   9720
aatttacgcg gaacatttat gttaacgcaa cctatttta agaagatgct caaaaaaaga   9780
gtcggttgca ttatcaacct tgctagtatt gtgggtctcc atggtaatac gggacaagct   9840
aattatgcgg caagcaaggc aggtatcatc ggccttacta aatctattgc ccaagaagga   9900
gcacgccgtg gaattcgttg caatgcgatt gctcccggaa tgattactag tgatatgact   9960
gaaaaattat ctgagcgagt aaaagaacaa attctcagtc gcatccccct caaccgctta  10020
ggacagtcag aagaagttgc taagaccgca aaattttag cagaaaacga ttatttgact  10080
ggtcaaacca ttgtagttga cggtggcatg acaatttagg aggaactaaa tgacaagagt  10140
tgtaataaca ggaatgggtg ctgttgctcc taatggtaac ggtattcaag aatttataag  10200
taatagtttt gcaggcaaag ttggaattaa agcgatcaag aaatttgatg ccaagtcgac  10260
aggaattacc gtggcaggtg aaattgacga ttttgaccct aatgatgtca ttggaaggaa  10320
agccgcgcgc cgaatggatc tttattctca atacgcctta caaagtgcga ttgaagcaat  10380
ggaaatggcg gagattaacg aaacaaatac caagccagtc gacatgggtg ttatctatgg  10440
atctggaatt ggcggtttga caactattca agagcaaatt atcaaaatgc atgataaggg  10500
tcctagacgg gtatcaccaa tgtttgttcc aatgtcaatt gctaacatgg cagccggtaa  10560
tatttccatt cactttaatg cgcaaaatat ttgtacatcg attgtgactg cttgtgccac  10620
```

-continued

```
tggaactaat gcaattggtg aagcctttcg tcaagttaaa gcaggtcgcg ctaaagtaat   10680
gatcgctggt ggatcagagg cttcggtgaa tgagatcggg attgctggtt ttgcggcatt   10740
aacagcatta tcacaagcaa ctgatccgct taaagcttct ttgccatttg ataaggcacg   10800
tcaaggattt gttttgggtg aaggcggtgc aacacttgtt ttagaggatc ttgagcatgc   10860
gcaaaaacgc agtgctaaca ttcttggtga gattgtcggt tatggtgcta cctcggacgc   10920
ttaccatatt acatccctg atccaactgg tgcaggggcg gcaagagcaa tggaactggc   10980
aattaaagaa gctggaatta gtcctagcga aatttcctat attaatgccc acggaaccgc   11040
tactcatgct aatgatgaag gcgaatccaa agcaatcaat caggtatttg gttccgatag   11100
taatgttcgc gttagttcaa cgaagggaat gaccggccat ttgcttgggg ctgcgggcgc   11160
aattgaggca gtcttaacag tagccgcttt acaaaaggga caattaccgt tgaatatagg   11220
ttgctttaat caagatccaa aatgctcggt taaccttgtg acggcagaaa ataggaacgc   11280
ctcaaccgcc cgttacgcaa taagcaattc ttttggtttc ggtggtcata atgctgtttt   11340
agcctttaag aaatgggagt gatctatctt ggaatttaaa gaaattcaaa cattaatgca   11400
aaattttgaa gattctgata ttcgtgaatt agaaataaat caagattcct ttcagctcta   11460
tttaagcaaa aataagcaaa cccacaagca tgaaaatctt ataacaaccg aaaaaacaga   11520
gcaaacgact tcagctaaga aaaaagcaaa cgaacaacta actttacctt cgcaaaatat   11580
aactgcgccc ctagtcggaa cagtctatct ccaaccaacc cccgatgcag atccctatgt   11640
taaaagtggc gaccacgtaa aaaagggga tgttgtttgt gtgattgaag caatgaaaat   11700
gatgacagag ataaaaagcc cttttaacgg aaccattact tcaatttgtg taagcaatga   11760
agaattagtt gaagtagaac aaccgctttt ctcagttcag gaggataaag acaatgccta   11820
ataaaacttt agatataact gaaattcaaa aaatccttcc gcatcgttac ccgatgttgc   11880
taattgacca agttgatgaa ttaatccctg gtaagaaggc cattacacac cgtaatgtca   11940
cgattaatga gaggttttt aatggtcatt tccccgaaaa tccagtttta ccaggagcat   12000
tgattgttga atcattggcg caaacaggtg ccgtcgctct cttatctcaa gaagagttcc   12060
aagggaaaac agcctatttt ggtggaattc ggtcagcaga atttcgtaag gtagtccgtc   12120
cgggcgatac gttaaggtta gaagtcagac tagaaaaagt tcacaaaaat attggaattg   12180
gtaaaggcat tgcaacggtc gatggcaaaa aagcctgtac agccgaatta acttttatga   12240
ttgggtaggt ggtttaatgt tttccaaagt actagtggct aatcgtggtg aaattgctgt   12300
caggataata cggtcattac gggagctagg aattaagaca gtagctatct attcaactgc   12360
agaccgcgaa agtcttcatg ttcaactagc ggatgaagct gtatgcgttg gaactgcccg   12420
ggcccaagat tcatatttga atgcgaaaaa cattttagaa gctgctcttg gtacaggtgc   12480
ccaggcaatc catcctggct ttggctttct atcagaaaat gcggaatttg cgacaatgtg   12540
tgaagaatgc ggaattacgt tcatcggtcc ccaagcctca gtgattgact taatgggaaa   12600
taaggagcat gcacgggagc aaatgaaaaa atcaggggtg cctgtgattc ctggaagcga   12660
tgactatatt accaatgtta atgacgctgt tgaggtcgca aacaagattg ggtatccaat   12720
tttgttaaaa gcagctgctg gtggtggcgg taaagggatc cgacgaatta acgatcataa   12780
ccagatgcgg caaatattta gcgaggccca aaacgaagcc cgactttcgt ttaatgatga   12840
ccgaatgtac cttgaaaaga ttatggagaa tgttaaacac attgaggtcc aagtatttcg   12900
tgataatttt ggcaatgccg tttttctttcc tgaacgtgac tgctcgattc aacggaataa   12960
acaaaaattg attgaagaaa gtccttgtgt cctagtaaat gaacaagagc gaaaaacgct   13020
```

-continued

```
aggacaaatt gcaatgcgag ccattaatgc gattaactac cataatacgg ggacaataga   13080
atttctaatg gacaaggacc atcactttta ctttatggaa atgaacactc gtatccaggt   13140
tgaacataca gtgacggaga tggtaactgg gatcgactta gtgaaggcac aggttattgt   13200
cgctgcgaat gaaccacttc cctttaccca acaggatatt caggttcatg gacatgcaat   13260
tgagtgtcgg ataaatgctg aaaatcctaa acaaaacttt atgccagtga ctgggacgat   13320
taattactta tatcttccag tcggtaattt ggggatgcgc attgacactg ctatttatcc   13380
tggcagtaag atcactcctt attatgattc aatgatcgct aaggtaattg cccttggtca   13440
agatcgccaa gaagctattg aaaaaatcaa acgacttta aatgaaatgg taattacggg   13500
cgtaacgacc aatcaaaatt tccatttagc aatcctaaac aatcctaaat ttttggcagg   13560
aacagcttca acaacgtttc ttgaagactt cttcttgcca caatggaaaa aggagctgac   13620
agcgtgaaat tatatgatca aaataatact ttaagtgaac ggcacatcaa agcagataaa   13680
aatgctgatg aaagggtccc agatcaaatg tggttaaggt gtccacattg tcatcaatta   13740
ctattcgcca agcagttaac acaatatgct gtttgtccca attgtgacta tggattacga   13800
atacctgccc gccatcgact ctcgtggtta gtagattcat ttaaagaatt cgataaggat   13860
ctccagacaa agaatccgtt acattttcct ggataccaag aaaaaatcag caaacttcaa   13920
agacaaacta agctgaatga ttcagtccta actggtgaag cttcaattaa tgatcagcta   13980
ttttcactag gtattatgga tccaacattt attatgggat ccctcggaac tgttaccggt   14040
gaaaagataa cgcgcttatt tgaatatgca actatccatc gtcaagcagt agtactattc   14100
actgcttcag gcggggcacg gatgcaagaa ggaattatgt cgctaatgca gatggcgaag   14160
atttcacaag caataaatga gcatgctgct gccggccttt tatacattgt gatcttaacc   14220
gatccaacaa ctggtggagt aacagctagt ttcgcaatgg acggagatat tattctcgct   14280
gagccccatg cacttgttgg ctttgcaggc cgtcgagtta ttgaacagac gattcatcag   14340
caaattcctg ttgatctcca atcagctgaa aacatcctgc atcatggatt tattgatcga   14400
attgtaaaac gtcaagatga aaaaaagctg cttgaatggc tattaaaaac agggagcgtt   14460
gctaatgaat gaacaattat cagcaagcga gattgttaaa cgtgctcgca atgacaataa   14520
aattacgggg atggagatta ttcaaaatgt tttcccagat tttgttgagt tgcacggcga   14580
ccgggcaggc ggggatgatc ctgcaatcgt tggtggaatc gctactttcc atcagcaagc   14640
agttaccgtc attaccactg atcgaggaaa aacaacagaa gaaaaaatca taaagcattt   14700
tggctcacca atgcctagtg gttatcgcaa ggcactccgc ttaattaagc aagcagttaa   14760
atttaagcga cctgtattct gttttgttaa taccgcagga gcatttccta gcaaggaagc   14820
cgaagaaaat gggcaaggaa gtgcgattgc ccaaaacatt ttacaaataa gtcagcttgc   14880
cattccaatt atcacgatta tttatggtga aggaggtagt gggggagcct tagcattggc   14940
atgtggagat gaagtatgga tgttagaaaa cagtacttat tctattttat ctcctgaagg   15000
gtttgcctcc atcatgtgga aagatagtac gaaagcagat aaagcggcag aattaatgca   15060
aatggtgccg caagctttat taaaacaagg gattatcgaa ggaattattc cagaaagcga   15120
agagcatcgt aaaacttgca aaaatatcga gcaggtttta ctaaagcgat taaacaagct   15180
gcaagaatta ccgccaaacc aacttctagc aaacagaaaa aaacgttatc gaaagtttta   15240
aggaggataa tatgggaaat atattaacag gaaaaaagat cgttgttatg ggagtagcta   15300
ataagcgttc tattgcatgg ggatgtgcac aaatgatggc tgaacaaggt gcccaagtta   15360
```

-continued

```
tctatactta tcagaattcc agaatgaaaa aaagcttaca acggttagta gatgatgaag   15420
atcaattaat tgaatgtgat gtagcagatg atgaaagtat tgaccaagcc tttacgatta   15480
tcaaggaacg tttttacaaaa gtagatggaa ttgtacacgc aattgctttt gcaaaaagag   15540
aagaattagc tggttcaatc cttggtgcta gtcgcaaagg ttatgcaatt gcgcaagata   15600
tttcgtctta ctcccttatt gctgtcgcta aggttgctaa tgagttaaat ctattaaata   15660
atcctgcaag tattgttacc ttaacttatt ttggctcaga acgtgctatc cctaactata   15720
atgtaatggg aattgctaaa gctgcccttg aagctagtgt tcgctattta gcacgggatt   15780
taggacaaaa acgaatccgt gttaacgcaa tctctgctgg cgcggttaag acattagcag   15840
ttacaggtat taaaggtcat gatgaacttt taaagatgtc ccaagcaaga actgttgacg   15900
gagaagatgt gactattagc gaaattggga atgtgtgtgc attcttaatg agcgatttat   15960
caactggagt tactggcgac accatttatg ttgataaggg ggtacatttg atttaaaaat   16020
ataaatttta aagactgaga aatgagtttt tttcagtctt tttgctgtct tttagaagga   16080
aaacataaca atagcaagaa ctttttttaa ttttttctaa aaagttcttg ctattttata   16140
gctcagttgg tattattaat aacgttgtga aagacgagtt aataattttg agaaaaattg   16200
tttaatatat ttaaaaatgg cccgttagtc aagtggttaa gacaccagcc tttcacgctg   16260
gtatcgtggg ttcaaatccc gcacgggtca cttttgcgga agtagttcag tggtagaaca   16320
tcaccttgcc atggtggggg tcgcgggttc gaatcccgtc ttccgcttag ccagttctat   16380
tatgccgggg tggcggaatt ggcagacgca caggacttaa aatcctgcgg ttagtgataa   16440
ccgtaccggt tcgatcccgg tcctcggcac tatttcggga aatagctcag cttggtagag   16500
cacctggttt gggaccaggg ggtcgcaggt tcgaatcctg ttttcccgat ctggctaaac   16560
agctaagagg taatcttctt agctgttttt ttggatatct gtcaactggt atggttgact   16620
aaaaattttt ttagtgcgcc cggcatgggt attagctagg tggtgaaagt ccgctatggg   16680
ccgtagtagt cggaaccatg agctgaggac aagggtgtcc accgtgaggt ggaatctgaa   16740
ggaagtctaa ggcaaagtac tgcatcgatg aacaagaagt agctataagg ctgaaattaa   16800
ctggataagg ctgctagaca agttgaagtc caatactact cgaagttggt ctcagtaaag   16860
ctaacgatga catggtacga aagctaatat tcttacccgg ggagatctgg cctacacgtt   16920
tccgacaagc agtactaacg cagccattaa ttagtttttt gaaataaaat aaacttttt   16980 gaaaaaagta ttgctttttta taggataact tgataatata atattcgtcg ctgatatgcg   17040
ggtatagttc agtggtaaaa ccacagcctt ccaagctgtt gtcgcgagtt cgattctcgt   17100
tacccgcttt taattaattt aatatggccc gttagtcaag tggttaagac accagccttt   17160
cacgctggta tcgtgggttc aaatcccgca cgggtcattt ttggaggatt agctcagttg   17220
ggagagcatc tgccttacaa gcaggggggtc acaggttcga gccctgtatc ctccattgaa   17280
caattttaat agttgttcaa cattttaata taattgggct atagccaagc ggtaaggcaa   17340 cggttttttgg taccgtcatg cgctggttcg aatccagcta gcccaattag tctaaaacag   17400
tgagtaaaaa ttactcgctg ttttttatta gaaaaaatag gcaatctaat aacgtaggct   17460
aaaagcgaac atcattggat tgcccaataa ttagcataat ttattcacgt cgtaacataa   17520
tatgccagac aaagaagccg actccaataa ttaacgccaa ccatgcccat agttgcaatg   17580
gaagatagat agtacacgtt aacaagccta aaacccaact gattagcatc atcgataatc   17640
cagcaatatc gccacctaaa ccatcaatac cacaagtagc gatatagacg attcctgatg   17700
ccagatataa tagcgaaaca attaattcgg ctgttccggc ataaatagga attgcaggat   17760
```

-continued

```
taggattccc aaaacctcct caagtcttat tctacccgga tgattagaat ttataaagaa   17820
ttacagtttt tctatttaca aatagagcag ggggaacaaa aaatcaaacc agaaattatc   17880
ttctgatttg attggatctt atttagttgt atcttttact tttttcaagg cttctaaaaa   17940
tacttcataa ggttgtgcac cagtgattga atacttatta ttaatcacaa atagcggtgc   18000
acttggcatt ccaatcataa atgcgcgccg ttcatttttt cgaacttcat cttcatactg   18060
attagattca agaacttttt taacatcagc aacaggtagt ccgatttcat tcattgcaac   18120
agttagagct tcatagtccg cgattgattc attatcatta aaataaagtt gataaagacg   18180
tttaacagcc ttattaagta atgcttggtc atttaaactc tcaatgtatt ttattaagcg   18240
atgagcagct aatgtattaa caggaatcgc attttccatc ttaattggta aatcaatatc   18300
ggcagcaagt tgatcaattt tatgtatttg tgtaacagct tcttgcttag ttagttgatg   18360
agtttttgca taatattctg tcattgataa atcagttgtt gttggcaacg ttggatctag   18420
ttgaaatgac ataaatttta atggtgtctg atcggcaatc tttaattctt taagcgcccg   18480
ttgtaattgt gtaattccca tatagcaata tgggcacgca atatcagccc agtattgaat   18540
ttccatagat gatcgctcct tataaatata tattaattta atctaatcat aaaataagcg   18600
aagttgctag taaatacgta aagagggaac gatttatttt aaaattaaca tgtcattaaa   18660
attatagttt taatgcgact gaatttaaaa ttcccccccag aatatcaatt tttagctttc   18720
tcaaaagaat ttatttaatg cttatttta actttaataa aacttttct aaacaaaact      18780 aatacttttg atttatgttt taaaagattt atgtaatact attgatgaag tctatgtcaa   18840
aagtatttta aaaggagttt ttatcatgaa acatacgctt aaagttgatc aagtacgtga   18900
cggtttatgg ctagattcag atattacgta tacgcaagtt cctggatggc ttggtaatac   18960
aacgcgagat ttgaagcttt cagtcattcg gcattttcaa actaatgatg atacacgtta   19020
cccagtaatt ttttggtttg ctggtggcgg ctggatggat actgatcaca atgttcatct   19080
gccaaatttg gttgattttg ctcggcatgg ttatattgtt gttggtgtcg aatatcgtga   19140
tagcaataaa gttcagtttc ctgggcaatt ggaagatgct aaggctgcta ttcgttatat   19200
aagagctaat gccaagcgct ttcaagctga tcctaatcgg tttattgcga tgggagaatc   19260
agctggtggt catatggcaa gtatgttagg tgttactaat ggtcttaacc aattcgacaa   19320
aggtgctaat ttagattact ccagtgatgt tcaagtagcg gttcctttt atggtgtagt    19380 tgatcccta accgctaaaa caggaagtgc atcaaacgat tttgattttg tttaccgtaa    19440
cttgcttggc gctgaacctg aagctgcaaa tcccctcacg tatgtaaatt ctacttctac   19500
gccctttctt atctttcatg gtacggagga tgtcgttgtt ccaatcaaag atagtgaaaa   19560
gctttatgat gtattagttg aaaacaacgt tcctactgaa ttatacgaaa ttgaaggtgc   19620
aagtcacatg gatgtaaaat ccttcaacc acaggtattt aaaattgtga tggacttttt   19680
agataagtat ttaacccggc catagatcat ttcttgcctt tactactaaa aagcaaacta   19740
ataacaatcc aactttcaca ttattgacaa aatcaaaaag caccatgaaa ttacttttc    19800 acggtgcaac tattgttaat atttatctac ttggcttcca tcaatggaga aatagacaac   19860
ttgatttgca aacctaatcc agcagcatat ttatttaatg taggcagcgt agggattgaa   19920
tctaaattct cgattttagc caattgaggt tgtgtcatac cgattttttt tgcaaattct   19980
gtttgcgaaa tgccctgttt aattctttgt acttctaaaa aagacaaggt atcaacaatc   20040
gataattctt cttttgttgc agccgtctga tgcttatcta tatcttccca ttttctcatt   20100
```

-continued

```
atttacccttt cctttcgtac caatcgtcaa gtagcgacaa ggctctttct atctgacgag   20160
gatctgtttc atccttttc ttagcataat gatttaataa tacaaaatta tttttcttcc   20220
atactccata aaatactctt tctggcatag gtcgtaactc ccatagttga tgcctataac   20280
cctttaattt ttttgcttgt ggtgtatgca acacaggacc aagagcttgt aacatcttaa   20340
tttgatggcg cattttttaaa taaattgctt tatcttgctt ttgtttactt tgcgaaattt   20400
tctcgaaata atcaccaatt tcactatttc cattttttatc ttcgtaaaaa actacttcat   20460
acatgcacta tttcctttat tatagcttat ttattactaa ttatagcaag attgctatag   20520
ctttactact attaaaatat attccataat caaaaatttt tctattgaaa gcacccgcac   20580
actcaattaa atcaaataag tttacggcaa tgattatttt tggtgcacaa aaattgccga   20640
tgttccccag ctttacaaac tttcaccatt tcataccatt ttaactaaac aaaagctccg   20700
gtaaaatgcc gttatatcag cattttatcg gagcttcttt tttatacaat cttaaaaaaa   20760
tgcgtccccc gagcatagaa gattgttgat atatcaacgt tttgaaggag ttagtgtgcc   20820
aaacgtgtgc gaacttaact aaaataaaaa agagcgccta tcagggcgcc ccacgttata   20880
ccggtacgga tcaagtaacg aactgaatcc aatttgcgtg ccgatacttc tcatctgata   20940
tttaaattat aacataatta ttttatgata caataattaa tgcgtgtcgg gagtaacgac   21000
ccaaactatc acgcaaaagg ggtgaattcc ccgtgacatt tatacttctc attctgatcg   21060
tgccgaacgg gctcgtcaag caactgatgc attatgcaaa ggttgtaatc aaaaaggctc   21120
tcaaacatct aattgatgaa ttacttggtt aattctgata ggaaatgtgc gagatgctat   21180
ttcagcggta gtgtttgcta tcgctgtttt ttattatact ttaagaatat agtcatggta   21240
tttttttacc ttagtaacta ttcagtttaa tgttactcta ttaaattttg aattccttta   21300
catccttaac ctctatcata ttacaatctt tatcttcaac gtagacgaat tctgacatat   21360
catcaatatc attgaaatct ttattagctg cgagttctgc agcatcctta aaaaaattag   21420
gccttttttc ttctattttg tccatcggta ctaaacattt taatatgtaa gttttgaaat   21480
gctcttgttc ccatcttgtt tgaagaggcc cttttaatgg cctacttcta atattatcta   21540
attcatatat ggcactatca aggtacctta aaatttcagg acacttataa atgcaagaat   21600
aatcaaaatg atatggtata aaaaagccac taattccgtt atcattttcc aaacgtgctg   21660
caatatcatt ccaacttcca ccagattcaa tcaggtatga gtgcccatta tatgaaataa   21720
aaggattatt attttttacag tagaaacgaa tattatttttt ttctaaaaat gatcctaaca   21780
aggtactaga atctgttata actttgctaa gtggttttaa tccatcatat aaatagttcc   21840
tttgctgtga agaacaagtt gtaaagtggt aaaaatatgc attttcaatt tcatctttttt   21900 tatatagttc taatgatctt tcagccattt catgagtcga taaatcaaat atcttgtatt   21960 ttttctttttc agacaccatg gttttctcct ttttatgata tatctaattt agattactat   22020
atgacaaaac accctagcaa ccattaatcg gctactaggg tgtttattac tataattttt   22080
cacttaaatc tgaattgttt gaccaatgaa aatcatatta ggatttgcga tgccattctt   22140
ttgagctaat gcttgccagg tcttgccaaa cttagccgca attccgctta gtgtgtcccc   22200
tgcttggaca gtataagcat tggattgtcc gttgccggct aagtagagtt tttgcccaac   22260
gtagatcaca ttcgggttag taatgtgatt acggcttacg aggtctgaga cagtggtgcc   22320
gaatttggtg gcaattccgg ataacgtatc gcctgattga acaaagtaag tattttcgtt   22380
tgatactttt ccggtgactt tgaggacttg gccgacatta atctggtttg gattaccaat   22440
accattgatt gctgctaggt tctgataagt agtcccgtat ttttctgcaa ttccactcaa   22500
```

-continued

```
tgtatcgccc ggctgaacaa tgtaggttcc agtagctggg tgaccaatat gttgaaccgg   22560
ctgtggtgct ggaataacag cttgcggaac attgcctgat actaaaccag tcgtaaaggc   22620
accgtcaaag tcataactag tatcaattcc catgatgcta tgatcagaat attgccaagc   22680
acttgcatta tcaatcccca gttcagtcac accatagcca gcaatccaaa tcttccggga   22740
atcaaagcca tgtgaattaa gaataccgcc agtgaagaag gacttcatgg agtaaatccc   22800
agtattcttg taaccaagag cttctacttc ttgaagaaag gctaaggata ctgattgata   22860
atctgcagtt gaatgaactt ccgcatcatc aatcatcaaa gtatcgtcat acataccaaa   22920
ttgcttagcg attttaacga agaatcgagc ttcattttgt gcatcagtca ctgatgtata   22980
acgagcaaag tggtaacagg aaacgcgcaa gccaaccgct aaggcattac gaatttgagc   23040
ggccgcacgt ggattaacat aagccgaacc atcttcggac ccttccgtta acttaacaac   23100
gacccctaat gcaccctgag ctttagcagc ttggaaaaag gcaacagtat ctggttgata   23160
acttgaaaca tcgatgaatt gattacgcat attattcttc ccctttcatt ggatcgattg   23220
ctggtgcttg gccggctgga atagtagcgg gtttagttgg ttgtgatgtc ggatcaacgg   23280
ttggtgtcaa tgcagacttt tcataagctg attgcacaag cgtttcaata gcgttaaggt   23340
caatattctt aataccctgc ttttgaagtg cttgttgaac aatacctgtt gcttgatgaa   23400
atttctcatg accagccatg tctttgccaa ctaaggaagc aacggcatta tctgcaagtc   23460
gttcagcaca agaccaagca gcacgagaag tttctgtttt ggcatgagtg actttagcgt   23520
gaataaatgt ctggctttgc tttaaggcaa aataaaagac cgttgagata acggccgtca   23580
tgatataggt tggaattgca ttaatgattg tgctcatgtt gtttctcttc tttctctaca   23640
taatctttgc tgagcttgta aatatgattc tttacccaag atggtaatgg tagtcccatt   23700
tggccccagt tttcgataat cgaaactagg taaaatagga aaaagaaaaa gacaagcgag   23760
tcgcctgcct gtcctaatcc gcataattct aacattggat aaacggttaa agtcaaaata   23820
ataactgcag catgtttcaa aagtccaccc gttcctttac tagaagttgt tcggtgcgta   23880
atgatacttt tgaaaaaacc tgtcacaata tcaatcacaa tcgcccaaac taaccattca   23940
atgagcacgt tgtcaatcat gctggcaaaa tattgaatgt atagaacgtg ttgtggcggt   24000
tgtgtcagta gtaagtgcat ttatagtggt cacctcctta taagggtaaa ataaaaacgc   24060
cctgtagagg acgtttaaaa ttatttaatt tttattaaaa gattcccaat ttccatcttc   24120
attattattg attttaatta ttaagtcgtt aagtttatta tcaatatcat tagctagctt   24180
atacgcactt gaatcacctc gtactctagt aatttcatat atttttcctt gacgaagttc   24240
ttcagtcaaa gatttaatat tatctatttc gttagaatat ttctgtttga gattcacttt   24300
atccccatct ccttaccgct aaaataaaag tgttatatta cgctgttact aaatatggaa   24360
tattattatc agataaccat tgaactgcat tattattaat ttttacaaca tcatctaaaa   24420
ttttatctaa attaaatgaa taaccaaata taaaaaattc atgcttatga ggatcgtata   24480
ctcttaaagt ttcatctttt gtaggagtga acactttgtc tccaactttt atagtttgat   24540
acaaattacc aattacttgt ttttcaacca ttatgtgctg acgtcggtta aatttaataa   24600
gtccttcatc aatatgttct aaactattcc tgaggcctct taaattttca ttttcgaccc   24660
tattaatata gaaatcatca gttacattca aaatttccct tacctttttt cgatcattac   24720
tatttttaga gttagaaccc catagaagct tagctatatc tgacgtatac aatgcaatat   24780
tttgtaaatt ataccaaatc atattatctt tataatattt ttcatgtttg gtattatata   24840
```

-continued

```
tattttttaat agcaataata gtaaaattac ataacagata agtttcacta attgcatact   24900
cctcgtcttt actattcata gtataatgtt gcataatatt taccattccc cttattaatt   24960
gtttagtaat attatcgtat cagtaattga aataattatg atattattat gaaaaattga   25020
agaaaaacca aaggctaata attaatttac aaaagtatgg aatcaaaatt ttaataaaat   25080
gccgcccata ataaaagccc cgctcgtttg agtgaggctt atttatgtat tgtgtatttc   25140
taaggcgact ataagtaatt accgttaagc taagaattca tttaattatt agccattttc   25200
tttagctttt ctttatcttc aatctgatac aagcgaatct tagtaattaa tccctgatac   25260
gcttttactt cattgggaaa attattagca ggagtaaatt tatcatcttc ttgggacaat   25320
tcagaaacat agaatacatt tcgataataa cctatataaa gtttatggtt cagtttccta   25380
tataatttat tttttttcaat aatttttgct tctttaggag tataaccatc ttgttttcgg   25440
tcaaaatagg cttcccattt aatgcactgt tcctgtgaat taatccgatt tgttttaaa    25500 ccaaatgctg ctaatggata cccacctaat ttgggattgt tacacaattc attatcatat   25560
tcgtaagcag tattaacaat atcttctaat gattttgaaa tattcaagat aaccacctct   25620
attttataga gtatcactaa tttagactac taaacaataa cttaaataat tttattgtca   25680
tgatttatgc tccttgaatt tcgtaattct gaccggttac cgtcttatat tcatctttag   25740
tgatcgctcc gcatcgtaca taaactttgt agaattctaa atcatggtta ccccagtcat   25800
tccaaaacat ttgaagcatt tgtaattgtg tcatcattat gccgttacct ccttagattt   25860
ttcgactgcc tgttgctgat taacagtcat aaacatttgt tgtaattgct tgatttgagt   25920
tgcttgttga gcattagtag cctgcaattt tgcatttgat tggttctgtt gcataatcat   25980
tgcttgcaaa atagtgattt gttgattggt attcccgttt gaatgcgaaa taatcgtcac   26040
aggaatttga ctatcattca taataaagct ctccttagta tatttttgtt tgataaaaca   26100
ctgttacagt tacccctgta ttttgtatag ctgagttatc aatgtttcta acgattaatc   26160
catcgccgtt tccagcttct gaaacactca attgccagcg gtcgccttct gcaacatagt   26220
taagtatttt cccagtaact ccaagttctt tattgatagc atccattgga agtgtcttga   26280
cctcttgcga attaagttga tcaatagcta taaatttagt aatcgtcttt aaattagaat   26340
tgtaatctgt ttgatgatct tgcaaactca ttcctagcga tgtattgcct aaactaatga   26400
gcgaagttgg cgttttatca gcataaaattc tcccagcttg aaaatgggct gagttttgat   26460
cgtaaaattt aactccagta ttaaaagcct ttccacctaa cttaaagtga tccacatcta   26520
gatatgttcc agtcgtacta ggcccaatat atagcccatt catgctttct ctttcagctc   26580
ctagcataat ctcgtttgct gtaaactcag cgttagtttg cagagtgagc aactgatcgc   26640
attttccccc aagtgcaagg taatcaatgt ggccctttga tagcataatt tttagattag   26700
cttgtccact tttatttgta acaaatggc tttcccaatg tttgatagtt agatcgtaag    26760
ttgaatcaat cactgatcca atagcattgt ctgctatatc aaacgtttcc tcccacacaa   26820
aagaatattc accgaaaccg gattgttgcg ataccgaatg ctgatacaat gtttgatagc   26880
aattatagtt ccaaagtttg attttgatcc caatattatg tgtgttatct gcatctgtac   26940
cagttacgtt taatatacat cctctgaaat aatacccttt aatcgaaata ttactatgaa   27000
acatggtatc aaaagaaacc ccatacttag ctgcacctcg ctctagcata atttgaatat   27060 catttttgatt tccatttcta aatttgaatg caatttgatc cacgtttagt gctggtgtta   27120
actttaacct caacgaaata tgagactgct tcaagtcaat agctaatgga ctttcaatta   27180
gataacatcc attcccatga acacttttat tattatcaac tgcataggtt agaatgcttt   27240
```

-continued

```
gaaggatttg gtaatcatca tttttaccat ctccatgtgc tccccatgtt tcaggtataa    27300
tttcattttc aataagttcc gctaatagtc ctgatgctaa ttgttctgca tgtttagttg    27360
ttgtatctgt gacataaaaa agccctcctc ctccatcatt tggttcataa tagccaagag    27420
ttcttgcgca catatctttg cttaaagcac tatcagcttt catggcagct acatttggat    27480
acacatgtgc atagttaatc gcaattgcct tcatcatttc ctgcttaaac gcctctgctt    27540
ccgcctgggt aaacaaattg tcttgcttaa tcttagcgtc tagtgcatct aaaccatttt    27600
gaacagtaac gccaagagct ttgagcgtgt tcattgattg ggtaaactta tcaataaagt    27660
cactggtcat cttggtgagc ttgtcggtac tgtcttggta cttggcttcg atttcgttaa    27720
ttaactcttc gacgggtgaa atatatgttc gtggtaccaa gccatcaatg accttatcag    27780
caaggacatc gaggtcgaat tccaaggtag tgatagagtt accgtctttg aggatgcgaa    27840
aaaaggcttg gcgataggaa ccagcgactg taaaggcatg gccgggcatg tcgaaacgga    27900
aacgtccggc ggttgggtca agggcaacgt agcctttatc atcaattact cggaagtcgc    27960
cggcggaatt cttaggaagt aatccttcaa accagacgtt acagccagtt aaatctagtg    28020
gtgtcccgtc ttcgttctta atattgacaa aaacttgacg catacttcgc tcatactgac    28080
gcgcttggac ccagttagta ttactgccat caaagttaac cttgaagtct tgtacattgt    28140
caacatgcgg acgccggtct tgaccgatca cataagttaa agtttgtgac attaaatcat    28200
tcctttctct ttcaaaatct gcatgacagc ttgttcaacc gtttcatagt cggtccctaa    28260
agccacatgc tcaattttct ttttccacgc ttcttgagcc tcttttagtt catctcgcgt    28320
ggctttttct tgttcgagtt ggtcgagacg agtattaatc tcctcgagta gcctaatcaa    28380
ttctttatac tgcctgtcac ggagattatc gtctttgtta tcctcatttt gaattatcgt    28440
taaattattt attaattgct ggcggaattt tcttccactc tgcaaatcta gattagtttc    28500
taaatccaaa tgaccatccc cctcctcact tcaaactact ccaatccgtc actctgtaac    28560
ctagatttac ctgggcccgt gatacgtatg ctttatcaga tccggaaaca ttaaaaacca    28620
gccttccttt agtagtgccg gctggaattt taatgttaac tgtgccggcg gattgccagg    28680
cgccattatt gacgatatag acaatattcg atttgccggc agaactacca tcgctcttca    28740
agaactcgac ataagtagta gcggaacttg aattatcggt cgcatttaac ttagccatga    28800
gacgacttga gatggaggag acaccgttga ggttaaattc attgcttctg agagtgcctt    28860
gctctacttc aattactgga ctgtcattat atttttcgct ggaaacagtt ccgccagtca    28920
tcatagttac caaattatgc tggccatttt gcatccagta aatattctgg tctactgctt    28980
ccatattctt atccgtctct ttcttatcat tcacgacttg cgttaatgac ttggattgct    29040
gatccatgct atttgctaat ccactaatcc ggagtcgttg ttcttcaaga gcttcttgta    29100
gacgtttagc tttctgattt tgataatcta aaatagttgt ttttgaatta tttaacgtta    29160
tttgattatc ttgtcccctta gcttccggat atatcgtata accgacagtc ttataactac    29220
ctgaatattt atctcgcgca agtactctta aaatttcacc agcaacaggt acaaatgaat    29280
ttccctgaag cgtgacttca atatttaaat ctggatcagg tttaagagta gttaaggcat    29340
atttacgcat tgcatccgca tcttgaaatc tttttcatcaac aagatcaggt ccaggatgtt    29400
ctccccattc gtcaattgac ttttgatcaa ctaccataaa cggttgaaaa taatactctt    29460
cctgtgattc tgtggttgta tcatttccga cagtatcatt ggtttcttta ccaccgatac    29520
catcacgaat aacttgtaag ggatcaagcc aggttccatc atttgaccag gcacttttca    29580
```

-continued

```
atgcagtcat taaattcttt tgcttagtaa ttccaatatg aagatggcta gtatcacggt   29640
ggccaataac atcccccgtc ttaatttctt ggccaacttg aacagtaata tctcctcgat   29700
tcaaaaatgc ttcttggtag caaattaaat aatcattcga cacaatagtt atatagtttt   29760
ccagtccagc aatgtatcca atatcctgga ctttcccacc atgaatcgca tgaacatcgc   29820
gtccaggatg atcgacagaa ccaaaatcaa ggccatcgtg aaaaccatta gttcgcccca   29880
ctccatcttg agggtgtgtt ccaaaagttt gccccaatga aaaatgacct tctccaacat   29940
ctgggaaagg ccatccccac ggattaggtg gtgaaatgat caatttatct ttcgtgattg   30000
gggcaccatg aggactccaa ccagtaacac cattaatttg tcctagtgca ttaggaatat   30060
tgaagaacgc aattaactgg tcaaaaccct ttaagatatt tgtatagggc tcccgacaat   30120
aagtattaaa agttcctcgc ttaaattgaa gtaacccaag cgccggacca gaaccatcgc   30180
catcgggatc agttcctggt tgcggaatcg tctcgtttcc acctgattcc aaatgaattt   30240
gtgcccgtaa aacattaagc tgctgagcat tcggtttttat tccataaaag ctagcagcat   30300
actgaataac tggtgtccaa tcaccgttga ctggctcagt tggtccatta gcattagttc   30360
cacctgtccc ggtataaaca gtgtgctgaa cctcatgctt accaccaaca caacgaatca   30420
tattaataat tgattgactg tcccgagtag ttttaactga ctttgcatcc cttggaaaat   30480
caatcactcg accattatcc ttatagaact catcttctga ataaactcgt atcttcttgt   30540
tatccggata tataactgca cttggccata actcagtaat cttactaagc atctctttac   30600
cactgccgct atcgaactta gaagttgact gcttatcaaa attaccatga acttcatagc   30660
taaagcctag cttatttcca tcaatccaag cctttagtaa gtcctcaact ccataagact   30720
gatccttact agcattacta tcctgattgt tatttaaggt aaggtcactt cgtttataaa   30780
ttcgactaat ctcattatag acatgccaag cagtgatatt tttcgtatta gtatcaaagt   30840
tttcaacaca atttttttaca atatattcct gtccctcaag cacaatcgaa ctttcaacat   30900
ctaatggatc atacaatgct gaatcgtaat caaatactga aaaagtcaat tgaaaggtcg   30960
aattcttaga ccactcgctt tgcattgttg gccagagaat aatgtctccg attggctcct   31020
tagttgtctc tttatgaggt gtcatcaata ctaaactaat tgtcctcacc tcctaaccaa   31080
gatacataaa tgggaaactg aatgtaattt ccaaatcatc tgcaccagta acttcaaagt   31140
cattctttcc aggcgctaaa gtaatatacc cataatcggt attggcactg tctgggttat   31200
tattcttaaa tgttcgccgt ccctttagca agagagtatc gtttccagat agattttgat   31260
tgtacgtcca agaagtatta gtagttgtat tctttactgt gaattttcca ccattatgct   31320
taatagtaat ttttagatca tgacgctgtt caacaggatc gattgtaata tcactatcgt   31380
taaggataga aaacttattc tggcctttga aatggtatga aggagtttcc tcatccatgt   31440
tcatattcaa gtctaagaaa tcctcatctt tcatctcatc cgtatgcaat ttactaaatc   31500
gcattccgct tggattttca aaaggcactt caaacgtaca atagttaact tcttctggtt   31560
cgcttttaat ctcaaaggaa ctagcccgac agtaacggac aatatccggc tcaactcctg   31620
ttcttaacct aaagattcct ttttgtgcaa aaacgcgata aatctcatgc tttgccatct   31680
taaaatcttt tcgatcaaag aactgcaata agaacttagc ggtgatcgtc gtttggccat   31740
aacgggaata actccaaatt tgaccatctt gttgggaatc atcacgataa ttattaataa   31800
cactaggcga ttcagttaag ccaagaaaag ttaagtggtc agtaatatct gtgctggcca   31860 cttcttttttg atcatcaatt ttaatgtaaa gaatgtttac agcgattacg accacctcct   31920
aaagatgttg attatcaaat aatgcttgat cagttccttc aatcccataa aactggttct   31980
```

-continued

```
tgtcaaaggc gccggcttta attgcagaaa gttgagctgc atttaagccc agcattgtcc   32040
caaagcggtt gagcatctgg tccatccgat ctaacatctc tttttgcatt ccattattac   32100
tttggccacc gttattataa ttatttacaa cttgggtgct ttgcatattg ggcttaaagt   32160
tagttaatac cgaaacagca tcatcagtac cattagcata ttgtggtaag tgcttaaaca   32220
tcttagcagt atcgctagct ttaacaactt ttgttcctcg tggtgctgga aagactacat   32280
tacgcccata aggaataaat ggtgtttcac ctgggaattg aactaactca cgaaagacgg   32340
ggccaggttg atcattaact tccatcaatc cacctttatg gtaattagtt ccctgagcat   32400
gctttgattt atgaaaaata acattaactg ttttctcaat agtattaggt atactcataa   32460
aattatggat tgcatcaagt gctgttttaa ttggcccaga agctttatca ttagcttttg   32520
caatttttgc tggtcccgta tttgatccag caaaagcatt tacaccattg cgagcactat   32580
acattggtcc actagcatta tcaacggcta aagcattttt aggagcgcca ggatttgaac   32640
tagcaaaaac atcgacacca ccagtagcat ttctcatcgg accactagca ttgtcaattg   32700
ccagtgcatt ctttggttct cccggattag catgacgcca agattgaagg gcatcgttag   32760
cagcttttag atttccacta gctttatcat cagcaatgat ttgttttgca gcactaaccg   32820
gcatcccctt ccacagccca taatcagtga tcagttgctg tagttcgggt ccacccttag   32880
catttacgat tgcttgctgt tgcttaggac taagttgatt ccagcgacca attttattga   32940
gcgcatccat taatcgacca gcaccctgag tagtaaccaa agcacgttgt tgcttaaacg   33000
aaagactatt ccaaacacca gcctgcacta atgcatcaac taattgtgga gttcctttag   33060
cgtcaataat cgcttcctgt tgtttttaagg ttaaattatt ccactgtccg gaactttgca   33120
aggcttcata aattggctta gttgccttat tagtaattac tgcttcctgt tgtttttaatg   33180 acaaggaatt ccatgcaccg gattcaagca gaatgtcggc catttcttgc ttacctttag   33240
ccttaacaat tgcttctttg gtcttaagat caagattatt ccattctccc gacttctcta   33300
aagcttgaac aattgtttca ctaaagccgt ctttcaacca agctttctgc tctttccaac   33360
tcatgctatc ccatttacca ttttcgatta atgcagctgc caccatttgt tgagcattgg   33420
tacttaactt accttccttt ttcagaagtt taatttggtt ccattgatct ttagaattaa   33480
cagccttatt aacttcctcc tgggcattag tccgaacttt accagttttg ggatcgaaaa   33540
ctaagtcatt ccacatatca gcggcttttt tagcttttcc acttaattta gtagtattta   33600
ccgctaagct ttgtaggttt gtttcggcag ctttggattg ccgcttaatc tcatcagtgc   33660
catctttata actaagtccc atactttttta ggtcattctt aattaattta gtactttcac   33720
cattagcacg ggccaggcga atatattcgg cagctgcttt attcgtgtaa tctgttaatg   33780
ctttcttatt agcacgcata ccgaccttat acagttcaga atctttttccg tagcgtttag   33840 caagcattga agactgcttc ttgtattggt tttccatttc agcagtttca ctggttatat   33900
ctcccatttt tgttgagcgt tgttgcatag acatatgctt aatatcgtta ttaaggacag   33960
ccattgcttt agcacgctta cttccactta atttaagaat tttcatctca tcgttaagca   34020
tttcctgctg gttgttcttt aacatgactc gctgagtatc atttaattgt gaaactttttt   34080 tattgtggtc agatagaatt gtttgaacac gctgattggc attatctgca tcattcacat   34140
atgaattata ttgtttttttc tccttttcta actcatcgtc aatagcttta gatatttctg   34200
gagacagacc ttttttctgcc tttttggcat tagcaaaatg ttgttttgca ctattttcaa   34260
tattagtaaa ctcacggtca aaatcagcag ctaatttctt tgttgaagtt gaggcagcaa   34320
```

-continued

```
catccatatc tgacagagtg ttctgaattc cttgagaagt cgactgcatt tttgataaag   34380
ccttatcagc agctgcacca acatcagatc cccaacgatt cgttcgttgt gatgattcga   34440
cagctttctt accccaaagc tcccaaacag taattccacc ggcaatggct aaagtagcaa   34500
ctccagcaac agcggcaact gttcctaaag atactccagc cgcagcagta gcagcacctg   34560
cttcacctgc agctacaccg gtaccttgta aagcgacagt cgcagcacca acaccgttag   34620
cagcttgaac cgcccgacca cctgcaccag tcatggttgt tccaaacttt gcagcttgaa   34680
atgttgattt tgaaaaagct gagccaataa cgtctaaccc actggctcct agtttcattg   34740
cagtttgtac acggccgatt ccggaagcaa tttttccaaa ggcaagaact gtcttcccag   34800
caccactagt cagtttaccc aatgctagga acaacgggcc tgcaccagca gtgaacaggg   34860
tagttgttac aattgccttc tggacagctg gtgataaatc accaaagcca tgtgcaagtc   34920
tggaaaggcc ttgaaccatt ggaataatag atggtaagac gtactttgcc atatccattc   34980
cagcgttagt taaagattcc ttgaagattg ctaattgtgc tttaggagat tgaaggtttt   35040
tctgtgacaa gtcgccgata taatcccgct tggcagagtt ttgaacttct ttattaagtt   35100
cacgtaaccg attagcgttt tcggttaaaa ttgccccagc ttgttgtcca gttgttccaa   35160
ataacgcatg aaaaatatca ttcttttggt gaccagataa gcctttcata tggtcattta   35220
acgtcttaaa aatagacgac attgatttta actttccact cttagtaaga aaatctttag   35280
tacttaaatt aatacttgct aaagcttttt gaccattagc ggttggcgta attagtgaat   35340
tgataacctt tcgtagaccg gtaccagctt tgtctgcttc tagaccatta ttagacaaga   35400
tccccattgc actagcagtt tctgagagac taaaacctgc ttgatgagca gttgagccaa   35460
catatgacat tcccacacca agtgattgaa aatcagttga tgtggcatcg gcagcatagg   35520
ctaactcatt taatgtttta gtagatctac gctgcatgac tgtagcattc ttgattggac   35580
gtcctgcttt atcagtagcc agtccaaaag attccattgt ctgcgaagca actttgatta   35640
catcattaaa gtcatcccca gtggccacag atgctttaag ttcgttccgc attactccaa   35700
ttgctgcttt agatgtataa ccacgcttta ctagatcttg atacccggca gcaatctttt   35760
gctgactaac accgtactcg tcagaatact ttcgggcatc tgcagtcatc gttttatatg   35820
cggcattcgt ttctgcagct gattctccgg aagttcgaat aacgttcttg acctttgtca   35880
tttgatcttg gaagtcaacg agtttcttag cggaatatgt taaccctgcc gcaattggag   35940
ctgttaaata agtcgacatc cctcgaccga cacctgatat tttagaacca acattggtgg   36000
ccacatttcc aaaatgttga gtgcgattag caagttgtgt ccacttattc gactgcaatt   36060
caatatcacg attaagagct tgcattcgtc cacgtaattg ttcaatttgc gcagacgttt   36120
tattatattg ggttgctgcc ttagttcgtg actgctcgct cctggtagta tcatccattg   36180
ctttcttagc attctggagt tgcgcattat aattgcgcat ttgttgactc atagtcgcat   36240
aagcagcacg catattatta atacttccac cggatgcttt cagtgccgct tcttgcgcac   36300
gcaaagcatt ggctgttgat ttaatttgcg cttttaaaac accattagcc gctttaaacg   36360
gatcaatatc caaactaaca gttgctgcca aatgtcctaa tgattgggtc attatttaac   36420
ctcctttcct agaataagaa tgggaatgct ttatcaatgg ttgtctgctt ttcttcaaag   36480
acgtaattca ttaatttcaa atctgaaagt gttagcttac tgacctcatt ccatttatat   36540
ccatcgcgca ttttattttt aatgaaatct gtgagactct tgattgaatc atcaatcatc   36600
tcaacagtta ttttttttggc ttttcgttat ccttttttctc ttctaagtca tcttcactta   36660
gaggagaacc gagagtttca ttaattgcat taacaatgct aattaaccct tctatagccg   36720
```

-continued

```
taactcctga aagaacatcc tttttagtca atccattctt ccaaaaatta gcagcaaact   36780
cagcccgtaa acttaataat cgttcattat ctttatctgt tggcaatttt ttgggatcag   36840
agtacatcac tatttcttga cgttgaacct ttaatgcatc taatagattt tcaagcattg   36900
gggcttcttt tcgttcatag attgtttctt tgccatctgt ttttactttt aatttatatg   36960
gcatttccat atcctcctca tcgtctcact taactcgtct ctgtctgatt aattagttac   37020
cctttatcaa caacagtttc tggtttagta tcttttgtat tggttggatc agttactgga   37080
gcttcttccc caaagaccat tgcatggaac ttagcaaaat caaatccttc attatcttcc   37140
cgaccgatta aaaggatggt tccagtatcc gcatccccac gcggaacgaa attaccttca   37200
atttcatctg cttctgggtc tggagcaccg tcctgagtct tgattgaaat acctggtaag   37260
gagaacatcc ccttggttaa accaacccaa caatgcttcc cgtttgaaag ctttgtccgg   37320
aacatagtag caacataatt tggtacaaga ttcttagtat aaacttctgt accgttctga   37380
atatcaattc catacaagtc tttcttcatg atggaatcaa tatcataaag gttgatggtt   37440
tccttagctt cggtaattcc accagaaaga accaagtaag ggccgtcatc ggctgctaac   37500
gtctttaatt cgttagtcag ctccagctta acttcactta acccgctcat ctttcgggta   37560
tctttaatct tttcgttctc gtctagcacc ccatattcaa aattagaggc cccaaactta   37620
gcaacttttg catttggtgt tcccattaaa tatcattcct ttcttcaaac ccttcaaagt   37680
tagctgtgac cattatgcaa ttatccaagt ccggatccgg ataagaattc ttgtagtaac   37740
gttcaaagcc atgactgtgg agggtttcat atattcgttc ttgaatatcc attagccggt   37800
catcattctc ttcacgaatc caaaaatcaa cttgtacacg tgggtattca aaaaagcgag   37860
cattgtcact gtaaattgca tcatccccag gtaggggggt gatccgaatc cacggtgctg   37920
aactcgcttt aataaatgga tcatcaggcg tactagtaaa aattggaaca tatgataatt   37980
tatcttgtcg caactcatcc atcatcacga ctaggcactc atcattcgtt agataatcgg   38040
ctacttgcat ctctggagtt ttcatacttt caagtcctca ataaatttag ccaatatttt   38100
cttcttagca gcatttcttg aatcttcaac aaagtgttgt ggatcttgct tagcagttcc   38160
agcatcgggg aagtgagcaa tccatccttt atctttgtca taaccaacat cgacagaata   38220
atctccaccg ttagtcttga gattaccgtg tttagtatga tcttttaaag gagtcttgcc   38280
tgaatgatca gagcctttag aagccacagg cgtccatttt cttaattctt cttgaaagac   38340
tttagcacca tcacgggttg cttttcgtgc cttcttttct tccgtctttt caagtttagt   38400
taagttagca atcagctctg cttcaccggt cactgccatt ttggacaacc tcctgggcgg   38460
taatttttgt tagatctcgc tttgcataat caggatccat tcccgtgatt tcataccatt   38520
ttcctcgcca gttaattaac caattcgatt gaatttcctt acgagttttg aaagcaatta   38580
aaaacgtggg tgattctttt ctgaacccca cgtttgaact gtttttggaca aattcacgga   38640 ctgacagctt aggaacttct gcccacacgg taaattcctt aactttctga tccttgatcg   38700
gtcgatgagt ttccggattg atccccattt ggactgagta aaatgttatc cgttccgtca   38760
tgttccgtag tttcatcggt attcacctca ctacttattt gattaataag gccatcaatt   38820
cctgatgaaa gaactggtcg gtaactatct gcagtaattc ctcgctcgta gaagtcttct   38880
ttcacctgct tcataagtgc aatttttgaat cgcggttcgt cagagtagtc agcaggctta   38940
ctctcccatt taattgccct tgcaatcatc aatgcggcag catcaacaat tattttaaga   39000
atttcatcat caaagtcctg gtcaattttg cagtagtttt ttagattggc aaagaattgt   39060
```

-continued

```
tcatcactcg agaaagtgtg gtctgtttcc atcctactca cctagctttg ctaacagttg   39120
atccttagta tcggttgaag tataggcaat tccatgatca tctaagtact ttttgattgt   39180
gtctaccgta tcagcactag tcggtttaac gtccgccccg ttgtcggacg gcgttatttt   39240
gacgctgctg atggaccagt aacaaagtaa ccagcgtttt catcggcctt cttcacatct   39300
aaacgaagaa ccgcttggag atattgacca taaatgtcat tatcaaccca ccgtacctgg   39360
agatcttttc gatttgctaa aataattgca cggtatggat caccaacaaa ggcatgagct   39420
tcaccctttg ctccaaataa gtcatcttca attacagcaa cgttgattcc agagaccgct   39480
ttaccagacg gactagaaat actatcttga agtaagtaac gtccattctt atctttcaat   39540
gtatcaagcc agttgtagaa gctttggctg gcaataatca tcttattgta agccacatct   39600
aaatcgacat tccaaatttt ctttaggtca tcgattgcat tagagccatc aacggtctta   39660
gctgaaaatc ccttaaaaat tgtagcaata gccgcattct ttgtatttaa ggattgttct   39720
tttgcgtttc gagcaactaa tccagttaaa tcaattgctg aatcatcaat cgattcttgt   39780
gaaataggaa ttgctccacg ataggtctca atttgccatg ctaccttaag aaattcaggt   39840
ttttgaagat caggattctt tgcaagttct tcaacagtat gcatttgagc agttgccttt   39900
ttaagaattg gataactacc agaagcagtt gtggcgttaa atacttgaac aaattggcta   39960
agatcagtta ctgtttaat ttcattttca ggattgtaaa tgattgattc aggaatagta   40020
acgcttgcgt ctgaagaagt aattccagta gtaccatcac gatgttcttg gtgaagatat   40080
gcgttgaaat tacgtttttc ttcattttcg tcctcgttat tttgagaacg cttatgagga   40140
tctggagctg gattaccctt agctgcttta cggtaaagct taaggtcatc ttcaatactc   40200
cgaacttcct tttcagcagc ttcaatttca gaacgtaatg acttagctcg tgttaagtct   40260
tcatcagttg cgtcttcatt tgagagcagt tggcgcattt cattagtttt ttcgttaatt   40320
aatgctcgct taccttcttt ttgagcaagc aattctttaa ttttttcgcg aaacatttaa   40380
tttcctcctt cgagtgtctt caataattct tgtcgttcta attcacgtaa catctttta   40440 cgtttctgat cagtagcatc tctattttct tggctctgca tttgcttaac catattgatc   40500
gaacgctgac cgacctgaac ttctgtatcc ggataagcag gtgttgtaac tactgataca   40560
tcgaacaaac gatcaatttg tcgaatggtt cgttcataat caactccatc ctggtcagat   40620
tcttcccaat cttgggcctc atctgtgttg gccaccgtaa aagcaaagct gcattgatta   40680
ataacgcctg ccttgatatt ggcgatcaaa tcacgcgcaa atgatgtatc agttggctta   40740
acagtgaatt tcaagccaat tgcatcagaa gataaagtca tgttcacccc tgatcgtccc   40800
agtacctggt taggatcgtg attgatcgtc gctactacat ttgacatatc agcgtcatcg   40860
aacgctcctg gagcaatttg ctcaataaag cgagtaaagc cacccaaaac ttcggatggc   40920
ttattgtatt tggctgcata accttcaatt actggttcat catcttcatc agttgccgtt   40980
ctcatctgaa ttggcatcat taactgtcga gtttccaagt cgcttgtcat cgattccacc   41040
tcccttcgct gttgattgtt tctgatactc ttctttttta tcaaggaaga cagtattcaa   41100
ggttgattgg aaacggtcta agtctggatt gtcagatttg actaacccca tccgaactcg   41160
tccttcatta ggagtaatga cgttatttgt aactcccttt tgtacatcgt ccattgacat   41220
ccctgtttct ttgcgtgtat caaattcgat gtggcagtta tgacgttgcc gatcagtcag   41280
cattgtcatt tccaaattac ttgcaatcgg cttgaagtaa taaggtaaat cagaagtaat   41340
aaagtcttca tttaattgtt taatcgattg gttaggacta ttaactgcta atttatatgc   41400
tggaatatgc aacgctttgg caatttgagc agttgaatag ttgttgctgt taattagttg   41460
```

-continued

```
caaaacattg gtatcaatct caattggcga gtaatcgaat gtatcatcag taacgattgg  41520
gctaccggca ttgctattag cttgtgcata ttcaaacgcc tttctagttt taagacgcgc  41580
ttccggactt aacttacctt tagcctttag taatccacct ttaagacctg acttaaagaa  41640
ccgccgtaaa gtcttaattc catcatcctg taatccaatc tcatcagcca aagacaacaa  41700
cggcgaccgg ccatgaatac catcgtaggt aaagaacata aaatgaatta catcttcagc  41760
cggcacaacg attgtttgac caccgccttt ttgattgata ggtgtaaatt cgtatttaat  41820
attcgttaca tcagaatcat caatataggt ttgcgatggt ggaaaatatt gtatttctaa  41880
cggtgctttt gtatgaggat cacgaattat tcttgaaaaa ccatccccag ttaaaattgc  41940
gttaactgtc attaggaaac gccaatgata agcagataac atatcgtttg ggtgcttatt  42000
cagcaaataa tcaacacttt tgatattctt tactgcattt ttaccatcat ccaaaatgac  42060
aatcggaaat cgagctacat tactagcaac atgagagact gcagtcagca catcagagtt  42120
tctaagagca ccgattccac tataagatgg catattgcta aaccccggaa gaatcccctg  42180
gtcaatataa tcttgtgccc attcgcgttt ctcggtatga aataacactc agcttcaccc  42240
cctttcataa gagataaaag ccattacgaa taattcaatt gaaataatta gtaagccaat  42300
cttcgtggaa aataaaaagc ctgtaactgc taaacagata caagctaata tgaacagcaa  42360
aaccggttcg tttagtttcc agaatttcat ggcatcaccc ggagaagaaa tttcaagtct  42420
tcatccgtaa tctcaaattt ctcaatatac ggggcaagct ttctcagtcg ttccaatcgt  42480
cccttgattt cattaagtgc gggagttaca tcaatcttca ttccttcttc accgtcgtat  42540
agatacttag ccatgtctat tcctcctcga ttcctttgat aaattcaatt gcttccttag  42600
ttaaggccaa tggatggaaa tattctccat ctgaacagtc attgatgatc ttcccttttta  42660 ataggtgctc cacatcattt ttagtgataa aggtggtcca gttgctatcg ttgccatatt  42720
catctagttg cttaatatca tggctaaatt tatcttttc agaaaccaaa gtcatcatta  42780
aacacatcct catctgttaa ataatcatca atattttcac ggaaacaaat tgcatatgcg  42840
tctagcaatg catcggcagc atcaatctta tttgaataac ggttcttatc aatccggaca  42900
ccattgttat ctgatttaag gatcgcgtta gccattgcgc cagttaaaat ttcattgtca  42960
gaatgtcgaa ctcgcttatc taaaatatca tccctaaatt gcttggttgg cattgaaaga  43020
gttagtgttc cttgacgaac agatatctgt tgccattccg gatgaccttt ttcaatctga  43080
gttaacaagg ttccatattg tgcggggtca taacaaattg cctgaacatc aagattgtgt  43140
tctctgacaa agccatccag ccattcatat acccgttcaa catcaataac tccagattca  43200
agcttcgtaa tttcacactg gcccatccct tgcaaccgga cataatctaa ccggtctgct  43260
ttaatctttg cttccaaacc atatttagta ccgacaaacg cataagaatc cgcataccaa  43320
tacccctctt gaggaattaa ccaactaatt gcataaaggt cagatgattt accaacgtca  43380
atcccaaacc aaactcgttg accatcaatg tcaattggat caatttgagc tgcattccaa  43440
gtatcaatat ccatataact atcctcttcg gcttgtcgcc acatattaaa gttcttaact  43500
agaacagaat tctttgtccc tttctgttta gcttctttcc accgctttgc caaatatcca  43560
tatacctggt cttgcaaagc cgggacactc agaattggat tggatttaat ccaggtactt  43620
ttatcatcaa cttctgatac attatcttgt tcagcaatgt aggcaaaata agtatcatca  43680
gtaatttcac ctttcaaaac cttcgttgca tagggatatt caattgtatg cattggaaca  43740
ttcaaatcaa agccggctgt tgaaataatc atgataagtg agttatgaag taaggcctga  43800
```

-continued

```
ccggattcta gtaattccat catttcagtg gtcttacttg cagcatactc gtctaggatt    43860
ccaacatgag gttcaaaacc atcaaccgtt cccgtttcct tggaaagaga ccgaacataa    43920
gaataatcat caaggttact aattaaatca cgattaactt ttgtcccacg ttttgtatca    43980
ccatcactgg aacgtagagc attgaggcgt ttcttaatca tattaaaaac gatgttcgct    44040
tgctttttat cgttagcggt acaaaatatt tgccgggaga attcaggtga gttacccatc    44100
aagaactcat acaatgcaat tccggaaata aggatcgact taccattttt tcgtgccatt    44160
gataacattc cttttcggaa gcgccgttca gatggcttgt cttttttcca ccagccatac    44220
atattagcaa taatgaaacg ctgaaaatct gctaaaggat acgcccgcat cgttttttgga    44280 tccggaagta tttccatgaa ttgaataacc ttattagcac gttcattatc ataaaaatat    44340
tcaaagtcat cgttatccgc cttttttaaga tcatttaagt accttttttgc agctaaaatc    44400 acctttttac cagcaactat tttgccggcc acgacctttt cagcataatc tttagcgtaa    44460
ttcatcatga aatcctaaac ttatcacgca aggattgatg ctcttccttg tcagtttgtg    44520
gcatgttcat ctgcagccgc gaattaacat taagcccaag atcagatgca agaccctta    44580 ttgccctggt tgctttatca attgtcttaa ttgcgttatt gattttagca atgttctttc    44640
ttttcttgga ctgttcctta tttaattgaa cggaagcatc tttataaatg ctgtaccagg    44700
tacaatacaa ttccaattcg ctccggtcca agttacgcaa tggcagcttt ccgatagaac    44760
caataattcg ccgatattcc gctttggcca ccttatctaa atgtgccggc ggagtctttt    44820
gcaactcagg taaaccatcg gcagccataa attctgcctt atattttgct tcttgttcaa    44880
ccactctaag gtggcctgtt gactgcgata ataattttg ctttcttgcc aa             44932
```

```
<210> SEQ ID NO 12
<211> LENGTH: 12924
<212> TYPE: DNA
<213> ORGANISM: Artificial Sequence
<220> FEATURE:
<223> OTHER INFORMATION: Based on Lactobacillus reuteri sequence

<400> SEQUENCE: 12
```

```
ctatacaagc gcccgcaatt gttgaatcat gcttaacact tggtaagggg tatttgacat      60
gtcaatacct ctattttgat accaaaattg cgccaacatc tgaacagcga acgtatattg     120
ttcatactgg gttaagtctg ctgtgggggtt tacagcgttt tgtacataag ccttagcgtt    180
ctttagataa tccttgatta attggtcttc ttcttcaccg tcaagatata aggcttgctt    240
aaagttgtct acttcccact gctctacatc aaatttcatt aatttcacct tcttttagaa    300
cacatctagg tctaactttt tagcaacatc tactataaat tgatcacgta acttgtacgc    360
ttttgtagtg ctacaccata tatcgccagt tgctactagg ttctttatcg tcttatgatt    420
agggttaaaa tagcattctt taattatctt ctgggtacag tccccagcgt cttgtaatgc    480
taagtcaata gcttctttct cacgtttttaa gcggtgcata tatctatctt ggtcaatggt    540
tattaacata tcatcgtaat aagtccatgg tcgattgata gcacgtccac cacctacatt    600
ttcatctctt ttgcggatag ggtgcattag ttcaaactta cggctttttta gtttcttatt    660 aattgaagga taatctttca gtattactat tactagactt tttacttctt ttcgcattaa    720
tacacctcat aaaaaaagag tgggcgatat tgcccaccct gtgctagtag ctattattta    780
ctttcggtcg ccttagttgt ggttaaagag agattaaaag cagcgtcatt actaattggt    840
tggtagtcat tacggacgat aacagataaa ccttgactgt aactgtcgaa cttgtcccat    900
tgggctgtaa cttgattacg ccggaatact gctaccgctt ctgaaatatc acctaaaatc    960
```

```
attggatgtg aaccgtctgt gttatctggt aagaacttat tactaatctt aacaacgggt   1020
tggccaagta aagaaaatcc actaggagcg gttacatctg gttgtaataa gtaacgtcct   1080
tcattgtctt tcaaagtatc taatacttgg aaagctgatt gatttactaa ccatgtagaa   1140
gtactttgta aggctgggtc aaggtcaacg ttgaatactt gcttcaagtc gtcaacatta   1200
gctacggttt tcttagtaaa gttatcgcct tgtaatacct tgataatttc agcgttatca   1260
gtgttatcaa ctaacttttg aagttggttc tttacttcag atacaatatc aacttctgaa   1320
tcgtcaacaa cttcatttga tagtgcaatc ttaccggcac gggtctttac atcaaacttc   1380
acatcttcaa acatattagc gtctacatca gcaatttctg cttgttcttc cttagtagta   1440
agtaccgctg tgttgtaacg ggtagcgatt ggataatgac cggaaccagt ccctacagtc   1500
tttacagtag cgtactttgc taagttataa gcactgttct ttaagtctag gactggagta   1560
acaacttctt ctggaataac ggcttctgcc cccttagttg ttaatccgtc acgggtttca   1620
ccacgtgaac gaatgaagct ttcaaaggcg ttagctggtt gttctgtatt gtttttgggg   1680
tctaagattg tgtgttgcat tttattatgt tcctcacttt cgataaattg gttgtaacta   1740
cgaatgcttg ttttatctac atcaacattt gtctgatcat atgaaggcac tgtaacggtt   1800
gaaacctcaa ataaatcttt aatctgatta acggtgcgtg taatttgtcc gttgtcgtca   1860
cgtgtccaac tgtcagaacc atcatcaaca tcaaaacgga aagacataga attaatgttc   1920
ccattcttaa cattattaag agtgtcactt gcgtaactta cacttgggtc aatagttgcc   1980
ttgaagtgaa gccccttatc gtccacatca agttgtaatg aaccagcctt aacgcttgct   2040
agtggcttag tgtagtcgtg ttgatcaagc ataactacat tggataggtc tacgttatca   2100
agggcgctag ggtcaatcac ttcaacaaaa ccgcctaagt ccttgctggg ttgattaaag   2160
agtaacgcat agccttcaac tgtattaggc tgtgaggctt gcgtttcatc ttggttatct   2220
tgctggtctt ttgttgggtc ttctttaggg cttaccgttt gtaaacctgc gttagttgtt   2280
agtcgtttct ccattggctg taactcctcc ttctttttca ataaaattat ctccattagt   2340
taccggcact aaattaagta aggctcgggc ttcattgcgt gtgtagatac cgttaacata   2400
accatcaact gccatctgct gttgagcgga cgggtcaagg cttaatagct tgctattatc   2460
aaagctaaaa tcttgcccta gcttgtagtt caattcagaa gtaaagcaat cttcatagtg   2520
ctgtaaagta ccttgtaaat actgaacgtt actttgttgt tggttgctat gctcgttttc   2580
tacacctaaa cgctcgggtg gtagtccgaa cgctttcgca atttgacggg tattccagtc   2640
attagaattt actagcttta acacgtctgt attaagtggt aggcttttaa cgtccatacc   2700
atcatcagta acaattgtgt taagtgaatt attgccggta gttgcctcat caaattgttt   2760
tctaatgttc tctttaccat ccgaactaag atcagcttgg tggacttgga caactgttgt   2820
gccatgaatt ccattattaa agaatccagt cattaacctg tttccagccg cctgtatctt   2880
catttcatct tttagcgcat acagtggcga tagtccgact aaaccatcac gggtaaaata   2940
cttaaaatgt aagatgttag aagaggcaat tactcgctta atacgtccat ctgggctgta   3000
tgtgtaagtc agcttttgcg ttacatcatc ttgctggaca gttaatttat tgttaggaat   3060
aaaatttagc gtgtgtgaac ttaaatcaat ttcggcaaac gcattaccat ttaatagcat   3120
ttcaaccgct agggcgtact tgaaacttct gccgtccatt aactcgttag gatgatcatt   3180
aatcatcttg ttatataggc tagaactaga cttaatcgga ttactggcaa gatcaccagc   3240
gatagaacta attgcagcaa atatatcact attacgtaaa gccgaagcac taacgtaact   3300
```

```
attagggtca ttactagaaa gacttactag agcgtctaga aaggggtctt gtgcgcttgt    3360
agtcgttgtt ctcttactaa ataggcccat tatctaccct cctttacttg tgattatcag    3420
aatagttaat catgaaagct agaacaatca tttcaatacc aagaaagcca atcccaaaca    3480
accaaccggt taatcctata gcactgatct ccattagaac gcctccggtg atcaacaaaa    3540
ccggtttaat atagctagaa aagattttta gcagtttcat agtattcatt tgtacgttct    3600
tgctcctttc tcttagtgaa gtaatcataa ccagccgccc aagcatccat aagagcagca    3660
aggcaatcta ttttattttg ctttctagtc ttgtctaata acgcttgacc attaaagtta    3720
tatttcaata ttgcatttcc tacgttgtaa gctaacatct gattgttagt gtgaagaatg    3780
ttaccagcaa ttaattcttc cttaaaagtc ccaattggta ccgataaatt cttataggat    3840
tgtgttaatt gaagttgtgg tagtcctgcc cgttcaaaac gattaacaag atcagcccat    3900
ttataagggt caaatactaa gaatttaaca tttagattat acttaccgat taggtccatc    3960
acgaaatcat atacggaatc ataatcaatc aagccacttt ctaatgaact gattgaacat    4020
tctccacgtt tagcagccat ttcataatca attccatcac gttttgattt agtaacaatt    4080
ccaccataac gagatacaaa ggcgtgggaa tcagcgtaaa actttccatc ttctaacgga    4140
actaaccaac taatcgccgt taaatctcgg ctttttgata gatcagcacc aatataaaca    4200
tctctattac taatatctgg agcttttttca atcaatccat gttcccaatc ttgcgtacta    4260
atatatgaat tttcattctg ctgtacaaac atattcatat tctttacaag tacgttatta    4320
atattatttt gttttgtggc tacatctaaa tcattttgaa tgtgttccct cattgtctta    4380
gcaatcttag gattactcat caaaggatta gctttaatcc acattgtggg gtcgaatatt    4440
tcttcttttt tatcaagaca atacataacc gcaaagtaac gatcattctt aattttgccg    4500
ttgagtatat cggctgcata gtcccattca tttttgaagg gtgaattaag attaaaacca    4560
gcagtagaaa taatcgctag aataccattg tcttgttgag ccatacctga attcaaggcg    4620
tttagaatag tgttatcttt agcttggtga tattcatcga ctacgcccag tgtcgggtta    4680
taaccgtccg tactgtgggt atcagtagat agtggaattg cgaagctacc tgtctttttg    4740
tcagtcaccc gttgtttatt gattttcact cgttgcctta aatactttga attacgccgt    4800
aagtttctta gttggtcact cataatatca aacgcaaggt gtgcctgctg ggaactgtta    4860
gcagtaaata gtatttgtcg attacgggct ggttgctttt ccataagaag agacacaacg    4920
ccaatcgctg ccagtaagaa gctctttcca tttttacggg cttcacttaa tagaatccga    4980
ttgaagcgca atgaattatc gtctacctgt cgccaaccat agatattaga taagataaac    5040
acttcaaatg gctctagctt caatggttca ccgtttgttt gtggtaagct ctcaacaaat    5100
ttaataacct taccagcata cgtttcagaa taataataag gaaagtcatc ggtcttttgc    5160
tttttcatgt cgtctaagaa gcgctggcaa gcatgaataa ctaacttacc ggcgattaac    5220
tcacctttaa caactgaatt agcatactga atagctctat ccattatgac aacatctctt    5280
caaactcatc agtaggagct tcttcactca ttgccttgtg gacttctagg cgtacccgtg    5340
attgtgggct aagtgccatt tgactatcaa ttgacttcat ttctttaata gccttatcac    5400
gtgccatgta gtaaggtgac tgctgtaatc ctcgttttgt atcaataact accccagtac    5460
gatcaatctc tttagtacat ttgataattg ttgaatacaa agtacagtga gtagcgatta    5520
aactaacatc tagttcgcta ataggggcac tcttctttaa gagtgggaca attctacgcc    5580
attccttttt tgctacatca tcaagccatt taggggcgtg agatgttaag tttgggtatt    5640
ctgccaatgc tttttcagcg tcttcacgtt gtgcttttttc tgccttagta atatgacctt    5700
```

-continued

```
ctggacgggt cttcattggt tgagccaact atttaacctc cttctattta tttggtgaca    5760
ccatgtcact atttgtttaa aaaaataaaa aaaacatcat ttcatattca attatcgtat    5820
tatttaaccc ttattatacc atatttgaat agtttgttaa gttcaatgcc taaaagttat    5880
aataaaaaat ccttgacatt tgaggctcta aattatttaa taaagttgaa aagaaaacca    5940
tacaaaataa aaagaaacgt cttgaaatct tcggatttta aggcgttttt ttgtaaaggg    6000
agaatttttt taaaagaaac ccccaccatt acggctccta ccggtctata ccaatagcgg    6060
gggtattaaa attatttcag ctattcatat ttattttcct ttctcgttga tgatctttc    6120 ttgtctttc tcggtgacaa cgatagcaaa gtgattgtag attagttgaa tccaatcttt    6180
tactccaatc ttcacgtata ggtacaatgt ggtcaactaa atcagctttt tttactattc    6240
cctttcgtaa acacataaca caaactgggc ttttctggag cgtttgacgg cttaatttaa    6300
cccacttact cgttttgtag aatctattat agtcatgagg agctttggcg cttctttcca    6360
ttcgcttttt gtatactttt ctattgtatt catgtttctg ttctttggtc atctttttat    6420
agttatctcg ttgccaatgt ttacgcttgt cttcatattc tttttgtaga tattgatgtt    6480
ttttacaaaa atattgacct actggaatca cctctcgaca accagcagca ctacaaaacc    6540
ttactacact catttgataa cctcctatga aaaaagggca tcgcataaca cgacacccTt    6600
agcacttact tattaattaa ttccattgcc ttactatatg cttcaagcct gcttatgtgc    6660
cagcttttaa catcgttaac cgttctctta atgcaagctt caagctccat tgtatcggcg    6720
ctgtaagggt cacactcgct tagtctatac cttgccatca tcacccagtc ttggcgactt    6780
tcctctgcgt ccttgcatac tgccacttgt gcaatacact ttactagctc ttggttgtct    6840
ggtagtccta gatcaatcgc taatggtaat ggactgccat ttactgagac taattttaaa    6900
ctataaagcg tagtatacat atgataatta gaaggatcat caccgcttgc ctcaatcatt    6960
acattaataa agttgttata ctctgggtgc gtgttgactg ttaatttact catccccatt    7020
tcacctctta tttatgacta tcaagcttgc gtaaggttac aatatcatac gccaataact    7080
catcatcaat tgaccaacca gcaactttat agatactgcc attgtattgt gcttctggat    7140
atttcttcat gtccgttaaa tctttcttgt gacgaactac caatataaca tcatcagtaa    7200
ttgaactacc tgcctcacta atagcttgac tagcactgat tgaatagtta ccacaatgta    7260
ctgtcacatc tcctacaaaa cctgtcatga tcataccagt attcgggtta cgtttccccg    7320
taccaccttc atgaccgaat gtgaccttat gctttaatcg tgtaattgcg tatttattac    7380
ttcgcattta attattcctt tctgcctgta cttgcagata caagcaatag tagaacgttt    7440
gcagccgttc tagtgaaatc tactgttact ttattttTaa ctccttaata ggcttttcac    7500
ctatccggtg gtatgtggtc actgcctcaa aataaaagta cggtaaaagc agttttaatt    7560
gttaattttc atctcttcaa ttgaaaatag ttttTactTt tatcggttac cccgtttcaa    7620
gtacccacaa tcgcctttat atcaacattt atatggtaac cgataggata taaaggtaac    7680
cgatacattg cagttactta atatagtaac ccgaaactat cggttacctc aaaatgcttt    7740
cggttacctt taaatagctt tatatcaagc tttataagaa cttctgcaaa ggtaaccgat    7800
aaatataaaa ctataactaa ttttttaagag caattccttt ataacctTta acatttttac    7860
cgttaatctt aactgtagtg tgtttgtatc ctcgtgctat tagctctttc gcaaacttac    7920
gattactaag acaaggaaca gcagtatttt tacaatactc tttgtaatta tcatatagat    7980
atactgattt ttctttatct ttctcatttg tagtacagca atcattaatc caattaccga    8040
```

-continued

```
tattgtcatt agcatttacc cagcttcgct tttgctgttc catgtattca gtcactggaa    8100
acttaccaga atcaagtgct tttttataag attttaagca ttcataggca aatgctggca    8160
tttctctttt aaagtcttgc tctttgaatt gctctttaaa atgtttaatc ttatggaacg    8220
ttacaataat tggtcgtctt ttaaatccgt ctgtaaaatc attgaaggct ggtaaatcat    8280
tagcgctaaa aatcaattta gcttcatttt caagtttaaa tggatcttta tatttaaatt    8340
gagctgttgt agtgtcgtca ccagttaatg ttttaataat attagtctgt tccataaatt    8400
tggggcttat atcagcaaaa acattagcag ctttatgata cagctgagaa gtagcaaatt    8460
tagcttcttt ttggtcggat aatgcttcta aagaaacgtt tgaaacgtta ggcttcccta    8520
ttaactccat tagtttattt agaaatgtag atttaccatc cccacccaac ccgtatagaa    8580
tcatataaat ttgaaagtcc ttaaaactac ctgctaaagc aaaaccaata aaggctttta    8640
ctgtttcaat tgctgttagg tcatattcat cttgtagttt tccagtatca tcacggattt    8700
ctttagttga gggtactaat gattgtttta accatttatt ccacgttgta gctttttcctt    8760 ttgtttctaa ttcatatggt ctattttgta aaagatagtt ctctggtgaa ttatcttcta    8820
aagtgtccgt catcaagttg taagtgtgtt taccaaacac tgctttataa ggtgctggtt    8880
gatcaaatgg attgtcttct acaatttctt gtgaatctaa ggcaattaat ttagaaaccg    8940
atgctaataa gttcgttctc catattccat gaggtacaat ttcatttttg attgattttt    9000
caatgactga atcagcgtaa tttttccatt gtctactttt aggatcgaac caatagccgt    9060
gttctataaa ttggttggat gtaaagtgat actttttttc taaatattta gccaacttaa    9120
tttcatcaac cagtttattt cctttatcac ttacagttaa ccattctgga aaactattgt    9180
tatttactaa gtcatcaata ttagccatat ttttcctctc tttacatggt aatttagcgt    9240
ttgtatttaa gactgataat ctctacttcg ccttttgttt tgatatattc aaagcttttc    9300
ccgtctaaac ttgtttcttc gtatatattg tcccaatcga ctattgattg atcttcgttt    9360
tgactagcat tattccaata cttaaagagt ggtgtacggt gcagtattcg gttaacttgt    9420
ttaacgtcat cccctgtgta gtagagaaga taaaaacaca ttgcaccaat agcaggttta    9480
acgctatgat atttattttag gtagtaggaa attatttcct cattatttttt ataaagagca    9540 ataaattttc tactactttt actactaaca gctcgttcta taaccttgta atcatcgtta    9600
tagtattcaa gtgctttctg aaactgtttc tttgcgtact cattaaggggg atgtgacgtt    9660 gaattaataa ttttttccat cttgtcacta tctaataaag gattaacgga tagttttttct    9720 tcaaaactta acactattaa tcacgtccca cctattgcaa ttgatcatga atttgatcta    9780
acttatccaa caaaatacta gatagtgcta acaatgcttt cttacgtgat actactgttt    9840
gagcaaccgt agacacttgt tcatcactca ttgctgcata attgtctact cgtacaattg    9900
gagcaaaaac atcatttaac tgatcataca gtgcttgggc tattccggtt gtttcttcaa    9960
cattggaatc tgcttccac aactgatttt caaacgctag ttcttggttc ttatcttttt    10020
ccattgttta aaccctccac tcatgttaga atgaaagaga attaaatatt agtaattcgt    10080
ccaacatccc ccgtaaagat tgttggcttt tttattagct aaatttaatt ctctaagttt    10140
tatttagtcg ttgttagtgt ctgaattggc gttctcacta tcaacggctt ttttattacc    10200
atccataaag tcgtttttcaa aatcagttaa agttttatat tgaattgcta aatctttaat    10260
ttctttagcg accttaataa tttcatctgc tgaggaaatc ggatcatctg caattatttc    10320
tccattttct ttagtgatag taccttcaaa acaatcttca gtaattgaat ttatataact    10380
gccagcttta acaatcctgt cttctatatc aataattctt ttacttaata tttcttattc    10440
```

-continued

```
aaattttttta gtgtataaac tcatttctta ttactcctta aaataagtta ctaattgcaa    10500
caacaatacc cagcaatggt aaaaacgttg ctagataagc ccaaaggcgt tggtctggtg    10560
aagtccacca gtaagctaaa atcttaccat caatttttttg taacatatgt ctcacctcct    10620
cctatttatt tctctacaat cacttgccag ccagctgtgc gattattact tagaattttc    10680
ttttacccaa cggtcaacat cttcacgttt atatacatat tttcctccaa cctttgatga    10740
tggaaaattt cgggtcttaa tccaacgatc aatagttgtt cgagaaacac ttagataatc    10800
cgcagtttgg cccttattca taaactctgg ttcggtttta acagtcttag catcttgtaa    10860
cttattgttc tctagctttt tagccacagc ttcagctaac tgatcaatga actgatctaa    10920
aatagctgta ctcattatta tcacctcttt atttcatatc gtaattacaa tatataacat    10980
aatgaaatat tatgcaacaa caaaataaaa tatattgtgt tttgtattgt tattttcggt    11040
tatgtataat atattaacta tacaaggagg aattaatgtg aaagaaattt catctgacca    11100
gaaaataggt tctaacattg cactaattcg taaagctaaa aagatgactc aaaaagactt    11160
agcaagaaaa attggaatat cacaaccagc cttggggaat tatgaacgtg gccagcggat    11220
tatacctgct tcgatttttc acagtttacc tcaaatatta gatgttcctc tagattttct    11280
agtctatgga attcccaaca atattacctt tcatgattta gcaacgctcg attccgtatc    11340
tctcaaaaag aaagctgctc atattgaaaa tgatagaagt attattgaac gtgggttagg    11400
gcgtgacgac ataaaaagac atttattagc tgctgttttg cttgataatt atggttatct    11460
tgtgtaccca gatgaatcta gcaatgacaa agaacatgaa caacttaaaa aatttgtttg    11520
gaatacatta gatggattac ttaccggcgt accaattacc aatgaaataa attttaaaca    11580
aattaatgaa caatttgaat tacttgcaaa tacgtattta agcctaatta ttgacgaaga    11640
ggcaaatcgc tatcctgctt tccgcaagga tttaccaccc ttcaaagaaa aacttacaca    11700 gttttttaaat gataacggat attttaaaat tttaaaaaaa taattttaaa cctttctcta    11760
caatctcttg ccagccagct gtgcgattgt aggaggaaag taaaaatgtc agtatacaag    11820
gataaaagaa atggtacgtg gtatgttaaa taccgcatta atggtaaatc aaccagtaag    11880
cgaggtttca aattaaaatc ggacgctgta gcgtgggaac aagaaaaagc tgtggagctt    11940
aaaaaatatg gtcaaatgaa taaccataac atgaccgttg aagagctatc aaaaaaatgg    12000
ttgccagtat atgaacagac tgggatagaa aattctacta ttcataaaac aaaacaaatc    12060
attaaaaatc atattctacc ccgcattgga aactataaag ttgctgatct tagcattgag    12120
ttattaactg aagttgctgc taaatggaaa gaagaattag taaagagtga cccttttaac    12180
tatactaagc gaatgttaga ctacgcagta caattaagag cgatcccaac taatccaatg    12240
aattctgtag taaagcctcg taaaaaacat gacaaaacat ttactaacaa taatttcttt    12300
aatgaaaagc aacttcacaa ttttatcaag tgtataaaaa aagactacga agaaaaaaat    12360
cctcgtgctt tcatggttct atggttagcc cttttttactg gcatgagaaa acaagaactt    12420
caagccttga cgtggcaaga tgttaaattt acaaaaagcg gtggaataat ccatattaac    12480
aaggctatta agaacgcaaa acatccctat cttggtggcc ctaaaaccgc taactcttat    12540
cgctggattt caatagataa aaaaactgct tcctatctaa aaagatggaa acagcaacag    12600
atagatattt taactaaact aggttttaat ccacaccaaa aagagcaatt gattttctct    12660
acctacacta aaaataaaat tgtttttaggt gcagaattgg acaagccgtt aaataaagta    12720
attgttagaa ataatctaaa gaaagttaca ttccatggat tacgtcatac ccatgctaca    12780
```

```
catttggctt ctattggtac ccagccaaaa ttaatagcag atagattagg cgatacaatg   12840
gaaactgttc ttgaagttta tattaatgca gatactgaac cagaacaagg aatcgccgac   12900
aagttcgccg atagtttagt ataa                                          12924
```

```
<210> SEQ ID NO 13
<211> LENGTH: 36497
<212> TYPE: DNA
<213> ORGANISM: Artificial Sequence
<220> FEATURE:
<223> OTHER INFORMATION: Based on Lactobacillus reuteri sequence

<400> SEQUENCE: 13
```

```
ttaaaattga ctaagtgcct ggacgatttt gtcatcagtt ttactttat attcatcaat     60 caagtaggcg tatgtgttca ttgtggttgt gatatcatta tgtccaagtc tcttgctaat    120
tgcataaata tctattccgt tacttaacag taaagcaacg tgactatgac gtaaactatg    180
gaaatgaaaa ttcttctttg ataattttgt atcactcata atttgtcgaa gcgtttttatt   240 taatgctgta ctagtaggga tagtattaaa ttgatccata aaaacaaggt tacttgatga    300
attattgcgc aattgtttaa gtagtaatag tagtttttca ttaactttta ttttacgtgt    360
agatgattca ttcttggtgg gtttaaagcg atgtgtatta aaatgttcgt ctgtttcgtc    420
tcttcctttt acctctctcc atgctttatc aatattaatg gtatgatgaa tgaaatcaat    480
atcattccag gtaagagctt gaatttcttc ttttctcatt ccagtatata tcgcagtgac    540
tatcatataa cggcttgtat atcttctatt agtaattcca ttgattgtag tagttaataa    600
tttccttatt tcagttacat tagggtattc taccttcatt gttttgctag tattggcagc    660
taaagtaaca cctttagtaa aatctttaag cagataatca tcaaggatag cagattgtac    720
gcaagaccgt attattgaat taagcttctt tacacttgct atagcatgag ttgctccata    780
cttgttaata aattcttgat atttagaacg gttaatttct ttaatagaag cttcttttgaa   840 ataatcatta attagattac cgattataat ataacgattc agagttacac ttgatatttt    900
aggttgctta taagtattaa cccattcttc gtaataatca ctaaaagcaa ttttttttctc    960 aatgtgtatt ccgcgattaa gattagtttc catttcagct gcccactttt tagctagtgc   1020
ttttgttgca aaaccagctt tggactttga aaaacgtttt ccttcagtat cttttccactg   1080 aattcttaca gaccattttc cgcttctttt atatatttga gccatacttg tccctccatt   1140
attaaattgt gtataatgaa agggttgata gaatttgttt ggacgcaatt aatatcaacc   1200
cttggtccac tgacagttgc cgctgtcggt gggctttttt agtttaaata gctttttacg   1260
tcatcaattt agttggacga gaaatttagc ttttgtttag cttctttaat tgattaataa   1320
tttcttgatt ttgcttaatt gttatccaat tttgctgttt gattattctt aattcatgaa   1380
aaagggcttt tgtatcatta cttgtaaaag taggataggc acctgttaat ttttcggcaa   1440
ctgctatatc ttttacagat tcgagaattt cgtcatctaa actttctaaa cgattttctt   1500
taatatattt atctttgtct ttagcaaatc catctttacc attgaaaata ctcatttta    1560 gctttctcct atcttttttaa tttttacatt gtaaagagcg ttatttaaat cattacagtt   1620
cctaagatag gaaaaagcgt ttttttaaaag tttattcatc ctttgactcc ttatattcct   1680
aaaatttgtt tctttttagc atcaaattct tctttgttaa tgattccatc atcaagtagt   1740
tgttttaatt ctcttaattg cgaaaggtca ttactagaat tggattgtgc tgatgtctgc   1800
ttaaaatctg cagctgcctg tttaataagtc tcagccatct ttttagcagg gtagggttgc   1860
atattttcta tttgagttgt aatagctccg ttggttactg caatagatcc caacattaaa   1920
```

```
cctttagaat atgaaacgcc attaatcata tcaaggggaa tgtcagttga tttactacca     1980
taaatcaggc cgtggtcaag aaaaattacg cgcttattag tacaaaccgc aagaatggaa     2040
ttagtttcaa cgaaagcatt agcagcataa agtatttttt ctccaccatc gacatctatt     2100
atgtctggca aggctttgat ttccttttta gtaccgaata gattttctac attggcatcc     2160
tttaactgtt gcttaataac atccaatttt tcttgttcgc ctttgttgat ttcgtcaatt     2220
gctgcttgta aagtatcagc tttttacca gcgctatcag caattgaatc aagtttctca     2280
gttactttag atagctttga tttatacaaa tcaggatgtt ctttgtaagg tacggtagaa     2340
tgaatcccta ataaactttc aatttcacta gcggtatggg aactaatgaa attgctaagt     2400
ttaattggaa cacggtaagt atttgctgga cgtttgggat caagtctgtt ggcatctttg     2460
ccacaaatta aatatccatc tttggtaatg caagaagcct ttaacattcc cagggcatca     2520
ttacatatga agcatctctt tttactcatt tggatcacct tattccattg tcactgaata     2580
tttaactaat ttaccaacaa ttcgacctgg atgctcttca tcaagaatta ttggatcata     2640 gttttttatta tctggcatta gcataactaa attgccttga tgcttaatac gtttttaaagt     2700 agcttcgtta tcatcgtcaa caagaactgc agctatctca ccatcttcaa cttcaggttg     2760
ctctctaata atggctaatg cgccattagg aatggtaggc tccatgctat cacctttaca     2820
acgaagacca aaaagtgttc cactaggaac tggtttttca aagatttcat cagtataacc     2880
ttcgatattt tcttcagcag taatcggatc gccacaagca atttcaccaa tgattggaat     2940
tgaaacaact tctaatcctt ctttaggata aataatatta gaaggtttct tttctctggt     3000
agggaaaaag tcatcaacat ttacattaaa aatttcagct aatttaaata aaacatcttg     3060
atttgccttt ctagatccta actcatatct agtcacagtt gctcttgtcg tatcaagttt     3120
gtctgcaagt tgttctactg aaaggccacg ttgttcacga aaatttctga ttttttgacc     3180
aatgaattta cttagttcca ttttatgtac ctctcttatg taactaatta tataacttgc     3240
gttaccgaaa tggaatattt tttatctttt tcgaaaaaaa tagttgcatt tgttccagaa     3300 tggtttaat atataattgt tccaaattgg aacggaaagg agagataata tgcagtcaag     3360
attatatgat ttacgaaaac atgttaaagg aatgactcaa caacaaatgg ctgattatct     3420
aaatattagt gtcaaagctt atcgtgataa ggaaaatggt aaaaatcaat ttactcaaga     3480
tgaaatgttt gctattagta aattatttga tcttaatatt gacactattt ttttgcctcg     3540
taagttccat attggaacaa agggctaaga gaggtgacac aaaatgcaag catcgctaga     3600
tgaacaagat taccaagtaa ttactaatga ggttctcagg cgtattaagg aatgttacaa     3660
cttagtgcct aaacaagatg tccaaactga caaatgggtc ggtatcaagg aattcacgag     3720
taagttgccc gttataaagg acaaggaatg ggtcagaatg tttctcctta cacttccagt     3780
ctttaagaac tgggttatca atttgaatgc aggtcaaggt catcgaacta aggtaaatgt     3840
gaccaaggca ttgccttgga ttatgtctca tcaagctgat attgattgga accagtcatt     3900
gccacgttag gaggtgaaca gatggcacaa ccgatatttg taaaaggaat ttttggaaga     3960
cgaattatag tttctcaatt tgaacaaacg tctgatttta ttttgcaaaa gaaaaacgct     4020
gacctaataa aagaagccag cggatttca aaaaacaaga aattgtttac tcgttatcaa     4080
ggtaaagact ttcaaattat ggagcaatta aagtggcaac ccagtgttct ttttgatgat     4140
gccagtaaga accgtagtag ccacagattt aaggacacca atggaaactg actttagagt     4200
gttagtagct ttctttgttt gtttccaaac ctcatcatct cgaatggaat caagtagttc     4260
```

-continued

```
atgcccagac caagtgatgt catagacagt taattggcga accattttat taataaatgg   4320
tttggcacta atgaaaccgc ctgagtagag ctgataaagg gtataaacaa tatcattttt   4380
atcaaaggtc tcattagcaa taacatttgc aatttgagaa tctgtaaaac cttggtaaag   4440
catttgcaat tgctgttttt ctaatgataa aagaacatac ctaacacagt cttgcttcaa   4500
tttcacaatt ttcaccacct ttattttgaa ttaatcaaag tatagcagaa agggagagca   4560
gttaaatggc gttggtaatt ggattaccaa tattaattat tgcaatgtgt ttgttatatg   4620
cattggtgta cagcttattg tatgagcgga ataaaccatt gctattgaaa gaaaagtatc   4680
ggaagaaaca ttgaaaggag gtgatatgaa cttttggtaaa tttatttctt ttgttgtttt   4740
ttatctttgt tataatgccg cttttgtatc aatttttgaa ttacatcaga aggcaaattg   4800
aaaatttctt ttggaaaaaa agccataaaa ataagaacga atgaaatgaa agtagctgta   4860
aattcaaatt gttctttggt ctgagttatt aatagcccag taatagtaga aagaataatt   4920
gctatttttg aaagatcatc caagtatttt tcgcttattt gaaatcctaa agtttctgta   4980
agccagccaa ggataaacaa tggaaaagaa aagaagccag ttagaaaaag aatagtaatt   5040
aagcaatcaa atattctgag tttttggaat tcaaaaatta cagcatctgg attagcagca   5100
tatgtaatat gtagagctaa ataagtaaaa cagatgaggc agaagataca aaccataaag   5160
tcggttagtt tcttactata gtaattaaat ttggttaaaa acttaaaaat tttacgcata   5220
atgattttcc ttttgtactg agttaatcaa agtatagcaa atgaaaggat ggtagtttaa   5280
tgagtaaatt aattgcgcta atcgttggtg cttggatcat gtattgttca atgattggct   5340
cttatgatgg agcgatggcg atcctagcag tttatcttct gctagtggtt cttgatccac   5400
taaataaaaa aggtacgact gccgcaaaca gtcgtaccga taaataaata atctacgagg   5460
taattatata tgaatgagtt taatttatca aaattaaatg ccagggttgg cgataattgt   5520
gtatttgtat cgaatttggc agttcgctat caaagcgctg ctactcctga agagcgaatg   5580
gcaatggcca tcaaaatgga gaatgctgct acgatgttac gcatttcagc tgagcgtttg   5640
gccactgaaa ctaagaatgt ttacggaggt aagaacaatg actaacgaag aaaagattaa   5700
ggcaattaaa caaattcttg gaccagaata cgaggaggta gccattttcg ctgctaaaaa   5760
atcagaaatt cgtgacgaac gtactaattc attagttgat gcggatcccg gaacggtagc   5820
agccatgatt atgaattggt tacatactaa tccgatagca gcttcaattg tcaaagcaac   5880
tattgatact ttggaaactg atccaactgc tgatttattt gcacagattt ttctaggagg   5940
taagaactaa tgaatttatt tgaattaaac gacaactaca aaacacttgc tagtcgggat   6000
gacttagatc caactattct aaaggataca ttggaatcaa ttaaggatga tcggaagacc   6060
aaattggaca atcttgcttc atgggcagat catttgaagt cagaaattga ttttatgacc   6120
gacaaaaaga agtcatggga agaagaaatt acttaccgaa aaaataaact tacttggatc   6180
aagaaatata ttactgaagt tcttgatgat gccggtatta agaaaataac tactgaaaat   6240
cacttactta gtgcccggaa ctttaaggcc tcaaccatta ttgatagtga taagaagctt   6300
ccggataagt tcaaaattac tgagacgact actaagccag ataagcaggc catttaccaa   6360
gcactcaaag ctgagaagaa agtaccagga gcacatttaa aagctaaccg taacacggtg   6420
attaaataat gtttgaactc cgtgattatc agcaagaaac gattgataac atcatgaatt   6480
ctataagtgc tggtcaccgt tctatcatgg ttcaacagcc gccacgaacg gggaagacag   6540
ttattatggc cgagattgct agacgagcaa cggcaaaggg taaccgtatc ttgttcgtgg   6600
ttcatcggca agaaattgtc cagcaggtta tcaagacttt caaagctaat gatgtaaata   6660
```

-continued

```
tggatttagc taaaatcggc atggttcaaa cgattacccg acacgttaat aatttggacc   6720
caccggcgat aattttttgtt gatgaggccc atcatgttct ggctaaatca tatcgaagga   6780
ttcttgatgc ttttccgaaa gcttataagt tactgtttac cgctactcct tatcggttag   6840
gtggacaggg ttttactgat gtggctgatg atttaattat tggcaaatca gtcccctggt   6900
taattgacca tcacttttta gcaccagttg attattacgc tccttcttac attgatactg   6960
ccaagttaaa agtaaaacga actggtgaat atgacactga ttcaatcaaa aaagccatga   7020
agcctaaaat ctacgggaat gcggttaagc actatttgaa acttgctacg ggaatgcaag   7080
ccattgccta tacctataac gttgatagtg caattaagtt agccaatgca tttaatggct   7140
atgggataac tgcaagcgcc gtttccggaa aaacgcccaa agaagaacgg aataaaatca   7200
ttgaggacta tcgccaagga aaaattcaaa ttgtaaccaa tgcagaatta tttacagagg   7260
gcctagattt accaaatgtt gattgtgtca ttatgttacg gccaactcaa tcattatcgt   7320
tgtacttaca atttgcaatg cgctcaatga atccacggga aggtaagact gcaataatta   7380
tcgatcacgt gggaaatgtt gaacgattcg ggctgccgac tgatgagcgg caatggacat   7440
tagaaggtag cggaaaaaat aaacaacaac caggaacaac gcttaaacct gtatcagtat   7500
gtccgatatg ttttgcttcg ttttatcgta caagtgatat ttgcccttat tgcggggcgg   7560
cattaggaga agaaaaagaa attgaagtcg ttgatgatgt tcaactaaaa aaagttacta   7620
agtcacggct agcgattatt aagaaaattc aatcgtcagc aattatgaat aatgttgctg   7680
gcaagcgtcc aaacgaattg aagaatctga aagaaataca agcctatgcc aaattaaaag   7740
gttacaaacc aggctgggct taccactacg ctaaacagcg tggatttatt aagaagtgag   7800
gttgatatta tgagtatttt gccaccaaat aagccacaga aggcacggcg agttccaaga   7860 aattactttta tctacggaga tacaatgtcc ggaaagtcat atctagctga acgttttcca   7920
agtccgctat ttcttaacac cgatggtaat agtgagatga acaccgcacc aagtattcaa   7980
ttaaagaatg tccgaaagag cgatggaagc ttgaaagagt cagtgattga tcaactagac   8040
aagattattc ttgctcttgg tactgaaaat catggttaca aaacagtagt tattgatgtg   8100
attgatgatg tagtaacact aattgaacag gccatctgtt atgacaatgg agtagaaacg   8160
ctgggggatg ttccttacgg caagggatat gcacaattta ataccgtctt tcaagcattt   8220
gtcactgagc taaaagcctt accactgaat acggtttaca ttagccggtt aatgatgcta   8280
actgatgaat cttctggcca caccgaagac cgaccatcac taaaacagaa atattacaac   8340
gtggttaacg gaaattgtga tttagtgatt gaaactaagc gctatggtga ccgttatatc   8400
cggatggtta aagatcgacg aattcattat gtcaaagatg atattactga tccggcaatc   8460
ttacgggtac ttgaacatgt aaatggcgtc tttgataagc caaagcagac tactacaaaa   8520
gagcagaatg aaattgttaa caaaattaaa aagcaaaatg taaaggaagg ttaatgaatt   8580
atgagtttac gagatgcaat gaataaagct actgaaggtt ttgatccaaa gaatgattca   8640
gttaataaat ttaagggact ggaaagtggt aaatataccg ttgtagttgc aaaagtagaa   8700
aaccatgaaa ctccttggaa tgctgaacag cttaactttg agttagaagt tgtcgatgga   8760
gaatcagccg gccaaaaaga attcttacaa attggattag atgaattaac ttctaagggt   8820
aatcccaatc caatgctaga aactaattta cgattggttt ctaagttagc agcaattcta   8880
ggtgttgaaa ttcccgatga agtttgggat gacgatactt taatctacga gaacttggct   8940
aaagcatttg caccggcagt aggaaagacc atgattatgg atttgaaggt tcgaccaaac   9000
```

-continued

```
aagaagaacc cccaatatcc ataccgtaat tatgactttg atgaagcgga acagccggaa     9060
acgccagaag ttacagatga tgaaatgccc ttttaagtaa atatttgagt cagtgaactt     9120
ataacaccgt atggctggga ggccattaag gaggaaaaat gaaaaatcta gttaattacg     9180
ccttagccta tcaagcaaag ggtttaagcg tcctcccaat tgctggcaag cgtccactaa     9240
ttaagtttgc tgatcgtgat ccacttaccg ccgaagaaat aaagaccatc tggatagaac     9300
atccatatgc tcaaattgcg ttgcggactg ataagttctt cgttgttgat atagaccgca     9360
accatgctga taacattgat ggtttttgaat caattaagca attaccagcg gaatattttc     9420
cggaaacttt aacccaaacc accaagcatg gtggccgaca gttattttat ttgaaacgtt     9480
cagatatgcg agttaatcag ttaattggtt atttaccagg tgttgatgta aaggcccacc     9540
aaaataatta tgttgtggtt gcgccatcag aaggttacca atggctgaat aagaagccga     9600
ttgttacggc tcctaagtcg ttagtagtga atattaacca aatgcgagcc agtaaccggc     9660
gaagttctcc agatgattta gttttttaaac cacgtgaacg caactcaact actgacttac     9720
ttgagaccat cgcaaatgga ttgggagata aaggaataag aaataaaaac ttagctggaa     9780
tgattggtgc tttattgttt cggggagtag aaccaaagtc tgcttatcaa ttagcgatga     9840
tttgtaatga gaatacgccc gatccactac cagaagaaga agtgaaccgg acatttcaat     9900
caatgctaag acgtgatttg agaaacgggg gtgaaatacg tggcggataa tataattcgc     9960
aaaccaattg aatttgaatt aaatactcaa ggcaatccta aaactaatag tttgaagaat    10020
attggtttaa tccttgatgg cgatccacta ctgcatggca ccttcaaata taacgagttt    10080
gcttattcaa ttgatgttgt taaggacatt ccacagctat ttattgaaaa ggggcaactt    10140
gatgatagct attcagcaat tatgctccgt tacattgagg atgagtatgg ggtgatgttt    10200
caagaaaaat tgttaaatat ggcaatcact gttgaagcaa aaagccaccc atataatccg    10260
gttaaagagt atatggaaaa gtgctataag aattgggacc acaaagaacg aatcaaagac    10320
ttcctaccag tctatttagg agtacccagt ggtgaagtaa caacgctgca gacaaaatta    10380
ttcttagtcg gagcggtgat gaaagtctat aagccggaaa gtaaatttga ttgggtgttt    10440
gatttagttg gtggccaagg cgttggtaaa actactttac ttaaaaagtt agcccatggt    10500
tggtatacag accaatttac ggacttcaaa gacaaggata atttttgccaa tatgctgcgg    10560 gcattgattg ttaatgacga tgaaatgacg gccacaaata attctgactt tgaaaatttg    10620
aagaaattta tctcagctga agaattagag ttccggccac catatggacg acatacaatc    10680
cgccggccaa agaattttgt tatggcccgg actactaacg aatcaaccta tttgaaagat    10740
aaaaccggtg agcggcgttt cttacctaac atggctgata agtcccaagc aatggctaat    10800
ccggtaactg atcttgatga tacgatggtc aatcacattt ggggtgaagc tgttggcctc    10860
tacaaagaag gctttttcttt catattgacg aaggagcagc agaagctcat tgaggataat    10920
cgaaagatat ttatgtacat tgatgaaact gaaaatcaaa ttgaacgggt tctcagtact    10980
tgggacgatg actggattga aagctcagaa attgctcatc aattaggtga agataatctg    11040
gttaagaatc gttcattagc caaaaagatt aagtatgtaa tggataaccg gcatgattgg    11100
aaagcaggac aacggcgaat taaaggaatt agtcatcgtg gttatagaaa agtgcataca    11160
gataatacac tatgaatata gttaagtgta tgcagaaaaa acctattaca tcaacgttta    11220
ttaaggtttg catacactac tacactattt taataataaa aaataaatat atataaatac    11280
tatatatgcg ttataaaaag ttgaaagtta gtgtatgcgt gtatgcagta actaaatccg    11340
ttgagagagt aagaattaag ctgtatacac tactgtatgc atagtgtatg caaggaggaa    11400
```

```
aatatgaatg aattaaaaaa catcagcaca tcagaattac ttgatgaact gattgaacgt    11460
aatgcattat ttcgtgtaga ttgtggtctt tatcggaatt gggagttgaa gggaaaatat    11520
caatttagcg atattaaatt gcctagcgca tatcctattt atgtaggaaa ttcaattatt    11580
gaccgcatga ttaagtggga gtgtgagcat tgacgagtga acataaaatt caaaacgata    11640
tccgggttgc actatcaaaa catcagtgta cagtgttccg ggtaaatgtc ggttcggtaa    11700
aaacaccaga tggaagattt ttttcagctg gtgtacctag tggtcacccg gacttatatg    11760
gatttcgttg gtcggatcat caagtatttt atattgaagt gaaaaacgaa aaaggtaagc    11820
ctagagcgga tcaaattaga tttcatgaaa tgctaactaa acgagaaatt attcatggaa    11880
tcgctaggtc tgctggagat gcagtaaaaa ttgttgagga aggattgatt ggttatggat    11940
atgaaaataa aaaagaacca ccacaacaag taaaattagt tgaagtaatt caggttataa    12000
cctctcgtgg agctggaaca aaggaggatc cgataagaaa gattattcag tattggagca    12060
aagaaggcac attattagca gaaagttttg gaaactaatt tttctttgag tcacgtttct    12120
ctatgtgctt tagttgtttt tcaggaagac tattataaaa cttatcaatt tgatttggct    12180
gtgttattaa attgtctgta attatattta acagatttaa aagacttttc gccatttctt    12240
ggttatcagt taagtctatc tcaccaggat gaacagcatt atttccaaca attcttacaa    12300
tatcaaacgc ttgttgtaat ttagccggaa gtcccttaga tactagatca ccaatacgat    12360
tatctaatga atgtttattg gaaaattctt ttgttagttt atctattgcc agacgagaca    12420
aagcagcaga tgctcttggt gaatctctaa gtacttttgc cgcttcaata taaatttgtt    12480
taatatcatc gggcatatct ggattaggag ctgttaattt taaaggaaaa ctaggaaaga    12540
taagtatatc ttcattggat tgccgattat gaaaccaaat agaatctaaa taacatgaag    12600
tgcattttgc aactattaaa ttatattcgt attgttttga ttttattttt tctgcatatt    12660
tccaatcaaa ttgagcatat acatgacaat aaggacaaat aataggagct ttccctgtaa    12720
aatcattact aaaatatttta gtcattaaat tcacctcaaa taagattata gcgtaaagga    12780
gtagatgtaa tgctacacaa atatagaaag ttaccaattg tggaagctga acagtttgat    12840
gggtcagatg aaatgattga aaggtattca gtgcatgtat ttaatcctaa tttagctaaa    12900
aacatcttct ttataggtat gaacgttcta gctattggtg attggattgt taaggatgaa    12960
tatgggaatt atcaagtggt agctgatgat atattccgta aaagttatga gaggtgcgac    13020
taatgcacat ttatgaagta atcgttgtag ctgtatttgg cacagatatt agccactttg    13080
ttgttgctaa gaatgccgat aatgctaaga aaattattct tgattattac agcactcgtg    13140
atgatggtat caggccaact gtgacaatgt atgacctaac aacaaaatta atcaatctta    13200
ataactacat tgatgaggtg atgcttggat gagattaagt gacaaaatta ttatgacttc    13260 cttttttactg ttattaattg tttcagtcgt cttatcaata gttacgggaa gtaaagtctg    13320
gatatggatt tttcttttc tgatgacact tgagatgctt tacaaaattt ggcgttagga    13380
gcgtgactaa tgaaagcaag atgtggcgat tggagtactg atgtttatcc agttgaaccg    13440
tttgtttatg aagtagcagc tgatggtaag aaagaatttt atcaatcagc atgggatgct    13500
tttagttctg aattgcatat gaaaaatgtg acggcgaaga ttatcaaaat accagttgtt    13560
ccaatgagta atgatgaaat taaagcagag agtgttgcat ttgaattagg cgaaaaaagg    13620
cattatccac atgtggaaga attcactaat agtaaaccga ggaggaaagt tacatttctt    13680
caggttgcgg aagcttttgc aattataacg tggattattt taataattct tataataagt    13740
```

-continued

```
acggcgttta tgtaggaggt aagttactaa tgacatttga agaggcgtta aaacatgaag   13800
aaaataatgt gccagtattc tatagcgatc gaaaatatta tgtaatcggg cacaatgagt   13860
taaccgaaca atttacaatt cgtgagctaa gtggtaatcc gttatttacg gtgccggttg   13920
atgtacaagc ggaggaattg tcatgagtat taaaattaat gcgcaaacag ttgtatttaa   13980
gggacaaagt tttattccta gcaaaagtaa ctgtgagtat tgtcaatttc catttaagaa   14040
gttaatggtt actaaagcat ctccagatcc atcagttaag acagaagtac caatcaaagt   14100
tgacggtgag gtatttaatt attgtcctca ttgtggacgg aatttacaag ggtgaggcaa   14160
tgttactttt aattgtatta atgatgattg tctttattgc tgggttccta ttgggtaaga   14220
aaaatccatg acgaaaaaag gacccaccgt aaaagatgtg tcctcactaa aaatatttaa   14280
ccataattat tatatcagat agcgagggta cgtcatgcaa acaagtttga atttagatat   14340
tgattgtctg aaaactgcaa gaaaggttac tgactttctt gataagaagc tggatcgcta   14400
tctggcttta tcggggaagc aacgtttga tttgaagtca ccagggatgg acggaatgcc   14460
taaagctccc agccatggta acggtagtga aaatcgaatg ctgaatatct ggttggcaga   14520
agaggttgtt gattgtgtgg gttgcgctat gcggaatatg acaaaggaat cacaacggat   14580
tttactaaat cggtattcgg atcagatgtt aacgtataac attgctaggg agctaagtat   14640
tagttcagca acgtatagtc gaaagcagga aaaagcgctg tgtgagtttg cggaccggtt   14700
tgaatttcag ttagttaagc acggtattca tactgaaatt gatgatctac acgtttatct   14760
tgacgaggaa gattgataaa ttgatgatag attattgagc gagcaattca tgatagaaat   14820
gtgataatag tattgtcgaa tgattcgata ttcatataat aatcttccca aatgaagtct   14880
agctattatg gctaggcttt tgtattatgt ttaattgggt gatttttata tgattgaata   14940
cttaaaaaca ttttttggagg ctttgagtat gaagccaaaa actaaatttg ttggagttat   15000
ttttggaata gtacttttat gcttaaaacc attttttaatt caatataata tgaaatggtt   15060
ttacaataag ttttcttgga ttattatttt aattacttta ttttttgtag cctcattaat   15120
aattgaagta atagttgaag tatacgaatg gggtagaaac aagtataaca aacataaagt   15180
tgaaagagat tacgaaaaat atatcttagg cttgtctgat aaaaagttgg caattgtaaa   15240
gaaactttac gctaatgaac atcaccaagg atatttaaga caaaacgata ctaatgttat   15300
tgaattggtt aatatgtacg taattatgca acttaataat gaaattatag taagagaaag   15360
ccaagttgaa gatataaacg atcctgaatt tcttttttgta ttacagccac cggctttaca   15420
catcatagaa aagaattcag aaaaatttaa ataaatttaa ttagtttagc ttaacggctg   15480 acttttttact ttttaggagg tgagtagcat tactcaaaaa ttaacacaga agcaacaacg   15540
atttgtcgat gagtacatta tttcgggtaa tgctactcag gcggcaatta aagctggata   15600
ttctaagaag acagctaagc agtctggtgc tgaaaaccta gcaaaacctt acttaaaagc   15660
tgcaatcgaa aaacgcaatg ctgaaattca atccgagaaa acagctgata tgacagaggt   15720
gatggaatat cttacttcag ttatgcgtgg tgagcaaaca gaatcggttg ctactgctaa   15780
gggtatttat gaagacgttg aagtgtcggc aaaaagatcgt attaaagctg ctgaattaat   15840
tggaaagcgt cacggcgcct ggactgataa aaaggttatt tctggtgatg ttcagattga   15900
tgtgggaatg ggggattatg atgatgaaga gtgaagaaca atggagaaaa atcaaagatc   15960
atcctcatta cttggttagc aataaaggta atgtttacag tgagtataaa ggcggcttgc   16020
ttaaacagat gaaagatgct tatggatatt ctcaggttaa tttaaaccgc cgctccaaaa   16080
aggtgcatcg tttagtagcg gaagctttta tcccaaaccc agacaaattg cctgaagtta   16140
```

-continued

```
atcataaaga cgaagataaa aataataacc aggtggataa cttggaatgg tgtactagca   16200
agtacaacat gaattatggt gacgtggaga aaaggtcaat tctttcacaa caaagccata   16260
gtacttggaa aatttatcaa tatgatttaa acggtaattt ggtaaaagta tggaattcag   16320
cgagagaagc cgacagacat ggattcaacc gtagaagtgt gtatcgctgt tgtgatgggg   16380
aaataaaatc tttcaaagga tacatatggt caagacaaaa gaaggtgata ccatgccaaa   16440
catcaaacta aattttccta aaccatacaa cgttttcaat aaacaaattt ttgataactt   16500
gtttgattac agtcatttcg ttgaggtttg gtactgactt atggcggtgc atcttctggt   16560
aaatcgcatg gtgtggtaca gaaagttgta cttaaatcac tccaacactg gaaacatccc   16620
cgcaaagtgc tatggctgcg gaaagttgat cgaacaattc aagaatctat cttcgctgac   16680
gtaattgact gtttatcaaa ttggcaattg ttatcgttat gtagagtaaa taaatcaaac   16740
cgtactgttc atttaccgaa cggtgcggtt ttcctgttta agggtatgga tgacccagaa   16800
aagattaagt caatcaaagg gttatctgat gtggtaatgg aagaagcttc cgaatttaca   16860
caggacgact tcacgcagct taccctacgt ctccgtgaac ctaagcataa gaaacgacaa   16920 ttgtttgta tgtttaatcc agttagcaaa ttgaactgga cttataagca atggtttgat   16980
ccgaaagtga aagttaatcc ggaacgagta tcaattcacc aatcaactta caaggataat   17040 cacttttgg acgctgataa cattgcaacg attgagaact aaaaacaaac caacccggcc   17100
tactataaaa tctatacgct gggcgagttt gctacattgg ataagctggt ctttccagag   17160
tttgaaaaac gtcggttaag tattcgaacc ttatcacagc ttccctcgta cttcggcttg   17220
gactttgggt acactaacga tgaaacagcc tttatgcacg ttaaagtgga tgagagtacc   17280
cgtaaaattt acgtgatgga agagtacgct aagcacggta tgttgaacga tgatattgcc   17340
cgaataatta aacaaatggg ttatagcaag gaagttatta ctgctgatgc tgctgagcct   17400
aaatcgattg ctgaaattaa acgcgatggt atctcgcgga ttcgtccagc taaaaagggg   17460
aaggacagca ttatacaggg actttcattt atgcagcaat atcacttagt cgttgatgac   17520
cggtgtgtga aaacgattga ggaattggaa aattatacat acaagaagga caaacaaact   17580
ggtgaataca ccaatgagcc tgtcgatagt tacaaccacg aaatcgatgc tatcaggtat   17640
gctttatctg aaatcaacgg aatggctagt ccaaaggcaa ctgtaatgaa aaatatttat   17700
atttaggtgg tgattgaatg gaaacagtaa acggtaaagg acaaattta gatggccata   17760 tttttatcta tccagctgat gaagaagaac ttgatccgca tgatttactg tcgttcatga   17820
gaagaaatat tcagtatgct aaggattaca agcataatat gcaaatgtat ctaggtaatc   17880
acgatatctt agatcaacag cggcggatgt atgggccaga taatcggcta gtagcaaatt   17940
taccgcatta tattgttgat acttataatg gattctttac tggaatccca cctaagatta   18000
ctttagatga taagaatgag aacgaagcat tacagcaatg gaatgacact aattcgttcc   18060
aggacaaatt gagtgaaatt agtaagcaaa cggatatcta cggacgttcg tttgctttta   18120
tttatcaaga tgagaacgca gacacttgta ttgcttatgc ttctcctaca gatgccttca   18180
tggtttacga tgtacggtt gctagaaaac cttttgcttt tgttcgttac tggaaagata   18240
ctgaaagcgg attatggacc ggaatggttt attacgctaa taaaattaaa acctttaaag   18300
gtagtgttgt tgaagattca gatcaaaata atatgtataa tttagtgcca gcagttgaat   18360
tttatggaaa tgaagagcgg caaggtgttt ttgataatgt gaaaacctta atcgacgaat   18420
tagacagagt gttatcacag aaagctaacc aagtggaata ttttgataat gcttacctta   18480
```

```
aaattcttgg tcttgatta gatgaggatg gtgatggtag accggatgct aatttaattg    18540
gtaatcaaat gattttattcg cctaatgctg atgctgctaa tgccgatgtc gaattcattt    18600
caaaaccaga tggtgataat atgcaagaac atattattga ccggcttgtt tcaatgattt    18660
accaggtaag tatggttgct aaccttaatg atgaagcgtt tgctggtaat agttctgggg    18720
tggctttgca atataagtta cttccaatgc gaaatatggc agctaataaa gagcgtaaat    18780
ttactcaggc actccggaag ttatatcgaa tagtgtttag tgctgatcaa gtagtcaaag    18840
ataaggaagc ctggcaagac ttgctctttg atttcaaaca aaacttaccg attgatgttt    18900
ctgaagaagc tgatactta caaaaactat caggggttgt gtcaaaagaa actgcattcc    18960
gaaatagtcg tttaattgat gatcctaaaa aagaagttga gcgtatgcaa aaagagaagc    19020
aggaagaaat aaaccaagcg cttcaacatt ctgcttctgc tacagatcaa atgctaatgg    19080
atgatcaaaa agaaaatgat aaagagatag ttggtttccg gaagaacggt gaatccgatg    19140
acgaagaaga ataattattg ggctgatcgt attgctcggg aacgtaaatg gcaagaagag    19200
caattaagta aagatgctca atttaatcag cgccttcaac agtattatga tcaagcaatt    19260
gtccagatta ataaagacat tgaagatcag ataaaattctt tagctgtccg gaataaagtt    19320
tcttatgctg aagctcaaaa agaagtgtcc actaccgata ttgctgatta tgaaacagaa    19380
gctaagaagg tagttcagga agctaatcgt ttaagagcac aagggaagca tgttacttac    19440
aatgatttct ctgatgaagt taatgaacga ttgaggaatt ataatacggc gatgcgtatt    19500
aaccgattga atttattgaa atctaaaatt ggtttatcga tggttgaagc cggaatgaat    19560
attgatgctg atatgcaagc taaaattggt aaagattata ctgatgagct aaaacgtcag    19620
tctggtattc tagatcattc taccgaaaat agttcgtttt ggacttctaa agatgttgcg    19680
aaacaagtaa tgaagcaaat taatggagca acttttagtc aacgaatttg ggctaatcaa    19740
gatactttga aagctcaact tgatacggtt atcaccaacg gaattttaac tggtaagaat    19800
ccgcgagttg tagcaagaca attaagagat aaagtaaaag tcactgttaa aaatcacagt    19860
tatgttactg aacgtattgc caggacagaa tcagcacggg ttcagtattc tgctcagatt    19920
gaattaatca aaaagaatgg ttatcaattt gtccactgga ttgcggagcc aagagcctgt    19980
gatgagtgtc gaaagattgc gacgcaagat aatggctttg gtgatggtat ttatcgaatt    20040
aataaagttc ctaaaatacc agacgatact catcctaatt gtcgctgttc aattagtgag    20100
acatgggtcg atggtcaacg caatatagca ttatctgatg atgaacaggc ggcattgaat    20160
aattatatta gttcagattc atataagatt aatgatgatt tgaggcgtaa taagatttct    20220
aaaaataaga aacaatttat tgaaaactta gatgccgcat tggctaaaat gccaatttat    20280
catagtagca agccactcca gcgtgattat ttctttgata acaagaagc attggatgat    20340 tttattagta attttgaaat tggtggagtc ttcactgatt catcatacat ttcaacttct    20400
aaaatttatt atggacaggg caaagagaca attcatgtta ttattaaatc aagtaagaca    20460
ggaagagata tctctgagtt taattttaat gagcaggaag tattattccc cagaaatagt    20520
aagtttagga ttgatgatgc atacgttgat gataacggga agatgacaat ggtttggagt    20580
gaattagatg agtaacaagc ctttttactga taaacgttgg cgagataatt ctttggaagg    20640
cgttaaattt gataattcaa aagtaacgtc agaacaaaag aagaagacag aagaattcca    20700
tgagttattc aaaaagacgt ttgctaaaca attaaaagaa aaacactcac ataaaaagta    20760
ggtgatccaa tgggaaataa tgatttcttt acggtaacgt acaaaatact aagttatctt    20820
aagtattgtt atgaaaatgg aattaatcct gatcctaata ttcttaatgc tgatacattt    20880
```

-continued

```
aatattagta aagttcaatt tggaagaact ctacaaatgt taagcgagca tggttatatt   20940
tcaggagtga gatttacaca agccaaaatc gaaggtactg ttgttggtgg actccacaat   21000
acgtcaataa cggttgaagg tctgcaatat ttagctgaaa actcaatgat gaaaaaagca   21060
tatcgaattt ttaaagaagt cagagattgg cttccgggtt tctaagcatt cacaaattag   21120
tgagtgcttt ttgttttgga ctttttactt gttgcagtcg ttaaagaaca acccggatat   21180
tacagtccac cggactataa acgaggtgta tttatgtttg aaaaattacc aatgcgttta   21240
caattctttg ctgaagatcc aacgccagat ccagataatg atggtgcacc tgaaggaact   21300
gatgatggag ataacggtaa aagtgaaaag acatttactc aagcagaatt aaacgatatt   21360
gtcaaagccc gagtcaatcg agccttgaag aataagcaag aggaaattga ccaggctaag   21420
agtgaagcta ctaaacttgc caagatgaat aaggatcaaa agcaagaata taagcttcaa   21480
caaactgaaa aacgtgccca agatgctgaa gcagaattgg cccgttataa aatgcgtgat   21540
acagcgaagc aacaattaat tgatggcggt tatgacaatc caactgatga agatatcgat   21600
ttaattgtta ctgataaagc agaaacaact aaagaacgtg gtgaagcatt tcttaaagct   21660
tataaccgaa ttaaagaaaa tgttcgtcaa gaactattaa agggaaagtc accacgaatt   21720
aatggtgctc ctgctactgc aatgactaaa gaacaaattg caaagatcaa ggatcccgtc   21780
aaacgggtcc aagccattcg ggataactta tcccaatatg aaaaataaaa ggaggaatat   21840
aaaatggctg aaactaattt aacgacaagt acagacctag ttgcacaatc tatcgacttt   21900
gtagaacaat tctctggagg aatccaaact ttattgaatg cattgggagt tattcgtatg   21960
cagccaatga ctactggttc acagattaag atttacaagt cagaagtaac taaggtcgat   22020
ggtaatgttg ctgaaggggga agttattccg ttaagtaagg ttactcgcaa gctagctaat   22080
actttgacat taggatttaa aaagtatcgt aaggtaacta ccattgaagc tattcagtca   22140
gctggtggtg ctacacctgc tatcgtggat actgataata agctacttcg agaaattcaa   22200
aaggatgtta agaaggactt atttaattac attaccaagt ctgatgcaaa caagactacc   22260
gcctctggtg acgattttca aaaggcaatg gcggcagctt taggacaact ttcagttaag   22320
tgggaagact acgacacaca aactgtcgcc tttgctaatc cgcttgatct atatgcatgg   22380
ttaggtaacc aaactcttac tgttcaatct gcctttggtt tgcaatacat tcagaatttc   22440
cttggctttg acactattat tctaagtgct gaagtaccac agggaacgat tgctacaaca   22500
gttgcagata atatcaatta cttctacgct ccaatttcat ccgttggtca gttatttaac   22560
atgacttctg atgaaactgg tttaattggt gtaactcatg atgcagttaa taacaatttg   22620
tcatacgaaa ctgttgtaac aatggctaat gtattgacta cagaacgttt ggacggcatt   22680
gtattgtcaa caatcagtgg tgctaagtct gctggtaagt aggtgattga atggaccaga   22740
atacggtttt gcaaaactta aaagtaatgc ttgaaattaa aaatgatgac cgtgatgctt   22800
tgctgaaact aatcattgat aatacagacc aagcattgcg atttaagcta gaactaactg   22860
aagacgaaaa tttacctgga gaactaggtt atattgaatt agaagtttca gttcgacgat   22920
tcaatcgact gcaaaacgaa gggatgagtc aatatagtca agaaggggaa agtattactt   22980
ttaattcttc agattttgat gatttccttg atgatattga tttgtggaaa cgacgacacc   23040
agaaagatgt taaatctttta ggtgccgttt cttttattaa tccttatgcg gggatgagta   23100
aaaatgcgaa aaacacagat aattaagttt tattttcaag atgaaaatgg ctataatcca   23160
tatgcagaag aagacacgat tactagtcct aagctagtag cacaacggta tgccaatgtt   23220
```

-continued

```
actgatgtag ggacaaatcg cctagttgaa ttatttagca ggctagatca gaacgccaag    23280
gtaattcgat tggagtctcc agtaaatgac tcttggtcat atctgactat tgatgattgt    23340
cctatcaagt atcgtcttga aacctgtcgg aaaccattaa aaggcacaac gctgattgta    23400
ggtgaagcca gtggctaatt cttttaaggt tgatgttaaa ggtactaaag aactagcgaa    23460
tttcttaaag aagaataaag atttgactcc agttaaacgg atagtcgcaa aacatggagc    23520
aggtctcaaa aagcaaacgc agcaaaatat gaacaatttg tataagggcc actacgaatg    23580
gaagaagggg gctgggctaa caatggttag ccctaccggg aatactagac ggtccgtaac    23640
aaatacaatt tctaataatg gtttaacagc aacggttgct ccacaaactg aatatttccc    23700
atatcttgaa tatggaactc gctttatggc agcacgaccg acattacatc cagcgtttgc    23760
aattgagtct atgaaatttg ctaatgattt gaataagtta tttaagtagg tgagaaaatg    23820
tcaccaagta ttgaaattta tgatgcagtt tttgctcagg tccaaaagca ttatcagacc    23880
tacgatcacc caccgcagtt aaatgaacca gttacctatc cattcgtggt tgttgatgat    23940
agccagtcga ttttgacgaa ctataaaaca gccacaggaa tgcgggtaac tttaatagtc    24000
catgtgtggg ggaagtctaa ccaacgtaag actgttacta agatggttga tgaaattagt    24060
cgtctgggga tgcaagcagt tcggacgaaa cattatgctt ggcaaggacg acctaatgag    24120
caagaacaac aattattaac tgatacgagt gttccgaata ctgtgttaaa gcacggttat    24180
ttaacactcg tttttgattt gaaataaagg aggataaata tggcaacata tccagtattg    24240
gaagggaaga atgcagttct ttttgaacga ctattagaaa atgcaaggaa agagccggca    24300
caattgatcc cgtatcaaac atcactaagt tatgatccta aacgggatac tgattcaaca    24360
actacgaaga tggggaatgt tcctactgct tctaatattg aaacagattt agaagtagag    24420
ttcctaaatg caatttccaa agctgcagat gatgtttatg attctttgta ctttaataag    24480
aagattgaag tatggaaggt tcatattgat cgagtccggt cagatggcaa agtttatgcc    24540
gaatatatgc aaggaattgt gtcagaagac tctaatgata acgacccaga cgatcattca    24600
actcgggatg tgacctttac gattgatggc gtggccaaac gtgggtgggt cactctaccg    24660
ccagaaatca aggaagaaat tgactatgta ttccgtggct tggcacagct taaaggcgat    24720
gacgacaacg gtgaaggtga agcttttgct gatggcgatc gtggtgctgg tgcaaatgaa    24780
gcagtaacaa ctgaatagga ggaagattat gaagttaaaa attaatggtc aagaccaatc    24840
atttgtattc ggagttaagt ttttgcgaaa acttgatgct tatcggggcg ctgaacaaga    24900
aatccaagga gttaaggtta agctaggaat ggggctagcc atgatgcttc cccaattaat    24960
gactaaggat gcggccgctt tggcagacgt gttgtactgt gcggctaagt ctagcattaa    25020
gttagataca attgatgatt atattgataa ttgcaaggac ttggattcat tatttaatcg    25080
ggtaatgaat gaaattaagg caagtaatgc cgctaagccg attgcaaaaa atctaaaagc    25140
ctagatggtc ctgagcttag ttcagaacaa agctatcacg aaattctttt gaattcgttg    25200
gcttatctag gctttcataa tatttcagaa attgaagaaa tgggattggc tgaatatcag    25260
ctccggatgg aagcctataa cctccaacgg gttagccagg aacgagactt agcattgcaa    25320
gctttcctta atcagtcggt acaagcgacg aaagggagcg aaaagcaccc aattccgaag    25380
tataagaagt ttagccaatt tttttgattat gataaatttg ttgatgatgt tcgtgggcac    25440
tatgagcctg actatcagcc aacaagcaag gccagccttg aaaagaaacg aaatgatcta    25500
atcgtcaagc ggtggcgtga attccggaag atgaaacaaa aacagagagg aggtaatggc    25560
tagtgtcaca atcaatgaga gttgaagcgg tattatcagc atacgatgag agttttagcg    25620
```

```
caaccttaga taaggcgctt aaatcgatta ataatttagg ccgtgaaacc cagtcaacct   25680
ctcaaactgt tagtgcaggt ggttctagta tttccagtac cttttaaatcg atggctggag   25740 caatgggtgt agttgcgatt gctggtaaag catgggacgt tgttaaagat tcaatgagtg   25800
gcgccattaa ccggtttgat acattaaaca agtatccggt agtaatgaag gctttgaatt   25860
attcaactaa ggatgttgca aagtcaaccg ctatcttatc taagggaatt gatggattac   25920
ctacttcttt gcaagacgtt acaagtgttg cccaacaatt agcgccatta actggtagtg   25980
caactaaggc ttctaagtcg gcgattgcct tgaataatgc cttccttgcc tccggtgcta   26040
gtgttgccga tacctctcgt ggacttcaac aatacacaca aatgctttca actggtaaag   26100
tcgatttaat gtcttatcga acattgatgg aaaccatgcc aattgcatta cgtaaagtcg   26160
ccaattcatt tggttttact ggtaagtctg ctgaacaaga cctttataaa gctttgcagt   26220
caggacaaat tacggtagat cagttgaatg atcgtttttat caagctgaat ggtggagtta   26280
atggttttgc tcaattagca aagaaaaata gtgaaggtat cggtacatct tttgcaaact   26340
taaaaaatgc cgttgtcaaa aatctggcaa atatgttatc ggcaattgac aatggtttta   26400
agcaagcggg ctttggaagt attgcacaag tcctagacaa catgaagggt agtattaatt   26460
ctgcttttca agttattgga ccagttgtta ctaatgctac tgttgtagtt cttaattttg   26520
caaaggttat aggcggagcg cttaaatctg ctttcagtaa tgatattttt aaaacagcag   26580
ttgtgggaat attaggcttt gtgggtgcag ttatggcagc ccataaggtt atttcaatat   26640
ttacaacatt aagatctgca atagttggtt taagtgtgat tacaaaagct ggtaatttgg   26700
caatggcgtt tagtgaagca atgtcaacac ttgctaaaac ttctaagatt gctggtggag   26760
cgatgaaagc attcagtgcg gtggcctcat taggtccctg gggaattatt gctgttgcaa   26820
ttgcagctgt ggttgcagcc ttaacttatt tctttaccca aacgaaaacc ggtagggctt   26880
tatggcaaag ttttactacg tggttatctg gagtatggca gagtttggtt ggagtggcta   26940
ctactgtttg gaatgcaatt ggtaatgcta ttaatgcagt agttaatttt attaaacctt   27000
attggcaagg attattaaca ttctttaccg gaatctggac atcaattgtg gcgggtgttg   27060
ctccaatttg gcaagggtta gttaatgtct ttaatagcat tatcagtgca attttagccg   27120
tttggcaggc tttagctcca attattgttc cgattgtagc tggtgtagtt gctatcattg   27180
gggcaaccct aattacgatt gttaccgtct ttcaaactgt gtgtaatatg cttgtaccca   27240
ttgttcaagt tgtatggcaa ttaatttcaa cagttgtatc tactgctatt acgatgctag   27300
gtacaataat ccaaacaggc ttggcaatta tcgttgctat ttggaatgtg gtctggaata   27360
cattcagtat tgttgtaagt acggtatgga acgttattac tactattata tctaccgtgc   27420
tgaacgttat tgcgggaata attcaagcta tcactgctgc aatacaaggc gattggtcag   27480
gagcttggaa tgcaattcag aatgttgtat caactgtttg gaatgcaatt gccagtatta   27540
cttctagtgt attgaatgga ataaaaggaa tctttgatgg tgtaatgaat ggtttaaaga   27600
gtattacttc tagtagttgg aatggtatta aatcgctatt cagtgaaggt gttaatttca   27660
ttaaatcagt tgttcatata gatttaggtg ctgctggtag agctatcatg aattcacttt   27720
ggaatggaat gaaatccatt tggaatagta ttaagaattg ggttagcggt attgctgatt   27780
ggattaaaga acataaagga ccaatcagtt atgaccgtaa gttacttatt ccagctgggc   27840
aagcaattat gaatggtctt aataacggat tgattaatgg attcagtgaa gttcaatcaa   27900
acgttagtga tatggctaat caaattcagc aagctattac taatccaggc tttgatattg   27960
```

-continued

```
gagcaagtat tggtaacttg ggttcaatta attcaaatta tactggtagc ctggcaattc   28020
aagatagtca gttacaaatg cagaataatg ctttgcttcg tcaattactt aataaagaca   28080
cgacaatggt tcttgacgat ggcactcttg ttggctatac agcggatcaa tacgattatc   28140
gcttgggtca aaatacagca ttgaaggata ggtggagccg atgaaattct aaataatga   28200 ctattctttt cgtggattag acccacaaa ggatgatcca gaatacttag aaaatgcaga   28260
atatatcgac tttgccggtt ttaattcttc tgattatgat tggtggttga ttgatcgaac   28320
agcaactacg ccagaagaac aagaaattac agaaagcgtc ccttacatgc aaggagaata   28380
tgatttctca atgtatgatc aggaacgttt ttttaagacc cgtgagttga cttataagtt   28440
tgtatatttt ggtgaagttt atcaggatcg taaagcttac gaagaggagc ttaaacggca   28500
attactgcca catggtttca ctaaactaat tgattctcat gatcctgttt actactggtc   28560
agctaagtgt actagtgttg aggttgagga tgaccaagaa aagggaatgc tcacagcaac   28620
tattactttc aaggcttatc cttttgctta tactaatcat aacgagggca ccgattattg   28680
ggatgatgtc gcatttgatc attggatttg gcaaccagtt aaattcaatg ttaacggtga   28740
tcaggatgtt aatgttaaga atatcggctc acgaccagtc gaatgctcat ttcaattgac   28800
agggtccata actttgaaga acgattcaat tggtgaagta ggtttaactc aagacaattt   28860
taaaacaacc acgattgtat tagagatggg tgacaataaa atgcatctat ccggaaacgg   28920
gacaattgaa tttcaattta agcgtgagga gatgatttag tgtaccgaat tattggttat   28980
aatgaaccaa cagataaagc aggatttatt gtactggatc cccgagttaa tcgtcatatt   29040
agttcgggaa aactcacgct taaagaatct aatattgatg atttgactat tacggttaat   29100
caagcaagtc cattatggga caacgtaagg ccttatcata ctcatgttaa cgtttatgat   29160
gataatgaac ttatttttcg tggacgagct atcaaaccta aaaagtcgat ggaagaaagc   29220
ggacaattca ttcgtgaata tgtttttgaa gatattgaag catatctcat ggatagcacc   29280
caaagatttt atgaaggtgt tggtcaaacg cccaaagaat ttttacaaac tttaatcgat   29340
gttcataatt cacaggttcc tgactataaa aagtttcaag tccggaatgt aaatgtcact   29400
aataataagg atgaccaata tcgacaaatt gattatccca aaactagcga tgctattaat   29460
gataaattag ttaaatctct tggtggttat attgtgacta cttacaacgc taacggaata   29520
aactacattg actacttaac ggatattggg gttgatcata aagatgatac tcctattcag   29580
ttagctaaaa atatgaagtc tgcaagtatg caaattgatc ctactaaggt gattacaaga   29640
ctgattccac tgggaaagac actagaacca tcaaaagttg atgtaagtga tgatgatgga   29700
gagggcggtt ctggatcatt agatagccct gaagaatttt gtaaatcaga aattaatgct   29760
acttggggta gtgatattaa taatatgaaa caagattttg ccgctcgttc ttcgagagtt   29820
cgggcttggg gagtggacgt taatcgttta tatgatgtgg tgaaaaatgc tggagtaagt   29880
cctgaatggt tctttgctta tgaacttcaa gaacaaggaa cttactatgg atggcttaac   29940
catacttatc gacacggtga tgcgtatagt gatgcgcaat ctgtttgtga gtggattaaa   30000
aattgttcaa atagtaattc cattaatcca gcatggagcg caccggaagg atcaatggcg   30060
ccgaatcaag cattagcgga taaatggaat caagagtttg gaaaaggtac tattggccgc   30120
gtttatttac aagggactgc cgctgctgtt tgggatttag ctggtcaaac gcctaatcca   30180
gctattggaa agccaattag tggatgcatt tcttgtatta aacgttgggg tggtcattct   30240
aatgcagctg gtggtacatg gggatggcct tttcctgatg ttggggaagg tcattttttct   30300 caagttcaga gtttcggaaa tgatggcgga tatcgtcaaa atagttatca cgatggtgtg   30360
```

```
gattttggat caatagatca tcctggtaga gaagtgcatt gtattcatgg tggaacggta   30420
actatcaaat cagctatggg tggcttaggt aattttgtgg ttattcatac gccggaagga   30480
ttcaatatcg tttatcaaga agcttttagt tctccctcta atattattgt tagtgttggg   30540
caaaaagtaa aaactggtga tgtaattgga tatcgtgata cagaccatgt tcatattggc   30600
gtaactaagc aagattttta tcaagcagtt cgaaattctt tttctcctgc aggtggttgg   30660
ctagatccag taaaactaat taaagaaggt ggcgatgggt ctaaaccaca agaaggaaag   30720
aaagatcaaa ctgttgataa tagtaatgct gcacgtccta aattaaccat tactactgtc   30780
aataacggta gagactatat tgatattcct gatttacaaa aagaattcgg tattattgag   30840
ggaactgttg aatttgataa tgtagatgat ccgaatgttt taatgcaaca agctcaaaca   30900
tggataaagg ctcaaagaat acctcaaagt tgggaagtta cagctttaga attacatatg   30960
acaaacttca aatcttttaa ggttgctgat aggtacatgt ttattaatcc aaatgttgca   31020
aaaccccaat tattacgaat tactcaaaaa gaaattgatt tactaaagcc ccatgcgtct   31080
tcattaacga ttggtgataa gacgatgggg cttactgatt atcagttaga aaatcaagtc   31140
aattttcaac aatttaagga aattcgagtg atggttaatc aggttgtcca aacccaagag   31200
caatctgcta ataacaataa taaggttatg caaaattttg ctagtagtgc tgatcttgca   31260
caaatgagac aggatctaag aaatcttcaa gatgataacg atcgtgctcg caaaggaatg   31320
gtttccttag aagaattcaa taaactaaag gaacaagtag aaaaactaac aacaggaggc   31380
gatgataatg gcaagtgaaa cctatgatta tgagtcattt gataatacgg atcatactat   31440
gaaacaaatc gctgacgcta ttcgtcacaa gggttatgga aaagatgtgc gtgaggcaat   31500
tgcacagggc ttcgaaaact tagataaaca tttaagtagt attgaagaag aactgaaaca   31560
acaagaaaag aaaaagtcat cgtctatgga tgatattttt aattcttttg gtaagaagga   31620
gtgatgataa atggcaaaag agattagtaa tctgattacc tttaacacct acaaatttga   31680
acgaggcggc cttttggttg atatgtttaa ccaatttaat gctcgtgtag gagatcaagg   31740
aacggaatta gccatccagt gggaaactag taagactgaa actaaaatta atttaaaaga   31800
acgaggatta catttctttg ggacaggttc agttggacag taccttgaaa aattagaaga   31860
tggaactggc tttaagatgt ctgcagatgc atctaccgtt gaatgggaag ataaagatga   31920
agctggtagt ttagacgatg gaattacggt tgttaagttg ccaaaacaat ttttccctca   31980
aaaaggtatt ttctttggtt actttggcct aaaagataga caaggtaata tctttactag   32040
tgttaatgtt tggttccgtg ttcttggcgg tgttccaacg atgggggctg ctattcctta   32100
ctttgttact gaatttgatg aagtattaga gcgatgcaat ggtaagatta ttgacgcttt   32160
agcagaatta cgtgaaaagt accaggcaga agttaagaag aatgaggata tgtctgcgga   32220
aacaagagca gcgttgagta aacttgctga tgctgttggt gcaattcaag cgcagattga   32280
tgcaggtaat gtaattacac gtaaagaata taataatctt gctaatcaga ttgataatcg   32340
ccttagtaaa atgacacaga acattgagag tttttcatca ctcgatgact aaaaagctca   32400
atatcctaat ggaaaagatg gactctttgt tactaatgac aataatcata agtatcaata   32460
caagaatgga tcatgggtag atgaaggtat atggacagtt actacctttg atccagaaac   32520
gcgacgacgc cttacatacc ttgatacatc taattctatt ttgcaaaaat cactcagtga   32580
attgactaaa gaagtcgttg atataaattg gtttttaggc gaaattgatg caaatactgg   32640
taaaattaca cctcacgaaa gttttaatcg tgcatactca tcactcaaag taattggtaa   32700
```

-continued

```
atcacatgct tttgaatttt tgcttaatac tgattatttg caatatatta gtatttttga   32760
attcaattca aatggggaga ttattaagca cgatagtgtt ggcgataaag cgatatatac   32820
atttgaaaag gatacgactg cggtaaggtt tcagattact agtactgctg ctactatgaa   32880
gcaaaatgat ttacgcgata ctattcaaaa tagtgggcta aaaattatcg atcgaggaca   32940
ccgttcagta attaatgata ttgatcattt atatatccgt gaacatttaa tgccgattga   33000
agcaattgaa ggctatacaa ttaacactaa tgttgattat ggtgaaactg ttgatgtatc   33060
acatccaata gtaacgtctg cgtttcaata tattaatcaa gtatgtaagc cgggcgatat   33120
tttcgtaatt aataatctat ctggaggctt taacgcaatg gcttgggcct ttattgatag   33180
cgagaaccgg ttaattcaaa aatctgaagt aaacttatct caatctcagg ttactttata   33240
tgcgccaagt aatgctgcaa aattaattat caataaatatg gatagtaact gtacagcata   33300
tagatatact ccggataaag aacatttagc taaaattaat attgctttaa ctaccaatat   33360
tcatcgaaat atcaagttag cttatcaaac aggagaaaca gtctcattaa ttcctgaaaa   33420
agtaagtaat tacaaatata ttatattaga ttgtaatttt aatgatgctt tcagaataaa   33480
gggttatggt ggattgaatc cacgattata tggatttatt tctgagcaaa acacattaat   33540
gaatgttgcg cctgcaaatg ttaatgatca attaactgat gtctttatca aaacgccaaa   33600
aggcgccaaa aaattagtag ttaatttcaa tcttgatcaa caagtaaatc ccaaacaaat   33660
tgctgaactt tataagcttc cagacattaa tgttattact gagcaaaaaa taaaaaagaa   33720
tttattgaat caacaaacag tcgatacatt aatttctagt tatatgaatg gtatattact   33780
tggtaaagat ttagccaatc atcttgcgga ttttgctaaa agcggcgata aaatggttca   33840
tgtatcaacg ttttataaag ttaacgatac tcttttttatg tcttattatg ctaatacaag   33900
atcggcttac gaagatccaa cccagcatac agcacgatta gtttatgcac cgtttgagaa   33960
tctaaatcaa caaacgtaca tcgatgtagc cgacattgga caagaatata atggtcaaaa   34020
gattgaagca atatacgatt ctttgcttct taaaacaagt gatgattcat atatgatcta   34080
tgcctttact gctaaggtag gtggtaagtt ctatatgctt taccgtcgtt ttgatcctaa   34140
gactaagctg ttgagcgata ttcatacaat gaatttttaaa gttggagtaa tgacgtcgac   34200
atttgataca gtaagcgttc atgatttgtt agctaaggca ggaattgact atgattatga   34260
agatcgtgat atttcctttg tccaaaaatt aagtccacgg attgaagatg gcgtagtgca   34320
atactatgca ggtatcggaa tcttacattt ttgctttgta gtaaaatcaa gcgacttaat   34380
caactggact tttgtcagta ctccagactt tatgtacaag ccagaatttg aaccttctgt   34440
atatgttaag ggagacaatg tttattattt ttgtcgtcag cgagggacag aaggtaatgc   34500
agttttagct aagtataata tccctaatgg tcaatggtcg aatccgattc ttgtaccaga   34560
tactcaatca cgctatgact tttttcgagaa taatagtcag ttgtaccttg ttcattcacc   34620
gctagaccgt aatcatatta gtttgatgca gattgatcag aatgttctgg aaaagagcta   34680
tgaagtagca acagcagtag tacaagattg cttctaccca tttactcaaa atattgatgg   34740
tcagatgtat atgagcttta cacaaagtag gcaacatatt tggctaaata aatttaatcc   34800
ccacagtctg ctagatagtg atgtagcaac tattttcagt aatttaattg agtagcaaaa   34860
catagtcgcc ttataaatac acaatacata gaaagttgca ttgcttaaat ggaaacttaa   34920
tgggcggctt atagactttt attatttaaa agagtatact ggaattattc tttttattgg   34980
gaggaaatat aaaagtgaca actaaagtga gagataaatc gcttgatatt atccggggga   35040
gcatccttct agttgtcttg ggtcatatat ctgggatacc ttttgagtta aaaaagtaca   35100
```

-continued

```
tatattctttt tcatatacca ctgttctttt ttgtttcggg atatttgttc aactttgcta    35160
aatacaggta tttttcttat aaagagttta taaaatataa agctaaaaaa tatatcctac    35220
cttatttcag aatggggttg atatgtttgc ttctatttgg catagtttat ccactatttg    35280
ctgaagggtt tagtaaacag tatatgcttc aatctacaaa atatgtttta ggtttactat    35340
actcgcgtgg aggtcctaat tatatggcct ggagttcgcc actttggttt ctaacagcct    35400
tatttattgc agagattatt tttttgtgg ttctaaaatt taattttaaa tatccattaa    35460
tagtgtttgg aatcttagct atattgagtt atatttactc gattacaatt aaaattccgt    35520
taccgtggaa tattgatgtt gcaatgtttg cagtgttatt catgtaccta ggctttatta    35580
cacacaaata taatttaact aagcacatta acttaccggt tttcttactt ttgattgtta    35640
tttttgtatt atctgtagct tacaataatg agattgacat gaatttaaga aactatggca    35700
atggattttt aacaattatt agtggaacaa taggtactgt tatatgcttg caaattgcgc    35760
gattgttaaa agagaataag atattagagt tttatggtaa aaacacatta tttatcatgg    35820
gctacacgta tgctgtgttt aattgtattt tggctttaag cagccatttt agtactgtaa    35880
agaatgttgt agcttcgttt ttgattcaaa ttataatttt aactttatta atagtactga    35940
agaatttatt caaacaaata aaaaagccca tttatgcata tactaggaaa attaacaatt    36000
aaaaaaacta atacgtccta ctcagggcgt ttttatttta ccttcaaagg agatgatcaa    36060
cattgcccta tcatttattt atgctgcacc aaatgcagac attagttgat gataaactaa    36120
tgtgggcttt tacaatcgtg atgattgtag atttaattac gggaatgatt aaaccgtatt    36180
atgcaaagaa aacaattaag aaaactaata gttcagttgg aatccctggg ataattaaac    36240
acacagtaat ttatttagtg gtagtaattg cttatccata tctttatacg attggagcaa    36300
gcacgatggc taccactttt ttaattgctt ggatttatca atatttaatt tcaattgtag    36360
aaaattggac agagatgggg tggtggttgc ctaaaccaat catggatttc tttgaagcca    36420
aattagctaa ggatcaagaa gattatgacc catctaagta caattttctt ggtaaatata    36480
aaggaggtaa aaagtaa                                                    36497
```

<210> SEQ ID NO 14
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 14

```
ttaaagtatt aaaatagatg taaaatttat tttttttcaaa agaaatttta attgtacact      60
gttggtattg aacggggtta aacaaaggta aattagcatt tctgcggatt aagataaata     120
gaaaaatgtt aaagaacacc ttaaaaagat taattttttta taattggacc gtatcaattt     180
gtaaaaaggt tgactttttg aaaaaaaagt ttatcattaa cattgtaaat ttaatgattt     240
acgttatgtt gttatagagc acaggacgta ttgatttata tagaaggagt gtttattaga     300
```

<210> SEQ ID NO 15
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 15

-continued

```
atgaatggac agatgtttta atcgctagaa tagaaggaaa gaaagtcgca acaaatacgg      60
tttctagtac gtggcaggaa cgactaggta agcagattga cgaattaata gaaaaacatt     120
agtcaaatac atttacaaat gaacagatag ttgatattat atttaagaat tcttcttcag     180
agcctaagat taaagctttc aattggcgaa aagaagttgt acaatatgta taaaggtatg     240
tcagtcaccg aatcagatga tctggcatta tacttgtaaa ttatcaggag gttttcatta     300

<210> SEQ ID NO 16
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 16
atctcacgtg cgatccatta cactaagggc gcgtcaacaa atattatact atcttaaata      60
agaatgaatt gcaagcatta tttgaaaatt ttaattaaaa taacgcttac atcagaaaaa     120
tgttgtgatt gaatagacaa ttttttttgaa gatggtatca taagtatcgt aggagttgta     180
ttattgctta gaccttacca ctgcgtcact tacaatggtt gagagttgcg atgctgatgt     240
aatgtgataa actaagcaag tacactaatt atgttttttc ctaaaggagg aatttgcagt     300

<210> SEQ ID NO 17
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 17
ttgtttaaga tatctttcaa agctgcggaa ttttccag cttttttagt tagttttgtt        60
ttcataagct ataattttaa ccgattccaa atttctttta aaagttttt tgatctagac     120 cattaattga taaacgctta ccaaagacta atcaacaagc catttagcgg tagtggtcca     180
ttttaacttt ctaagacatc ttctcagaaa acgtttcctt tgatagtgca gattgtgctt     240
taagagtata taattgtcac ggtataagaa ttttctgaaa tttcagaagg agtgaacatt     300

<210> SEQ ID NO 18
<211> LENGTH: 449
<212> TYPE: DNA
<213> ORGANISM: Artificial Sequence
<220> FEATURE:
<223> OTHER INFORMATION: Based on Lactobacillus reuteri sequence

<400> SEQUENCE: 18
ctcctctatt attattcctg atcaatttta aattaatctc cctagatagg tatattttag        60
cacaggtcac caacgttcca aagtttaatc tatgtttaaa ctttaatttt caaaaaaatg     120
ctatactatg ttcacgatac tttaaggaaa ggtgattaca atagtgagtc tcttaattgc     180
tattcttatc tgctggttgc tatggaagat tgggggttta acggttaagt tcattggtct     240
aatccttctt attctattaa tcgggacatt aattcatgtt ttactttggc cagcgatcct     300
tttagcagtt attatcttag gagcaggttt attcactaac taatttatct ataaaatctt     360
atagtaattt ttctgcggaa tgttataatc attactgtga gagaaatctc aaataatgta     420
tacataagat gaaagggaga ctgtttatt                                      449

<210> SEQ ID NO 19
<211> LENGTH: 250
```

```
<212> TYPE: DNA
<213> ORGANISM: Artificial Sequence
<220> FEATURE:
<223> OTHER INFORMATION: Based on Lactobacillus reuteri sequence

<400> SEQUENCE: 19
acaaatacgg tttctagtac gtggcaggaa cgactaggta agcagattga cgaattaata      60
gaaaaacatt agtcaaatac atttacaaat gaacagatag ttgatattat atttaagaat     120
tcttcttcag agcctaagat taaagctttc aattggcgaa aagaagttgt acaatatgta     180
taaaggtatg tcagtcaccg aatcagatga tctggcatta tacttgtaaa ttatcaggag     240
gttttcatta                                                            250

<210> SEQ ID NO 20
<211> LENGTH: 3017
<212> TYPE: PRT
<213> ORGANISM: Artificial Sequence
<220> FEATURE:
<223> OTHER INFORMATION: Based on Lactobacillus reuteri sequence

<400> SEQUENCE: 20

Met Val Ser Lys Asn Asn His Gln Phe Tyr Gln Gln Lys His Ala Glu
1               5                   10                  15

Arg Lys Gln Arg Trp Gly Ile Arg Lys Leu Ser Val Gly Val Ala Ser
            20                  25                  30

Val Leu Leu Gly Thr Thr Phe Met Leu Tyr Gly Asn His Ala Val Leu
        35                  40                  45

Ala Asp Thr Val Thr Ser Pro Ser Asp Asp Val Thr Arg Ser Thr Thr
    50                  55                  60

Thr Gln Gly Gly Asn Lys Asp Lys Val Thr Glu Gly Thr Thr Glu Gly
65                  70                  75                  80

Thr Thr Ser Thr Pro Gln Thr Ser Gly Asp Ser Thr Asp Lys Gln Ala
                85                  90                  95

Asn Gly Gln Asn Val Asn Gln Gln Val Pro Thr Thr Asp Thr Glu Glu
            100                 105                 110

Ala Thr Asn His Gln Asp Thr Pro Gln Gly Gln Asp Thr Thr Gln Asn
        115                 120                 125

Thr Thr Asn Val Asp Lys Lys Asp Thr Glu Val Thr Pro Ala Asn Asp
    130                 135                 140

Ala Thr Thr Pro Thr Thr Gln Lys Ile Thr Ala Lys Phe Thr Thr Ala
145                 150                 155                 160

Lys Phe Thr Thr Ala Lys Phe Thr Ala Ala Lys Phe Lys Val Leu Ala
                165                 170                 175

Ala Arg Pro Val Met Lys Val Ala Gly Thr Ala Ser Leu Pro Ile Ser
            180                 185                 190

Asn Gln Asp Ile Lys Leu Asp Ser Gln Pro Met Leu Thr Glu Ile Ile
        195                 200                 205

Asn Lys Pro Thr Asp Asn Trp Val Tyr Asn Asn Leu Lys Trp Tyr Gln
    210                 215                 220

Asp Thr Ser Thr Glu Lys Ile Lys Glu Ile Leu Gln Asn His Thr Ala
225                 230                 235                 240

Asn Asp Glu Ser Gly Arg Tyr Tyr Phe Ala Gly Val Ala Asn Tyr Asn
                245                 250                 255

Glu His Tyr His Ala Ile Tyr Leu Leu Ala Arg Ser Asn Asn Leu Asn
            260                 265                 270

Asp Asn Ser Leu Tyr Val Thr Ile Leu His Thr Gly Leu Gly Lys Asn
```

-continued

```
              275                 280                 285
Ile Gln Glu Ala Val Val Ala Pro Gly Glu Ser Lys Lys Val Glu Tyr
    290                 295                 300

Ser Gly Thr Thr His Thr Pro Ile Phe Thr Asn Tyr Asp Gly Thr Ser
305                 310                 315                 320

Ala Ser Ile Asp Leu Asp Gly Ile Glu Lys Gly Asp Asn Ile Tyr Gly
                325                 330                 335

Met Val Val Gly Phe Ala Tyr Gly His Asn Thr Gly Ile Lys Gly Asp
                340                 345                 350

Pro Ala Ser Met Gly Asn Gly Phe Val Met Thr Pro Ile Pro Thr Lys
                355                 360                 365

Met Thr Thr Thr Ile His Tyr Ile Asp Gln Ala Thr Gly Asp Glu Ile
    370                 375                 380

Ala Val Pro Lys Ser Phe Glu Gly Val Ala Tyr Gln Lys Tyr Thr Ile
385                 390                 395                 400

Thr Gly Glu Ala Pro Thr Ile Asp Gly Tyr Thr Leu Lys Lys Ser Pro
                405                 410                 415

Glu Thr Thr Gly Tyr Ile Ser Pro Tyr Lys Val Gly Glu Ser Tyr Asp
                420                 425                 430

Phe Arg Leu Asp Lys His Val Val Ile Lys Gln Thr Val Ile Asp Ala
                435                 440                 445

Gln Gly Leu Val Arg Val Thr Ala Tyr Tyr Asp Gly Glu Val Leu Asn
    450                 455                 460

Asn Thr Thr Arg Tyr Leu Gly Asn Lys Leu Asn Val Asn Asp Arg Met
465                 470                 475                 480

Ser Phe Ile Ser His Gly Lys Trp Tyr Thr Tyr Ile Asn Gln Ile Thr
                485                 490                 495

Ser Thr Asn Asp Gly Ile Val Tyr Tyr Tyr Ala Lys Asp Gly Ser Glu
                500                 505                 510

Asp Lys Ser Glu Val Arg Val His Tyr Ile Asp Val Thr Gly Ser Lys
                515                 520                 525

Asn Ser Ile Phe Val Pro Gly Asp Gly Glu Glu Val Ala Thr Asp Lys
    530                 535                 540

Ile Ser Gly Lys Leu Gly Glu Asn Tyr Asn Tyr Asp Val Asn Leu Pro
545                 550                 555                 560

Thr Asp Tyr Asn Leu Ala Thr Asn Gln Ala Asn Thr Val Asn Gly Thr
                565                 570                 575

Tyr Thr Ile Asp His His Asp Glu Tyr Val Tyr Val Val Lys Lys Thr
                580                 585                 590

Ser Ala Glu Leu Asp Pro Thr Val Pro Ala Lys Thr Lys Val Asp Asn
    595                 600                 605

Pro Thr Ser Leu Thr Ala Asp Glu Lys Lys Thr Ile Glu Asp Lys Ile
    610                 615                 620

Val Glu Ala Asn Lys Asp Lys Phe Pro Glu Gly Thr Gly Val Thr Val
625                 630                 635                 640

Ala Asn Asp Gly Lys Ala Thr Ile Thr Tyr Pro Asp Lys Ser Val Asp
                645                 650                 655

Thr Ile Glu Gly Asn Gln Leu Val Glu Glu Lys Thr Ser Ala Glu Lys
                660                 665                 670

Leu Asp Pro Thr Val Pro Ala Lys Thr Lys Val Asp Asn Pro Thr Ser
                675                 680                 685

Leu Thr Ala Asp Glu Lys Lys Thr Ile Glu Asp Lys Ile Val Glu Ala
    690                 695                 700
```

-continued

```
Asn Lys Asp Lys Phe Pro Glu Gly Thr Gly Val Thr Val Ala Asn Asp
705                 710                 715                 720

Gly Lys Ala Thr Ile Thr Tyr Pro Asp Lys Ser Val Asp Thr Ile Glu
                725                 730                 735

Gly Asn Gln Leu Val Glu Glu Lys Thr Ser Ala Glu Lys Leu Asp Pro
            740                 745                 750

Thr Val Pro Ala Lys Thr Lys Val Asp Asn Pro Thr Ser Leu Thr Ala
        755                 760                 765

Asp Glu Lys Lys Thr Ile Glu Asp Lys Ile Val Glu Ala Asn Lys Asp
        770                 775                 780

Lys Phe Pro Glu Gly Thr Gly Val Thr Val Ala Asn Asp Gly Lys Ala
785                 790                 795                 800

Thr Ile Thr Tyr Pro Asp Lys Ser Val Asp Thr Ile Glu Gly Asn Gln
                805                 810                 815

Leu Val Glu Glu Lys Thr Ser Ala Glu Lys Leu Asp Pro Thr Val Pro
            820                 825                 830

Ala Lys Thr Lys Val Asp Asn Pro Thr Ser Leu Thr Ala Asp Glu Lys
            835                 840                 845

Lys Thr Ile Glu Asp Lys Ile Val Glu Ala Asn Lys Asp Lys Phe Pro
        850                 855                 860

Glu Gly Thr Gly Val Thr Val Ala Asn Asp Gly Lys Ala Thr Ile Thr
865                 870                 875                 880

Tyr Pro Asp Lys Ser Val Asp Thr Ile Glu Gly Asn Gln Leu Val Glu
                885                 890                 895

Glu Lys Thr Ser Ala Glu Lys Leu Asp Pro Thr Val Pro Ala Lys Thr
            900                 905                 910

Lys Val Asp Asn Pro Thr Ser Leu Thr Ala Asp Glu Lys Lys Thr Ile
            915                 920                 925

Glu Asp Lys Ile Val Glu Ala Asn Lys Asp Lys Phe Pro Glu Gly Thr
        930                 935                 940

Gly Val Thr Val Ala Asn Asp Gly Lys Ala Thr Ile Thr Tyr Pro Asp
945                 950                 955                 960

Lys Ser Val Asp Thr Ile Glu Gly Asn Gln Leu Val Glu Glu Lys Thr
                965                 970                 975

Ser Ala Glu Lys Leu Asp Pro Thr Val Pro Ala Lys Thr Lys Val Asp
            980                 985                 990

Asn Pro Thr Ser Leu Thr Ala Asp  Glu Lys Lys Thr Ile  Glu Asp Lys
            995                 1000                 1005

Ile Val  Glu Ala Asn Lys Asp  Lys Phe Pro Glu Gly  Thr Gly Val
    1010                 1015                 1020

Thr Val  Ala Asn Asp Gly Lys  Ala Thr Ile Thr Tyr  Pro Asp Lys
    1025                 1030                 1035

Ser Val  Asp Thr Ile Glu Gly  Asn Gln Leu Val Glu  Glu Lys Thr
    1040                 1045                 1050

Ser Ala  Glu Lys Leu Asp Pro  Thr Val Pro Ala Lys  Thr Lys Val
    1055                 1060                 1065

Asp Asn  Pro Thr Ser Leu Thr  Ala Asp Glu Lys Lys  Thr Ile Glu
    1070                 1075                 1080

Asp Lys  Ile Val Glu Ala Asn  Lys Asp Lys Phe Pro  Glu Gly Thr
    1085                 1090                 1095

Gly Val  Thr Val Ala Asn Asp  Gly Lys Ala Thr Ile  Thr Tyr Pro
    1100                 1105                 1110
```

-continued

```
Asp Lys Ser Val Asp Thr Ile Glu Gly Asn Gln Leu Val Glu Glu
    1115            1120            1125

Lys Thr Ser Ala Glu Lys Leu Asp Pro Thr Val Pro Ala Lys Thr
    1130            1135            1140

Lys Val Asp Asn Pro Thr Ser Leu Thr Ala Asp Glu Lys Lys Thr
    1145            1150            1155

Ile Glu Asp Lys Ile Val Glu Ala Asn Lys Asp Lys Phe Pro Glu
    1160            1165            1170

Gly Thr Gly Val Thr Val Ala Asn Asp Gly Lys Ala Thr Ile Thr
    1175            1180            1185

Tyr Pro Asp Lys Ser Val Asp Thr Ile Glu Gly Asn Gln Leu Val
    1190            1195            1200

Glu Glu Lys Thr Ser Ala Glu Lys Leu Asp Pro Thr Val Pro Ala
    1205            1210            1215

Lys Thr Lys Val Asp Asn Pro Thr Ser Leu Thr Ala Asp Glu Lys
    1220            1225            1230

Lys Thr Ile Glu Asp Lys Ile Val Glu Ala Asn Lys Asp Lys Phe
    1235            1240            1245

Pro Glu Gly Thr Gly Val Thr Val Ala Asn Asp Gly Lys Ala Thr
    1250            1255            1260

Ile Thr Tyr Pro Asp Lys Ser Val Asp Thr Ile Glu Gly Asn Gln
    1265            1270            1275

Leu Val Glu Glu Lys Thr Ser Ala Glu Lys Leu Asp Pro Thr Val
    1280            1285            1290

Pro Ala Lys Thr Lys Val Asp Asn Pro Thr Ser Leu Thr Ala Asp
    1295            1300            1305

Glu Lys Lys Thr Ile Glu Asp Lys Ile Val Glu Ala Asn Lys Asp
    1310            1315            1320

Lys Phe Pro Glu Gly Thr Gly Val Thr Val Ala Asn Asp Gly Lys
    1325            1330            1335

Ala Thr Ile Thr Tyr Pro Asp Lys Ser Val Asp Thr Ile Glu Gly
    1340            1345            1350

Asn Gln Leu Val Glu Glu Lys Thr Ser Ala Glu Lys Leu Asp Pro
    1355            1360            1365

Thr Val Pro Ala Lys Thr Lys Val Asp Asn Pro Thr Ser Leu Thr
    1370            1375            1380

Ala Asp Glu Lys Lys Thr Ile Glu Asp Lys Ile Val Glu Ala Asn
    1385            1390            1395

Lys Asp Lys Phe Pro Glu Gly Thr Gly Val Thr Val Ala Asn Asp
    1400            1405            1410

Gly Lys Ala Thr Ile Thr Tyr Pro Asp Lys Ser Val Asp Thr Ile
    1415            1420            1425

Glu Gly Asn Gln Leu Val Glu Glu Lys Thr Ser Ala Glu Lys Leu
    1430            1435            1440

Asp Pro Thr Val Pro Ala Lys Thr Lys Val Asp Asn Pro Thr Ser
    1445            1450            1455

Leu Thr Ala Asp Glu Lys Lys Thr Ile Glu Asp Lys Ile Val Glu
    1460            1465            1470

Ala Asn Lys Asp Lys Phe Pro Glu Gly Thr Gly Val Thr Val Ala
    1475            1480            1485

Asn Asp Gly Lys Ala Thr Ile Thr Tyr Pro Asp Lys Ser Val Asp
    1490            1495            1500

Thr Ile Glu Gly Asn Gln Leu Val Glu Glu Lys Thr Ser Ala Glu
```

```
        1505                1510                1515

Lys Leu  Asp Pro Thr Val Pro  Ala Lys Thr Lys Val  Asp Asn Pro
        1520                1525                1530

Thr Ser  Leu Thr Ala Asp Glu  Lys Lys Thr Ile Glu  Asp Lys Ile
        1535                1540                1545

Val Glu  Ala Asn Lys Asp Lys  Phe Pro Glu Gly Thr  Gly Val Thr
        1550                1555                1560

Val Ala  Asn Asp Gly Lys Ala  Thr Ile Thr Tyr Pro  Asp Lys Ser
        1565                1570                1575

Val Asp  Thr Ile Glu Gly Asn  Gln Leu Val Glu Glu  Lys Thr Ser
        1580                1585                1590

Ala Glu  Lys Leu Asp Pro Thr  Val Pro Ala Lys Thr  Lys Val Asp
        1595                1600                1605

Asn Pro  Thr Ser Leu Thr Ala  Asp Glu Lys Lys Thr  Ile Glu Asp
        1610                1615                1620

Lys Ile  Val Glu Ala Asn Lys  Asp Lys Phe Pro Glu  Gly Thr Gly
        1625                1630                1635

Val Thr  Val Ala Asn Asp Gly  Lys Ala Thr Ile Thr  Tyr Pro Asp
        1640                1645                1650

Lys Ser  Val Asp Thr Ile Glu  Gly Asn Gln Leu Val  Glu Glu Lys
        1655                1660                1665

Thr Ser  Ala Glu Lys Leu Asp  Pro Thr Val Pro Ala  Lys Thr Lys
        1670                1675                1680

Val Asp  Asn Pro Thr Ser Leu  Thr Ala Asp Glu Lys  Lys Thr Ile
        1685                1690                1695

Glu Asp  Lys Ile Val Glu Ala  Asn Lys Asp Lys Phe  Pro Glu Gly
        1700                1705                1710

Thr Gly  Val Thr Val Ala Asn  Asp Gly Lys Ala Thr  Ile Thr Tyr
        1715                1720                1725

Pro Asp  Lys Ser Val Asp Thr  Ile Glu Gly Asn Gln  Leu Val Glu
        1730                1735                1740

Glu Lys  Thr Ser Ala Glu Lys  Leu Asp Pro Thr Val  Pro Ala Lys
        1745                1750                1755

Thr Lys  Val Asp Asn Pro Thr  Ser Leu Thr Ala Asp  Glu Lys Lys
        1760                1765                1770

Thr Ile  Glu Asp Lys Ile Val  Glu Ala Asn Lys Asp  Lys Phe Pro
        1775                1780                1785

Glu Gly  Thr Gly Val Thr Val  Ala Asn Asp Gly Lys  Ala Thr Ile
        1790                1795                1800

Thr Tyr  Pro Asp Lys Ser Val  Asp Thr Ile Glu Gly  Asn Gln Leu
        1805                1810                1815

Val Glu  Glu Lys Thr Ser Ala  Glu Lys Leu Asp Pro  Thr Val Pro
        1820                1825                1830

Ala Lys  Thr Lys Val Asp Asn  Pro Thr Ser Leu Thr  Ala Asp Glu
        1835                1840                1845

Lys Lys  Thr Ile Glu Asp Lys  Ile Val Glu Ala Asn  Lys Asp Lys
        1850                1855                1860

Phe Pro  Glu Gly Thr Gly Val  Thr Val Ala Asn Asp  Gly Lys Ala
        1865                1870                1875

Thr Ile  Thr Tyr Pro Asp Lys  Ser Val Asp Thr Ile  Glu Gly Asn
        1880                1885                1890

Gln Leu  Val Glu Glu Lys Thr  Ser Ala Glu Lys Leu  Asp Pro Thr
        1895                1900                1905
```

-continued

```
Val Pro  Ala Lys Thr Lys Val  Asp Asn Pro Thr Ser  Leu Thr Ala
    1910             1915             1920

Asp Glu  Lys Lys Thr Ile Glu  Asp Lys Ile Val Glu  Ala Asn Lys
    1925             1930             1935

Asp Lys  Phe Pro Glu Gly Thr  Gly Val Thr Val Ala  Asn Asp Gly
    1940             1945             1950

Lys Ala  Thr Ile Thr Tyr Pro  Asp Lys Ser Val Asp  Thr Ile Glu
    1955             1960             1965

Gly Asn  Gln Leu Val Glu Glu  Lys Thr Ser Ala Glu  Lys Leu Asp
    1970             1975             1980

Pro Thr  Val Pro Ala Lys Thr  Lys Val Asp Asn Pro  Thr Ser Leu
    1985             1990             1995

Thr Ala  Asp Glu Lys Lys Thr  Ile Glu Asp Lys Ile  Val Glu Ala
    2000             2005             2010

Asn Lys  Asp Lys Phe Pro Glu  Gly Thr Gly Val Thr  Val Ala Asn
    2015             2020             2025

Asp Gly  Lys Ala Thr Ile Thr  Tyr Pro Asp Lys Ser  Val Asp Thr
    2030             2035             2040

Ile Glu  Gly Asn Gln Leu Val  Glu Glu Lys Thr Ser  Ala Glu Lys
    2045             2050             2055

Leu Asp  Pro Thr Val Pro Ala  Lys Thr Lys Val Asp  Asn Pro Thr
    2060             2065             2070

Ser Leu  Thr Ala Asp Glu Lys  Lys Thr Ile Glu Asp  Lys Ile Val
    2075             2080             2085

Glu Ala  Asn Lys Asp Lys Phe  Pro Glu Gly Thr Gly  Val Thr Val
    2090             2095             2100

Ala Asn  Asp Gly Lys Ala Thr  Ile Thr Tyr Pro Asp  Lys Ser Val
    2105             2110             2115

Asp Thr  Ile Glu Gly Asn Gln  Leu Val Glu Glu Lys  Thr Ser Ala
    2120             2125             2130

Glu Lys  Leu Asp Pro Thr Val  Pro Ala Lys Thr Lys  Val Asp Asn
    2135             2140             2145

Pro Thr  Ser Leu Thr Ala Asp  Glu Lys Lys Thr Ile  Glu Asp Lys
    2150             2155             2160

Ile Val  Glu Ala Asn Lys Asp  Lys Phe Pro Glu Gly  Thr Gly Val
    2165             2170             2175

Thr Val  Ala Asn Asp Gly Lys  Ala Thr Ile Thr Tyr  Pro Asp Lys
    2180             2185             2190

Ser Val  Asp Thr Ile Glu Gly  Asn Gln Leu Val Glu  Glu Lys Thr
    2195             2200             2205

Ser Ala  Glu Lys Leu Asp Pro  Thr Val Pro Ala Lys  Thr Lys Val
    2210             2215             2220

Asp Asp  Pro Thr Lys Leu Thr  Asn Asp Glu Lys Lys  Glu Val Glu
    2225             2230             2235

Asp Asn  Ile Arg Asp His Asn  Thr Gly Leu Pro Glu  Gly Thr Lys
    2240             2245             2250

Ile Ala  Val Gly Asp Asn Gly  Asp Thr Thr Ile Thr  Tyr Pro Asp
    2255             2260             2265

Lys Ser  Val Asp Thr Ile Glu  Gly Asn Gln Leu Val  Glu Glu Lys
    2270             2275             2280

Thr Ser  Ala Glu Lys Leu Asp  Pro Thr Val Pro Ala  Lys Thr Lys
    2285             2290             2295
```

-continued

```
Val Asp  Asp Pro Thr Lys Leu  Thr Asn Asp Glu Lys  Lys Glu Val
2300            2305             2310

Glu Asp  Asn Ile Arg Asp His  Asn Thr Gly Leu Pro  Glu Gly Thr
2315            2320             2325

Lys Ile  Ala Val Gly Asp Asn  Gly Asp Thr Thr Ile  Thr Tyr Pro
2330            2335             2340

Asp Asn  Ser Val Asp Thr Ile  Pro Gly Asp Lys Val  Val Glu Gly
2345            2350             2355

Lys Ser  Asp Ala Ala Lys Asn  Glu Pro Lys Val Pro  Gly Asp Lys
2360            2365             2370

Val Lys  Val Asp Asp Pro Asn  Lys Leu Thr Glu Asp  Glu Lys Ser
2375            2380             2385

Glu Val  Val Lys Ala Val Glu  Asp Ala Asn Lys Asp  Glu Asn Gly
2390            2395             2400

Lys Ser  Thr Leu Pro Glu Gly  Ser Lys Val Thr Val  Gly Asp Asn
2405            2410             2415

Gly Asp  Val Thr Val Thr Tyr  Pro Asp Gly Ser Lys  Asp Thr Ile
2420            2425             2430

Pro Gly  Asp Lys Val Val Glu  Gly Lys Gly Thr Glu  Gly Gln Thr
2435            2440             2445

Asp Ala  Asp Lys Asn Glu Pro  Lys Val Pro Gly Asp  Lys Val Lys
2450            2455             2460

Val Asp  Asp Pro Asn Lys Leu  Thr Glu Asp Glu Lys  Ser Glu Val
2465            2470             2475

Val Lys  Ala Val Glu Asp Ala  Asn Lys Asp Glu Asn  Gly Lys Ser
2480            2485             2490

Thr Leu  Pro Glu Gly Ser Lys  Val Thr Val Gly Asp  Asn Gly Asp
2495            2500             2505

Val Thr  Val Thr Tyr Pro Asp  Gly Ser Lys Asp Thr  Ile Pro Gly
2510            2515             2520

Asp Lys  Val Val Glu Gly Lys  Gly Thr Glu Gly Gln  Thr Asp Ala
2525            2530             2535

Asp Lys  Asn Glu Pro Lys Val  Pro Gly Asp Lys Val  Lys Val Asp
2540            2545             2550

Asp Pro  Asn Lys Leu Thr Glu  Asp Glu Lys Ser Glu  Val Val Lys
2555            2560             2565

Ala Val  Glu Asp Ala Asn Lys  Asp Glu Asn Gly Lys  Ser Thr Leu
2570            2575             2580

Pro Glu  Gly Ser Lys Val Thr  Val Gly Asp Asn Gly  Asp Val Thr
2585            2590             2595

Val Thr  Tyr Pro Asp Gly Ser  Lys Asp Thr Ile Pro  Gly Asp Lys
2600            2605             2610

Val Val  Glu Gly Arg Gly Thr  Glu Gly Gln Thr Asp  Ala Asp Lys
2615            2620             2625

Asn Glu  Pro Lys Val Pro Gly  Asp Lys Val Lys Val  Asp Asp Pro
2630            2635             2640

Thr Lys  Leu Thr Glu Asp Glu  Lys Ser Asp Val Glu  Gln Ala Ile
2645            2650             2655

Lys Asp  Ala Asn Lys Asp Glu  Asn Gly Lys Ser Thr  Leu Pro Glu
2660            2665             2670

Gly Ser  Lys Val Thr Val Gly  Asp Asn Asp Asp Val  Thr Val Thr
2675            2680             2685

Tyr Pro  Asp Gly Ser Lys Asp  Thr Ile Pro Gly Asp  Lys Val Val
```

-continued

```
            2690                2695                2700

Glu  Gly  Lys  Gly  Thr  Glu  Gly  Gln  Thr  Asp  Ala  Asp  Lys  Asn  Glu
     2705                2710                2715

Pro  Lys  Val  Pro  Gly  Asp  Lys  Val  Lys  Val  Asp  Asp  Pro  Asn  Lys
     2720                2725                2730

Leu  Met  Glu  Asp  Glu  Lys  Ser  Asp  Val  Glu  Gln  Ala  Ile  Lys  Asp
     2735                2740                2745

Ala  Asn  Lys  Asp  Glu  Asn  Gly  Lys  Ser  Thr  Leu  Pro  Glu  Gly  Ser
     2750                2755                2760

Lys  Val  Thr  Val  Ser  Asp  Asn  Gly  Asp  Val  Thr  Ile  Thr  Tyr  Pro
     2765                2770                2775

Asp  Gly  Ser  Lys  Asp  Thr  Ile  Pro  Gly  Asp  Gln  Val  Ile  Glu  Gly
     2780                2785                2790

Lys  Ser  Asp  Ala  Asp  Lys  Asn  Thr  Pro  Asn  Val  Pro  Gly  Gly  Asp
     2795                2800                2805

Lys  Val  Lys  Val  Asp  Asp  Pro  Thr  Lys  Leu  Thr  Asp  Asn  Glu  Lys
     2810                2815                2820

Asn  Ala  Val  Lys  Asp  Lys  Val  Asp  Glu  Ala  Asn  Ser  Asn  Leu  Pro
     2825                2830                2835

Asp  Gly  Thr  Lys  Val  Thr  Val  Gly  Asp  Asp  Gly  Thr  Thr  Thr  Ile
     2840                2845                2850

Thr  Tyr  Pro  Asp  Gly  Ser  Thr  Asn  Thr  Ile  Ser  Gly  His  Asp  Leu
     2855                2860                2865

Val  Thr  Gly  Lys  Thr  Asp  Ala  Asp  Lys  Tyr  Pro  Leu  Asn  Pro  Gly
     2870                2875                2880

Gln  Ala  Val  Asn  Val  Val  Asp  Pro  Asn  His  Leu  Thr  Gln  Ala  Glu
     2885                2890                2895

Gln  Asp  Gln  Val  Lys  Glu  Ala  Ile  Gln  Thr  Thr  Asn  Pro  Thr  Ala
     2900                2905                2910

Pro  Ile  Ala  Thr  Ile  Thr  Val  Asp  Thr  Ala  Gly  Asn  Val  Gln  Val
     2915                2920                2925

Thr  Phe  Ala  Asp  Gly  Ser  Thr  Thr  Thr  Leu  Gln  Ala  Asn  Leu  His
     2930                2935                2940

Lys  His  Val  Thr  Glu  Ala  Thr  Thr  Gly  Ser  Ala  Ile  Lys  Pro  Gly
     2945                2950                2955

Val  Gly  Thr  Asn  Gly  Gly  Gln  Thr  Lys  Gly  Ala  Thr  Ser  Thr  Asn
     2960                2965                2970

Gln  Thr  Ala  Thr  Lys  Gln  Gln  Ala  Gln  Gln  His  Leu  Pro  Gln  Thr
     2975                2980                2985

Gly  Asp  Gln  Pro  Ala  Thr  Trp  Ala  Met  Leu  Ser  Gly  Leu  Gly  Val
     2990                2995                3000

Ala  Phe  Leu  Gly  Leu  Leu  Gly  Leu  Lys  Lys  Lys  Arg  Glu  Asp
     3005                3010                3015
```

<210> SEQ ID NO 21
<211> LENGTH: 1472
<212> TYPE: PRT
<213> ORGANISM: Artificial Sequence
<220> FEATURE:
<223> OTHER INFORMATION: Based on Lactobacillus reuteri sequence

<400> SEQUENCE: 21

```
Met  Glu  Ile  Lys  Lys  His  Phe  Lys  Leu  Tyr  Lys  Asp  Gly  Lys  Lys  Trp
1                5                   10                  15

Cys  Cys  Ala  Ala  Ile  Ala  Thr  Thr  Val  Leu  Gly  Ile  Gly  Leu  Ala  Ile
```

```
                20              25              30

Gly Ser Pro Ser Val Leu Ala Asp Ala Asp Thr Ile Thr Ser Thr Ser
        35              40              45

Asp Ala Asn Asn Ser Leu Val Lys Asn Asp Asn Thr Ser Asp Thr Asp
    50              55              60

Ser Asn Ser Glu Ser Thr Phe Thr Asp Thr Asn Lys Asn Ser Thr Asn
65              70              75              80

Glu Lys Glu Ile Asn Glu Asn Lys Asn Ile Asp Ser Ser Gln Gln Ile
                85              90              95

Asn Gln Glu Gln Thr Lys Ser Asn Asn Ser Glu Glu Gln Thr Thr Pro
                100             105             110

Val Asn Val Lys Ala Glu Asn Thr Asp Ile Lys Asp Ser Ile Pro Glu
            115             120             125

Lys Ser Thr Pro Asn Ser Phe Lys Glu Ile Asn Gly Ser Thr Tyr Tyr
        130             135             140

Tyr Gly Glu Asn Gly Asp Leu Tyr Arg Asn Gln Phe Tyr Asn Asn Trp
145             150             155             160

Gly Arg Thr Tyr Tyr Phe Gln Ala Asn Gly Ala Arg Leu Asp Asn Gly
            165             170             175

Phe Tyr Asn Asn Trp Gly Arg Thr Tyr Tyr Phe Gly Ser Asp Gly Ala
        180             185             190

Arg Trp Asp Asn Arg Phe Tyr Asn Asn Trp Gly Arg Thr Tyr Tyr Phe
    195             200             205

Gln Asn Asp Gly Ser Arg Leu Asp Asn Ser Phe Tyr Asn Asn Trp Gly
    210             215             220

Arg Thr Tyr Tyr Phe Gly Val Asp Gly Ala Arg Trp Asp Asn Arg Tyr
225             230             235             240

Met Val Lys Trp Gly Arg Ala Tyr Tyr Phe Gly Asn Asp Gly Ala Leu
            245             250             255

Leu Gln Asn Gln Leu Lys Ser Ile Asn Gly Ile Asn Tyr Trp Ile Asn
            260             265             270

Asn Glu Gly Ile Ile Pro Leu Lys Asn Gln Phe Leu Thr Ala Asn Glu
        275             280             285

Asn Gln Leu Phe Tyr Phe Asp Gly Asn Gly Ser Leu Val Val Asn Lys
    290             295             300

Phe Tyr His Asn Trp Gly His Thr Tyr Tyr Phe Gly Ser Asp Gly Ala
305             310             315             320

Arg Tyr Thr Asp Gln Phe Leu Asn Arg Asp Gly Lys Val Tyr Tyr Phe
            325             330             335

Asp Asn Gln Gly Ile Met Tyr Gln Asp Gln Tyr Tyr Lys Asn Trp Gly
            340             345             350

His Thr Tyr Tyr Phe Gly Ser Asp Gly Ala Arg Tyr Thr Asp Gln Phe
        355             360             365

Leu Asn Arg Asp Gly Lys Val Tyr Tyr Phe Asp Asn Gln Gly Ile Met
    370             375             380

Tyr Gln Asp Gln Tyr Tyr Lys Asn Trp Gly His Thr Tyr Tyr Phe Gly
385             390             395             400

Ser Asp Gly Ala Arg Tyr Thr Asp Gln Phe Leu Asn Arg Asp Gly Lys
            405             410             415

Val Tyr Tyr Phe Asp Asn Gln Gly Ile Met Tyr Gln Asp Gln Tyr Tyr
        420             425             430

Lys Asn Trp Gly His Thr Tyr Tyr Phe Gly Ser Asp Gly Ala Arg Tyr
        435             440             445
```

-continued

```
Thr Asp Gln Phe Leu Asn Arg Asp Gly Lys Val Tyr Tyr Phe Asp Asn
    450                 455                 460

Gln Gly Ile Met Val Thr Asn Gln Val Arg Val Ile Asp Gly Lys Gly
465                 470                 475                 480

Tyr Glu Phe Asn Asp Asn Gly Glu Ala Thr Glu Thr Ser Asp Met Gly
                485                 490                 495

Gln Thr Arg Asp Thr Val Ala Lys Glu Val Ala Gln Ala Leu Thr Asn
                500                 505                 510

Gln Gly Ile Lys Gly Val Lys Tyr Asp Trp Arg Asn Thr Asn Asn Asp
                515                 520                 525

Tyr Gln Glu Leu Ala Leu His Asp Ile Ala Gln Glu Val Ala Gln Gly
    530                 535                 540

Asp Thr Asn Pro Asp Lys Asn Val Ile Glu Lys Lys Leu Gln Ala Asn
545                 550                 555                 560

Asn Leu Leu Ser Gly Lys Val Leu Val Val Tyr Ser Thr Asp Phe Thr
                565                 570                 575

Asn Asp Asp Pro Gln Lys Ile Thr Asn Thr Phe Met Asn Ser Tyr Asp
                580                 585                 590

Phe Thr Asn Ala Asp Asn Ser Val Leu Gly Val Gly Ala Asp Leu Asn
    595                 600                 605

Lys Asn Lys Leu Val Ile Ile Leu Phe Lys Pro Gly Glu Lys Ala Glu
    610                 615                 620

Gln Pro Gln Ala Thr Ser Thr Ile Ser Ala Ser Ile Ser Asp Ile Phe
625                 630                 635                 640

Lys Lys Ala Gly Val Asn Val Asp Val Asp Asn Gly Leu Thr Lys Gly
                645                 650                 655

Ser Val Val Asn Ser Ala Asp Leu Gly Asn Ala Leu Thr Asn Gly Thr
                660                 665                 670

Ala Glu Leu Leu Lys Gly Asp Lys Gly Thr Ile Ile Ser Gln Glu Val
                675                 680                 685

Leu Lys Ala Ile Phe Ala Ala Phe Ala Gly Asn Thr Ser Ala Val Glu
    690                 695                 700

Gly Thr Lys Asn Tyr Tyr Asn Gly Asn Asp Ala Tyr His Tyr Glu Phe
705                 710                 715                 720

Trp Leu Glu Gly Gln Ser Ala Asp Asp Lys Leu Asn Asn Phe Leu Ala
                725                 730                 735

Leu Asn Lys Gly Ala Lys Tyr Gly Asp Gln Leu Lys Val Asn Tyr Thr
                740                 745                 750

Ala Thr Leu Val Phe Gly Gln Glu Thr Gly Thr Asn Ser Asn Glu Ser
                755                 760                 765

Lys Val Pro Ala Ser Glu Arg Thr Asp Glu Gln Leu Asp Leu Ala Tyr
    770                 775                 780

Lys Thr Gly Thr Asp Thr Gly Leu Arg Tyr Asp Ser Val Lys Val Glu
785                 790                 795                 800

Lys Ile Pro Gly Met Thr Asp Asp Met Val Arg Gly Val Asp Val Ser
                805                 810                 815

Ser Tyr Gln Ala Leu Ile Asn Ala Gly Val Lys Phe Tyr Asp Phe Asn
                820                 825                 830

Gly Gln Glu Ser Asn Leu Phe Lys Ile Leu Lys Asp Ser Gly Val Asn
                835                 840                 845

Trp Val Arg Leu Arg Val Trp Asn Asp Pro Tyr Asn Ala Gln Gly Gln
    850                 855                 860
```

```
Pro Tyr Ala Gly Gly Asp Asn Asn Glu Glu Asn Leu Ile Lys Met Ala
865             870             875             880

Lys Glu Ala Ser Asp Asn Gly Leu Lys Leu Leu Ile Asp Phe Gln Tyr
            885             890             895

Ser Asp Phe Trp Thr Asp Pro Ala Gln Gln Ile Leu Pro Lys Ala Trp
            900             905             910

Arg Asn Leu Ser His Gly Glu Met Ser Gln Glu Val Tyr Leu Tyr Thr
    915             920             925

Ser Lys Ile Leu Asn Asp Leu Gln Lys Ala Gly Ala Ser Val Lys Met
    930             935             940

Val Gln Ile Gly Asn Glu Ile Thr Asn Gly Ala Phe Gly Leu Tyr Thr
945             950             955             960

Gly Arg Asn Gly Gly Gly Asn Trp Ala Ser Leu Trp Glu Thr Ser Asp
            965             970             975

Gly Asp Gln Val Ala Lys Tyr Ile Gln Ala Gly Ser Ser Ala Val Arg
            980             985             990

Arg Ile Asp Pro Thr Ile Lys Val  Ala Ile Gln Leu Glu  Thr Pro Glu
        995             1000             1005

Ile Asn  Lys Tyr Arg Gly Ile  Met Asn Val Leu Lys  Lys Asn Asn
    1010             1015             1020

Val Asp  Tyr Asp Tyr Leu Gly  Thr Ser Tyr Tyr Pro  Phe Trp Ser
    1025             1030             1035

Thr Thr  Gln Gly Asn Gly Trp  Tyr Asp Asn Val Asp  Leu Gly Tyr
    1040             1045             1050

Gly Ala  Asn Thr Pro Val Asn  Leu Glu Ala Ile Glu  Lys Met Ala
    1055             1060             1065

Trp Asn  Glu Phe Gly Lys Arg  Thr Val Ile Leu Glu  Ser Gly Trp
    1070             1075             1080

Leu Asn  Asn Thr Asn Asp Ala  Asp Gly Thr His Asn  Ser Val Gly
    1085             1090             1095

Glu Asn  Asn Glu Thr Thr Asn  Ile Asp Arg Tyr Ser  Ala Asp Pro
    1100             1105             1110

Gln Gly  Gln Val Asp Glu Ile  Glu Asp Met Tyr Asn  Ala Ile Ile
    1115             1120             1125

Ala Gln  Lys Gly Leu Gly Ala  Phe Tyr Trp Glu Pro  Ala Trp Ile
    1130             1135             1140

Pro Val  Lys Ala Gly Trp Asn  Asn Trp Gln Tyr Asn  Lys Leu Met
    1145             1150             1155

Ser Asn  Ile Tyr Gly Ser Gly  Trp Ala Ser Gln Tyr  Ala Lys Gly
    1160             1165             1170

Tyr Ala  Pro Asp Ser Val Leu  Tyr Tyr Asp Gly Lys  Glu Ala Trp
    1175             1180             1185

Gly Gly  Ser Ser Trp Asp Asn  Ile Ser Leu Phe Asp  Asp His Gly
    1190             1195             1200

His Pro  Leu Gln Ser Leu Asn  Val Tyr Asn Gly Met  Leu Asn Gly
    1205             1210             1215

Tyr Glu  Ser Pro Lys Asn Val  Lys Ser Ser Leu Ser  Thr Gln Leu
    1220             1225             1230

Val Lys  Ile Trp Asn Glu Thr  Asp Val Ile Pro Asn  Asp Gly Leu
    1235             1240             1245

Thr Glu  Gly Thr Lys Leu Ser  Thr Asp Leu Phe Gly  Thr Thr Gln
    1250             1255             1260

Leu Ser  Gly Asn Asp Gly Gln  Ser Ile Gly Asn Ala  Glu Leu Thr
```

-continued

```
           1265                1270                1275

Lys Leu  Ala Gly Arg Leu Lys  Asp Gly Ile Ser Ser  Lys Val Tyr
    1280                1285                1290

Thr Ala  Ala Asn Gly Ala Arg  Tyr His Tyr Ile Tyr  Trp Leu Glu
    1295                1300                1305

Gly Gly  Asn Asn Lys Val Asn  Thr Phe Val Ser Ala  Asn Lys Asp
    1310                1315                1320

Ala Lys  Tyr Gly Gln Pro Leu  Ile Ala Asn Tyr Ser  Ala Thr Val
    1325                1330                1335

Val Val  Asp Ser Glu Pro Gly  Thr Gln Val Ala Thr  Ser Pro Leu
    1340                1345                1350

Gln Ile  Lys Ile Ser Gln Val  Trp Asn Thr Val Asn  Asn Glu Glu
    1355                1360                1365

Ile Lys  Ile Asp Asn Pro Leu  Lys Gln Gly Asp Leu  Ile Thr Asp
    1370                1375                1380

Lys Ser  Asp Asn Ala Phe Ser  Gly Ile Leu Asn Ser  Lys Asp Ile
    1385                1390                1395

Lys Glu  Ala Leu Thr Gly Glu  Lys Gly Lys Asp Val  Ser Glu Ser
    1400                1405                1410

Thr Val  Asn Asp Val Lys Ser  Leu Leu Pro Lys Glu  Val Lys Gly
    1415                1420                1425

Ser Lys  Thr Tyr Thr Thr Ala  Asp Gly Asn Gln Tyr  Tyr Tyr Asp
    1430                1435                1440

Phe Trp  Leu Ala Ser Val Glu  Thr Ser Asn Val Asn  Tyr Gly Glu
    1445                1450                1455

Pro Ile  Ile Val Asn Tyr Thr  Ala Ser Leu Lys Trp  Leu Gly
    1460                1465                1470

<210> SEQ ID NO 22
<211> LENGTH: 1063
<212> TYPE: PRT
<213> ORGANISM: Artificial Sequence
<220> FEATURE:
<223> OTHER INFORMATION: Based on Lactobacillus reuteri sequence

<400> SEQUENCE: 22

Met Glu Lys Thr Met Lys Lys Lys Ala Leu Val Ala Thr Thr Ala Val
1               5                   10                  15

Ala Gly Ile Thr Leu Val Gly Glu Val Thr Thr Val His Ala Ala Asp
            20                  25                  30

Asn Val Gln Gln Pro Val Asn Glu Gln Asn Val Asn Gln Ser Ser Gln
        35                  40                  45

Glu Glu Lys Gln Ala Ala Gln Asn Leu Gln Asn Ala Gln Ser Asp Val
    50                  55                  60

Asn Thr Ala Thr Glu Ala Asn Ser Asn Ala Gln Asp Asn Leu Ala Ser
65                  70                  75                  80

Ala Asn Asn Asn Leu Ser Asn Ala Lys Lys Ala Val Ser Asp Gln Ala
                85                  90                  95

Ala Lys Val Ala Asp Ala Thr Lys Ala Gln Ser Asp Ala Ser Thr Lys
            100                 105                 110

Val Asp Asn Asp Asn Lys Val Val Ala Asp Ala Gln Gln Lys Ala Asp
        115                 120                 125

Gln Ala Thr Pro Ala Asn Ile Glu Asn Ala Lys Gln Ala Ile Glu Gly
    130                 135                 140

Gln Asn Lys Val Ile Asp Gln Asp Asn Glu Asn Ile Lys Tyr Ser Asn
```

-continued

```
145                150                155                160

Thr Asp Gln Asp Lys Ala Gln Asn Thr Leu Asn Asn Ala Gln Ser Asn
            165                170                175

Glu Asp Lys Ala Asn Ala Thr Leu Ser Asn Lys Lys Ser Ser Gln Ala
            180                185                190

Ser Ala Gln Asn Asn Val Lys Gln Ala Glu Asp Ala Leu Asn Gly Thr
            195                200                205

His Leu Val Glu Ala Gln Asn Ala Phe Asn Gln Ala Gln Ser Asn Val
    210                215                220

Glu Asn Ala Gln Ser Lys Tyr Asp Gln Ala Asn Asn Gln Leu Ser Asp
225                230                235                240

Ala Gln Lys Lys Val Thr Thr Asn Gln Asn Asp Leu Thr Ala Lys Asn
            245                250                255

Lys Ala Leu Asp Asn Ile Asn Asn Gln Val Asp Thr Asp Gln Asn Asn
            260                265                270

Val Asn Ser Asn Gln Ala Thr Ala Asp Ser Ala Ser Ser Ala Thr Gln
            275                280                285

Val Ala Gln Asn Ala Val Asp Gln Thr Lys Gln Ser Leu Asp Lys Val
    290                295                300

Ile Glu Glu Leu Asn Gly Phe Ser Glu Asn Thr Ile Lys Val Pro Ala
305                310                315                320

Gly Ala Gln Glu Ala Tyr Glu Ala Phe Ile Asp Ala Val Asp Asn Asn
            325                330                335

Ala Asp Gln Ser Gln Leu Asp Ser Leu Ala Lys Lys Met Tyr Asp Thr
            340                345                350

Leu His Gln Gly Gln Gly Thr Asn Gly Ile Asn His Phe Asn Ser Ser
            355                360                365

Lys Tyr Asp Gln Asn Gln Leu Val Asp Val Asp His Leu Thr Thr Asp
    370                375                380

Gln Leu Asn Glu Leu Thr Gln Phe Ala Ala Asp Met Ile Asn Ser Ala
385                390                395                400

Arg Lys Ala Trp Gly Ser Asp Lys Asn Ala Gly Thr Leu Ile Pro Thr
            405                410                415

Gln Gly Val Ser Glu Met Ala Gln Gln Ile Ala Lys Gly Tyr Val Ser
            420                425                430

Asp Asn Trp His Ile Ser Gln Gly His Asp Val Lys Arg Val Thr Ala
            435                440                445

Ala Ala Gly Leu Ile Gly Leu Asn Asp Ala Gly Gln Phe Tyr Glu Asp
    450                455                460

Ala Ser Glu Gly Tyr Val His Ala Trp Pro Trp Glu Lys Asp Ser Tyr
465                470                475                480

Thr Met Asp Asn Leu Lys Glu Ala Val Tyr Asp Ser Ile Leu Gly Met
            485                490                495

Leu Phe Ala Asp Asp Asn Ser Gly Asn Gly His Met Thr Asp Leu Leu
            500                505                510

Gly Leu His Val Asn Arg Lys Glu Asp His Gln Tyr Phe Gly Leu Ser
            515                520                525

Thr Asn Met Cys Pro Gly Ser Tyr Met Gly Gln Leu His Phe Ile Ile
            530                535                540

Val Glu Asn Asp Pro Ala Tyr Ile Lys Asp Pro Gln Thr Phe Asn Ala
545                550                555                560

Lys Gly Gly Thr Thr Lys Ile Glu Tyr Ile Asp Pro Lys Val Gln Leu
            565                570                575
```

-continued

```
Asn Gln Gln Lys Asp Ile Leu Thr Thr Thr Leu Ser Thr Gln Gln Ala
            580                 585                 590

Asp Leu Ala Thr Lys Gln Asp Ala Leu Asn Lys Ala Asn Gln Asn Leu
            595                 600                 605

Ala Asn Ala Lys Lys Gln Leu Ser Glu Asp Gln Asp Leu Gln Thr Val
            610                 615                 620

Ala Gln Gln Asn Arg Asp Ser Ala Gln Lys Ala Leu Asn Asp Ala Thr
625                 630                 635                 640

Ala Lys Val Ser Asn Leu Gln Ala Thr Val Asn Ser Leu Ser Gln Asp
                    645                 650                 655

Leu Asn Ser Ala Lys Ala Thr Leu Asp Gln Ala Lys Lys Thr Leu Glu
                    660                 665                 670

Ser Tyr Thr Ala Asp His Lys Ala Lys Leu Asp Asn Tyr Asn Asn Ala
            675                 680                 685

Lys Ala Ala Leu Asp Asp Ala Asn Lys Ala Val Ala Glu Ala Gln Ser
            690                 695                 700

Ala Val Asp Thr Ala Val Asn Glu Thr Lys Ile Ala Gln Asn Asn Leu
705                 710                 715                 720

Asp Gln Lys Lys Gln Ala Val Thr Asp Ala Gln Asn Lys Leu Ala Asn
                    725                 730                 735

Asp Gln Glu Tyr Leu Ala Thr Leu Lys Gln Asn Leu Ala Asp Leu Gln
            740                 745                 750

Asn Ala Pro Gln Asn Leu Gln Lys Ala Lys Asp Gln Leu Ala Lys Asp
            755                 760                 765

Gln Ile Ala Leu Asp Asn Ala Asn Lys Asp Leu Gln Asn Gln Lys Asp
    770                 775                 780

Ser Leu Asp Glu Leu Asn Lys Lys Leu Glu Asp Ala Gln Val Lys Val
785                 790                 795                 800

Asn Glu Ala Gln Ser Ala Ala Asn Val Thr Lys Ala Thr Leu Asp Gln
                    805                 810                 815

Ala Gln Ala Lys Leu Ser Asp Ala Glu Ala Thr Trp Lys Glu Leu His
            820                 825                 830

Asn Asp Ala His Arg Tyr Gly Asn Val Val Lys Val Thr Pro Ile Thr
            835                 840                 845

Met Glu Ala Gly Thr Ser Leu Pro Asp Pro Val Ile Glu Asn Gly Phe
    850                 855                 860

Thr Val Asn Thr Gly Thr Asn Gln Leu Phe Val Ser Leu Ala Ala Ile
865                 870                 875                 880

Asp Ser Ser Asn Asn Asn Ile Pro Gln Gly Thr Lys Ala Ser Trp Ala
                    885                 890                 895

Asn Arg Ser Lys Ala Leu Thr Asp Ser Gln Asn Ala Gly Ser Tyr Ser
            900                 905                 910

Glu Asp Ile Leu Ile Thr Phe Pro Asp Asn Ser Thr Val Thr Val Pro
            915                 920                 925

Val Asp Leu Thr Val Thr Ala Lys Lys Ile Thr Glu Asp Gln Lys Ala
    930                 935                 940

Thr Glu Gly Gly Tyr His Ile Val Asn Gly Ser Val Val Asp Lys Gln
945                 950                 955                 960

Asn Asn Leu Val Ser Gly Trp Thr Val Lys Asn Gly Gln Met Val Asp
                    965                 970                 975

Pro Glu Gly Asn Val Ile Lys Thr Thr Met Ser Thr Ala Gln Gly Val
            980                 985                 990
```

-continued

```
Thr Ile Glu Lys Asn Asn Ser Lys  Ser Gly Asn Thr Lys  Thr Asn Met
        995             1000              1005

Ile Gln  Thr Ser Leu Thr Ile  Ala Asn Asn Lys Ala  Thr Thr Asn
    1010             1015              1020

Lys Asp  Asn Gln Leu Pro Gln  Thr Gly Asn Tyr Asn  Asn Asn Thr
    1025             1030              1035

Lys Val  Leu Gly Leu Ala Gly  Ile Ala Leu Ala Ser  Ala Leu Thr
    1040             1045              1050

Met Phe  Gly Tyr Lys Lys Arg  Gln His Asn
    1055             1060

<210> SEQ ID NO 23
<211> LENGTH: 212
<212> TYPE: PRT
<213> ORGANISM: Artificial Sequence
<220> FEATURE:
<223> OTHER INFORMATION: Based on Lactobacillus reuteri sequence

<400> SEQUENCE: 23

Met Lys Ser Thr Thr Lys Lys Ile Leu Ala Ser Ser Leu Gly Val Ala
1               5               10              15

Gly Ala Met Ala Met Gly Thr Val Thr Ala Lys Ala Asp Thr Thr Val
            20              25              30

Thr Val Asn Ala Gly Asp Ser Leu Asn Gly Ile Ala Gln Lys Tyr Asn
        35              40              45

Val Ser Ala Asp Asp Ile Ala Thr Ala Asn His Leu Gln Asn Lys Glu
    50              55              60

Leu Ile Phe Val Gly Gln Lys Leu Thr Ile Pro Thr Lys Asp Lys Asn
65              70              75              80

Glu Thr Pro Ala Asn Asn Ala Glu Lys Lys Asp Gln Ala Ser Lys Asn
            85              90              95

Ser Gln Ser Leu Gln Asp Ser Val Asn Lys Ala Met Ser Tyr Leu Gly
            100             105             110

Thr Pro Tyr Val Trp Gly Gly Asn Lys Pro Gly Gly Phe Asp Cys Ser
        115             120             125

Gly Leu Val Gln Tyr Cys Tyr Gly Ile Pro Gln Arg Thr Thr Tyr Glu
    130             135             140

Gln Gln Ala Leu Gly Pro His Ile His Asp Asn Val Leu Asn Ala Pro
145             150             155             160

Tyr Gly Ala Leu Val Phe Tyr Gly Ser Asp Asp Ala Pro Tyr His Val
            165             170             175

Ala Ile Ser Leu Gly Asp Gly Arg Ile Ile Gln Ala Pro Asn Glu Asn
            180             185             190

Glu Thr Val Lys Ile Thr Asp Gln Gln Tyr Phe Pro Gly Asn Tyr Tyr
        195             200             205

Val Val Met His
    210

<210> SEQ ID NO 24
<211> LENGTH: 1029
<212> TYPE: DNA
<213> ORGANISM: Artificial Sequence
<220> FEATURE:
<223> OTHER INFORMATION: Based on Lactobacillus reuteri sequence

<400> SEQUENCE: 24
atggaaagcc gtaataacaa taacctgaag ggcatcgatg tgagcaactg gaagggcaac     60
```

```
atcaatttc aaagcgtcaa aaatgacggt gttgaagttg tttacattaa ggcaaccgaa        120
ggcaactact tcaaagacaa atatgctaag caaaactacg agcgcgctaa agaacagggt        180
ctgcgtgtgg gcttctacca ctttttccgc gcaaacaaag gtgccaaaga tcaggcgaac        240
ttcttcgtga attacctgaa cgaaatcggt gcggtcaatt atgactgtaa actggcactg        300
gacatcgaga ctaccgaagg cgtcggtgcg cgtgacctga cctctatgtg catcgagttc        360
ctggaagagg tgaagcgtat tacgggtaag gaagttgtcg tgtacaccta taccagcttc        420
gcgaacaata atctggattc ccgtctgtct agctatccgg tgtggattgc gcactatggc        480
gtcaacaccc cgggtgcgaa caatatctgg agcgagtggg tgggtttcca gtacagcgag        540
aatggctccg tcgccggtgt cagcggtggc tgcgatatga acgaatttac caatggtatc        600
tttattgact cgaacaattt cacgttggac aatgcaacga ccaaaaatgt tagcattaag        660
ctgaacattc gcgccaaggg tacgaccaac agcaaagtta ttggtagcat tccggcgaac        720
gaaaagttta agatcaaatg ggttgatgaa gattacctgg gttggtatta cgttgagtat        780
aacggtatcg tgggttacgt taacgccgat tacgtcgaga aactgcaaat ggcgaccacg        840
cataatgtta gcacctttct gaatgtacgc gaggagggtt ccttgaatag ccgtattgtg        900
gacaagatca acactggcga catctttcgt attgactggg ttgatagcga tttcattggt        960
tggtatcgtg tgacgacgaa aaacggcaag gtcggctttg ttaatgcaga gtttgtgaaa       1020
aagttgtaa                                                                1029
```

```
<210> SEQ ID NO 25
<211> LENGTH: 738
<212> TYPE: DNA
<213> ORGANISM: Artificial Sequence
<220> FEATURE:
<223> OTHER INFORMATION: Based on Lactobacillus reuteri sequence

<400> SEQUENCE: 25
atgacaacag taaatgaagc attaaataat gtaagagctc aggttgggtc cggtgcgtct         60
gttggcaacg gcgaatgcta cgctttggct agttggtacg agcgcatgat tagtccggat        120
gcaactgtcg gacttggcgc tggtgtgggc tgggtcagcg gtgcaatcgg cgatacaatc        180
tctgccaaaa acatcggctc atcatacaac tggcaagcta acggctggac agtttccaca        240
tctggtccat ttaaagcagg tcagattgtg acgcttgggg caacaccagg aaaccettac        300 ggacatgtgg taatcgtcga agcagtggac ggcgatagat tgactatttt ggagcaaaac        360
tacggcggga aacgttatcc cgtccgtaat tattacagcg ctgcaagcta tcgtcaacag        420
gtcgtgcatt acatcacacc gcctggcacg gtcgcacagt cagcacccaa ccttgcaggc        480
tctcgttcct atcgcgagac gggcactatg actgtcacgg tcgatgctct caatgttcgc        540
agggcgccaa atacttcagg cgagattgta gcagtataca agcgtggtga atcatttgac        600
tatgatactg tcatcatcga tgtcaatggc tatgtctggg tgtcttacat aggcggcagc        660
ggcaaacgta actacgttgc gacgggcgct accaaagacg gtaagcgttt cggcaatgct        720
tggggtacat ttaaataa                                                       738
```

```
<210> SEQ ID NO 26
<211> LENGTH: 543
<212> TYPE: DNA
<213> ORGANISM: Artificial Sequence
<220> FEATURE:
<223> OTHER INFORMATION: Based on Lactobacillus reuteri sequence

<400> SEQUENCE: 26
```

-continued

```
atgtcgaaga tttttggttt agatgcgggt cattgtacga gcggcgcaga tacgggtgcg      60
cagggcaatg gttacaaaga acaagacttg acccgtcaag ttgttaccta tctgagcgaa     120
tacttggaga aagagggcca cactaccaag tactgccatt gcaatagcgc gagcacggtt     180
aacgaatccc tgcgctatcg tgtgaacaaa gccaactcca tcggtgtcga ctacttcgtg     240
agcatccacc tgaacgccgg tggcggcgtt ggtaccgaaa cgtacatctg cgcgcgtggc     300
ggcgaggccg agcgcgtggc gaaacgcgtc aattctaaac tggtgcagta cggttatcgt     360
gaccgtggtg tcaaggttgg taatctgtat gtgattaaga acaccaatgc accggctatc     420
ctggttgaga tctgtttcat tgacagcagc agcgatgtgg caaagtttaa cgcgaaggca     480
atcgcgaaag cgattgctga gggtctgctg dataaaacca ttggtgaagt cgagaataag     540
taa                                                                   543
```

```
<210> SEQ ID NO 27
<211> LENGTH: 1107
<212> TYPE: DNA
<213> ORGANISM: Artificial Sequence
<220> FEATURE:
<223> OTHER INFORMATION: Based on Lactobacillus reuteri sequence

<400> SEQUENCE: 27
atgcgtaatc aattcatcga tgtttcaagt tatcaaccag atactgttgc ctttttccaa      60
gctgctaaag ctcagggtgc attaggggtc gttgttaagt taacggaagg gtccgaagat     120
ggttcggctt atgttaatcc acgtgcggcc gctcaaattc gtaatgcctt agcggttggc     180
ttgcgcgttt cctgttacca ctttgctcgt tatacatcag tgactgatgc acaaaatgaa     240
gctcgattct tcgttaaaat cgctaagcaa tttggtatgt atgacgatac tttgatgatt     300
gatgatgcgg aagttcattc aactgcagat tatcaatcag tatccttagc ctttcttcaa     360
gaagtagaag ctcttggtta caagaatact gggatttact ccatgaagtc cttcttcact     420
ggcggtattc ttaattcaca tggctttgat tcccggaaga tttggattgc tggctatggt     480
gtgactgaac tggggattga taatgcaagt gcttggcaat attctgatca tagcatcatg     540
ggaattgata ctagttatga ctttgacggt gcctttacga ctggtttagt atcaggcaat     600
gttccgcaag ctgttattcc agcaccacag ccggttcaac atattggtca cccagctact     660
ggaacctaca ttgttcagcc gggcgataca ttgagtggaa ttgcagaaaa atacgggact     720
acttatcaga acctagcagc aatcaatggt attggtaatc caaaccagat caatgtcggc     780
caagtcctca aagtcaccgg aaaagtatca aacgaaaata cttactttgt tcaatcaggc     840
gatacgttat ccggaattgc caccaaattc ggcaccactg tctcagacct cgtaagccgt     900
aatcacatta ctaacccgaa tgtgatctac gttgggcaaa aactctactt agccggcaac     960
ggacaatcca atgcttatac tgtccaagca ggggacacac taagcggaat tgcggctaag    1020
tttggcaaga cctggcaagc attagctcaa aagaatggca tcgcaaatcc taatatgatt    1080
ttcattggtc aaacaattca gatttaa                                        1107
```

```
<210> SEQ ID NO 28
<211> LENGTH: 2439
<212> TYPE: DNA
<213> ORGANISM: Artificial Sequence
<220> FEATURE:
<223> OTHER INFORMATION: Based on Lactobacillus reuteri sequence

<400> SEQUENCE: 28
```

-continued

```
gtgtaccgaa ttattggtta taatgaacca acagataaag caggatttat tgtactggat        60
ccccgagtta atcgtcatat tagttcggga aaactcacgc ttaaagaatc taatattgat       120
gatttgacta ttacggttaa tcaagcaagt ccattatggg acaacgtaag gccttatcat       180
actcatgtta acgtttatga tgataatgaa cttattttc gtggacgagc tatcaaacct        240
aaaaagtcga tggaagaaag cggacaattc attcgtgaat atgttttga agatattgaa        300 gcatatctca tggatagcac ccaaagattt tatgaaggtg ttggtcaaac gcccaaagaa       360 ttttttacaaa ctttaatcga tgttcataat tcacaggttc ctgactataa aaagtttcaa      420
gtccggaatg taaatgtcac taataataag gatgaccaat atcgacaaat tgattatccc       480
aaaactagcg atgctattaa tgataaatta gttaaatctc ttggtggtta tattgtgact       540
acttacaacg ctaacggaat aaactacatt gactacttaa cggatattgg ggttgatcat       600
aaagatgata ctcctattca gttagctaaa aatatgaagt ctgcaagtat gcaaattgat       660
cctactaagg tgattacaag actgattcca ctgggaaaga cactagaacc atcaaaagtt       720
gatgtaagtg atgatgatgg agagggcggt tctggatcat tagatagccc tgaagaattt       780
tgtaaatcag aaattaatgc tacttggggt agtgatatta ataatatgaa acaagatttt       840
gccgctcgtt cttcgagagt tcgggcttgg ggagtggacg ttaatcgttt atatgatgtg       900
gtgaaaaatg ctggagtaag tcctgaatgg ttctttgctt atgaacttca agaacaagga       960
acttactatg gatggcttaa ccatacttat cgacacggtg atgcgtatag tgatgcgcaa      1020
tctgtttgtg agtggattaa aaattgttca aatagtaatt ccattaatcc agcatggagc      1080
gcaccggaag gatcaatggc gccgaatcaa gcattagcgg ataaatggaa tcaagagttt      1140
ggaaaaggta ctattggccg cgtttatta caagggactg ccgctgctgt ttgggattta       1200
gctggtcaaa cgcctaatcc agctattgga aagccaatta gtggatgcat ttcttgtatt      1260
aaacgttggg gtggtcattc taatgcagct ggtggtacat ggggatggcc ttttcctgat      1320
gttggggaag gtcatttttc tcaagttcag agtttcggaa atgatggcgg atatcgtcaa      1380
aatagttatc acgatggtgt ggattttgga tcaatagatc atcctggtag agaagtgcat      1440
tgtattcatg gtgaacggt aactatcaaa tcagctatgg gtggcttagg taattttgtg       1500
gttattcata cgccggaagg attcaatatc gtttatcaag aagcttttag ttctccctct      1560
aatattattg ttagtgttgg gcaaaaagta aaaactggtg atgtaattgg atatcgtgat      1620
acagaccatg ttcatattgg cgtaactaag caagattttt atcaagcagt tcgaaattct      1680
ttttctcctg caggtggttg gctagatcca gtaaaactaa ttaaagaagg tggcgatggg      1740
tctaaaccac aagaaggaaa gaaagatcaa actgttgata atagtaatgc tgcacgtcct      1800
aaattaacca ttactactgt caataacggt agagactata ttgatattcc tgatttacaa      1860
aaagaattcg gtattattga gggaactgtt gaatttgata atgtagatga tccgaatgtt      1920
ttaatgcaac aagctcaaac atggataaag gctcaaagaa tacctcaaag ttgggaagtt      1980
acagctttag aattacatat gacaaacttc aaatctttta aggttgctga taggtacatg      2040
tttattaatc caaatgttgc aaaaccccaa ttattacgaa ttactcaaaa agaaattgat      2100
ttactaaagc cccatgcgtc ttcattaacg attggtgata gacgatggg cttactgat       2160 tatcagttag aaaatcaagt caattttcaa caatttaagg aaattcgagt gatggttaat      2220
caggttgtcc aaacccaaga gcaatctgct aataacaata taaggttat gcaaaatttt       2280 gctagtagtg ctgatcttgc acaaatgaga caggatctaa gaaatcttca agatgataac      2340
gatcgtgctc gcaaaggaat ggtttcctta gaagaattca ataaactaaa ggaacaagta     2400
```

-continued gaaaaactaa caacaggagg cgatgataat ggcaagtga                                    2439

<210> SEQ ID NO 29
<211> LENGTH: 154
<212> TYPE: PRT
<213> ORGANISM: Artificial Sequence
<220> FEATURE:
<223> OTHER INFORMATION: Synthetic construct

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Gly Ser Gly Arg Thr Gly Ser Leu Tyr
            20                  25                  30

Ser Met Gly Trp Phe Arg Gln Ala Pro Gly Lys Glu Arg Glu Phe Val
        35                  40                  45

Ala Ala Ile Thr Trp Arg Pro Ser Ser Thr Tyr Tyr Ala Asp Ser Val
    50                  55                  60

Lys Gly Arg Phe Thr Ile Ser Arg Asp Asp Ala Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Arg Pro Arg Gly Gly Leu Ser Pro Thr Pro Gln Ala Tyr Asp
            100                 105                 110

Tyr Trp Gly Gln Gly Thr Gln Val Thr Val Ser Ser Ala Ala Ala Ser
        115                 120                 125

Gly Ser Leu Glu Gln Lys Leu Ile Ser Glu Glu Asp Leu Asn Gly Ala
    130                 135                 140

Ala His His His His His His Gly Ala Ala
145                 150

<210> SEQ ID NO 30
<211> LENGTH: 141
<212> TYPE: PRT
<213> ORGANISM: Artificial Sequence
<220> FEATURE:
<223> OTHER INFORMATION: Synthetic construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Thr Ile Asn
            20                  25                  30

Asp Met Gly Trp Phe Arg Gln Ala Pro Gly Lys Gln Arg Asp Trp Val
        35                  40                  45

Ala Thr Ile Val Ser Asp Gly Ser Thr Ala Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ala Arg Arg His Tyr Gly Gln Gly Thr Gln Val Thr Val Ser Ser Ala
            100                 105                 110

Ala Ala Ser Gly Ser Leu Glu Gln Lys Leu Ile Ser Glu Glu Asp Leu
        115                 120                 125

Asn Gly Ala Ala His His His His His His Gly Ala Ala
    130                 135                 140

```
<210> SEQ ID NO 31
<211> LENGTH: 462
<212> TYPE: DNA
<213> ORGANISM: Artificial Sequence
<220> FEATURE:
<223> OTHER INFORMATION: Synthetic construct

<400> SEQUENCE: 31
gaggtgcagc tcgtggaaag tggcggaggt cttgttcagg ctggggggatc gctccgtctg      60 agctgtgcgg ggtctggcag aacaggtagt ctctattcca tgggttggtt tcggcaggcc     120
ccgggtaagg agcgggagtt cgttgcagcg attacgtgga ggcccagctc tacctactac     180
gcggacagcg taaagggacg attcaccatt agtagagacg acgcaaagaa tactgtatat     240
ttgcagatga attcgttgaa gcctgaggac accgctgtct attttttgcgc ggcgcgaccg     300 aggggcggtc tctccccgac acctcaagca tatgattact ggggacaagg gacccaagtc     360
actgtatcca gtgcggccgc gagcggcagc cttgaacaaa agctgataag cgaggaggat     420
ctcaatggtg ctgcacatca tcatcaccat cacgggggcag cg                       462

<210> SEQ ID NO 32
<211> LENGTH: 423
<212> TYPE: DNA
<213> ORGANISM: Artificial Sequence
<220> FEATURE:
<223> OTHER INFORMATION: Synthetic construct

<400> SEQUENCE: 32
gaagttcagc ttgtagagtc cggtgggggt cttgtacagc ccggcgggag cttgcgactc      60
tcatgcgctg cttccggaag cattgcgaca ataaatgata tgggttggtt tagacaagcc     120
cccgggaagc agcgtgactg ggtcgcgact attgtgagtg acggcagcac ggcttatgcg     180
gactcagtga aagggagatt tacgatttcg cgagataacg cgaaaaacac tgtatacctg     240
cagatgaatt cactcaagcc ggaagataca gctgtgtatt attgttctgc ccgacggcac     300
tacggacagg ggacccaggt cacagtctcg agcgctgccg ccagtgggtc actcgagcag     360
aagctgatat cagaggagga ccttaacggt gcggcgcacc atcaccacca tcatggtgcg     420
gcg                                                                    423

<210> SEQ ID NO 33
<211> LENGTH: 148
<212> TYPE: PRT
<213> ORGANISM: Artificial Sequence
<220> FEATURE:
<223> OTHER INFORMATION: Synthetic construct

<400> SEQUENCE: 33

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Thr Asn
            20                  25                  30

Val Met Gly Trp Tyr Arg Gln Ala Pro Gly Lys Gln Arg Glu Phe Val
        35                  40                  45

Ala Gly Ile Thr Ile Gly Gly Thr Ala Arg Tyr Pro Asp Ser Val Lys
    50                  55                  60

Gly Arg Phe Thr Ile Ser Arg Asp Asn Thr Gln Asn Thr Val Tyr Leu
65                  70                  75                  80

Gln Met Asn Asn Leu Lys Pro Glu Asp Thr Ala Val Tyr Tyr Cys Asn
```

```
                    85                  90                  95

Ala Val Leu Pro Ser Asp Gln Arg Arg Trp Ser Trp Gly Gln Gly Thr
                100                 105                 110

Gln Val Thr Val Ser Ser Ala Ala Ala Ser Gly Ser Leu Glu Gln Lys
        115                 120                 125

Leu Ile Ser Glu Glu Asp Leu Asn Gly Ala Ala His His His His
    130                 135                 140

His Gly Ala Ala
145

<210> SEQ ID NO 34
<211> LENGTH: 143
<212> TYPE: PRT
<213> ORGANISM: Artificial Sequence
<220> FEATURE:
<223> OTHER INFORMATION: Synthetic construct

<400> SEQUENCE: 34

Glu Val Gln Leu Val Glu Ser Gly Gly Gly Leu Val Gln Thr Gly Gly
1               5                   10                  15

Ser Leu Arg Leu Ser Cys Thr Ala Ser Gly Thr Ile Asp Met Thr Tyr
                20                  25                  30

Gly Leu Ile Trp Tyr Arg Gln Ala Pro Gly Lys Glu Arg Glu Leu Val
        35                  40                  45

Ala Ser Ile Arg Arg Asp Gly Arg Thr Asn Tyr Ala Asp Ser Val Lys
    50                  55                  60

Gly Arg Phe Thr Ile Ser Ile Asp Asn Ala Lys Asn Ser Ile His Leu
65                  70                  75                  80

Gln Met Asn Ser Leu Lys Pro Asp Asp Thr Ala Arg Tyr Tyr Cys Asn
                85                  90                  95

Ser Pro Tyr His Ala Leu Trp Gly Gln Gly Thr Gln Val Thr Val Ser
            100                 105                 110

Ser Ala Ala Ala Ser Gly Ser Leu Glu Gln Lys Leu Ile Ser Glu Glu
        115                 120                 125

Asp Leu Asn Gly Ala Ala His His His His His His Gly Ala Ala
    130                 135                 140

<210> SEQ ID NO 35
<211> LENGTH: 444
<212> TYPE: DNA
<213> ORGANISM: Artificial Sequence
<220> FEATURE:
<223> OTHER INFORMATION: Synthetic construct

<400> SEQUENCE: 35
gaggtacaac tggttgagag tgggggtggt ttggtgcaag ccggaggttc cttacgtttg      60
tcttgcgcgg ctagtgggag catcttttca acaaacgtaa tggggtggta ccgccaagcc     120
ccaggtaagc agcgggaatt tgtggccggg ataacgatcg gaggaactgc gaggtatcct     180
gatagtgtga aagggcgttt cacaattagt cgagataata cacagaatac tgtctatctc     240
caaatgaata atctcaagcc cgaagacaca gcagtttatt attgtaatgc cgttctcccc     300
tctgatcagc gtcgatggag ctggggacaa ggcacccagg ttacggttag cagcgcggca     360
gcgtctggtt cgctcgagca aaagctcata tctgaggagg acctgaacgg ggcagcccac     420
catcaccacc atcacggagc agct                                            444

<210> SEQ ID NO 36
```

-continued

```
<211> LENGTH: 429
<212> TYPE: DNA
<213> ORGANISM: Artificial Sequence
<220> FEATURE:
<223> OTHER INFORMATION: Synthetic construct

<400> SEQUENCE: 36
gaggtacagc tggtggagtc cggcggtggt ttggtgcaaa ccggggggtag tctgcggctt      60 agttgcacgg cgtctgggac aatagacatg acttatggtc tcatatggta caggcaagcg     120
cctgggaaag agagggaact cgttgcgagt atcagaaggg acggccgcac aaattacgct     180
gattcagtga aagggcgctt cactatctcg atcgataatg cgaaaaacag tattcacctt     240
caaatgaact cccttaagcc cgatgatacc gccaggtatt attgcaacag cccatatcac     300
gcactttggg gtcagggtac gcaggtaaca gtgtctagtg cggcagcctc tggtagtttg     360
gagcaaaagt tgataagtga ggaggactta aatgggcgg cacatcacca ccaccatcat     420
ggggcggct                                                             429

<210> SEQ ID NO 37
<211> LENGTH: 1001
<212> TYPE: DNA
<213> ORGANISM: Artificial Sequence
<220> FEATURE:
<223> OTHER INFORMATION: Synthetic construct

<400> SEQUENCE: 37
aaattaaaag gctggatttt ttcggccttt ttttagtgca ataattatt ttttacgtat       60 ttatattata gggctaatca ctaaactaat aattagtggt tgaagcgctg aaaattttct     120
gctattttat taatagtttg ataataaat aatgatattt aatataaaga gggataaacg      180
aaataatgaa atcaacaaca aagaaaattc ttgcatcgtc gttaggggta gctggcgcaa     240
tggcaatggg cacggtaact gcaaaggctg atacgaccgt tacggtcaat gctggcgata     300
gtttgaatgg gattgctcaa aagtataatg ttagtgcgga tgatattgca accgctaatc     360
acttgcaaaa taaagagttg attttttgtgg gacaaaagtt gacaattcca accaaagata     420
aaaatgaaac agaagttcaa ttagttgaaa gtggtggtgg tttagttcaa ccaggtggta     480
gtttacgttt atcatgtgct gcaagtggtt caattgcaac tattaatgat atgggttggt     540
ttcgtcaagc accaggaaag caacgtgatt gggttgctac tattgttagt gatggttcaa     600
ctgcttatgc tgatagtgtt aaaggtcgtt ttactatttc acgtgataat gctaagaata     660
ctgtttacct tcaaatgaat agtcttaagc cagaagatac tgcagtttac tattgttcag     720
ctcgtcgtca ttatggtcaa ggtactcaag ttactgttag ttcagctgca gctagtggtt     780
cattagaaca aaaattaatt tcagaagaag atttaaatgg tgcagctcat catcatcatc     840
atcatggtgc agcttacttc cctggaaatt actatgttgt gatgcattaa tattcccttt     900
cacctcacct ttaataattt aaattagtaa ttatcttgcg catcacaaaa gagtgctata     960
tactatttca gattagaaag ttttatgagg gagacaaatt g                        1001

<210> SEQ ID NO 38
<211> LENGTH: 1393
<212> TYPE: DNA
<213> ORGANISM: Artificial Sequence
<220> FEATURE:
<223> OTHER INFORMATION: Synthetic construct

<400> SEQUENCE: 38
gaagtacaaa gttactttaa ctataatgaa aaacaagaca atataaagaa aacaacatat       60
```

-continued

```
aaggttcagt tcataactga ttagatttat aataaatatt gtaaatcgga caaaaataaa      120
ttaattttca attaattcaa aaaaaccata tttttttcgt tttggcatat ttggatttgc      180
tacactaaag atgatcaaga aaggggaaaa gataatcttc aatcttgtgt acttagtttg      240
ttaattaatt tataaattta gggaggaaac ctatcatgga aaagactatg aaaaagaaag      300
ctttagttgc aactactgct gtagccggta ttactttagt aggagaggtt actactgttc      360
atgccgctga caatgtacaa caagaagttc aattagttga aagtggtggt ggtttagttc      420
aaccaggtgg tagtttacgt ttatcatgtg ctgcaagtgg ttcaattgca actattaatg      480
atatgggttg gtttcgtcaa gcaccaggaa agcaacgtga ttgggttgct actattgtta      540
gtgatggttc aactgcttat gctgatagtg ttaaaggtcg ttttactatt tcacgtgata      600
atgctaagaa tactgtttac cttcaaatga atagtcttaa gccagaagat actgcagttt      660
actattgttc agctcgtcgt cattatggtc aaggtactca agttactgtt agttcagctg      720
cagctagtgg ttcattagaa caaaaattaa tttcagaaga agatttaaat ggtgcagctc      780
atcatcatca tcatcatggt gcagctaaga agattacaga agatcaaaaa gcaacagaag      840
gcggttatca tattgttaat ggatctgttg tagataagca gaataacttg gttagtggtt      900
ggactgttaa gaatggtcaa atggttgatc ctgaaggtaa cgttatcaaa acaacaatgt      960
ctacagccca aggtgttact attgaaaaaa ataatagcaa gtccgggaat acaaagacaa     1020
acatgattca aacttcttta actattgcta acaacaaggc aacaacaaac aaagacaacc     1080
agttaccaca aactggcaat tacaacaaca atacaaaggt attaggatta gctggtattg     1140
cacttgcatc tgctttaact atgtttggat acaagaagcg ccaacataac taattttctt     1200
acttgatggg tttctaaata aaaaatggac tacttcagct caaggtagcc catttttatt     1260
attatagtga agcagttatt cttacgtata accagactaa aatataataa aaatctatta     1320
tatattaatc aacatctcgg tttaatcgtt aaaactcctc tgagagctaa ttgttaatat     1380
tgagttgtat agt                                                       1393
```

```
<210> SEQ ID NO 39
<211> LENGTH: 1419
<212> TYPE: DNA
<213> ORGANISM: Artificial Sequence
<220> FEATURE:
<223> OTHER INFORMATION: Synthetic construct

<400> SEQUENCE: 39
```

```
gcaatgcaca agatgctgaa acaaaggcac aacaaatgc agatcaagct tcaccagcta       60
atattcaaaa ggcacaagat gctattgcta atcaagaaac tcaaattagt aaagacaccg      120
atgctattaa tgacgctaac aaagccgtta gcgatgcaca aagcacagtt gatgcagcgc      180
aaaaaaagtt aatgatgcaa ctactgctcg tgacaatcaa caaaagaatg ttgatactgc      240
tagtgatgca gttaagaatg ctcaagctat tcttgacaac agtgatcagg ctaaaaagga      300
agcccaagat gctttgaaca aggctaacca aaaagttgct gatgatacta ctgccgttaa      360
caacaaacaa actgatgtta acaatgcagc agaagctaag aagaatgcag atgaggcatt      420
gaagaacgcc aatgatgcgc aaacttctgc acaaagaat aaagatgcta agcaagcaat      480
tgctgatgag gcaagtgtag aagttcaatt agttgaaagt ggtggtggtt tagttcaacc      540
aggtggtagt ttacgtttat catgtgctgc aagtggttca attgcaacta ttaatgatat      600
gggttggttt cgtcaagcac caggaaagca acgtgattgg gttgctacta ttgttagtga      660
```

-continued

```
tggttcaact gcttatgctg atagtgttaa aggtcgtttt actatttcac gtgataatgc      720
taagaatact gtttaccttc aaatgaatag tcttaagcca gaagatactg cagtttacta      780
ttgttcagct cgtcgtcatt atggtcaagg tactcaagtt actgttagtt cagctgcagc      840
tagtggttca ttagaacaaa aattaatttc agaagaagat ttaaatggtg cagctcatca      900
tcatcatcat catggtgcag ctgctgaaaa ggaagctaaa gataatggct accatatcga      960
aaataaccaa gttgttgacg ctaaaggtaa tagtgtcaat ggctggacag ttaagggcaa     1020
ccaaattgtt agtccaacta atgctactgt agatcccgct gtttctgtaa ccaccaatgt     1080
caatgttgat agtaaaggtc aagtacaacc acaaactagt gttactgcta atagtgttaa     1140
gactgtagct gcaactgaat cagcaaatcc agtagcaact actactgtgc aaacccgcga     1200
acaatacaag caacaattga agagcaataa tcaattacca caaactggta ataatgatag     1260
tgctgttctt tcacttgctg gagtagcact tgcagcaatg ttgagtttgt tcggtattaa     1320
gaaacgtgaa tactaattta gaaaatgtaa gtattattat gtaaaaaggt tcaaccaaat     1380
tggctgaacc tttttgtcta aaatttaagg agaagtttt                            1419
```

```
<210> SEQ ID NO 40
<211> LENGTH: 739
<212> TYPE: PRT
<213> ORGANISM: Artificial Sequence
<220> FEATURE:
<223> OTHER INFORMATION: Based on Lactobacillus reuteri sequence

<400> SEQUENCE: 40

Met Asn Lys Ala Asn Gln Lys Val Ala Asp Asp Thr Thr Ala Val Asn
1               5                   10                  15

Asn Lys Gln Thr Asp Val Asn Asn Ala Ala Glu Ala Lys Lys Asn Ala
            20                  25                  30

Asp Glu Ala Leu Lys Asn Ala Asn Asp Ala Gln Thr Ser Ala Gln Lys
        35                  40                  45

Asn Lys Asp Ala Lys Gln Ala Ile Ala Asp Glu Ala Ser Val Ala Leu
    50                  55                  60

Ala Asp Ala Asn Thr Ala Val Lys Asp Ala Gln Ala Lys Val Asp Ala
65                  70                  75                  80

Ile Asn Asp Lys Leu Ala Asn Phe Asn Thr Ile Thr Leu Pro Ala Gly
                85                  90                  95

Tyr Lys Asp Asp Leu Ile Ala Tyr Tyr Asn Tyr Phe Gly Asn Ser Asn
            100                 105                 110

Tyr Asn Gln Asp Glu Ala Asn Asn Leu Ala Gln Asp Leu Leu Lys Tyr
        115                 120                 125

Arg Asp Gln Ala Met Ser Gln Asn Lys Phe Lys Asp Asn Leu Ser Asp
    130                 135                 140

Asp Arg Val Val Asp Ile Asp Asn Leu Asn Ser Thr Asp Arg Ala Glu
145                 150                 155                 160

Leu Ser Gln Phe Val Ala Ser Leu Ile Asn Gln Val Arg Thr Gln Met
                165                 170                 175

Gly Thr Asn Leu Val Ile Ser Ser Pro Ala Ala Asp Asp Tyr Ala Glu
            180                 185                 190

Gln Val Ser Gln Asn Tyr Asn Lys Asp Asn Trp Asn Ser Ala Asp Asn
        195                 200                 205

Gly Lys His Asp Gln Ser Ala Leu Asn Asn Ala Thr Asp Gln Leu Asn
    210                 215                 220

Ile Ser Trp Asn Gly Glu Asn Met Gly Leu Asp Gln Ser Ile Phe Thr
```

-continued

```
225                230                 235                 240

Thr Asp Tyr Thr Val Leu Thr Asp Gly Thr Lys Leu Pro Thr Gly Asn
            245                 250                 255

Lys Gln Thr Ile Asn Asp Leu Lys His Leu Ile Tyr Asp Asp Phe Ile
            260                 265                 270

Ser Met Met Phe Asp Asp Ala Asp Ser Ala Trp Gly His Ala Thr Asn
            275                 280                 285

Phe Ala Gly Ile Asp Asn Phe Ala Ala Glu Lys Gln Ala Val Gly Phe
            290                 295                 300

Ser Leu Asp Lys Phe Tyr Asn Thr His Tyr Asp Leu Val Glu Ala Asn
305                 310                 315                 320

Gln Lys Val Glu Glu Asn Ser Tyr Thr Leu Pro Ser Ile Asn Ala Leu
            325                 330                 335

Thr Gln Lys Leu Ala Asp Ala Lys Asp Asp Leu Ser Ile Lys Gln Thr
            340                 345                 350

Asp Gln Ala Ser Lys Gln Lys Ala Asn Asp Asp Ala Gln Asn Ala Leu
            355                 360                 365

Ser Ser Ala Asn Gln Val Leu Val Ala Ala Gln Asn Asp Val Lys Asp
            370                 375                 380

Lys Thr Ala Thr Ala Gln Glu Ala Asn Asp Asn Leu Thr Thr Ala Gln
385                 390                 395                 400

Asn Asp Leu Ala Thr Leu Gln Asn Gln Leu Ser Ala Asp Gln Ala Asn
            405                 410                 415

Gln Lys Gln Ala Gln Thr Thr Phe Asp Ser Phe Asp Ala Asp Leu Ala
            420                 425                 430

Thr Lys Gln Ala Asn Leu Gln Lys Ala Thr Asp Ser Leu Lys Ala Glu
            435                 440                 445

Gln Gly Arg Leu Ala Ile Ala Gln Ala Asp Leu Asp Asn Ala Asn Lys
            450                 455                 460

Ala Leu Ser Asp Ala Asn Asn Asn Leu Ala Gln Lys Lys Gln Val Val
465                 470                 475                 480

Glu Asn Asp Asn Glu Thr Leu Lys Val Asp Asn Asp Lys Leu Val Gln
            485                 490                 495

Leu Gln Asn Asn Leu Ser Asp Leu Gln Asn Ala Pro Lys Leu Leu Ala
            500                 505                 510

Ala Ala Lys Glu Gln Val Ala Thr Ala Gln Lys Ala Leu Ala Asp Ala
            515                 520                 525

Gln Glu Ala Tyr Asn Val Ala Asn Asp Lys Leu Thr Ser Leu Lys Gln
            530                 535                 540

Thr Ala Ala Gly Thr Thr Thr Asn Val Ser Lys Ala Gln Gln Ala Leu
545                 550                 555                 560

Ala Glu Ala Lys Asn Asn Glu Asp Ala Ala Lys Glu Val Leu Asp Gln
            565                 570                 575

Ala Gln Gln Ala Leu Thr Glu Leu Arg Gln Lys Glu Ala Leu Ala Lys
            580                 585                 590

Gln Val Ala Glu Glu Gln Ala Lys Leu Ala Ala Glu Lys Glu Ala Lys
            595                 600                 605

Asp Asn Gly Tyr His Ile Glu Asn Asn Gln Val Val Asp Ala Lys Gly
            610                 615                 620

Asn Ser Val Asn Gly Trp Thr Val Lys Gly Asn Gln Ile Val Ser Pro
625                 630                 635                 640

Thr Asn Ala Thr Val Asp Pro Ala Val Ser Val Thr Thr Asn Val Asn
            645                 650                 655
```

```
Val Asp Ser Lys Gly Gln Val Gln Pro Gln Thr Ser Val Thr Ala Asn
            660                 665                 670

Ser Val Lys Thr Val Ala Ala Thr Glu Ser Ala Asn Pro Val Ala Thr
            675                 680                 685

Thr Thr Val Gln Thr Arg Glu Gln Tyr Lys Gln Gln Leu Lys Ser Asn
            690                 695                 700

Asn Gln Leu Pro Gln Thr Gly Asn Asn Asp Ser Ala Val Leu Ser Leu
705                 710                 715                 720

Ala Gly Val Ala Leu Ala Ala Met Leu Ser Leu Phe Gly Ile Lys Lys
                725                 730                 735

Arg Glu Tyr
```

```
<210> SEQ ID NO 41
<211> LENGTH: 185
<212> TYPE: DNA
<213> ORGANISM: Artificial Sequence
<220> FEATURE:
<223> OTHER INFORMATION: Based on Lactobacillus reuteri sequence

<400> SEQUENCE: 41
aaattaaaag ctggattttt ttcggccttt ttttagtgca ataattatt ttttacgtat     60 ttatattata gggctaatca ctaaactaat aattagtggt tgaagcgctg aaaattttct    120
gctattttat taatagtttg ataataaaat aatgatattt aatataaaga gggataaacg    180
aaata                                                               185
```

```
<210> SEQ ID NO 42
<211> LENGTH: 275
<212> TYPE: DNA
<213> ORGANISM: Artificial Sequence
<220> FEATURE:
<223> OTHER INFORMATION: Based on Lactobacillus reuteri sequence

<400> SEQUENCE: 42
gaagtacaaa gttactttaa ctataatgaa aaacaagaca atataaagaa aacaacatat     60
aaggttcagt tcataactga ttagatttat aataaatatt gtaaatcgga caaaaataaa    120
ttaattttca attaattcaa aaaaaccata ttttttttcgt tttggcatat ttggatttgc    180
tacactaaag atgatcaaga aaggggaaaa gataatcttc aatcttgtgt acttagtttg    240
ttaattaatt tataaattta gggaggaaac ctatc                              275
```

```
<210> SEQ ID NO 43
<211> LENGTH: 313
<212> TYPE: DNA
<213> ORGANISM: Artificial Sequence
<220> FEATURE:
<223> OTHER INFORMATION: Based on Lactobacillus reuteri sequence

<400> SEQUENCE: 43
gcaatgcaca agatgctgaa acaaaggcac aacaaaatgc agatcaagct tcaccagcta     60
atattcaaaa ggcacaagat gctattgcta atcaagaaac tcaaattagt aaagacaccg    120
atgctattaa tgacgctaac aaagccgtta gcgatgcaca agcacagtt gatgcagcgc     180 aaaaaaagtt aatgatgcaa ctactgctcg tgacaatcaa caaaagaatg ttgatactgc    240
tagtgatgca gttaagaatg ctcaagctat tcttgacaac agtgatcagg ctaaaaagga    300
agcccaagat gct                                                      313
```

-continued

```
<210> SEQ ID NO 44
<211> LENGTH: 46
<212> TYPE: PRT
<213> ORGANISM: Artificial Sequence
<220> FEATURE:
<223> OTHER INFORMATION: Based on Lactobacillus reuteri sequence

<400> SEQUENCE: 44

Ala Ile Lys Pro Val Pro Ser Pro Asn Gly Ile Phe Ala Ala Ser Phe
1               5                   10                  15

Glu Leu Asn Gly Thr Thr Trp Ile Phe Lys Tyr Lys Tyr Tyr Asp Ser
            20                  25                  30

Ser Lys Gly Tyr Trp Val Gly Ile Tyr Glu Ser Val Asp Lys
        35                  40                  45

<210> SEQ ID NO 45
<211> LENGTH: 64
<212> TYPE: PRT
<213> ORGANISM: Artificial Sequence
<220> FEATURE:
<223> OTHER INFORMATION: Based on Lactobacillus reuteri sequence

<400> SEQUENCE: 45

Leu Ala Ser Thr Leu Gly Ile Ser Thr Ala Ala Ala Lys Lys Ala Ile
1               5                   10                  15

Asp Ile Ile Asp Ala Ala Ser Thr Ile Ala Ser Ile Ile Ser Leu Ile
            20                  25                  30

Gly Ile Val Thr Gly Ala Gly Ala Ile Ser Tyr Ala Ile Val Ala Thr
        35                  40                  45

Ala Lys Thr Met Ile Lys Lys Tyr Gly Lys Lys Tyr Ala Ala Ala Trp
    50                  55                  60

<210> SEQ ID NO 46
<211> LENGTH: 38
<212> TYPE: PRT
<213> ORGANISM: Artificial Sequence
<220> FEATURE:
<223> OTHER INFORMATION: Based on Lactobacillus reuteri sequence

<400> SEQUENCE: 46

Glu Phe Ser Gly Gly Gly Gly Ala Glu Gln Arg Gly Ile Ser Gln Gly
1               5                   10                  15

Asn Asp Gly Lys Leu Cys Thr Leu Thr Trp Glu Cys Gly Leu Cys Pro
            20                  25                  30

Thr His Thr Cys Trp Cys
        35

<210> SEQ ID NO 47
<211> LENGTH: 35
<212> TYPE: PRT
<213> ORGANISM: Artificial Sequence
<220> FEATURE:
<223> OTHER INFORMATION: Based on Lactobacillus reuteri sequence

<400> SEQUENCE: 47

Ser Asp Ala Thr Pro Met Thr Val Thr Pro Thr Thr Ile Thr Ile Pro
1               5                   10                  15

Ile Ser Leu Ala Gly Cys Pro Thr Thr Lys Cys Ala Ser Ile Val Ser
            20                  25                  30

Pro Cys Asn
        35
```

-continued

```
<210> SEQ ID NO 48
<211> LENGTH: 36
<212> TYPE: PRT
<213> ORGANISM: Artificial Sequence
<220> FEATURE:
<223> OTHER INFORMATION: Based on Lactobacillus reuteri sequence

<400> SEQUENCE: 48

Ser Glu Ala Thr Pro Met Thr Val Thr Pro Thr Thr Ile Thr Ile Pro
1               5                   10                  15

Ile Ser Leu Ala Gly Cys Pro Thr Thr Lys Cys Ala Ser Ile Val Ser
            20                  25                  30

Pro Cys Asn Asp
        35

<210> SEQ ID NO 49
<211> LENGTH: 154
<212> TYPE: PRT
<213> ORGANISM: Artificial Sequence
<220> FEATURE:
<223> OTHER INFORMATION: Synthetic construct

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Ala Gly Ser Gly His Thr Gly Ser Leu Tyr
            20                  25                  30

Ser Met Gly Trp Phe Arg Gln Ala Pro Gly Lys Glu Arg Glu Phe Val
        35                  40                  45

Ala Ala Ile Thr Trp Arg Pro Ser Ser Thr Tyr Tyr Ala Asp Ser Val
    50                  55                  60

Lys Gly Arg Phe Thr Ile Ser Arg Asp Asp Ala Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Arg Pro Arg Gly Gly Leu Ser Pro Thr Pro Gln Ala Tyr Asp
            100                 105                 110

Tyr Trp Gly Gln Gly Thr Gln Val Thr Val Ser Ser Ala Ala Ala Ser
        115                 120                 125

Gly Ser Leu Glu Gln Lys Leu Ile Ser Glu Glu Asp Leu Asn Gly Ala
    130                 135                 140

Ala His His His His His His Gly Ala Ala
145                 150

<210> SEQ ID NO 50
<211> LENGTH: 143
<212> TYPE: PRT
<213> ORGANISM: Artificial Sequence
<220> FEATURE:
<223> OTHER INFORMATION: Synthetic construct

<400> SEQUENCE: 50

Glu Val Gln Leu Val Glu Ser Gly Gly Gly Leu Val Gln Thr Gly Gly
1               5                   10                  15

Ser Leu Arg Leu Ser Cys Thr Ala Ser Gly Thr Ile Asp Met Thr Tyr
            20                  25                  30

Gly Leu Ile Trp Tyr Arg Gln Ala Pro Gly Lys Glu Arg Glu Leu Val
        35                  40                  45

Ala Ser Ile Arg Arg Asp Gly His Thr Asn Tyr Ala Asp Ser Val Lys
    50                  55                  60
```

-continued

```
Gly Arg Phe Thr Ile Ser Ile Asp Asn Ala Lys Asn Ser Ile His Leu
65              70                  75                  80

Gln Met Asn Ser Leu Lys Pro Asp Asp Thr Ala Arg Tyr Tyr Cys Asn
                85                  90                  95

Ser Pro Tyr His Ala Leu Trp Gly Gln Gly Thr Gln Val Thr Val Ser
            100                 105                 110

Ser Ala Ala Ala Ser Gly Ser Leu Glu Gln Lys Leu Ile Ser Glu Glu
        115                 120                 125

Asp Leu Asn Gly Ala Ala His His His His His His Gly Ala Ala
    130                 135                 140
```